(12) United States Patent
Finney et al.

(10) Patent No.: US 12,331,117 B2
(45) Date of Patent: *Jun. 17, 2025

(54) ANTIBODY MOLECULES WHICH BIND CD22

(71) Applicant: UCB Biopharma SRL, Brussels (BE)

(72) Inventors: Helene Margaret Finney, Slough (GB); Stephen Edward Rapecki, Slough (GB); Kerry Louise Tyson, Slough (GB); Michael John Wright, Slough (GB)

(73) Assignee: UCB Biopharma SRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,688

(22) Filed: Aug. 23, 2022

(65) Prior Publication Data

US 2023/0065921 A1    Mar. 2, 2023

Related U.S. Application Data

(60) Continuation of application No. 16/778,523, filed on Jan. 31, 2020, now Pat. No. 11,472,879, which is a division of application No. 15/743,756, filed as application No. PCT/EP2016/066991 on Jul. 15, 2016, now Pat. No. 10,590,197.

(30) Foreign Application Priority Data

Jul. 16, 2015    (WO) ................. PCT/EP2015/066369
Jan. 20, 2016    (GB) ...................................... 1601077

(51) Int. Cl.
*C07K 16/28*        (2006.01)
*A01K 67/0278*      (2024.01)
*A61K 39/00*        (2006.01)

(52) U.S. Cl.
CPC ...... *C07K 16/2803* (2013.01); *A01K 67/0278* (2013.01); *C07K 16/2851* (2013.01); *A01K 2267/01* (2013.01); *A61K 2039/505* (2013.01); *C07K 2317/24* (2013.01); *C07K 2317/31* (2013.01); *C07K 2317/35* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Hiuse et al. |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 6,183,744 B1 | 2/2001 | Goldenberg et al. |
| 6,306,393 B1 | 10/2001 | Goldenberg et al. |
| 6,368,596 B1 | 4/2002 | Ghetie et al. |
| 6,809,185 B1 | 10/2004 | Schoonjans et al. |
| 6,818,749 B1 | 11/2004 | Kashmiri et al. |
| 7,074,403 B1 | 7/2006 | Goldenberg et al. |
| 7,183,076 B2 | 2/2007 | Arathoon et al. |
| 7,321,026 B2 | 1/2008 | Leung et al. |

(Continued)

FOREIGN PATENT DOCUMENTS

| | | |
|---|---|---|
| CN | 1326878 C | 12/2001 |
| CN | 103214578 A | 7/2013 |

(Continued)

OTHER PUBLICATIONS

Yu et al., "Rationalization and Design of the Complementarity Determining Region Sequences in an Antibody-Antigen Recognition Surface," PLOS One 7(3):e33340 (2012).

Zahnd et al., "Directed in Vitro Evolution and Crystallographic Analysis of a Peptide-binding Single Chain Antibody Fragment (scFv) with Low Picomolar Affinity," J Biol Chem 279(18):18870-18877 (2004).

Zhang et al., "PowerBLAST: a new network BLAST application for interactive or automated sequence analysis and annotation," Genome Res 7(6):649-656 (1997).

(Continued)

*Primary Examiner* — Phuong Huynh
(74) *Attorney, Agent, or Firm* — MEDLER FERRO WOODHOUSE & MILLS PLLC

(57) ABSTRACT

The present disclosure relates to antibody molecules comprising a binding domain specific to CD22, said binding domain comprising SEQ ID NO: 1, 2, 3, 4, 5 and 6 or 7. The disclosure also extends to pharmaceutical compositions comprising said antibody molecules and use of the antibody molecules/compositions in treatment.

20 Claims, 46 Drawing Sheets

Specification includes a Sequence Listing.

(56) References Cited

U.S. PATENT DOCUMENTS

| | | |
|---|---|---|
| 7,338,659 B2 | 3/2008 | Leung et al. |
| 7,355,012 B2 | 4/2008 | Pastan et al. |
| 7,491,514 B2 | 2/2009 | Leung et al. |
| 7,495,081 B2 | 2/2009 | Leung et al. |
| 7,541,034 B1 | 6/2009 | Fitzgerald et al. |
| 7,641,901 B2 | 1/2010 | Goldenberg et al. |
| 7,777,019 B2 | 8/2010 | Pastan et al. |
| 7,825,224 B2 | 11/2010 | Vilen et al. |
| 7,829,086 B2 | 11/2010 | Hilbert et al. |
| 7,837,995 B2 | 11/2010 | Goldenberg et al. |
| 7,910,103 B2 | 3/2011 | Goldenberg et al. |
| 7,939,073 B2 | 5/2011 | Goldenberg et al. |
| 7,982,011 B2 | 7/2011 | Pastan et al. |
| 8,088,378 B2 | 1/2012 | Chen et al. |
| 8,153,768 B2 | 4/2012 | Kunz et al. |
| 8,226,945 B2 | 7/2012 | Ebens et al. |
| 8,389,688 B2 | 3/2013 | Jones et al. |
| 8,409,577 B2 | 4/2013 | Thompson et al. |
| 8,420,086 B2 | 4/2013 | Govindan et al. |
| 8,481,683 B2 | 7/2013 | King et al. |
| 8,524,865 B2 | 9/2013 | Ebens et al. |
| 8,545,850 B2 | 10/2013 | Chen et al. |
| 8,591,889 B2 | 11/2013 | Dimitrov et al. |
| 8,658,168 B2 | 2/2014 | Ghetie et al. |
| 8,664,363 B2 | 3/2014 | Jones et al. |
| 8,669,349 B2 | 3/2014 | Johnson et al. |
| 8,691,531 B2 | 4/2014 | Chen et al. |
| 8,722,857 B2 | 5/2014 | Chen et al. |
| 8,747,857 B2 | 6/2014 | Kunz et al. |
| 8,809,502 B2 | 8/2014 | Pastan et al. |
| 8,835,611 B2 | 9/2014 | Kunz et al. |
| 8,852,599 B2 | 10/2014 | Zhang et al. |
| 8,871,201 B2 | 10/2014 | Kantor et al. |
| 8,968,741 B2 | 3/2015 | Ebens et al. |
| 9,138,485 B2 | 9/2015 | Govindan et al. |
| 9,139,649 B2 | 9/2015 | Chang et al. |
| 9,181,343 B2 | 11/2015 | Rabuka et al. |
| 9,192,664 B2 | 11/2015 | Chang et al. |
| 9,279,019 B2 | 3/2016 | Dimitrov et al. |
| 9,371,396 B2 | 6/2016 | Leung et al. |
| 9,475,883 B2 | 10/2016 | Chang et al. |
| 9,499,632 B2 | 11/2016 | King et al. |
| 9,518,115 B2 | 12/2016 | Chang et al. |
| 9,580,461 B2 | 2/2017 | Linke et al. |
| 9,592,304 B2 | 3/2017 | Fitzgerald et al. |
| 9,598,492 B2 | 3/2017 | Dimitrov et al. |
| 9,642,918 B2 | 5/2017 | Bruederle et al. |
| 9,663,576 B2 | 5/2017 | Chang et al. |
| 9,695,236 B2 | 7/2017 | Johnson et al. |
| 9,701,748 B2 | 7/2017 | Chang et al. |
| 9,845,355 B2 | 12/2017 | Chen et al. |
| 9,856,323 B2 | 1/2018 | Short et al. |
| 9,896,506 B2 | 2/2018 | Chen et al. |
| 9,944,703 B2 | 4/2018 | Chang et al. |
| 9,975,949 B2 | 5/2018 | Sun et al. |
| 10,358,493 B2 | 7/2019 | Finney et al. |
| 10,370,447 B2* | 8/2019 | Finney .................... A61P 35/02 |
| 10,590,197 B2* | 3/2020 | Finney .................... A61P 29/00 |
| 10,618,957 B2* | 4/2020 | Finney .................... A61P 5/14 |
| 10,618,979 B2 | 4/2020 | Wright et al. |
| 10,774,152 B2 | 9/2020 | Finney et al. |
| 10,774,157 B2 | 9/2020 | Wright |
| 10,829,566 B2 | 11/2020 | Rapecki |
| 10,954,312 B2 | 3/2021 | Finney |
| 11,261,252 B2* | 3/2022 | Finney .................... C07K 16/18 |
| 11,472,879 B2* | 10/2022 | Finney ............... A01K 67/0278 |
| 2003/0027247 A1 | 2/2003 | Wang et al. |
| 2003/0202975 A1 | 10/2003 | Tedder et al. |
| 2005/0033031 A1 | 2/2005 | Cuoto et al. |
| 2005/0048578 A1 | 3/2005 | Dongxiao et al. |
| 2006/0115832 A1 | 6/2006 | Hoon |
| 2006/0252130 A1 | 11/2006 | Boehm et al. |
| 2006/0275844 A1 | 12/2006 | Linke et al. |
| 2007/0071675 A1 | 3/2007 | Wu et al. |
| 2007/0141672 A1 | 6/2007 | Shin et al. |
| 2011/0076270 A1 | 3/2011 | Aversa et al. |
| 2011/0190157 A1 | 8/2011 | Kipps et al. |
| 2012/0178111 A1 | 7/2012 | Diamandis et al. |
| 2013/0142787 A1 | 6/2013 | Chang et al. |
| 2013/0209463 A1 | 8/2013 | Rotman et al. |
| 2013/0336977 A1 | 12/2013 | Thompson et al. |
| 2014/0099254 A1 | 4/2014 | Chang et al. |
| 2014/0212425 A1 | 7/2014 | Chang et al. |
| 2014/0248278 A1 | 9/2014 | Tuscano et al. |
| 2015/0239974 A1 | 8/2015 | Chang et al. |
| 2016/0229911 A1 | 8/2016 | Rabuka et al. |
| 2016/0304611 A1 | 10/2016 | Chevallier et al. |
| 2016/0363597 A1 | 12/2016 | Leung et al. |
| 2017/0058031 A1 | 3/2017 | King et al. |
| 2017/0081404 A1 | 3/2017 | Finney et al. |
| 2017/0145097 A1 | 5/2017 | Dimitrov et al. |
| 2017/0151356 A1 | 6/2017 | Govindan et al. |
| 2017/0204178 A1 | 7/2017 | Finney et al. |
| 2017/0204183 A1 | 7/2017 | Finney et al. |
| 2017/0226207 A1 | 8/2017 | Yamajuku et al. |
| 2018/0086843 A1 | 3/2018 | Short et al. |
| 2018/0201678 A1 | 7/2018 | Finney et al. |
| 2018/0201679 A1 | 7/2018 | Chen et al. |
| 2018/0237521 A1 | 8/2018 | Finney et al. |
| 2018/0273620 A1 | 9/2018 | Finney et al. |
| 2018/0334513 A1 | 11/2018 | Wright |
| 2018/0334514 A1 | 11/2018 | Wright |
| 2018/0346603 A1 | 12/2018 | Bhatta et al. |
| 2018/0346604 A1 | 12/2018 | Rapecki |
| 2018/0355063 A1 | 12/2018 | Finney |
| 2019/0322739 A1 | 10/2019 | Finney et al. |
| 2020/0024346 A1 | 1/2020 | Finney et al. |
| 2020/0157215 A1 | 5/2020 | Finney et al. |

FOREIGN PATENT DOCUMENTS

| | | |
|---|---|---|
| EP | 0392745 A2 | 10/1990 |
| EP | 0438474 A1 | 7/1991 |
| EP | 0463151 A1 | 1/1992 |
| EP | 0546073 A1 | 6/1993 |
| EP | 1049787 A1 | 11/2000 |
| EP | 1156826 A1 | 11/2001 |
| EP | 1178826 A1 | 2/2002 |
| EP | 1242457 A1 | 9/2002 |
| EP | 1431311 A1 | 6/2004 |
| EP | 1442061 A1 | 8/2004 |
| EP | 1448584 A2 | 8/2004 |
| EP | 1543839 A1 | 6/2005 |
| EP | 1570267 A1 | 9/2005 |
| EP | 1689783 A1 | 8/2006 |
| EP | 1784219 A2 | 5/2007 |
| EP | 1998799 A2 | 12/2008 |
| EP | 1999148 A2 | 12/2008 |
| EP | 2032606 A2 | 3/2009 |
| EP | 2097097 A2 | 9/2009 |
| EP | 2176295 A1 | 4/2010 |
| EP | 2176296 A1 | 4/2010 |
| EP | 2247620 A1 | 11/2010 |
| EP | 2252631 A2 | 11/2010 |
| EP | 2295073 A1 | 3/2011 |
| EP | 2474557 A2 | 7/2012 |
| EP | 2502937 A2 | 9/2012 |
| EP | 2657253 A2 | 10/2013 |
| EP | 2706069 A1 | 3/2014 |
| EP | 2788020 A1 | 10/2014 |
| EP | 2841459 A1 | 3/2015 |
| EP | 2861622 A2 | 4/2015 |
| EP | 2869850 A1 | 5/2015 |
| EP | 2874650 A1 | 5/2015 |
| EP | 3045475 A1 | 7/2016 |
| EP | 3178929 A1 | 6/2017 |
| EP | 3110445 A1 | 9/2017 |
| EP | 3227336 A1 | 10/2017 |
| EP | 3269737 A1 | 1/2018 |
| RU | 2339696 C2 | 11/2008 |
| WO | 86/01533 A1 | 3/1986 |
| WO | 89/00195 A1 | 1/1989 |
| WO | 89/01476 A1 | 2/1989 |
| WO | 90/02809 A1 | 3/1990 |

(56) References Cited

FOREIGN PATENT DOCUMENTS

| | | |
|---|---|---|
| WO | 91/05568 A1 | 5/1991 |
| WO | 91/09967 A1 | 7/1991 |
| WO | 91/10737 A1 | 7/1991 |
| WO | 92/01047 A1 | 1/1992 |
| WO | 92/02551 A1 | 2/1992 |
| WO | 92/18619 A1 | 10/1992 |
| WO | 92/22583 A1 | 12/1992 |
| WO | 93/06231 A1 | 4/1993 |
| WO | 93/11162 A1 | 6/1993 |
| WO | 93/11236 A1 | 6/1993 |
| WO | 95/15982 A1 | 6/1995 |
| WO | 95/20401 A1 | 8/1995 |
| WO | 96/26964 A1 | 9/1996 |
| WO | 98/11918 A1 | 3/1998 |
| WO | 98/20734 A1 | 5/1998 |
| WO | 02/072832 A2 | 9/2002 |
| WO | 03/012069 A2 | 2/2003 |
| WO | 03/031581 A2 | 4/2003 |
| WO | 03/048327 A2 | 6/2003 |
| WO | 03/093320 A2 | 11/2003 |
| WO | 04/039840 A1 | 5/2004 |
| WO | 04/051268 A1 | 6/2004 |
| WO | 04/081051 A1 | 9/2004 |
| WO | 04/106377 A1 | 12/2004 |
| WO | 05/003169 A2 | 1/2005 |
| WO | 05/003170 A2 | 1/2005 |
| WO | 05/003171 A2 | 1/2005 |
| WO | 05/016950 A1 | 2/2005 |
| WO | 05/026210 A2 | 3/2005 |
| WO | 05/113605 A1 | 12/2005 |
| WO | 05/117984 A2 | 12/2005 |
| WO | 05/118642 A2 | 12/2005 |
| WO | 06/004910 A2 | 1/2006 |
| WO | 06/119897 A2 | 11/2006 |
| WO | 07/060406 A1 | 5/2007 |
| WO | 07/085837 A1 | 8/2007 |
| WO | 07/087453 A2 | 8/2007 |
| WO | 07/146968 A2 | 12/2007 |
| WO | 08/070569 A2 | 6/2008 |
| WO | 08/119353 A1 | 10/2008 |
| WO | 09/012268 A1 | 1/2009 |
| WO | 09/040562 A1 | 4/2009 |
| WO | 09/099728 A1 | 8/2009 |
| WO | 09/120178 A1 | 10/2009 |
| WO | 09/155724 A2 | 12/2009 |
| WO | 10/027524 A1 | 3/2010 |
| WO | 10/035012 A1 | 4/2010 |
| WO | 11/025904 A1 | 3/2011 |
| WO | 11/061492 A2 | 5/2011 |
| WO | 11/086091 A1 | 7/2011 |
| WO | 11/130305 A2 | 10/2011 |
| WO | 11/131746 A2 | 10/2011 |
| WO | 12/023053 A2 | 2/2012 |
| WO | 12/116453 A1 | 9/2012 |
| WO | 12/151199 A1 | 11/2012 |
| WO | 12/162561 A2 | 11/2012 |
| WO | 13/012733 A1 | 1/2013 |
| WO | 13/060867 A2 | 5/2013 |
| WO | 13/068563 A2 | 5/2013 |
| WO | 13/078455 A2 | 5/2013 |
| WO | 13/085893 A1 | 6/2013 |
| WO | 14/001326 A1 | 1/2014 |
| WO | 14/011518 A1 | 1/2014 |
| WO | 14/011519 A1 | 1/2014 |
| WO | 14/011520 A1 | 1/2014 |
| WO | 14/011521 A1 | 1/2014 |
| WO | 14/066271 A1 | 5/2014 |
| WO | 14/096390 A1 | 6/2014 |
| WO | 14/131694 A1 | 9/2014 |
| WO | 15/021089 A1 | 2/2015 |
| WO | 15/057834 A1 | 4/2015 |
| WO | 15/101587 A1 | 7/2015 |
| WO | 15/181282 A1 | 12/2015 |
| WO | 15/197772 A1 | 12/2015 |
| WO | 15/197789 A1 | 12/2015 |
| WO | 16/009029 A1 | 1/2016 |
| WO | 16/009030 A2 | 1/2016 |
| WO | 16/168773 A2 | 10/2016 |
| WO | 17/009473 A1 | 1/2017 |
| WO | 17/009476 A1 | 1/2017 |
| WO | 17/093402 A1 | 6/2017 |
| WO | 17/093404 A1 | 6/2017 |
| WO | 17/093406 A1 | 6/2017 |
| WO | 17/093408 A1 | 6/2017 |
| WO | 17/093410 A1 | 6/2017 |
| WO | 18/112407 A1 | 6/2018 |

OTHER PUBLICATIONS

Zhu et al., "Remodeling domain interfaces to enhance heterodimer formation," Protein Sci 6(4):781-788 (1997).
Zhu et al., "Expression of CD22 and CD79b from patients with chronic lymphocytic leukemia," J Clin Hematol (China) 667-669 (2013).
English translation of Office Action in RU Appl. No. 2016149102, issued Feb. 1, 2019.
English translation of Search report in RU Appl. No. 2016149102, issued Feb. 1, 2019.
International Search Report and Written Opinion for PCT/EP2016/066991, mailed Nov. 14, 2016.
Office Action issued Nov. 4, 2020 in Chinese Patent Application No. 201680041760.4 (English translation).
Non-Final Office Action in U.S. Appl. No. 15/326,501 issued on May 16, 2018.
Notice of Allowance in U.S. Appl. No. 15/326,501 issued Nov. 6, 2018.
Notice of Allowance in U.S. Appl. No. 15/326,501 issued Apr. 10, 2019.
Final Office Action dated Jun. 17, 2021, issued in U.S. Appl. No. 16/513,002.
Non-Final Office Action dated Feb. 23, 2021, issued in U.S. Appl. No. 16/513,002.
Notice of Allowance dated Oct. 18, 2021, issued in U.S. Appl. No. 16/513,002.
Baxevanis, Expert Opinion: Drug Discovery, 3(4):441-452 (2008).
Cuzick et al., "Overview of the Main Outcomes in Breast-Cancer Prevention Trials," The Lancet 361:296-300 (2003).
Evans et al., "Vaccine Therapy for Cancer—Fact or Fiction?," Q. J. Med 92:299-307 (1999).
Hernandez-Ledesma, "Lunasin, A Novel Seed Peptide for Cancer Prevention," Peptides 30:426-430 (2009).
Houdebine, "Production of Pharmaceutical Proteins for Transgenic Animals," Journal of Biotechnology, 34: 269-287 (1994).
Kappel et al., "Regulating Gene Expression in Transgenic Animals," Current Opinion in Biotechnology 3:548-553 (1992).
Komenaka et al., "Immunotherapy for Melanoma," Clinics in Dermatology 22:251-265 (2004).
Non-Final Office Action dated May 3, 2022, issued in U.S. Appl. No. 15/743,761.
Schiffman et al., "The Promise of Global Cervical-Cancer Prevention," The New England Journal of Medicine 353 (20):2101-2104 (2005).
Wall, "Transgenic Livestock: Projects and Prospects for the Future," Theriogenology 45:57-68 (1996).
Gussow et al., "Humanization of Monoclonal Antibodies," Meth Enzymol 203:99-121 (1991).
Hanes et al., "Ribosome display efficiently selects and evolves high-affinity antibodies in vitro from immune libraries," Proc Natl Acad Sci USA 95:14130-14135 (1998).
Harris, "Processing of C-terminal lysine and arginine residues of proteins isolated from mammalian cell culture," J Chromatogr A 705(1): 129-134 (1995).
Hermiston et al., "CD45: A Critical Regulator of Signaling Thresholds in Immune Cells," Ann Rev Immunol 21:107-137 (2003).
Hernandez-Molina et al., "The meaning of anti-Ro and anti-La antibodies in primary Sjogren's syndrome," Autoimmunity Reviews 10: 123-125 (2011).

(56) References Cited

OTHER PUBLICATIONS

Hinnebusch, "Evidence for translational regulation of the activator of general amino acid control in yeast," Proc Natl Acad Sci USA 81 :6442-6446 (1984).
Hinton et al., "Engineered human IgG antibodies with longer serum half-lives in primates," J Biol Chem 279 (8):6213-6216 (2004).
Hoeller et al., "CD79a and Cycline are the most appropriate markers to discriminiate classical Hodgkin's Lymphoma from Primary Mediastinal Large B-cell Lymphoma Histopathology," J. Clin Exp Pathol. 56(2):217-228 (2010).
Hollinger et al., "Engineered antibody fragments and the rise of single domains," Nat Biotechnol 23(9): 1126-1136 (2005).
Holm et al., "Functional mapping and single chain construction of the anti-cytokeratin 8 monoclonal antibody TSI1," Mol Immunol 44:1075-1084 (2007).
Holmes, "Buy buy bispecific antibodies," Nat Rev Drug Discov 10(11):798-800 (2011).
Holt et al., "Anti-serum albumin domain antibodies for extending the half-lives of short lived drugs," Protein Eng Des Sel 21 (5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Hu et al., "Four-in-One Antibodies Have Superior Cancer Inhibitory Activity against EGFR, HER2, HER3, and VEGF through Disruption of HER/MET Crosstalk," Cancer Res. 75(1):159-70 (2015).
Idusogie et al., "Mapping of the C1 q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 19(4):1480-1490 (2014).
Kashmiri et al., "SOR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Klimka et al., "Human anti-CD30 recombinant antibodies by guided phage antibody selection using cell panning," British Journal of Cancer, 83(2):252-260 (2000).
Ko et al., "Engineering Antibodies for Dual Specificity and Enhanced Potency," Biotechnol Bioprocess Eng 20:201-210 (2015).
Kohler et al., "Continuous cultures of fused cells secreting antibody of predefined specificity," Nature 256:495-497 (1975).
Kontermann et al., "Dual targeting strategies with bispecific antibodies," mAbs. 4(2):182-197 (2012).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Kumar et al., "Molecular Cloning and Expression of the Fabs of Human Autoantibodies in *Escherichia coli*," J Biol. Chem. 275(45): 35129-35136 (2000).
Kussie et al., "A Single Engineered Amino Acid Substitution Changes Antibody Fine Specificity," J. Immunol. 152:146-152 (1994).
Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103 (11):4005-4010 (2006).
Li et al. "Study advance in molecular structure and function of CD45," Int'l J. Immunology 31 (5):346-349 (2008).
Lloyd, C., et al., "Modelling the human immune response: performance of a 1 OE11 human antibody repertoire against a broad panel of therapeutically relevant antigens," Protein Engineering, Design & Selection 22(3):159-168 (2009).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "VI-linker-Vh orientation-dependent expression of single chain Fv-containing an engineered disulfide-stabilized bond in the framework regions," J Biochem 118(4):825-831 (1995).
Luo et al., "Design and Applications of Bispecific Heterodimers: Molecular Imaging and Beyond," Mot Pharm 11:1750-1761 (2014).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Munodzana et al., "Conformational Dependence of Anaplasma marginale Major Surface Protein 5 Surface-Exposed B-Cell Epitopes," Infection and Immunity, American Society for Microbiology 66(6):2619-2624 (1998).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Pan et al., "Blocking Neuropilin-1 Function Has an Additive Effect with Anti-VEGF to Inhibit Tumor Growth," Cancer Cell 11(1):53-67 (2007).
Patten et al., "Applications of DNA shuffling to pharmaceuticals and vaccines," Curr Opin Biotechnol 8(6):724-733 (1997).
Paul, "Fundamental Immunology: Structure and Function of Immunogloblins", Third Edition, Chapter 9, pp. 292-295 (1993).
Persic et al., "An integrated vector system for the eukaryotic expression of antibodies or their fragments after selection from phage display libraries," Gene 187(1):9-18 (1997).
Peters, "Serum albumin," Adv Protein Chem 37:161-245 (1985).
Pfeifer et al., "Anti-CD22 and anti-CD79B antibody drug conjugates are active in different molecular diffuse large B-cell lymphoma subtypes," Leukemia 29:1578-1586 (2015).
Polson et al., "Antibody-drug Conjugates Targeted o CD79 for the Treatment of Non-Hodgkin Lymphoma," Blood 110(2): 616-623 (2007).
Polyak et al., "Blood: Alanine-170 and proline-172 are critical determinants for extra cellular CD20 epitopes; heterogeneity in the fine specificity of CD20 monoclonal antibodies is defined by additional requirements imposed by poth amino acid sequence and quaternary structure," Blood Journal 99: 3256-3262 (2002).

(56) References Cited

OTHER PUBLICATIONS

Portolano et al., "Lack of Promiscuity in Autoantigen-Specific H and L Chain Combinations as Revealed by Human Hand L Chain Roulette", The Journal of Immunology 150(3):80-887 (1993).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rodgers et al., "Switch-mediated activation and retargeting of CAR-T cells for B-cell malignancies," Proc Natl Acad Sci USA 113(4):E459-E468 (2016).
Roitt et al., Immunology, Moscow, MIR, pp. 110-111 (2000).
Rudikoff et al., "Single amino acid substitution altering antigen-binding specificity," Proc Natl Acad Sci USA 79:1979-1983 (1982).
Ryan et al., "Antibody targeting of B-cell maturation antigen on malignant plasma cells," Mol Cancer Ther 6(11):3009-3018 (2007).
Schoonjans et al., "A new model for intermediate molecular weight recombinant bispecific and trispecific antibodies by efficient heterodimerization of single chain variable domains through fusion to a Fab-chain," Biomol Eng 17:193-202 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 (9):6591-6604 (2001).
Singer et al., Genes and Genomes, Moscow, MIR 1:63-64 (1998).
Smith-Gill et al., "Contributions of Immunoglobulin Heavy and Light Chains to Antibody Specificity for Lysozyme and Two Haptens," The Journal of Immunology 139(12): 4135-4144 (1987).
Snyder et al., "Overview of Monoclonal Antibodies and Small Molecules Targeting the Epidermal Growth Factor Receptor Pathway in Colorectal Cancer," Clin Colorec Canc 5(Suppl.2): S71-S80 (2005).
Song et al., "Light Chain of Natural Antibody Plays a Dominant Role in Protein Antigen Binding," Biochem. Biophys Res. Comm. 268: 390-394 (2000).
Spang et al., "Heterodimeric Barnase-Barstar Vaccine Molecules: Influence of One versus Two Targeting Units Specific for Antigen Presenting Cells," PLoS One 7(9):e45393 (2012).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Stavenhagen et al., "Enhancing the potency of therapeutic monoclonal antibodies via Fc optimization," Adv Enzyme Regul 48:152-164 (2008).
Steurer et al., "Ex vivo coating of islet cell al log rafts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable oop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Veri et al., "Therapeutic Control of B Cell Activation via a Recruitment of Fcγ Receptor IIb (CD32B) Inhibitory Function with a Novel Bispecific Antibody Scaffold," Arthritis Rheum 62(7):1933-1943 (2010).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).
Wang et al., "Antibody Engineering Using Phage Display with a Coiled-Coil Heterodimeric Fv Antibody Fragment," PLoS One 6(4):e19023 (2011).
Wang et al., "Molecular Mechanisms of Burkitt's Lymphoma treated by Epratuzumab," Modern Oncology 19(11):2188-2190 (2011).
Ward et al., "Binding Activities of a Repertoire of Single Immunoglobulin Variable Domains Secreted from *Escherichia coli*," Nature 341: 544-546 (1989).
Wienands, "The B-cell antigen receptor: formation of signaling complexes and the function of adaptor proteins," Curr Top Microbiol Immunol 245:53-76 (2000).
Willcox et al., "Production of soluble α/β T-cell receptor heterodimers suitable for biophysical analysis of ligand binding," Protein Sci 8:2418-2423 (1999).
Winkler et al., "Changing the Antigen Binding Specificity by Single Point Mutations of an Anti-p24 (HIV-1) Antibody," J Immunol 165:4505-4514 (2000).
Wu et al., "Humanization of a Murine Monoclonal Antibody by Simultaneous Optimization of Framework and CDR Residues," J Mol Biol 294:151-162 (1999).
Xiao Foreign Medical Sciences, China Academic Journal Electronic Publishing House, (Section of Internal Medicine) 31 (3):93-96 (2004).
Yang et al., "CDR walking mutagenesis for the affinity maturation of a potent human anti-HIV-1 antibody into the bicomolar range," J Mol Biol 254(3):392-403 (1995).
Young et al., "Thermal stabilization of a single-chain Fv antibody fragment by introduction of a disulphide bond," FEBS Lett 377(2):135-139 (1995).
Yu et al., "Interaction between Bevacizumab and Murine VEGF-A: A Reassessment," Invest Ophthalmol Vis Sci 49(2):522-527 (2008).
Adair et al., "Therapeutic Antibodies," Drug Design Reviews Online 2(3):209-217 (2005).
Altin et al., "The role of CD45 and CD45-associated molecules in T cell activation," Immunol. Cell Biol. 75:430-445 (1997).
Altschul et al., "Basic local alignment search tool," J Mol Biol 215(3):403-410 (1990).
Altschul et al., "Gapped BLAST and PSI-BLAST: a new generation of protein database search programs," Nucleic Acids Res 25(17):3389-3402 (1997).
Ames et al., "Conversion of murine Fabs isolated from a combinatorial phage display library to full length immunoglobulins," J Immunol Methods 184(2):177-186 (1995).
Angal et al., "A single amino acid substitution abolishes the heterogeneity of chimeric mouse/human (IgG4) antibody," Mol Immunol 30(1):105-108 (1993).
Armour et al., "Recombinant human IgG molecules lacking Fcgamma receptor 1 binding and monocyte triggering activities," Eur J Immunol 29(8):2613-2624 (1999).

(56) References Cited

OTHER PUBLICATIONS

Arndt et al., "Costimulation improves the killing capability of T cells redirected to tumor cells expressing low levels of CD33: description of a novel modular targeting system," Leukemia 28:59-69 (2014).
Babcook et al., "A novel strategy for generating monoclonal antibodies from single, isolated lymphocytes producing antibodies of defined specificities," Proc Natl Acad Sci USA 93(15):7843-7848 (1996).
Bartalena et al., "Thyroid hormone transport proteins," Clin Lab Med 13(3) :583-598 (1993).
Beiboer et al., "Guided Selection of a Pan Carcinoma Specific Antibody Reveals Similar Binding Characteristics Yet Structural Divergence Between the Original Murine Antibody and its Human Equivalent," J. Mol. Biol. 296:833-849 (2000).
Bendig, "Humanization of Rodent Monoclonal Antibodies by CDR Grafting," Methods: A Companion to Methods in Enzymology 8:83-93 (1995).
Berger et al., "Antigen recognition by conformational selection," FEBS Lett 450:149-153 (1999).
Biolegend Data Sheet, FITC anti-mouse CD45.1 Antibody, (1), (Nov. 30, 2012).
Bradshaw et al., "Concurrent detection of secreted products from human lymphocytes by microengraving: cytokines and antigen-reactive antibodies," Clin Immunol 129(1):10-18 (2008).
Bree et al., "Pharmacokinetics of intravenously administered 125I-labelled human alpha 1-acid glycoprotein," Clin. Pharmacokinet. 11 (4):336-342 (1986).
Brinkmann et al., "Phage display of disulfide-stabilized Fv fragments," J Immunol Methods 182(1):41-50 (1995).
Brosterhus et al., "Enrichment and detection of live antigen-specific CD4(+) and CDS(+) T cells based on cytokine secretion," Eur J Immunol 29(12):4053-4059 (1999).
Bruhns et al., "Specificity and affinity of human Fcgamma receptors and their polymorphic variants for human IgG subclasses," Blood 113(16):3716-3725 (2009).
Burton et al., "Human antibodies from combinatorial libraries," Adv Immunol 57:191-280 (1994).
Caldas et al., "Humanization of the anti-CD18 antibody 6. 7: an unexpected effect of a framework residue in binding to antigen," Mol Immunol 39:941-952 (2003).
Campbell et al., "Rapid detection, enrichment and propagation of specific T cell subsets based on cytokine secretion," Clin Exp Immunol 163:1-10 (2010).
Carnahan et al., "Eptrauzumab, a CD22-targeting recombinant humanized antibody with a different mode of action from rituximab," Mol. Immunol. 44(6): 1331-1341 (2007).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "The Dock and Lock Method: A Novel Platform Technology for Building Multivalent, Multifunctional Structures of Defined Composition with Retained Bioactivity," Clin Cancer Res 13 (18 Suppl): 5586s-5591s (2007).
Chang et al., "Loop-Sequence Features and Stability Determinants in Antibody Variable Domains by High-Throughput Experiments," Structure 22:9-21 (2014).
Chen et al., "Enhancement and destruction of antibody function by somatic mutation: unequal occurrence is controlled by V gene combinatorial associations," EMBO J 14(12):2784-2794 (1995).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcy receptor IIb inhibitory receptor," Arthritis Rheumatol 66: 1153-1164 (2014).
Clargo et al., "The rapid generation of recombinant functional monoclonal antibodies from individual, antigen-specific bone marrow-derived plasma cells isolated using a novel fluorescence-based method," MAbs 6 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2): 257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dmitrova et al., "A new LexA-based genetic system for monitoring and analyzing protein heterodimerization in *Escherichia coli*," Mol Gen Genet 257:205-212 (1998).
Doerner et al., "Therapeutic antibody engineering by high efficiency cell screening," FEBS Lett 588:278-287 (2014).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig. Dis. 32:61-66 (2014).
Edwards et al., "The remarkable flexibility of the human antibody repertoire; isolation of over one thousand different antibodies to a single protein, BLyS," The Journal of Molecular Biology 334: 103-118 (2003).
Feldman et al., "Adoptive Cell Therapy-Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161 :2791-2797 (1998).
Gish et al., "Identification of protein coding regions by database similarity search," Nat Genet 3(3):266-272 (1993).
Gitlin et al., "The selectivity of the human placenta in the transfer of plasma proteins from mother to fetus," J Clin Invest 43: 1938-1951 (1964).
Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gold et al., "The B Cell Antigen Receptor Activates the Akt (Protein Kinase B)/Glycogen Synthase Kinase-3 Signaling Pathway via Phosphatidylinositol 3-Kinase," J Immunol 163:1894-1905 (1999).
Goldenberg et al., "Multifunctional Antibodies by the Dock-and-Lock Method for Improved Cancer Imaging and Therapy by Pretargeting," J Nuc Med 49(1):158-163 (2008).

\* cited by examiner pAkt S473 on B cells pPLCγ2 Y759 on B cells

Fig. 9
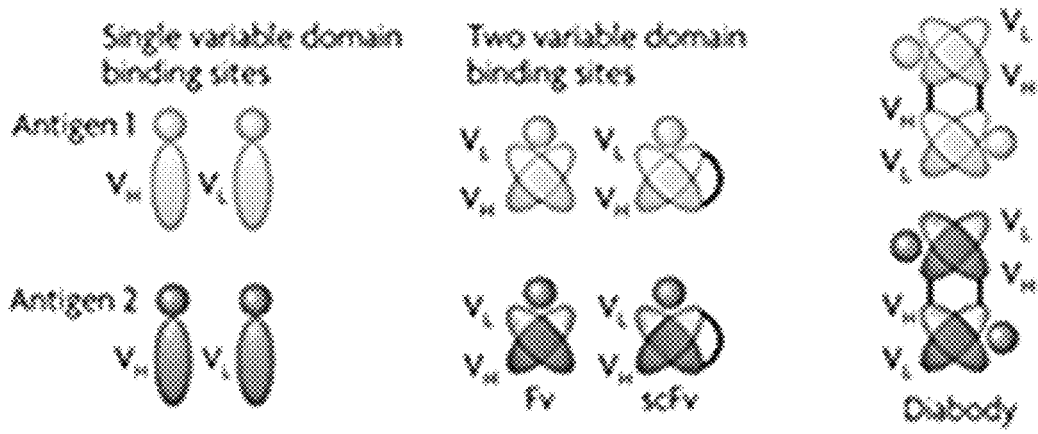
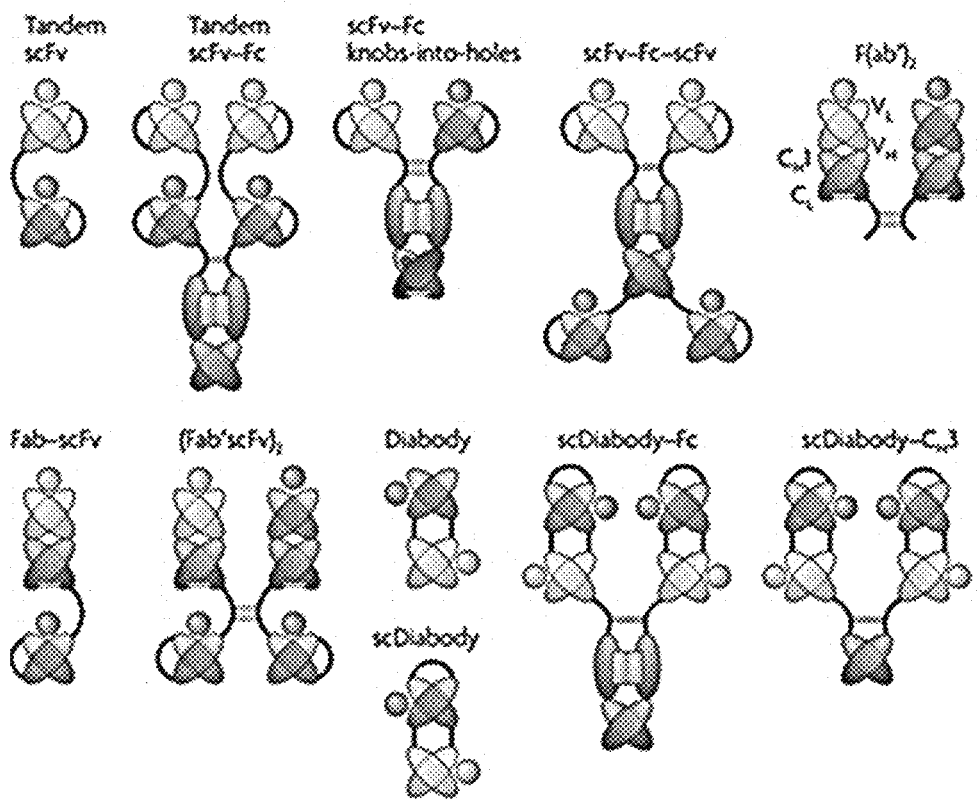

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -4.37 | 33.57 | 10.45 | 13.99 | 3.81 | 4.26 | 8.34 | 21.07 | 4.10 | 13.98 | 6.07 | 18.03 | 7.39 | 9.00 | 23.01 |
| 2 | 27.22 | 25.26 | 52.32 | 63.81 | 30.98 | 19.94 | 26.90 | 29.48 | 20.58 | 30.61 | 9.05 | 4.18 | 14.73 | 36.56 | 33.04 |
| 3 | 17.62 | 69.66 | 3.88 | 16.35 | 7.81 | -5.45 | 6.94 | 12.43 | 6.90 | 7.41 | 15.55 | 18.23 | 6.31 | 7.13 | 15.98 |
| 4 | 13.81 | 70.47 | -9.21 | 11.98 | 2.91 | -0.27 | 7.92 | 9.85 | 0.93 | 4.02 | 8.95 | 40.06 | 10.33 | 8.02 | 15.98 |
| 5 | 5.05 | 36.09 | -1.78 | -0.25 | 10.55 | -14.55 | 11.88 | 6.91 | -0.32 | -2.82 | 9.14 | 12.00 | 3.48 | 7.99 | 9.03 |
| 6 | ; | 21.62 | 7.24 | 15.79 | 16.88 | 2.69 | 2.50 | 14.87 | 9.48 | 4.44 | 11.14 | 20.93 | 12.37 | ; | ; |
| 7 | 10.54 | 35.72 | 2.40 | 16.16 | 14.92 | 1.39 | 2.23 | 14.14 | 5.64 | 10.62 | 8.02 | 17.58 | 9.49 | 10.65 | 10.80 |
| 8 | 8.03 | 26.05 | -7.89 | 3.46 | 7.85 | -19.33 | 0.26 | -5.98 | -2.08 | 0.09 | 7.83 | 5.13 | 2.60 | 9.59 | 9.47 |
| 9 | 13.56 | 32.14 | -4.74 | 2.87 | 9.63 | -7.13 | 5.17 | 10.72 | 0.79 | 1.69 | 9.22 | 13.63 | 2.49 | 15.70 | 10.52 |
| 10 | 15.35 | 54.98 | 13.21 | 17.70 | -2.07 | 6.11 | 21.65 | 23.25 | 9.94 | 10.33 | 16.30 | 41.50 | 13.23 | 6.52 | 16.72 |
| 11 | ; | -0.28 | -50.76 | -5.43 | -0.23 | -118.10 | -4.78 | -9.59 | 0.06 | -4.95 | 6.09 | 2.91 | -9.06 | ; | ; |
| 12 | 5.85 | 8.47 | 19.70 | 42.01 | 20.13 | 12.42 | 16.14 | 26.89 | 20.89 | 24.89 | 18.86 | 36.32 | 18.07 | 20.28 | 38.97 |
| 13 | ; | 31.56 | 22.19 | 28.34 | 15.50 | 13.12 | 14.23 | 27.59 | 22.46 | 14.25 | 16.00 | 26.84 | 16.21 | ; | ; |
| 14 | 9.13 | 40.70 | 10.80 | 14.58 | 5.88 | 8.89 | 7.52 | 22.68 | 6.27 | 9.04 | 7.34 | 33.39 | 11.20 | 7.01 | 14.84 |
| 15 | 9.38 | 33.18 | 7.13 | 11.20 | 15.92 | 11.35 | 9.90 | 19.81 | 9.80 | 10.62 | 13.98 | 28.99 | 15.26 | 13.77 | 25.64 |
| 16 | ; | 26.46 | -7.69 | 19.38 | 15.85 | -24.93 | 12.05 | 14.00 | 15.27 | 11.98 | 13.29 | 20.57 | 11.99 | ; | ; |
| 17 | ; | 22.79 | -4.70 | 19.07 | 17.98 | -37.56 | 10.99 | 11.71 | 15.83 | 8.61 | 10.98 | 21.28 | 9.71 | ; | ; |
| 18 | ; | 28.91 | 29.09 | 33.25 | 23.16 | 10.61 | 13.85 | 26.28 | 21.37 | 18.39 | 18.45 | 32.78 | 18.27 | ; | ; |
| 19 | ; | 33.63 | -15.93 | 2.00 | 15.54 | -24.55 | 11.73 | 10.55 | 7.32 | 4.45 | 15.19 | 20.88 | 10.61 | ; | ; |
| 20 | ; | 24.94 | -13.88 | 20.88 | 10.53 | -21.56 | 8.43 | 6.69 | 8.81 | 7.57 | 10.73 | 17.52 | 13.55 | ; | ; |
| 21 | ; | 23.94 | 6.89 | 22.70 | 22.45 | -3.18 | 13.33 | 21.28 | 15.88 | 10.81 | 15.92 | 25.96 | 17.22 | 9.14 | ; |
| 22 | 13.93 | 20.55 | -18.75 | -4.96 | 6.90 | -17.32 | 4.12 | -3.15 | -4.19 | -6.49 | 11.71 | 2.48 | -0.84 | ; | 11.88 |
| 23 | ; | 24.25 | -9.45 | 22.83 | 24.63 | -26.70 | 9.65 | 13.79 | 10.74 | 7.96 | 13.02 | 24.40 | 18.33 | ; | ; |

% Inhibition Syk

Fab-Y specificity antigen 1-23

Fig. 10

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0.81 | 22.29 | 11.45 | 10.78 | 5.39 | 1.60 | 7.43 | 5.90 | 2.24 | 3.29 | -2.71 | 10.80 | 0.99 | 6.90 | -4.08 |
| 2 | 19.70 | 18.61 | 44.00 | 50.83 | 23.17 | 19.01 | 24.57 | 21.47 | 25.89 | 39.80 | 12.35 | 0.52 | 18.91 | 28.55 | 25.89 |
| 3 | 17.93 | 61.18 | 3.00 | 15.38 | 5.38 | -0.12 | 4.05 | 3.77 | 6.84 | 12.78 | 11.01 | 16.71 | 2.97 | 9.17 | 4.89 |
| 4 | 13.34 | 55.83 | -3.82 | 7.24 | 1.41 | -1.39 | 6.75 | 0.89 | 3.12 | 3.12 | 4.16 | 40.49 | 1.71 | 5.13 | 1.10 |
| 5 | 0.34 | 25.18 | 0.51 | -0.83 | 7.36 | -1.41 | 11.49 | 4.08 | 5.59 | 2.99 | 5.76 | 11.67 | 2.84 | 5.90 | -2.08 |
| 6 |  | 20.71 | -0.85 | 6.04 | 0.40 | 3.49 | -2.60 | -0.87 | 3.41 | 0.22 | 1.34 | 12.34 | 3.36 |  |  |
| 7 | 10.95 | 27.95 | 1.38 | 15.86 | 11.27 | 2.40 | 2.48 | 4.45 | 6.13 | 16.07 | 3.18 | 12.77 | 3.92 | 5.85 | 0.37 |
| 8 | 7.73 | 24.86 | 4.02 | 6.23 | 3.56 | 0.49 | 2.68 | -1.16 | 2.39 | 1.45 | 4.10 | 8.50 | -0.84 | 3.01 | 0.97 |
| 9 | 7.37 | 28.27 | -0.02 | 3.22 | 6.39 | 1.35 | 4.75 | 4.08 | 4.92 | 4.09 | 3.10 | 10.50 | 0.62 | 5.82 | 1.80 |
| 10 | 17.08 | 28.23 | 7.72 | 5.65 | -6.55 | 1.40 | 21.89 | 6.66 | 5.90 | 5.11 | 7.61 | 35.77 | 1.50 | 4.32 | -0.06 |
| 11 |  | 47.69 | -10.93 | 1.38 | -0.58 | -24.94 | -1.36 | 0.83 | 3.58 | 3.88 | 5.92 | 11.18 | -4.57 |  |  |
| 12 | 6.05 | 11.76 | 9.02 | 29.48 | 4.92 | 1.15 | 1.89 | 5.75 | 7.23 | 20.95 | 5.44 | 17.92 | 3.37 | 16.34 | 8.67 |
| 13 |  | -3.88 | -0.99 | 7.30 | 0.40 | -1.40 | 1.83 | 6.41 | 8.91 | 3.25 | 2.76 | 11.84 | 5.41 |  |  |
| 14 | 4.40 | 23.78 | 1.77 | 5.61 | 4.01 | 1.73 | 5.95 | 2.45 | 4.05 | 6.85 | -0.60 | 20.60 | 5.45 | 4.11 | 0.05 |
| 15 | 4.96 | 28.11 | 0.87 | 3.43 | 5.41 | 1.77 | 1.89 | 1.80 | 3.72 | 1.96 | 2.29 | 14.57 | 5.26 | 2.36 | 0.11 |
| 16 |  | 25.80 | -5.77 | 4.50 | 2.41 | -6.86 | 4.89 | 2.52 | 5.19 | 3.07 | 3.38 | 9.47 | 1.17 |  |  |
| 17 |  | 22.39 | -6.98 | 6.73 | 2.99 | -10.27 | 2.35 | 2.13 | 6.02 | 2.08 | 3.10 | 10.86 | 2.03 |  |  |
| 18 |  | 19.53 | 2.43 | 12.36 | 2.08 | -1.05 | 1.09 | 4.25 | 6.70 | 4.90 | 4.40 | 12.49 | 4.34 |  |  |
| 19 |  | 19.90 | -12.22 | -2.38 | -1.61 | -8.05 | 5.97 | 1.78 | 5.27 | 4.83 | 5.92 | 15.60 | 3.16 |  |  |
| 20 |  | 35.50 | -8.67 | 2.95 | -0.16 | -6.71 | -3.46 | -4.91 | 4.13 | 2.31 | 6.52 | 10.96 | 4.25 |  |  |
| 21 |  | 21.53 | -6.86 | 2.36 | 1.10 | -6.49 | -0.95 | 5.08 | 4.96 | 3.55 | 3.97 | 10.88 | 3.63 |  |  |
| 22 | 14.73 | 19.03 | -5.00 | 0.58 | 3.97 | -0.08 | 3.70 | -1.25 | 1.72 | 0.99 | 11.40 | 7.99 | 2.80 | 8.39 | 4.58 |
| 23 |  | 19.72 | -16.22 | 0.75 | -1.16 | -11.03 | -3.57 | 3.30 | 3.57 | 1.23 | 4.90 | 8.22 | 4.20 |  |  |

Fab-Y specificity antigen 1-23

% Inhibition PLCg2

Fig. 11

Fab-X specificity antigen 1-15

| SP_Y | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -11.06 | 53.06 | -1.56 | 6.02 | -8.08 | -12.41 | 3.84 | -12.93 | -8.22 | -6.88 | -11.49 | -3.34 | -17.29 | -4.43 | -6.28 |
| 2 | 40.41 | 37.15 | 48.29 | 48.35 | 39.50 | 30.66 | 40.36 | 25.61 | 42.23 | 42.64 | 32.59 | 37.11 | 26.58 | 35.70 | 38.11 |
| 3 | 13.19 | 70.81 | 2.37 | 15.53 | 8.68 | 7.93 | 12.32 | 3.78 | 10.58 | 14.18 | 8.76 | -1.58 | 6.81 | 10.75 | 10.83 |
| 4 | 8.35 | 55.50 | -6.07 | 17.80 | 7.97 | 7.14 | 8.49 | 6.54 | 6.98 | 9.67 | 12.96 | 41.04 | 5.99 | 9.28 | 7.89 |
| 5 | -3.80 | 40.21 | -0.85 | 13.54 | 2.05 | -2.13 | 3.01 | -6.88 | 0.91 | 2.02 | 0.76 | 4.48 | -3.42 | 4.08 | 0.15 |
| 6 | -- | 40.39 | 6.67 | 19.26 | -4.86 | 12.95 | 3.52 | 2.59 | 6.73 | 5.65 | 5.28 | 4.77 | -1.03 | -- | -- |
| 7 | 0.53 | 46.36 | 4.87 | 18.78 | 4.08 | 0.72 | -1.43 | 5.07 | 4.69 | 11.49 | 6.48 | 5.72 | 4.78 | 0.73 | -3.71 |
| 8 | 6.61 | 37.54 | 5.72 | 16.25 | -1.45 | 2.38 | 0.64 | 0.17 | 1.10 | 2.08 | 6.50 | 7.59 | 2.18 | -4.37 | -4.53 |
| 9 | 0.51 | 42.34 | 0.85 | 9.41 | -0.30 | 1.07 | 2.86 | -2.56 | 0.51 | -0.55 | 2.07 | 2.49 | -2.84 | 4.54 | 0.16 |
| 10 | 11.13 | 52.32 | 3.75 | 12.57 | -4.41 | 3.82 | 15.78 | -3.15 | 5.70 | 4.26 | 1.77 | 22.73 | -4.88 | 7.65 | 8.05 |
| 11 | -- | 33.40 | -3.85 | 19.04 | 7.48 | 6.00 | 3.13 | 4.24 | 5.88 | 13.11 | 9.85 | 11.24 | 2.04 | -- | -- |
| 12 | 0.89 | 29.50 | -7.93 | 39.94 | 2.69 | 4.95 | -0.13 | -2.53 | 2.52 | 15.03 | -0.82 | 3.63 | -5.61 | 25.99 | 12.57 |
| 13 | -- | 35.33 | -4.80 | 10.35 | -4.98 | -7.46 | -7.91 | -6.47 | 3.78 | -0.83 | -4.68 | -3.84 | -0.54 | -- | -- |
| 14 | 1.62 | 44.02 | 0.91 | 16.05 | 1.80 | -2.56 | 1.09 | -4.49 | 3.94 | 5.30 | -0.19 | 8.15 | -5.85 | 5.21 | 0.88 |
| 15 | 2.25 | 36.02 | -2.44 | 10.00 | -0.22 | 0.37 | -2.20 | -2.11 | 2.41 | 1.84 | 3.23 | 2.79 | 2.51 | -2.19 | -4.62 |
| 16 | -- | 35.02 | -3.12 | 15.33 | 0.19 | -5.46 | 0.34 | -5.87 | 1.83 | 1.35 | -0.24 | -1.99 | -8.53 | -- | -- |
| 17 | -- | 33.56 | -4.92 | 16.87 | 1.78 | -2.20 | -0.71 | -2.12 | 3.07 | 1.17 | 0.98 | 0.80 | -2.14 | -- | -- |
| 18 | -- | 31.31 | -1.77 | 19.71 | -6.19 | -4.39 | -3.72 | -3.91 | 2.70 | 3.44 | -0.42 | -1.65 | -5.72 | -- | -- |
| 19 | -- | 50.00 | -2.93 | 9.92 | 2.01 | 9.54 | 10.19 | 2.60 | 11.44 | 9.84 | 7.96 | 9.17 | 3.37 | -- | -- |
| 20 | -- | 38.56 | -1.83 | 19.86 | 1.40 | 5.57 | 0.37 | 1.23 | 4.23 | 6.85 | 10.48 | 6.84 | 2.80 | -- | -- |
| 21 | -- | 38.74 | 1.67 | 11.59 | -5.60 | 8.23 | 0.58 | 6.00 | 6.99 | 5.11 | 3.12 | 3.73 | 3.44 | -- | -- |
| 22 | -2.71 | 40.50 | -2.45 | 12.91 | -4.39 | 6.77 | 1.58 | 4.97 | 1.66 | 2.93 | 18.10 | 8.41 | 8.06 | -2.35 | -4.93 |
| 23 | -- | 33.54 | -1.88 | 5.45 | -2.46 | 7.13 | 0.05 | -3.14 | 2.99 | 3.34 | 6.02 | 4.97 | -4.12 | -- | -- |

Fab-Y specificity antigen 1-23

% Inhibition AKT

Fig. 12

Fig. 13
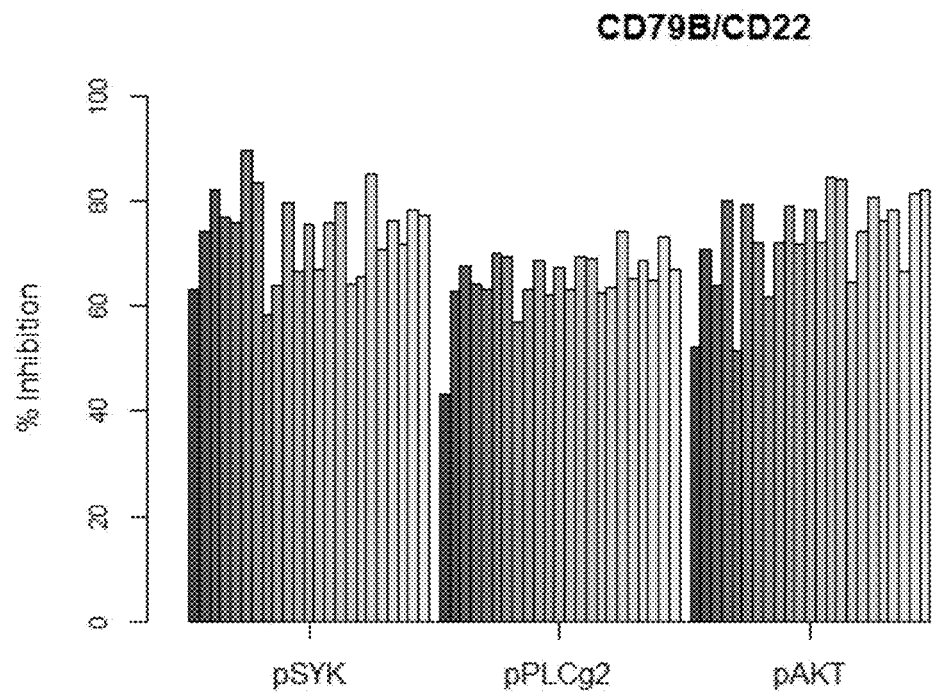
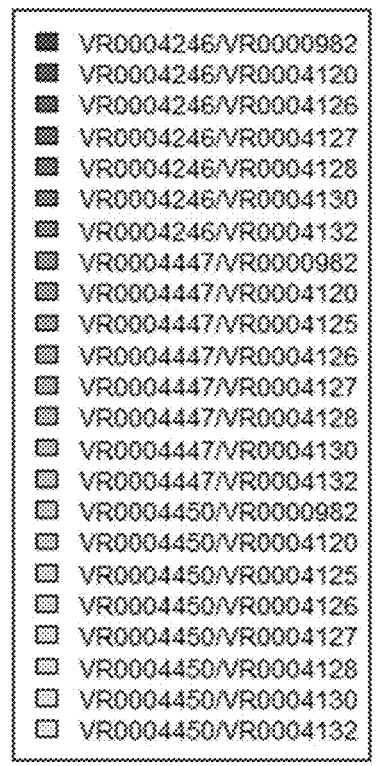

Percentage inhibition of CD27 expression on total B cells stimulated with a goat anti human anti-IgM antibody Percentage inhibition of CD27 expression on total B cells stimulated with a goat anti human anti-IgM antibody Fig. 27  Percentage inhibition of tetanus toxoid specific IgG production from human PBMCs Fig. 28  Percentage inhibition of tetanus toxoid specific IgG production from human B cells

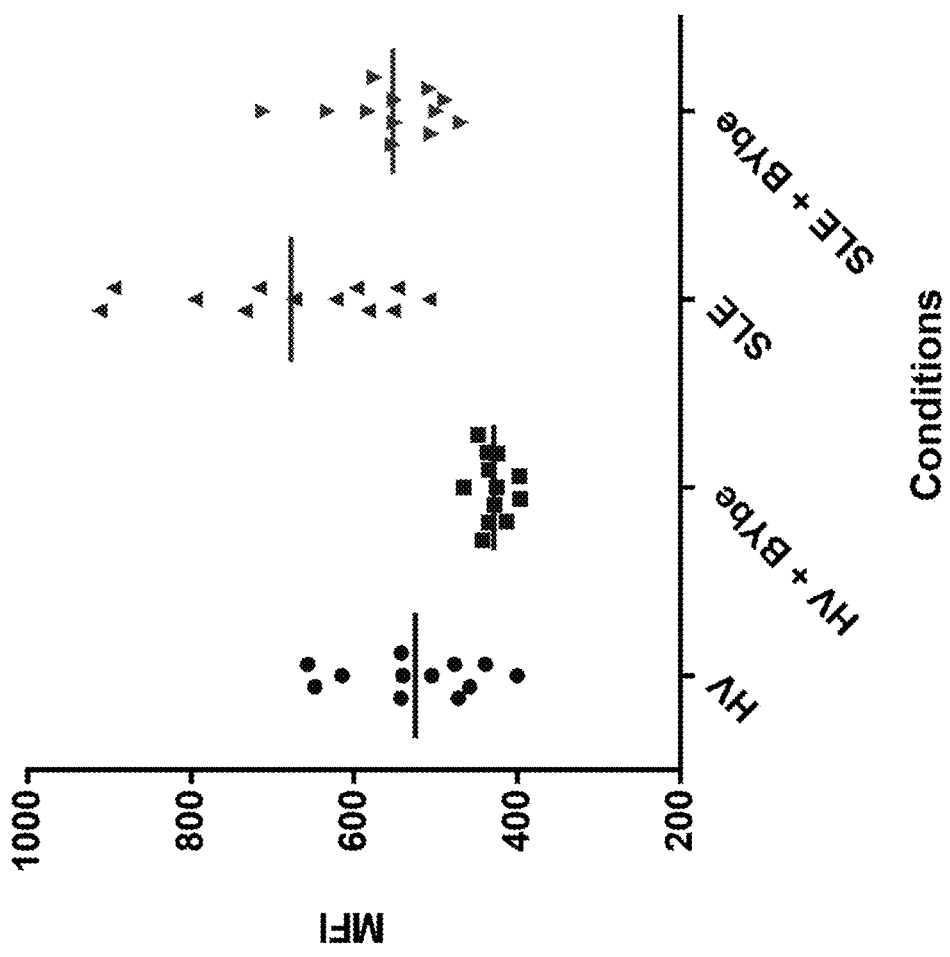
Fig. 31 Effect of CD79b & CD22 Specific VR4447/4130 BYbe on Anti-IgM Induced B cell NFκB Phosphorylation from 12 Healthy and 12 SLE Patient Samples

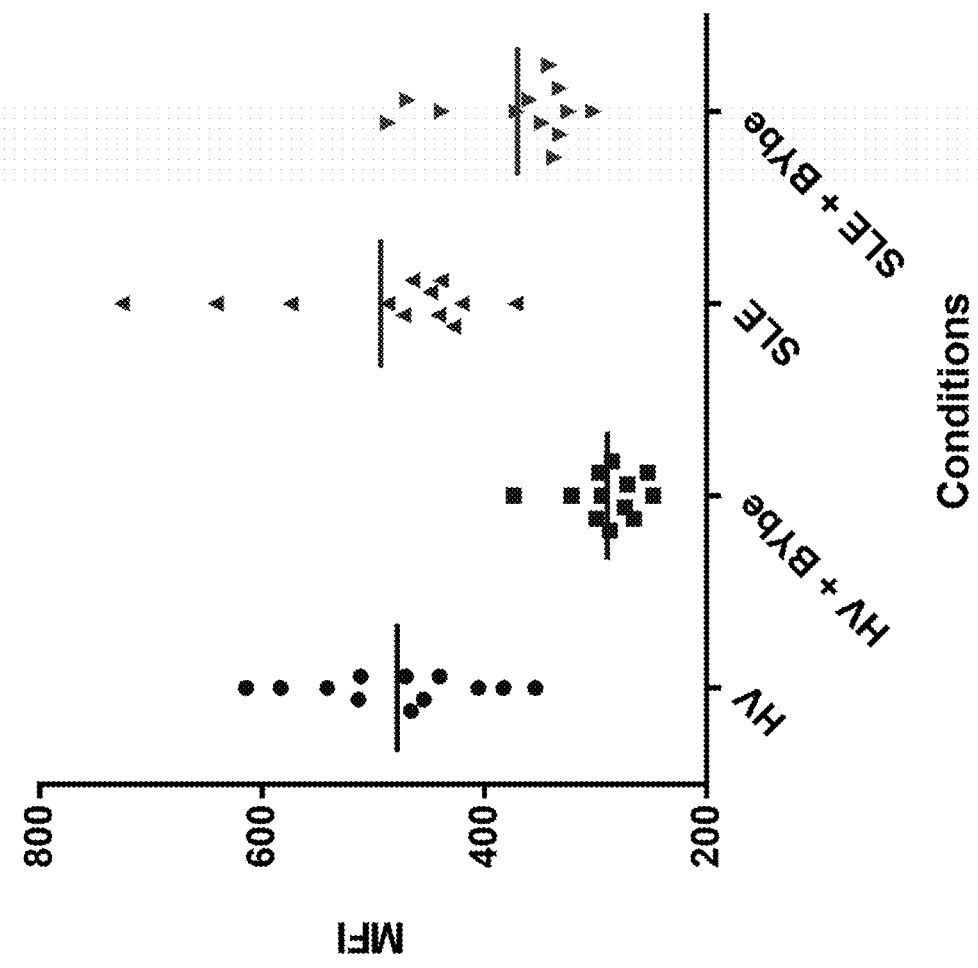
Fig. 32 Effect of CD79b & CD22 Specific VR4447/4130 BYbe on Anti-IgM Induced B cell Akt Phosphorylation from 12 Healthy and 12 SLE Patient Samples

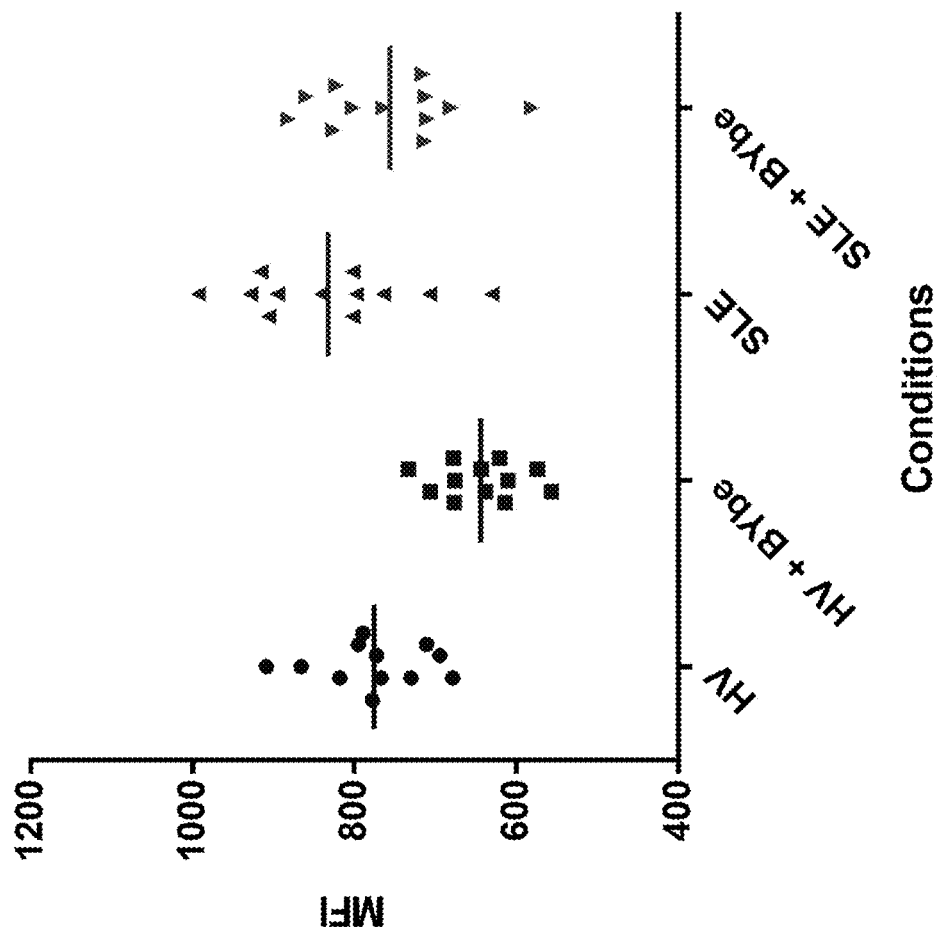
Fig. 33  Effect of CD79b & CD22 Specific VR4447/4130 BYbe on Anti-IgM Induced B cell Syk Phosphorylation from 12 Healthy and 12 SLE Patient Samples

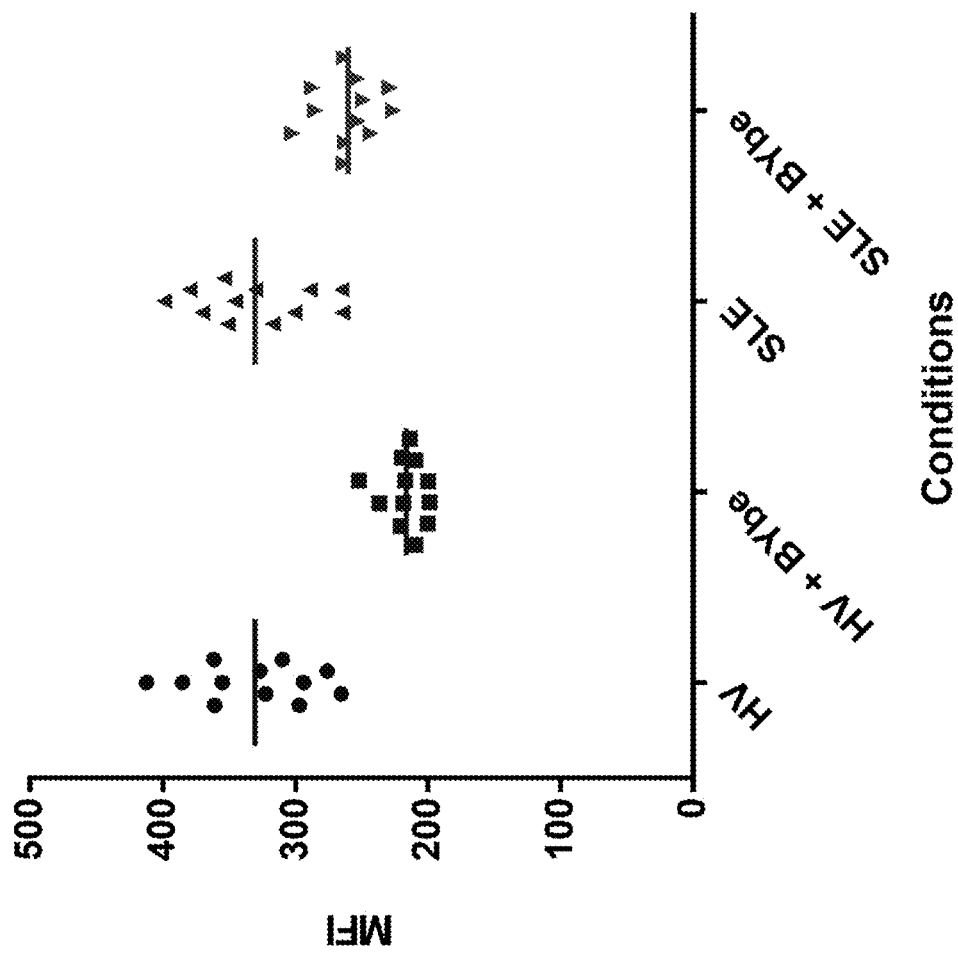
Fig. 34  Effect of CD79b & CD22 Specific VR4447/4130 BYbe on Anti-IgM Induced B cell ERK1 & 2 Phosphorylation from 12 Healthy and 12 SLE Patient Samples

Fig. 35

CD22 Antibodies

Ab 4120

SEQ ID NO: 29 CDRH1 GFSFSSSYYMC
SEQ ID NO: 30 CDRH1 variant GFSFSSSYYMS
SEQ ID NO: 40 CDRH2 CIYTGSSGDTYYASWAKG
SEQ ID NO: 41 CDRH2 variant SIYTGSSGDTYYASWAKG
SEQ ID NO: 60 CDRH3 GPYVGYGYDLQYLYL
SEQ ID NO: 69 CDRL1 QASQSISTALA
SEQ ID NO: 75 CDRL2 GASTLAS
SEQ ID NO: 81 CDRL3 QSYYGTSSGGSWA

SEQ ID NO: 102 Rabbit Ab 4120 VL region

AFELSQTPAS VEAAVGGTVT IKCQASQSIS TALAWYQQKP GQRPKLLIYG
ASTLASGVSS RFKGSGSGTE FTLTISDLEC ADAATYYCQS YYGTSSGGSW AFGGGTKVVV K

SEQ ID NO: 103 Rabbit Ab 4120 VL region gcattcgaat tgagccagac tccagcctcc gtggaggcag ctgtgggagg cacagtcacc
atcaagtgcc aggccagtca gagcattagc actgcattag cctggtatca gcagaaacca
gggcagcgtc ccaagctcct gatctatggt gcatccactc tggcatctgg ggtctcatcg
cggttcaaag gcagtggatc tgggacagag ttcactctca ccatcagcga cctggagtgt
gccgatgctg ccacttacta ctgtcaaagc tattatggta cgagtagtgg tggttcttgg
gctttcggcg gagggaccaa ggtggtcgtc aaa

SEQ ID NO: 104 Rabbit Ab 4120 VH region

QSLEESGGDL VKPGASLTLT CTASGFSFSS SYYMCWVRQS PGKGLEWIAC IYTGSSGDTY
YASWAKGRFT ISKTSSTTVS LQMTSLTAAD TATYFCARGP YVGYGYDLQY LYLWGPGTLV TVSS

SEQ ID NO: 105 Rabbit Ab 4120 VH region cagtcattgg aggagtccgg gggagacctg gtcaagcctg ggcatccct gacactcacc
tgcacagcct ctggattctc cttcagtagt agctactaca tgtgctgggt ccgccagtct
ccagggaagg ggctggagtg gatcgcatgc atttatactg gtagtagtgg tgacacttac
tacgcgagct gggcgaaagg ccgattcacc atctccaaaa cctcgtcgac cacggtgtct
ctgcaaatga ccagtctgac agccgcggac acggccactt atttctgtgc gagaggcct
tatgttggtt atggttatga tcttcaatac ttgtacttgt ggggccgggg accctcgtc
accgtctcga gt

SEQ ID NO: 106 4120 gL1 V-region IGKV1D-13 framework

AFELTQSPSS LSASVGDRVT ITCQASQSIS TALAWYQQKP GKAPKLLIYG ASTLASGVPS
RFSGSGSGTD FTLTISSLQP EDFATYYCQS YYGTSSGGSW AFGGGTKVEI K

SEQ ID NO: 107 4120 gH1 V-region - IGHV3-33 framework

EVQLVESGGG LVQPGRSLRL SCAASGFSFS SSYYMCWVRQ APGKGLEWIA CIYTGSSGDT
YYASWAKGRF TISKDSSKTT VYLQMNSLRA EDTAVYYCAR GPYVGYGYDL QYLYWGQGT LVTVSS

SEQ ID NO: 108 4120 gH2 V-region - IGHV3-33 framework

Fig. 35 Continued

EVQLVESGGG LVQPGRSLRL SCAASGFSFS SSYYMSWVRQ APGKGLEWIA SIYTGSSGDT YYASWAKGR
F TISKDSSKTT VYLQMNSLRA EDTAVYYCAR GPYVGYGYDL QYLYLWGQGT LVTVSS

SEQ ID NO: 109 4120 gH4 V-region – IGHV4-38-2 framework

EVQLQESGPG LVKPSETLSL TCAASGFSFS SSYYMCWVRQ PPGKGLEWIA CIYTGSSGDT
YYASWAKGRF TISKDSSKTQ VSLKLSSVTA ADTAVYYCAR GPYVGYGYDL QYLYLWGQGT LVTVSS

SEQ ID NO: 110 4120 gH5 V-region – IGHV4-38-2 framework

<u>E</u>VQLQESGPG LVKPSETLSL TC<u>A</u>ASGFSFS SSYYMSW<u>V</u>RQ PPGKGLEWI<u>A</u> SIYTGSSGDT
YYASWAKGR<u>F</u> TIS<u>KD</u>SS<u>KT</u>Q <u>V</u>SLKLSSVTA ADTAVYYCAR GPYVGYGYDL QYLYLWGQGT LVTVSS

Ab 4126

| | | |
|---|---|---|
| SEQ ID NO: 31 | CDRH1 | GIDFSSYYYMC |
| SEQ ID NO: 32 | CDRH1 variant | GIDFSSYYYMS |
| SEQ ID NO: 42 | CDRH2 | CIDPASSGTTYYATWAKG |
| SEQ ID NO: 43 | CDRH2 variant | SIDPASSGTTYYATWAKG |
| SEQ ID NO: 61 | CDRH3 | AYGSGGSGYIGCYFDL |
| SEQ ID NO: 62 | CDRH3 variant | AYGSGGSGYIGSYFDL |
| SEQ ID NO: 70 | CDRL1 | QASQNIGSGLA |
| SEQ ID NO: 76 | CDRL2 | YASTLAS |
| SEQ ID NO: 82 | CDRL3 | QSHDYSSVRSYGNA |

SEQ ID NO: 111 Rabbit Ab 4126 VL region

DIVMTQTPAS VEAAVGGTVT IKCQASQNIG SGLAWYQQKP GQPPKLLIYY
ASTLASGVPS RFKGSGSGTQ FTLTISDLEC ADAATYYCQS HDYSSVRSYG NAFGGGTEVV VK

SEQ ID NO: 112 Rabbit Ab 4126 VL region gacattgtga tgacccagac tccagcctcc gtggaggcag ctgtgggagg cacagtcacc
atcaagtgcc aggccagtca gaacattggt agtggtttag cctggtatca gcagaaacca
ggcagcctc ccaagctcct gatctattat gcatccactc tggcatctgg ggtcccatca
aggttcaaag gcagtggatc tgggacacag ttcactctca ccatcagcga cctggagtgt
gccgacgctg ccacttacta ctgtcaaagt catgattata gtagtgttcg gagttacggt
aatgctttcg gcggagggac cgaggtggtg gtcaaa

SEQ ID NO: 113 Rabbit Ab 4126 VH region

QQHLEESGGG LVKPGGTLTL TCKASGIDFS SYYYMCWVRQ APGKGLEWVA CIDPASSGTT
YYATWAKGRF TISKTSSTTV TLQMTSLTAA DTATYFCARA YGSGGSGYIG CYFDLWGQGT LVTVSS

SEQ ID NO: 114 Rabbit Ab 4126 VH region cagcagcacc tggaggagtc cgggggaggc ctggtcaagc ctgaggaac cctgacactc
acctgcaaag cctctggaat cgacttcagt agctactact acatgtgctg ggtccgccag
gctccaggga aggggctgga gtgggtcgcg tgcattgatc ctgctagtag tggtactact
tactacgcga cctgggcgaa aggccgattc accatctcca aaacctcgtc gaccacggtg

Fig. 35 Continued

```
actctgcaaa tgaccagtct gacagccgcg gacacggcca cctatttctg tgcgagggca
tatggtagtg ggggtagtgg ttatataggg tgctactttg acttgtgggg ccaaggcacc
ctcgtcaccg tctcgagt
```

SEQ ID NO: 115 4126 gL3 V-region - IGKV1-5 framework

DI<u>V</u>MTQSPST LSASVGDRVT ITCQASQNIG SGLAWYQQKP GKAPKLLIYY ASTLASGVPS
RFSGSGSGT<u>Q</u> FTLTISSLQP DDFATYYCQS HDYSSVRSYG NAFGGGTKVE IK

SEQ ID NO: 116 4126 gH12 V-region - IGHV3-7 framework

EVQLVESGGG LVQPGGSLRL SCAASGIDFS SYYYMCWVRQ APGKGLEWVA CIDPASSGTT
YYATWAKGRF TIS<u>K</u>D<u>S</u>AK<u>T</u>S <u>V</u>YLQMNSLRA EDTAVYYCAR AYGSGGSGYI GCYFDLWGQG TLVTVSS

SEQ ID NO: 117 4126 gH3 V-region - IGHV3-7 framework

EVQLVESGGG LVQPGGSLRL SCAASGIDFS SYYYMCWVRQ APGKGLEWVA CIDPASSGTT YYATWAKGR
F TISKDSAKTS VYLQMNSLRA EDTAVYYCAR AYGSGGSGYI GSYFDLWGQG TLVTVSS

SEQ ID NO: 118 4126 gH4 V-region - IGHV3-7 framework

EVQLVESGGG LVQPGGSLRL SCAASGIDFS SYYYMSWVRQ APGKGLEWVA SIDPASSGTT YYATWAKGR
F TISKDSAKTS VYLQMNSLRA EDTAVYYCAR AYGSGGSGYI GSYFDLWGQG TLVTVSS

SEQ ID NO: 119 4126 gH13 V-region – IGHV4-4 framework

<u>E</u>VQLQESGPG LVKPSGTLSL TCA<u>A</u>SGIDFS SYYYMCWVRQ PPGKGLEW<u>VA</u> CIDPASSGTT
YYATWAKGR<u>F</u> TIS<u>K</u>D<u>S</u>SK<u>T</u>Q <u>V</u>SLKLSSVTA ADTAVYYCAR AYGSGGSGYI GCYFDLWGQG TLVTVSS

SEQ ID NO: 120 4126 gH6 V-region – IGHV4-4 framework

EVQLQESGPG LVKPSGTLSL TCAASGIDFS SYYYMCWVRQ PPGKGLEWVA CIDPASSGTT YYATWAKGR
F TISKDSSKTQ VSLKLSSVTA ADTAVYYCAR AYGSGGSGYI GSYFDLWGQG TLVTVSS

SEQ ID NO: 121 4126 gH7 V-region – IGHV4-4 framework

EVQLQESGPG LVKPSGTLSL TCAASGIDFS SYYYMSWVRQ PPGKGLEWVA SIDPASSGTT YYATWAKGR
F TISKDSSKTQ VSLKLSSVTA ADTAVYYCAR AYGSGGSGYI GSYFDLWGQG TLVTVSS

Ab 4127

| | | |
|---|---|---|
| SEQ ID NO: 33 | CDRH1 | GFSFSNLYYMC |
| SEQ ID NO: 34 | CDRH1 variant | GFSFSNLYYMS |
| SEQ ID NO: 44 | CDRH2 | CIDISSSGSTYYASWAKG |
| SEQ ID NO: 45 | CDRH2 variant | SIDISSSGSTYYASWAKG |
| SEQ ID NO: 63 | CDRH3 | DYYSSDWGVRFNL |
| SEQ ID NO: 71 | CDRL1 | QASQSVYGNNELS |
| SEQ ID NO: 77 | CDRL2 | LASRLAS |
| SEQ ID NO: 83 | CDRL3 | AGYKSDSDDGTT |
| SEQ ID NO: 84 | CDRL3 variant 1 | AGYKSESDDGTT |
| SEQ ID NO: 85 | CDRL3 variant 2 | AGYKSDADDGTT |
| SEQ ID NO: 86 | CDRL3 variant 3 | AGYKSDTDDGTT |
| SEQ ID NO: 87 | CDRL3 variant 4 | AGYKSDSDEGTT |
| SEQ ID NO: 88 | CDRL3 variant 5 | AGYKSDSDDATT |

Fig. 35 Continued

| SEQ ID NO: 89 | CDRL3 variant 6 | AGYKSDSDDSTT |
| SEQ ID NO: 90 | CDRL3 variant 7 | AGYKSESDEGTT |
| SEQ ID NO: 91 | CDRL3 variant 8 | AGYKSESDDATT |
| SEQ ID NO: 92 | CDRL3 variant 9 | AGYKSESDDSTT |
| SEQ ID NO: 93 | CDRL3 variant 10 | AGYKSDADEGTT |
| SEQ ID NO: 94 | CDRL3 variant 11 | AGYKSDADDATT |
| SEQ ID NO: 95 | CDRL3 variant 12 | AGYKSDADDSTT |
| SEQ ID NO: 96 | CDRL3 variant 13 | AGYKSDTDEGTT |
| SEQ ID NO: 97 | CDRL3 variant 14 | AGYKSDTDDATT |
| SEQ ID NO: 98 | CDRL3 variant 15 | AGYKSDTDDSTT |

SEQ ID NO: 122  Rabbit Ab 4127 VL region

AIVMTQTPSS KSVPMGGTVT INCQASQSVY GNNELSWYQQ KPGQPPKLLI YLASRLASGV
PSRFSGSGSG TQFTLTISGV QCDDAATYYC AGYKSDSDDG TTFGGGTKVV VE

SEQ ID NO: 123  Rabbit Ab 4127 VL region gccatcgtga tgacccagac tccatcttcc aagtctgtcc ctatgggagg cacagtcacc
atcaactgcc aggccagtca gagtgtttat ggtaataacg aattatcctg gtatcagcag
aaaccagggc agcctcccaa gctcctgatc tatttggcat ccaggctggc atcgggggtc
ccatcgcggt ttagcggcag tggatctggg acacagttca ctctcaccat cagcggcgtg
cagtgtgacg atgctgccac ttactactgt gcaggctata aaagtgatag tgatgatggc
actactttcg gcggagggac caaggtggtg gtcgaa

SEQ ID NO: 124  Rabbit Ab 4127 VH region

QQLEESGGDL VKPGASLTLT CTASGFSFSN LYYMCWVRQA PGKGLELIGC IDISSSGSTY
YASWAKGRFT ISKTSSTTVT LQMTSLTAAD TATYFCARDY YSSDWGVRFN LWGQGTLVTV SS

SEQ ID NO: 125  Rabbit Ab 4127 VH region cagcagctgg aggagtccgg gggagacctg gtcaagcctg ggcatccct gacactcacc
tgcacagcct ctggattctc cttcagtaat ctctattaca tgtgttgggt ccgccaggct
ccagggaagg ggctggagtt gatcggatgc attgatatta gcagtagtgg tagcacttac
tacgcgagct gggcgaaagg ccgattcacc atctccaaaa cctcgtcgac cacggtgact
ctgcagatga ccagtctgac agccgcggac acggccacct atttctgtgc gagagattac
tattctagtg actggggtgt tagatttaac ttgtgggcc agggcaccct cgtcaccgtc tcgagt

SEQ ID NO: 126  4127 gL3 V-region - IGKV1-5 framework

<u>A</u>I<u>V</u>MTQSPST LSASVGDRVT ITCQASQSVY GNNELSWYQQ KPGKAPKLLI YLASRLASGV
PSRFSGSGSG T<u>Q</u>FTLTISSL QPDDFATYYC AGYKSDSDDG TTFGGGTKVE IK

SEQ ID NO: 127  4127 gH3 V-region - IGHV3-9 framework

EVQLVESGGG LVQPGRSLRL SCAASGFSFS NLYYMCWVRQ APGKGLE<u>LIG</u> CIDISSSGST
YYASWAKGRF TIS<u>KD</u>SAK<u>T</u>S <u>V</u>YLQMNSLRA EDTALYYCA<u>R</u> DYYSSDWGVR FNLWGQGTLV TVSS

SEQ ID NO: 128  4127 gH4 V-region - IGHV3-9 framework

Fig. 35 Continued

EVQLVESGGG LVQPGRSLRL SCAASGFSFS NLYYMSWVRQ APGKGLELIG SIDISSSGST YYASWAKGR
F TISKDSAKTS VYLQMNSLRA EDTALYYCAR DYYSSDWGVR FNLWGQGTLV TVSS

SEQ ID NO: 129 4127 gH6 V-region – IGHV4-38-2 framework

<u>E</u>VQLQESGPG LVKPSETLSL TCA<u>A</u>SGFSFS NLYYMCW<u>V</u>RQ PPGKGLELIG CIDISSSGST
YYASWAKGR<u>F</u> TIS<u>KD</u>S<u>S</u>K<u>T</u>Q <u>V</u>SLKLSSVTA ADTAVYYCAR DYYSSDWGVR FNLWGQGTLV TVSS

SEQ ID NO: 130 4127 gH7 V-region – IGHV4-38-2 framework

EVQLQESGPG LVKPSETLSL TCAASGFSFS NLYYMSWVRQ PPGKGLELIG SIDISSSGST YYASWAKGR
F TISKDSSKTQ VSLKLSSVTA ADTAVYYCAR DYYSSDWGVR FNLWGQGTLV TVSS

Ab 4128

| | | |
|---|---|---|
| SEQ ID NO: 35 | CDRH1 | GLDFSSYWIC |
| SEQ ID NO: 36 | CDRH1 variant | GLDFSSYWIS |
| SEQ ID NO: 46 | CDRH2 | CIVTGSSDNTYYASWAKG |
| SEQ ID NO: 47 | CDRH2 variant | SIVTGSSDNTYYASWAKG |
| SEQ ID NO: 64 | CDRH3 | GGGAGYSGAFDL |
| SEQ ID NO: 72 | CDRL1 | QASESISNYLS |
| SEQ ID NO: 78 | CDRL2 | ASSKLSS |
| SEQ ID NO: 99 | CDRL3 | QIYYSASGSRDWT |

SEQ ID NO: 131 Rabbit Ab 4128 VL region

DIVMTQTPAS VEAAVGGTVT IKCQASESIS NYLSWFQQKP GQPPKLLIYA
SSKLSSGVPS RFKGDRSGTE YTLTISDLEC ADAATYYCQI YYSASGSRDW TFGGGTKVVV E

SEQ ID NO: 132 Rabbit Ab 4128 VL region gacattgtga tgacccagac tccagcctcc gtggaggcag ctgtgggagg cacagtcacc
atcaagtgcc aggccagtga aagcattagc aactacttat cctggtttca gcagaaacca
gggcagcctc ccaagctcct gatctatgct tcatccaaac tgtcatctgg ggtcccatcg
cggttcaaag gcgatagatc tgggacagag tacactctca ccatcagcga cctggagtgt
gccgatgctg ccacttacta ctgtcaaatc tattattcgg ctagtggcag tcgtgattgg
actttcggcg gagggaccaa ggtggtcgtc gaa

SEQ ID NO: 133 Rabbit Ab 4128 VH region

QSLEESGGDL VQPEGSLTLT CKGSGLDFSS YWICWVRQAP GKGLEWIACI VTGSSDNTYY
ASWAKGRFTI SKTSSTTVTL QMTSLTAADT ATYFCARGGG AGYSGAFDLW GQGTLVTVSS

SEQ ID NO: 134 Rabbit Ab 4128 VH region cagtcgttgg aggagtccgg gggagacctg gtccagcctg aggatccct gacactcacc
tgcaaaggct ccgggttaga cttcagtagc tactggatat gctgggtccg ccaggctcca
gggaaggggc tggagtggat cgcatgcatt gttactggta gtagtgataa cacttactac
gcgagctggg cgaaaggccg attcaccatc tccaaaacct cgtcgaccac ggtgactctg
caaatgacca gtctgacagc cgcggacacg gccacctatt tctgtgcgag aggtggtggt
gctggttata gtggtgcctt tgacttgtgg ggccaaggga ccctcgtcac cgtctcgagt

Fig. 35 Continued

SEQ ID NO: 135 4128 gL1 V-region – IGKV1-5 framework
DI<u>V</u>MTQSPST LSASVGDRVT ITCQASESIS NYLSW<u>F</u>QQKP GKAPKLLIYA SSKLSSGVPS
RF<u>KG</u>D<u>R</u>SGTE <u>Y</u>TLTISSLQP DDFATYYCQI YYSASGSRDW TFGGGTKVEI K

SEQ ID NO: 136 4128 gH1 V-region – IGHV3-33 framework
<u>E</u>VQLVESGGG <u>L</u>VQPGRSLRL SC<u>KG</u>SGLDFS SYWICWVRQA PGKGLEWI<u>A</u>C IVTGSSDNTY
YASWAKGRFT IS<u>K</u>DSSK<u>TT</u>V YLQMNSLRAE DTAVYYCARG GGAGYSGAFD LWGQGTLVTV SS

SEQ ID NO: 137 4128 gH2 V-region – IGHV3-33 framework
EVQLVESGGG LVQPGRSLRL SCKGSGLDFS SYWISWVRQA PGKGLEWIAS IVTGSSDNTY
YASWAKGRFT ISKDSSKTTV YLQMNSLRAE DTAVYYCARG GGAGYSGAFD LWGQGTLVTV SS

SEQ ID NO: 138 4128 gH4 V-region - IGHV4-59 framework
<u>E</u>VQLQESGPG LVKPSETLSL TC<u>KG</u>SGLDFS SYWICW<u>V</u>RQP PGKGLEWI<u>A</u>C IVTGSSDNTY
YASWAKGR<u>F</u>T IS<u>K</u>DSSK<u>T</u>Q<u>V</u> SLKLSSVTAA DTAVYYCARG GGAGYSGAFD LWGQGTLVTV SS

SEQ ID NO: 139 4128 gH5 V-region - IGHV4-59 framework
EVQLQESGPG LVKPSETLSL TCKGSGLDFS SYWISWVRQP PGKGLEWIAS IVTGSSDNTY YASWAKGRF
T ISKDSSKTQV SLKLSSVTAA DTAVYYCARG GGAGYSGAFD LWGQGTLVTV SS

Ab 4130

| | | |
|---|---|---|
| SEQ ID NO: 37 | CDRH1 | GFDFSGGYDIS |
| SEQ ID NO: 48 | CDRH2 | CIYGGINSVTDYASWAKG |
| SEQ ID NO: 49 | CDRH2 variant 1 | CIYGGINAVTDYASWAKG |
| SEQ ID NO: 50 | CDRH2 variant 2 | CIYGGINTVTDYASWAKG |
| SEQ ID NO: 51 | CDRH2 variant 3 | SIYGGINSVTDYASWAKG |
| SEQ ID NO: 52 | CDRH2 variant 4 | SIYGGINAVTDYASWAKG |
| SEQ ID NO: 53 | CDRH2 variant 5 | SIYGGINTVTDYASWAKG |
| SEQ ID NO: 65 | CDRH3 | DVSNSDHYTRLDL |
| SEQ ID NO: 66 | CDRH3 variant 1 | DVSNADHYTRLDL |
| SEQ ID NO: 67 | CDRH3 variant 2 | DVSNTDHYTRLDL |
| SEQ ID NO: 73 | CDRL1 | QSSQSVYNTKDLA |
| SEQ ID NO: 79 | CDRL2 | GTSTLAS |
| SEQ ID NO: 100 | CDRL3 | QGGFSSSDLNV |

SEQ ID NO: 140 Rabbit Ab 4130 VL region
AAVLTQTPSP VSAAVGGTVS ISCQSSQSVY NTKDLAWYQQ KPGQPPKLLI YGTSTLASGV
SSRFSGSGSG TEFTLTISDL ECDDAATYYC QGGFSSSDLN VFGGGTKVVV K

SEQ ID NO: 141 Rabbit Ab 4130 VL region
gccgccgtgc tgacccagac tccatctccc gtgtctgcag ctgtgggagg cacagtcagc
atcagttgcc agtccagtca gagtgtttat aatacaaagg acttagcctg gtatcagcag
aaaccagggc agcctcccaa gctcctgatc tatggtacat ccactctggc atctggggtc
tcatcacggt tcagcggcag tggatctggg acagagttca ctctcaccat cagcgacctg

Fig. 35 Continued gagtgtgacg atgctgccac ttattactgt caaggcggtt ttagtagtag tgatttgaat
gttttcggcg agggaccaa ggtggtggtc aaa

SEQ ID NO: 142 Rabbit Ab 4130 VH region

QQQLEESGGD LVRPEGSLTL TCTASGFDFS GGYDISWVRQ APGKGLEWIG
CIYGGINSVT DYASWAKGRV TISKTSSTTV TLQMTSLTAA DTATYFCARD
VSNSDHYTRL DLWGQGTLVT VSS

SEQ ID NO: 143 Rabbit Ab 4130 VH region cagcagcagc tggaggagtc cgggggagac ctggtcaggc ctgagggatc cctgacactc
acctgcacag cctctggatt cgacttcagt ggcggctacg acatttcctg gtccgccag
gctccaggga agggctgga gtggatcgga tgcatttatg gtggtatcaa tagtgtcact
gactacgcga gctgggcgaa aggccgagtc accatctcca aaacctcgtc gaccacggtg
actctgcaga tgaccagtct gacagccgcg gacacggcca cctatttctg tgcgagagat
gttagtaata gcgatcatta ctcggttg gatctctggg gccaaggcac cctggtcacc gtctcgagt

SEQ ID NO: 144 4130 gL3 V-region - IGKV1-9 framework

<u>AAV</u>LTQSPSF LSASVGDRVT ITCQSSQSVY NTKDLAWYQQ KPGKAPKLLI YGTSTLASGV
PSRFSGSGSG TEFTLTISSL QPEDFATYYC QGGFSSSDLN VFGGGTKVEI K

SEQ ID NO: 145 4130 gH8 V-region - IGHV3-66 framework

EVQLVESGGG LVQPGGSLRL SCAASGFDFS GGYDISWVRQ APGKGLEW<u>IG</u> CIYGGINSVT
DYASWAKGR<u>V</u> TIS<u>KD</u>SSK<u>TT</u> <u>V</u>YLQMNSLRA EDTAVYYCAR DVSNSDHYTR LDLWGQGTLV TVSS

SEQ ID NO: 146 4130 gH3 V-region - IGHV3-66 framework

EVQLVESGGG LVQPGGSLRL SCAASGFDFS GGYDISWVRQ APGKGLEWIG SIYGGINSVT DYASWAKGR
V TISKDSSKTT VYLQMNSLRA EDTAVYYCAR DVSNSDHYTR LDLWGQGTLV TVSS

SEQ ID NO: 147 4130 gH9 V-region - IGHV4-4 framework

<u>E</u>VQLQESGPG LVKPSGTLSL TCA<u>A</u>SGFDFS GGYDISWVRQ PPGKGLEWIG CIYGGINSVT
DYASWAKGRV TIS<u>KD</u>SSK<u>TQ</u> <u>V</u>SLKLSSVTA ADTAVYYCAR DVSNSDHYTR LDLWGQGTLV TVSS

SEQ ID NO: 148 4130 gH5 V-region - IGHV4-4 framework

EVQLQESGPG LVKPSGTLSL TCAASGFDFS GGYDISWVRQ PPGKGLEWIG SIYGGINSVT DYASWAKGR
V TISKDSSKTQ VSLKLSSVTA ADTAVYYCAR DVSNSDHYTR LDLWGQGTLV TVSS

Ab 4132

| | | |
|---|---|---|
| SEQ ID NO: 38 | CDRH1 | GFSFSSSYWIC |
| SEQ ID NO: 39 | CDRH1 variant | GFSFSSSYWIS |
| SEQ ID NO: 54 | CDRH2 | CINSGTGGTAYASWAKG |
| SEQ ID NO: 55 | CDRH2 variant 1 | CINAGTGGTAYASWAKG |
| SEQ ID NO: 56 | CDRH2 variant 2 | CINTGTGGTAYASWAKG |
| SEQ ID NO: 57 | CDRH2 variant 3 | SINSGTGGTAYASWAKG |
| SEQ ID NO: 58 | CDRH2 variant 4 | SINAGTGGTAYASWAKG |

Fig. 35 Continued

SEQ ID NO: 59 CDRH2 variant 5    SINTGTGGTAYASWAKG
SEQ ID NO: 68 CDRH3             EWVSGYYKDAFDL
SEQ ID NO: 74 CDRL1             QASETISSRLA
SEQ ID NO: 80 CDRL2             SASTLAS
SEQ ID NO: 101 CDRL3            QGYYYSSGSDYG

SEQ ID NO: 149 Rabbit Ab 4132 VL region
DIVMTQTPAS VEAAVGGTVT IKCQASETIS SRLAWYQQKL GQPPKLLIYS ASTLASGVPS
RFKGSGSGTE YTLTISGVQC ADAATYYCQG YYYSSGSDYG FGGGTKVVVK
SEQ ID NO: 150 Rabbit Ab 4132 VL region
gacattgtga tgacccagac tccagcctcc gtggaggcag ctgtgggagg cacagtcacc
atcaagtgcc aggccagtga gaccattagt agtagattag cctggtatca gcagaagcta
gggcagcctc ccaaactcct gatctattct gcatccactc tggcgtctgg ggtcccatcg
cggttcaaag gcagtggatc tgggacagag tacactctca ccatcagcgg cgtgcagtgt
gccgatgctg ccacttatta ctgtcaaggc tattattata gtagtggtag tgattatggt
ttcggcggag ggaccaaggt ggtcgtcaaa
SEQ ID NO: 151 Rabbit Ab 4132 VH region
QSLEESGGDL VKPGASLTLT CTASGFSFSS SYWICWVRQA PGKGLEWSGC INSGTGGTAY
ASWAKGRFTI SNSSSTTVTL QMTSLTAADT ATYFCAREWV SGYYKDAFDL WGQGTLVTVS S
SEQ ID NO: 152 Rabbit Ab 4132 VH region
cagtcgttgg aggagtccgg gggagacctg gtcaagcctg gggcatccct gacactcacc
tgcacagcct ctggattctc cttcagtagc agctactgga tatgctgggt ccgccaggct
ccagggaagg ggctggagtg gagcggatgc attaatagtg gtactggtgg cactgcctac
gcgagctggg cgaaaggccg attcaccatc tccaattcct cgtcgaccac ggtgactctt
caaatgacca gtctgacagc cgcggacacg gccacctatt tctgtgcgag agaatgggtt
agtggttatt ataaagatgc ttttgatctc tggggccagg gcaccctggt caccgtctcg agt
SEQ ID NO: 153 4132 gL1 V-region – IGKV1-5 framework
DIVMTQSPST LSASVGDRVT ITCQASETIS SRLAWYQQKP GKAPKLLIYS ASTLASGVPS
RFSGSGSGTE YTLTISSLQP DDFATYYCQG YYYSSGSDYG FGGGTKVEIK
SEQ ID NO: 154 4132 gH1 V-region – IGHV3-21 framework
EVQLVESGGG LVKPGGSLRL SCAASGFSFS SSYWICWVRQ APGKGLEWSG CINSGTGGTA
YASWAKGRFT ISNDSAKTSV YLQMNSLRAE DTAVYYCARE WVSGYYKDAF DLWGQGTLVT VSS
SEQ ID NO: 155 4132 gH2 V-region – IGHV3-21 framework
EQ ID NO: 156 4132 gH4 V-region – IGHV4-4 framework
EVQLQESGPG LVKPSGTLSL TCAASGFSFS SSYWICWVRQ PPGKGLEWSG CINSGTGGTA
YASWAKGRFT ISNDSSKTQV SLKLSSVTAA DTAVYYCARE WVSGYYKDAF DLWGQGTLVT VSS
SEQ ID NO: 157 4132 gH5 V-region – IGHV4-4 framework
EVQLQESGPG LVKPSGTLSL TCAASGFSFS SSYWISWVRQ PPGKGLEWSG SINSGTGGTA YASWAKGRF
T ISNDSSKTQV SLKLSSVTAA DTAVYYCARE WVSGYYKDAF DLWGQGTLVT VSS

Fig. 35 Continued

CD79b Antibodies

Ab 4447

| | | |
|---|---|---|
| SEQ ID NO: 158 | CDRH1 | GFSLSNYAVS |
| SEQ ID NO: 159 | CDRH2 | IIYIETGTTWYANWAKG |
| SEQ ID NO: 160 | CDRH3 | EPYEPYDDSNIYYGMDP |
| SEQ ID NO: 161 | CDRL1 | QASQSVVSGNYLA |
| SEQ ID NO: 162 | CDRL2 | SASTLAS |
| SEQ ID NO: 163 | CDRL3 | LGEFSCSSHDCNA |
| SEQ ID NO: 164 | CDRL3 variant 1 | LGEFSSSSHDSNA |
| SEQ ID NO: 165 | CDRL3 variant 2 | LGEFSCSSHDSNA |
| SEQ ID NO: 166 | CDRL3 variant 3 | LGEFSSSSHDCNA |

SEQ ID NO: 167 Rabbit Ab 4447 VL region

AQVLTQTPSP VSAPVGGTVT INCQASQSVV SGNYLAWLQQ KPGQPPKQLI HSASTLA
SGV SSRFSGSGSG TQFTLTISGV QCEDAATYYC LGEFSCSSHD CNAFGGGTEVVVK

SEQ ID NO: 168 Rabbit Ab 4447 VL region

```
gcccaagtgc tgacccagac tccgtcccct gtgtctgcac ctgtgggagg cacagtcacc
atcaattgcc aggccagtca gagtgttgtt agtggcaatt acctagcctg gcttcagcag
aaaccagggc agcctcccaa gcaactgatc cattctgcat ccactctggc atctggggtc
tcatcgcggt tcagcggcag tggatctggg acacaattca ctctcaccat cagcggcgtg
cagtgtgaag atgctgccac ttactactgt ctaggcgaat ttagttgtag tagtcatgat
tgtaatgctt tcggcggagg gaccgaggtg gtggtcaaa
```

SEQ ID NO: 169 Rabbit Ab 4447 VH region

QSLEESGGRL VTPGTPLTLT CTVSGFSLSN YAVSWVRQAP GEGLEWIGII
YIETGTTWYA NWAKGRFTIS KTSTTVDLTI TSPSTEDTAT YFCAREPYEP
YDDSNIYYGM DPWGPGTLVT VSS

SEQ ID NO: 170 Rabbit Ab 4447 VH region

```
cagtcgctgg aggagtccgg gggtcgcctg gtcacgcctg gacacccct gacactcacc
tgcaccgtct ctggattctc cctcagtaac tatgcagtaa gctgggtccg ccaggctcca
gggagggac tggaatggat cgggatcatt tatattgaaa ctggtaccac atggtacgcg
aactgggcga aaggccgatt caccatctcc aaaacctcga ccacggtgga tctgacaatc
accagtccgt caaccgagga cacggccacc tatttctgtg ccagagaacc ttatgaacct
tatgatgata gtaatattta ctacggcatg gacccctggg gccaggcac cctcgtcacc gtctcgagt
```

SEQ ID NO: 171 4447 gL1 V-region - IGKV1D-13 framework

AQVLTQSPSS LSASVGDRVT ITCQASQSVV SGNYLAWLQQ KPGKAPKQLI HSASTLASGV
PSRFSGSGSG TQFTLTISSL QPEDFATYYC LGEFSCSSHD CNAFGGGTKV EIK

SEQ ID NO: 172 4447 gL2 V-region - IGKV1D-13 framework

AQVLTQSPSS LSASVGDRVT ITCQASQSVV SGNYLAWLQQ KPGKAPKQLI HSASTLASGV PSRFSGSGS
G TQFTLTISSL QPEDFATYYC LGEFSSSSHD SNAFGGGTKV EIK

Fig. 35 Continued

SEQ ID NO: 173 4447 gH1 V-region – IGHV3-48 framework

EVQLVESGGG LVQPGGSLRL SCA<u>V</u>SGFSLS NYAVSWVRQA PGKGLEW<u>IGI</u> IYIETGTTWY
ANWAKGRFTI S<u>KD</u>S<u>A</u>KNS<u>VY</u> LQMNSLRDED TAVYYCAREP YEPYDDSNIY YGMDPWGQGT LVTVSS

SEQ ID NO: 174 4447 gH3 V-region – IGHV4-59 framework

<u>E</u>VQLQESGPG LVKPSETLSL TCTVSGFSLS NYAVSW<u>V</u>RQP PGKGLEWIGI IYIETGTTWY
ANWAKGR<u>F</u>TI S<u>KD</u>S<u>S</u>KNQ<u>VS</u> LKLSSVTAAD TAVYYCAREP YEPYDDSNIY YGMDPWGQGT LVTVSS

Ab 4450

| | | |
|---|---|---|
| SEQ ID NO: 175 | CDRH1 | GFSLNNYVMV |
| SEQ ID NO: 176 | CDRH2 | IIYVSGNAYYASWAKG |
| SEQ ID NO: 177 | CDRH3 | DAGHSDVDVLDI |
| SEQ ID NO: 178 | CDRL1 | QSSQSIYNNNDLA |
| SEQ ID NO: 179 | CDRL2 | EASKLAS |
| SEQ ID NO: 180 | CDRL3 | QGGGSGGDGIA |
| SEQ ID NO: 181 | CDRL3 – variant 1 | QGGGSGGEGIA |
| SEQ ID NO: 182 | CDRL3 – variant 2 | QGGGSGGDAIA |
| SEQ ID NO: 183 | CDRL3 – variant 3 | QGGGSGGDSIA |

SEQ ID NO: 184 Rabbit Ab 4450 VL region

AIDMTQTPSP VSAAVGGTVT INCQSSQSIY NNNDLAWYQQ KPGQPPKLLI YEASKLASGV
PSRFKGSGSG TQFTLTISGV QCDDAATYYC QGGGSGGDGI AFGGGTKVVV E

SEQ ID NO: 185 Rabbit Ab 4450 VL region gccattgata tgacccagac tccatccccc gtgtctgcag ctgtgggagg cacagtcacc
atcaattgcc agtccagtca gagtatttat aataataatg acttagcctg gtatcagcag
aaaccaggc agcctcccaa gctcctgatc tacgaagcat ccaaactggc atctggggtc
ccatcgcggt tcaaaggcag tggatctggg acacagttca ctctcaccat cagtggcgtg
cagtgtgatg atgctgccac ttactactgt caggcggtg gtagtggtgg tgatggcatt
gctttcggcg gagggaccaa ggtggtcgtc gaa

SEQ ID NO: 186 Rabbit Ab 4450 VH region

QSVEESGGRL VTPGAPLTLT CTVSGFSLNN YVMVWVRQAP GKGLEWIGII YVSGNAYYAS
WAKGRFTISR TSTTVDLKVT SLTTEDTATY FCARDAGHSD VDVLDIWGPG TLVTVSS

SEQ ID NO: 187 Rabbit Ab 4450 VH region cagtcggtgg aggagtccgg gggtcgcctg gtcacgcctg ggcacccct gacactcacc
tgcacagtct ctggattctc cctcaataac tatgtaatgg tctgggtccg ccaggctcca
gggaaggggc tggaatggat cggaatcatt tatgttagtg gtaatgcata ctacgcgagc
tgggcaaaag gccgattcac catctccaga acctcgacca cggtggatct gaaagtgacc
agtctgacaa ccgaggacac ggccacctat ttctgtgcca gagatgctgg tcatagtgat
gtcgatgttt tggatatttg ggggccgggc accctcgtca ccgtctcgagt

SEQ ID NO: 188 4450 gL1 V-region - IGKV1-6 framework

Fig. 35 Continued

AI<u>D</u>MTQSPSS LSASVGDRVT ITCQSSQSIY NNNDLAWYQQ KPGKAPKLLI YEASKLASGV
PSRFSGSGSG T<u>Q</u>FTLTISSL QPEDFATYYC QGGGSGGDGI AFGGGTKVEI K

SEQ ID NO: 189 4450 gH1 V-region - IGHV3-66 framework
EVQLVESGGG LVQPGGSLRL SCA<u>V</u>SGFSLN NYVMVWVRQA PGKGLEW<u>IGI</u> IYVSGNAYYA
SWAKGRFTIS RD<u>S</u>SKNT<u>VY</u>L QMNSLRAEDT AVYYCARDAG HSDVDVLDIW GQGTLVTVSS
SEQ ID NO: 190 4450 gH3 V-region – IGHV4-59 framework
<u>E</u>VQLQESGPG LVKPSETLSL TCTVSGFSLN NYVMVW<u>V</u>RQP PGKGLEWIGI IYVSGNAYYA
SWAKGR<u>F</u>TIS <u>RDS</u>SKNQ<u>V</u>SL KLSSVTAADT AVYYCARDAG HSDVDVLDIW GQGTLVTVSS

Serum Albumin Binding Antibodies

| | | |
|---|---|---|
| CDRH1 dAbH1 | SEQ ID NO: 191 | Gly Ile Asp Leu Ser Asn Tyr Ala Ile Asn |
| CDRH2 dAbH1 | SEQ ID NO: 192 | Ile Ile Trp Ala Ser Gly Thr Thr Phe Tyr Ala Thr Trp Ala Lys Gly |
| CDRH3 dAbH1 | SEQ ID NO: 193 | Thr Val Pro Gly Tyr Ser Thr Ala Pro Tyr Phe Asp Leu |
| CDRL1 dAbL1 | SEQ ID NO: 194 | Gln Ser Ser Pro Ser Val Trp Ser Asn Phe Leu Ser |
| CDRL2 dAbL1 | SEQ ID NO: 195 | Glu Ala Ser Lys Leu Thr Ser |
| CDRL3 dAbL1 | SEQ ID NO: 196 | Gly Gly Gly Tyr Ser Ser Ile Ser Asp Thr Thr |

Heavy chain variable domain of anti-albumin antibody (no ds)     SEQ ID NO: 197
Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Gly Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser Heavy chain variable domain of anti-albumin antibody (ds) SEQ ID NO: 198
Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Cys Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser Light chain variable domain of anti-albumin antibody (no ds)     SEQ ID NO: 199

Fig. 35 Continued

```
Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile
Ser Ser Leu Gln Pro Glu Asp Phe Ala Thr Tyr Tyr Cys Gly Gly Gly Tyr Ser Ser
Ile Ser Asp Thr Thr Phe Gly Gly Gly Thr Lys Val Glu Ile Lys Arg Thr
```

Light chain variable domain of anti-albumin antibody (ds) SEQ ID NO: 200

```
Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile

Ser Ser Leu Gln Pro Glu Asp Phe Ala Thr Tyr Tyr Cys Gly Gly Gly Tyr Ser Ser
Ile Ser Asp Thr Thr Phe Gly Cys Gly Thr Lys Val Glu Ile Lys Arg Thr
```

Human CD22 SEQ ID NO: 201

```
MHLLGPWLLL LVLEYLAFSD SSKWVFEHPE TLYAWEGACV WIPCTYRALD GDLESFILFH
NPEYNKNTSK FDGTRLYEST KDGKVPSEQK RVQFLGDKNK NCTLSIHPVH LNDSGQLGLR
MESKTEKWME RIHLNVSERP FPPHIQLPPE  IQESQEVTLT CLLNFSCYGY PIQLQWLLEG
VPMRQAAVTS TSLTIKSVFT RSELKFSPQW SHHGKIVTCQ LQDADGKFLS NDTVQLNVKH
TPKLEIKVTP SDAIVREGDS VTMTCEVSSS NPEYTTVSWL KDGTSLKKQN TFTLNLREVT
KDQSGKYCCQ VSNDVGPGRS EEVFLQVQYA PEPSTVQILH SPAVEGSQVE FLCMSLANPL
PTNYTWYHNG KEMQGRTEEK VHIPKILPWH AGTYSCVAEN ILGTGQRGPG AELDVQYPPK
KVTTVIQNPM PIREGDTVTL SCNYNSSNPS VTRYEWKPHG AWEEPSLGVL KIQNVGWDNT
TIACAACNSW CSWASPVALN VQYAPRDVRV RKIKPLSEIH SGNSVSLQCD FSSSHPKEVQ
FFWEKNGRLL GKESQLNFDS ISPEDAGSYS CWVNNSIGQT ASKAWTLEVL YAPRRLRVSM
SPGDQVMEGK SATLTCESDA NPPVSHYTWF DWNNQSLPYH SQKLRLEPVK VQHSGAYWCQ
GTNSVGKGRS PLSTLTVYYS PETIGRRVAV GLGSCLAILI LAICGLKLQR RWKRTQSQQG
LQENSSGQSF FVRNKKVRRA PLSEGPHSLG CYNPMMEDGI SYTTLRFPEM NIPRTGDAES
SEMQRPPPDC DDTVTYSALH KRQVGDYENV IPDFPEDEGI HYSELIQFGV GERPQAQENV DYVILKH
```

Human CD79a SEQ ID NO: 202

```
MPGGPGVLQA LPATIFLLFL LSAVYLGPGC QALWMHKVPA SLMVSLGEDA HFQCPHNSSN
NANVTWWRVL HGNYTWPPEF LGPGEDPNGT LIIQNVNKSH  GGIYVCRVQE GNESYQQSCG
TYLRVRQPPP RPFLDMGEGT KNRIITAEGI ILLFCAVVPG TLLLFRKRWQ NEKLGLDAGD
EYEDENLYEG LNLDDCSMYE DISRGLQGTY QDVGSLNIGD VQLEKP
```

Human CD79b SEQ ID NO: 203

```
MARLALSPVP SHWMVALLLL LSAEPVPAAR SEDRYRNPKG SACSRIWQSP
RFIARKRGFT VKMHCYMNSA SGNVSWLWKQ EMDENPQQLK LEKGRMEESQ
NESLATLTIQ GIRFEDNGIY FCQQKCNNTS EVYQGCGTEL RVMGFSTLAQ
```

Fig. 35 Continued

LKQRNTLKDG IIMIQTLLII LFIIVPIFLL LDKDDSKAGM EEDHTYEGLD
IDQTATYEDI VTLRTGEVKW SVGEHPGQE
ASGGGRMKQLEPKVEELLPKNYHLENEVARLKKLVGERHHHHHH   SEQ ID NO:204
wherein the amino acids in bold are optional GCTAGCGGAGGCGGAAGAATGAAACAACTTGAACCCAAGGTTGAAGAATTGCTTCCGAAAAA
TTATCACTTGGAAAATGAGGTTGCCAGATTAAAGAAATTAGTTGGCGAACGCCATCACCATC
ACCATCAC SEQ ID NO: 205

52SR4 ds scFv sequence
DAVVTQESALTSSPGETVTLTCRSSTGAVTTSNYASWVQEKPDHLFTGLIGGTNNRAPGV
PARFSGSLIGDKAALTITGAQTEDEAIYFCVLWYSDHWVFGCGTKLTVLGGGGSGGGGS
GGGGSGGGGSDVQLQQSGPGLVAPSQSLSITCTVSGFLLTDYGVNWVRQSPGKCLEWLGV
IWGDGITDYNSALKSRLSVTKDNSKQVFLKMNSLQSGDSARYYCVTGLFDYWGQGTTLT
VSSAAAHHHHHHEQKLISEEDL- SEQ ID NO: 206
GATGCGGTGGTGACCCAGGAAAGCGCGCTGACCAGCAGCCCGGGCGAAACCGTGACCCTGAC
CTGCCGCAGCAGCACCGGCGCGGTGACCACCAGCAACTATGCGAGCTGGGTGCAGGAAAAAC
CGGATCATCTGTTTACCGGCCTGATTGGCGGCACCAACAACCGCGCGCCGGGCGTGCCGGCG
CGCTTTAGCGGCAGCCTGATTGGCGATAAAGCGGCGCTGACCATTACCGGCGCGCAGACCGA
AGATGAAGCGATTTATTTTTGCGTGCTGTGGTATAGCGACCATTGGGTGTTTGGCTGCGGCA
CCAAACTGACCGTGCTGGGTGGAGGCGGTGGCTCAGGCGGAGGTGGCTCAGGCGGTGGCGGG
TCTGGCGGCGGCGGCAGCGATGTGCAGCTGCAGCAGAGCGGCCCGGGCCTGGTGGCGCCGAG
CCAGAGCCTGAGCATTACCTGCACCGTGAGCGGCTTTCTCCTGACCGATTATGGCGTGAACT
GGGTGCGCCAGAGCCCGGGCAAATGCCTGGAATGGCTGGGCGTGATTTGGGGCGATGGCATT
ACCGATTATAACAGCGCGCTGAAAAGCCGCCTGAGCGTGACCAAAGATAACAGCAAAAGCCA
GGTGTTTCTGAAAATGAACAGCCTGCAGAGCGGCGATAGCGCGCGCTATTATTGCGTGACCG
GCCTGTTTGATTATTGGGGCCAGGGCACCACCCTGACCGTGAGCAGCGCGGCCGCCCATCAC
CATCACCATCACGAACAGAAACTGATTAGCGAAGAAGATCTGTAATAG   SEQ ID NO: 207

ANTIBODY MOLECULES WHICH BIND CD22

The present disclosure is a continuation of U.S. application Ser. No. 16/778,523 (now U.S. Pat. No. 11,472,879), filed Jan. 31, 2020, which is a divisional of U.S. application Ser. No. 15/743,756 (now U.S. Pat. No. 10,590,197), filed Jan. 11, 2018, which is a National Stage Entry of WO2017/009476 A1, filed Jul. 15, 2016, and claims priority from WO2016/009030, filed Jul. 16, 2015, and GB1601077.9, filed Jan. 20, 2016 all of which are incorporated herein by reference.

REFERENCE TO AN ELECTRONIC SEQUENCE LISTING

The contents of the electronic sequence listing (0089-0011US3 SL.xml; Size: 393 kilobytes; and Date of Creation Nov. 4, 2022) is herein incorporated by reference in its entirety.

FIELD OF INVENTION

The present disclosure relates to antibody molecules which are at least specific to the antigen CD22, formulations comprising said antibody molecules and use of any one of the same, in treatment. The present disclosure also extends to methods of preparing said antibody molecules and said formulations.

BACKGROUND OF INVENTION

Biological mechanisms in vivo are extremely complicated cascades of signals, which are difficult to deconvolute and understand. An example of such signalling is that required to activate B-cells. The B cell antigen receptor (BCR) is composed of membrane immunoglobulin (mIg) molecules and associated Igα/Igβ (CD79a/CD79b) heterodimers (α/β). The mIg subunits bind antigen, resulting in receptor aggregation, while the a/0 subunits transduce signals to the cell interior. BCR aggregation rapidly activates the Src family kinases Lyn, Blk, and Fyn as well as the Syk and Btk tyrosine kinases. This initiates the formation of a 'signalosome' composed of the BCR, the aforementioned tyrosine kinases, adaptor proteins such as CD19 and BLNK, and signaling enzymes such as PLCγ2, PI3K, and Vav.

Signals emanating from the signalosome activate multiple signaling cascades that involve kinases, GTPases, and transcription factors. This results in changes in cell metabolism, gene expression, and cytoskeletal organization. The complexity of BCR signaling permits many distinct outcomes, including survival, tolerance (anergy) or apoptosis, proliferation, and differentiation into antibody-producing cells or memory B cells. The outcome of the response is determined by the maturation state of the cell, the nature of the antigen, the magnitude and duration of BCR signaling, and signals from other receptors such as CD40, the IL-21 receptor, and BAFF-R.

Many other transmembrane proteins, some of which are receptors, modulate specific elements of BCR signaling. A few of these, including CD45, CD19, CD22, PIR-B, and FcγRIIB1 (CD32). The magnitude and duration of BCR signaling are limited by negative feedback loops including those involving the Lyn/CD22/SHP-1 pathway, the Cbp/Csk pathway, SHIP, Cbl, Dok-1, Dok-3, FcγRIIB1, PIR-B, and internalization of the BCR. In vivo, B cells are often activated by antigen-presenting cells that capture antigens and display them on their cell surface. Activation of B cells by such membrane-associated antigens requires BCR-induced cytoskeletal reorganization.

Autoreactive B cells are responsible for the production of pathogenic autoantibodies which can either directly or indirectly cause or exacerbate autoimmune conditions. Depletion of CD20 positive B cells has been used to successfully treat a number of autoimmune conditions and thus established conclusively that B cells play an important role in causing or maintaining a number of autoimmune diseases, such as rheumatoid arthritis, systemic lupus erythematosus, multiple sclerosis and type I diabetes mellitus. Although B cell depletion has been a successful therapeutic option evidence also exists that control of B cell growth and activation status can also be an effective way to modulate B cell function. Alternative strategies that do not deplete B cells and offer the flexibility of controlling B cells without long term suppression of B cell immunity, which has been shown to be associated with some side effects would therefore be desirable. In addition not all B cell responses or activities are harmful and evidence suggests that maintenance of regulatory B cell populations can be protective. Such an approach should be effective in diseases which have abnormal B cell function caused by inappropriate or excessive BcR signalling. Examples of such diseases include, but are not limited to, inflammation, autoimmunity and cancer. Of particular interest are diseases that either have a direct requirement for BcR signalling or require inhibition or stimulation of humoral immune responses.

Co-ligation of Fc gamma receptor IIb (CD32b) with the B cell receptor occurs to naturally regulate signalling, in particular when antigen is bound to antibody in small immune complexes. CD32b then recruits the phophatases SHP-1 and SHIP-1 which antagonise BcR activation. Although this natural regulatory mechanism can control B cell function, disruption of CD32b function caused by variation in the protein sequence of CD32b can lead to autoimmune disease and this receptor can be down regulated in autoimmune disease—e.g. as in the case of SLE. Alternative ways of blocking B cell activity are thus desirable as they offer alternative, non-natural, ways of regulating BcR function. These alternative mechanisms are likely to be particularly important when natural mechanisms are dysfunctional in the given disease.

CD22 is an inhibitory coreceptor of the B-cell receptor (BCR) and plays a critical role in establishing signalling thresholds for B cell activation. Targeting CD22 induces both physical down-regulation of BCR complex components on resting cells, which would likely result in less responsive B cells as well as limiting the extent of BCR signalling after BCR engagement. The overall effect is inhibition of B-cell activation, ultimately reducing subsequent autoimmune and inflammatory events mediated by B cells. Therefore modulation of CD22 function by antibodies can have therapeutic benefit in many diseases dependent upon B cell activation including autoimmunity, immunodeficiency, and malignancy, (see for example, CD22: an inhibitory enigma. Immunology. 2007. Vol 123: 314-325). The present disclosure provides a number of antibody molecules specific to CD22, which may be employed alone or in combination with an entity, such as an antibody or binding fragment thereof specific to a further B cell surface receptor (such as CD79), useful in controlling aberrant B cell functions, for example associated with certain diseases such as autoimmunity and cancer.

SUMMARY OF THE DISCLOSURE

Thus provided is an antibody molecule comprising a:

$$GX_1X_2FSX_3X_4X_5X_6X_7X_8$$ (SEQ ID NO: 1)

wherein $X_1$ is F, I or L (such as F), $X_2$ is S or D, $X_3$ is S, N or G (such as S), $X_4$ is S, Y, L or G, $X_5$ is Y or absent, $X_6$ is W, Y or D (such as W or Y, particularly Y), $X_7$ is M or I and $X_8$ is C or S (particularly S);

CDRH2 of formula (II):

$$X_9LX_{10}X_{11}X_{12}X_{13}X_{14}X_{15}X_{16}TX_{17}YAX_{18}WAKG$$ (SEQ ID NO: 2)

wherein $X_9$ is C or S, $X_{10}$ is Y, D, V or N, $X_{11}$ is T, P, I, G, S or A, $X_{12}$ is G, S, or A (particularly G), $X_{13}$ is S, I or T, $X_{14}$ is S, N or absent, $X_{15}$ is G, D, S, A or T, $X_{16}$ is D, T, S, N, V or G, $X_{17}$ is Y, D or A and $X_{18}$ is T or S (particularly S).

CDHR3 of formula (III):

$$X_{19}X_{20}X_{21}X_{22}X_{23}X_{24}X_{25}X_{26}X_{27}X_{28}X_{29}X_{30}X_{31}X_{32}X_{33}L$$ (SEQ ID NO: 3)

wherein $X_{19}$ is A or absent, $X_{20}$ is absent, G or Y, $X_{21}$ is absent, P or G, $X_{22}$ is absent, Y, S, D or E, $X_{23}$ is V, G, Y or W, $X_{24}$ is G, Y, S or V, $X_{25}$ is Y, S, G or N, $X_{26}$ is G, A, S or T, $X_{27}$ is Y, G or D, $X_{28}$ is D, I, Y, W or H, $X_{29}$ is L, G, S, Y or K, $X_{30}$ is V, Q, C, S, G, T or D, $X_{31}$ is Y, A or R, $X_{32}$ is L or F, $X_{33}$ is N, Y or D (particularly D);

and a light chain variable domain comprising CDRL1, CDRL2 and CDL3 from a lagomorph, in particular a light chain variable domain comprising a human framework and CDRL1, CDRL2 and CDRL3 from a lagomorph.

In one embodiment CDRL1 has a formula (IV):

$$QX_{34}SX_{35}X_{36}X_{37}X_{38}X_{39}X_{40}X_{41}X_{42}LX_{43}$$ (SEQ ID NO: 4)

wherein $X_{34}$ is A or S (particularly A), $X_{35}$ is Q or E (particularly Q), $X_{36}$ is S, N or T (particularly S), $X_{37}$ is I or V, $X_{38}$ is S, Y or G (such as S or Y), $X_{39}$ is T, S, G or N (such as S or N), $X_{40}$ is A, G, N, Y, T or R, $X_{41}$ is absent, N or K (particularly absent), $X_{42}$ is absent, E or D (particularly absent) and $X_{43}$ is A or S (particularly A);

CDRL2 has a formula (V):

$$X_{44}X_{45}SX_{46}LX_{47}S$$ (SEQ ID NO: 5)

wherein $X_{44}$ is G, Y, L, A or S, $X_{45}$ is A, S or T (particularly A), $X_{46}$ is T, R or K (particularly T) and $X_{47}$ is A or S (particularly A);

CDRL3 has a formula (VI):

$$AGYKSX_{48}X_{49}DX_{50}X_{51}TT$$ (SEQ ID NO: 6)

wherein $X_{48}$ is D or E (particularly D), $X_{49}$ is S, A or T, $X_{50}$ is D or E (particularly D) and $X_{51}$ is G, A or S; or CDRL3 has a formula (VII):

$$QX_{52}X_{53}X_{54}X_{55}X_{56}SX_{57}X_{58}X_{59}X_{60}X_{61}X_{62}X_{63}X_{64}$$ (SEQ ID NO: 7)

wherein $X_{52}$ is S, I or G (such as S or G), $X_{53}$ is Y, H or G (particularly Y), $X_{54}$ is Y, D or F (particularly Y), $X_{55}$ is G, S or Y (such as S or Y), $X_{56}$ is T, A or S (particularly S), $X_{57}$ is S, G, V or D, $X_{58}$ is G, S, L or absent, $X_{59}$ is G, R, S or N, $X_{60}$ is S, D or V (such as S or D), $X_{61}$ is W, Y or absent (such as W or Y), $X_{62}$ is A, T, G or absent, $X_{63}$ is N or absent (particularly absent), $X_{64}$ is A or absent (particularly absent).

In one embodiment, the sequence of formula (I) is as shown in formula (Ia):

$$GX_1X_2FSX_3X_4X_5YX_7X_8$$ (SEQ ID NO: 8)

wherein $X_1$, $X_2$, $X_3$, $X_4$, $X_5$, $X_7$ and $X_8$ are as defined above for formula I, in particular is a sequence of formula (Ib):

$$GX_1X_2FSX_3X_4X_5YX_7X_8$$ (SEQ ID NO: 9)

wherein $X_1$, $X_2$, $X_3$, $X_4$, $X_5$ and $X_7$ are as defined above for formula I.

In one embodiment, the sequence of formula (II) is as shown in formula (IIa):

$$X_9IX_{10}X_{11}GX_{13}X_{14}X_{15}X_{16}TX_{17}YAX_{18}WAKG$$ (SEQ ID NO: 10)

wherein $X_9$, $X_{10}$, $X_{11}$, $X_{13}$, $X_{14}$, $X_{15}$, $X_{16}$, $X_{17}$ and $X_{18}$ are as defined above for formula II.

In one embodiment, the sequence of formula (II) is as shown in formula (IIb):

$$X_9LX_{10}X_{11}X_{12}X_{13}X_{14}X_{15}X_{16}TX_{17}YASWAKG$$ (SEQ ID NO: 11)

wherein $X_9$, $X_{10}$, $X_{11}$, $X_{12}$, $X_{13}$, $X_{14}$, $X_{15}$, $X_{16}$ and $X_{17}$ are as defined above for formula II, in particular a sequence of formula (IIb) wherein $X_{12}$ is G.

In one embodiment the sequence of formula (III) is as shown in formula (IIa):

$$X_{19}X_{20}X_{21}X_{22}X_{23}X_{24}X_{25}X_{26}X_{27}X_{28}X_{29}X_{30}X_{31}X_{32}DL$$ (SEQ ID NO: 12)

wherein $X_{19}$, $X_{20}$, $X_{21}$, $X_{22}$, $X_{23}$, $X_{24}$, $X_{25}$, $X_{26}$, $X_{27}$, $X_{28}$, $X_{29}$, $X_{30}$, $X_{31}$ and $X_{32}$ are as defined above for formula III.

In one embodiment the sequence of formula (IV) is as shown in formula (IVa):

$$QASX_{35}X_{36}X_{37}X_{38}X_{39}X_{40}X_{41}X_{42}LX_{43}$$ (SEQ ID NO: 13)

wherein $X_{35}$, $X_{36}$, $X_{37}$, $X_{38}$, $X_{39}$, $X_{40}$, $X_{41}$, $X_{42}$ and $X_{43}$ are as defined above for formula IV; in particular is a sequence of formula (IVb):

(SEQ ID NO: 14)
$\text{QASQX}_{36}X_{37}X_{38}X_{39}X_{40}X_{41}X_{42}\text{LX}_{43}$ wherein $X_{36}$, $X_{37}$, $X_{38}$, $X_{39}$, $X_{40}$, $X_{41}$, $X_{42}$ and $X_{43}$ are as defined above for formula IV; in particular is a sequence of formula (IVc):

(SEQ ID NO: 15)
$\text{QASQSX}_{37}X_{38}X_{39}X_{40}X_{41}X_{42}\text{LX}_{43}$ wherein $X_{37}$, $X_{38}$, $X_{39}$, $X_{40}$, $X_{41}$, $X_{42}$ and $X_{43}$ are as defined above for formula IV; in particular is a sequence of formula (IVd):

(SEQ ID NO: 16)
$\text{QASQSX}_{37}X_{38}X_{39}X_{40}X_{42}\text{LX}_{43}$ wherein $X_{37}$, $X_{38}$, $X_{39}$, $X_{40}$, $X_{42}$ and $X_{43}$ are as defined above for formula IV; in particular is a sequence of formula (IVe):

(SEQ ID NO: 17)
$\text{QASQSX}_{37}X_{38}X_{39}X_{40}\text{LX}_{43}$ wherein $X_{37}$, $X_{38}$, $X_{39}$, $X_{40}$, and $X_{43}$ are as defined above for formula IV; in particular is a sequence of formula (IVf):

(SEQ ID NO: 18)
$\text{QASQSX}_{37}X_{38}X_{39}X_{40}\text{LA}$ wherein $X_{37}$, $X_{38}$, $X_{39}$ and $X_{40}$ are as defined above for formula IV.

In one embodiment the sequence of formula (V) is as shown in formula (Va):

(SEQ ID NO: 19)
$X_{44}\text{ASX}_{46}\text{LX}_{47}\text{S}$ wherein $X_{44}$, $X_{46}$ and $X_{47}$ are as defined above for formula V; in particular is a sequence of formula (Vb):

(SEQ ID NO: 20)
$X_{44}\text{ASX}_{46}\text{LAS}$ wherein $X_{44}$ and $X_{46}$ are as defined above for formula V; in particular is a sequence of formula (Vc):

(SEQ ID NO: 21)
$X_{44}\text{ASTLAS}$ wherein $X_{44}$ is as defined above for formula V.

In one embodiment the sequence of formula (VI) is as shown in formula (VIa):

(SEQ ID NO: 22)
$\text{AGYKSX}_{48}X_{49}\text{DX}_{50}X_{51}\text{TT}$ wherein $X_{48}$, $X_{49}$, $X_{50}$ and $X_{51}$ are as defined above for formula VI; in particular is a sequence of formula (VIb):

(SEQ ID NO: 23)
$\text{AGYKSDX}_{49}\text{DDX}_{51}\text{TT}$ wherein $X_{49}$ and $X_{51}$ are as defined above for formula VI.

In one embodiment the sequence of formula (VII) is as shown in formula (VIIa):

(SEQ ID NO: 24)
$\text{QX}_{52}\text{YX}_{54}X_{55}X_{56}\text{SX}_{57}X_{58}X_{59}X_{60}X_{61}X_{62}X_{63}X_{64}$ wherein $X_{52}$, $X_{54}$, $X_{55}$, $X_{56}$, $X_{57}$, $X_{58}$, $X_{59}$, $X_{60}$, $X_{61}$, $X_{62}$, $X_{63}$ and $X_{64}$ are as defined above for formula VII; in particular is a sequence of formula (VIIb):

(SEQ ID NO: 25)
$\text{QX}_{52}\text{YYX}_{55}X_{56}\text{SX}_{57}X_{58}X_{59}X_{60}X_{61}X_{62}X_{63}X_{64}$ wherein $X_{52}$, $X_{55}$, $X_{56}$, $X_{57}$, $X_{58}$, $X_{59}$, $X_{60}$, $X_{61}$, $X_{62}$, $X_{63}$ and $X_{64}$ are as defined above for formula VII; in particular is a sequence of formula (VIIc):

(SEQ ID NO: 26)
$\text{QX}_{52}\text{YYX}_{55}\text{SSX}_{57}X_{58}X_{59}X_{60}X_{61}X_{62}X_{63}X_{64}$ wherein $X_{52}$, $X_{55}$, $X_{57}$, $X_{58}$, $X_{59}$, $X_{60}$, $X_{61}$, $X_{62}$, $X_{63}$ and $X_{64}$ are as defined above for formula VII; in particular is a sequence of formula (VIId):

(SEQ ID NO: 27)
$\text{QX}_{52}\text{YYX}_{55}\text{SSX}_{57}X_{58}X_{59}X_{60}X_{61}X_{62}X_{64}$ wherein $X_{52}$, $X_{55}$, $X_{57}$, $X_{58}$, $X_{59}$, $X_{60}$, $X_{61}$, $X_{62}$ and $X_{64}$ are as defined above for formula VII; in particular is a sequence of formula (VIIe):

(SEQ ID NO: 28)
$\text{QX}_{52}\text{YYX}_{55}\text{SSX}_{57}X_{58}X_{59}X_{60}X_{61}X_{62}$ wherein $X_{52}$, $X_{55}$, $X_{57}$, $X_{58}$, $X_{59}$, $X_{60}$, $X_{61}$ and $X_{62}$ are as defined above for formula VII.

Examples of CDRs falling with the definition of formula (I), (II) and (III) are provided as follows:

```
                                          SEQ ID NO: 29
GFSFSSSYYMC
(for example as CDRH1)

SEQ ID NO: 30
GFSFSSSYYMS
(for example as CDRH1)

SEQ ID NO: 31
GIDFSSYYYMC
(for example as CDRH1)

SEQ ID NO: 32
GIDFSSYYYMS
(for example as CDRH1)

SEQ ID NO: 33
GFSFSNLYYMC
(for example as CDRH1)
```

GFSFSNLYYMS
(for example as CDRH1)
SEQ ID NO: 34

GLDFSSYWIC
(for example as CDRH1)
SEQ ID NO: 35

GLDFSSYWIS
(for example as CDRH1)
SEQ ID NO: 36

GFDFSGGYDIS
(for example as CDRH1)
SEQ ID NO: 37

GFSFSSSYWIC
(for example as CDRH1)
SEQ ID NO: 38

GFSFSSSYWIS
(for example as CDRH1)
SEQ ID NO: 39

CIYTGSSGDTYYASWAKG
(for example as CDRH2)
SEQ ID NO: 40

SIYTGSSGDTYYASWAKG
(for example as CDRH2)
SEQ ID NO: 41

CIDPASSGTTYYATWAKG
(for example as CDRH2)
SEQ ID NO: 42

SIDPASSGTTYYATWAKG
(for example as CDRH2)
SEQ ID NO: 43 cidisssgstyyaswakg
(for example as CDRH2)
SEQ ID NO: 44

SIDISSSGSTYYASWAKG
(for example as CDRH2)
SEQ ID NO: 45

CIVTGSSDNTYYASWAKG
(for example as CDRH2)
SEQ ID NO: 46

SIVTGSSDNTYYASWAKG
(for example as CDRH2)
SEQ ID NO: 47

CIYGGINSVTDYASWAKG
(for example as CDRH2)
SEQ ID NO: 48

CIYGGINAVTDYASWAKG
(for example as CDRH2)
SEQ ID NO: 49

CIYGGINTVTDYASWAKG
(for example as CDRH2)
SEQ ID NO: 50

SIYGGINSVTDYASWAKG
(for example as CDRH2)
SEQ ID NO: 51

SIYGGINAVTDYASWAKG
(for example as CDRH2)
SEQ ID NO: 52

SIYGGINTVTDYASWAKG
(for example as CDRH2)
SEQ ID NO: 53

CINSGTGGTAYASWAKG
(for example as CDRH2)
SEQ ID NO: 54

CINAGTGGTAYASWAKG
(for example as CDRH2)
SEQ ID NO: 55

CINTGTGGTAYASWAKG
(for example as CDRH2)
SEQ ID NO: 56

SINSGTGGTAYASWAKG
(for example as CDRH2)
SEQ ID NO: 57

SINAGTGGTAYASWAKG
(for example as CDRH2)
SEQ ID NO: 58

SINTGTGGTAYASWAKG
(for example as CDRH2)
SEQ ID NO: 59

GPYVGYGYDLQYLYL
(for example as CDRH3)
SEQ ID NO: 60

AYGSGGSGYIGCYFDL
(for example as CDRH3)
SEQ ID NO: 61

AYGSGGSGYIGSYFDL
(for example as CDRH3)
SEQ ID NO: 62

DYYSSDWGVRFNL
(for example as CDRH3)
SEQ ID NO: 63

GGGAGYSGAFDL
(for example as CDRH3)
SEQ ID NO: 64

DVSNSDHYTRLDL
(for example as CDRH3)
SEQ ID NO: 65

DVSNADHYTRLDL
(for example as CDRH3)
SEQ ID NO: 66

DVSNTDHYTRLDL
(for example as CDRH3)
SEQ ID NO: 67

EWVSGYYKDAFDL
(for example as CDRH3)
SEQ ID NO: 68

Examples of CDRs falling with the definition of formula (IV), (V), (VI) and (VII) are provided as follows:

QASQSISTALA
(for example as CDRL1)
SEQ ID NO: 69

QASQNIGSGLA
(for example as CDRL1 variant 1)
SEQ ID NO: 70

QASQSVYGNNELS
(for example as CDRL1 variant 2)
SEQ ID NO: 71

QASESISNYLS
(for example as CDRL1 variant 3)
SEQ ID NO: 72

QSSQSVYNTKDLA (for example as CDRL1 variant 4) SEQ ID NO: 73

QASETISSRLA (for example as CDRL1 variant 5) SEQ ID NO: 74

GASTLAS (for example as CDRL2) SEQ ID NO: 75

YASTLAS (for example as CDRL2 variant 1) SEQ ID NO: 76

LASRLAS (for example as CDRL2 variant 2) SEQ ID NO: 77

ASSKLSS (for example as CDRL2 variant 3) SEQ ID NO: 78

GTSTLAS (for example as CDRL2 variant 4) SEQ ID NO: 79

SASTLAS (for example as CDRL2 variant 5) SEQ ID NO: 80

QSYYGTSSGGSWA (for example as CDRL3) SEQ ID NO: 81

QSHDYSSVRSYGNA (for example as CDRL3) SEQ ID NO: 82

AGYKSDSDDGTT (for example as CDRL3) SEQ ID NO: 83

AGYKSESDDGTT (for example as CDRL3) SEQ ID NO: 84

AGYKSDADDGTT (for example as CDRL3) SEQ ID NO: 85

AGYKSDTDDGTT (for example as CDRL3) SEQ ID NO: 86

AGYKSDSDEGTT (for example as CDRL3) SEQ ID NO: 87

AGYKSDSDDATT (for example as CDRL3) SEQ ID NO: 88

AGYKSDSDDSTT (for example as CDRL3) SEQ ID NO: 89

AGYKSESDEGTT (for example as CDRL3) SEQ ID NO: 90

AGYKSESDDATT (for example as CDRL3) SEQ ID NO: 91

AGYKSESDDSTT (for example as CDRL3) SEQ ID NO: 92

AGYKSDADEGTT (for example as CDRL3) SEQ ID NO: 93

AGYKSDADDATT (for example as CDRL3) SEQ ID NO: 94

AGYKSDADDSTT (for example as CDRL3) SEQ ID NO: 95

AGYKSDTDEGTT (for example as CDRL3) SEQ ID NO: 96

AGYKSDTDDATT (for example as CDRL3) SEQ ID NO: 97

AGYKSDTDDSTT (for example as CDRL3) SEQ ID NO: 98

QIYYSASGSRDWT (for example as CDRL3) SEQ ID NO: 99

QGGFSSSDLNV (for example as CDRL3) SEQ ID NO: 100

QGYYYSSGSDYG (for example as CDRL3) SEQ ID NO: 101

In one example the present invention provides the CD22 antibodies described herein in any suitable antibody format. Accordingly in example the present invention provides anti-CD22 antibodies or fragments thereof containing one or more of the binding domains described herein comprising the CDRs provided herein above and in FIG. 35 including those rabbit CDRs derived from the following antibodies, antibody 4120, antibody 4126, antibody 4127, antibody 4128, antibody 4130, or antibody 4132. Said CDRs may be incorporated into any suitable antibody framework and into any suitable antibody format. Such antibodies include whole antibodies and functionally active fragments or derivatives thereof which may be, but are not limited to, monoclonal, humanised, fully human or chimeric antibodies. Accordingly, such antibodies may comprise a complete antibody molecule having full length heavy and light chains or a fragment thereof and may be, but are not limited to Fab, modified Fab, Fab', F(ab')$_2$, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Multi-valent antibodies may comprise multiple specificities or may be monospecific (see for example WO 92/22853 and WO05/113605). It will be appreciated that this aspect of the invention also extends to variants of these anti-CD22 antibodies including humanised versions and modified versions, including those in which amino acids have been mutated in the CDRs to remove one or more isomerisation, deamidation, glycosylation site or cysteine residue as described herein above. T Thus in one example there is provided an anti-CD22 antibody molecule of the present disclosure, (for example an antibody or binding fragment thereof) comprising a heavy chain or heavy chain fragment having a variable region, wherein said variable region comprises one, two or three CDRs independently selected from SEQ ID NOs: 1, 8 or 9, SEQ ID NOs: 2, 10 or 11 and SEQ ID NOs: 3 or 12, for example wherein CDR H1 is SEQ ID NO: 1, CDR H2 is SEQ ID NO: 2 and CDR H3 is SEQ ID NO: 3.

Thus one embodiment CDR H1 is SEQ ID NOs: 1, 8 or 9 and CDR H2 is SEQ ID NO: 2; or CDR H1 is SEQ ID NOs: 1, 8 or 9 and CDR H2 is SEQ ID NO: 10; CDR H1 is SEQ ID NOs: 1, 8 or 9 and CDR H2 is SEQ ID NO: 11; or CDR H1 is SEQ ID NOs: 1, 8 or 9 and CDR H3 is SEQ ID NO: 3; or CDR H1 is SEQ ID NOs: 1, 8 or 9 and CDR H3 is SEQ ID NO: 12; or CDR H2 is SEQ ID NOs: 2, 10 or 11 and CDR H3 is SEQ ID NO: 3; or CDR H2 is SEQ ID NOs: 2, 10 or 11 and CDR H3 is SEQ ID NO: 12.

In one example an antibody molecule according to the present disclosure comprises a heavy chain or heavy chain fragment having a variable region, for example comprising one, two or three CDRs independently selected from SEQ ID NOs: 29 to 68, in particular wherein CDR H1 has the sequence independently selected from SEQ ID NOs: 29 to 39, CDR H2 has the sequence independently selected from SEQ ID NOs: 40 to 59 and CDR H3 has the sequence independently selected from SEQ ID NOs: 60 to 68.

In one example there is provided an anti-CD22 antibody molecule of the present disclosure, (for example an antibody or binding fragment thereof) comprising a heavy chain or heavy chain fragment having a variable region, wherein said variable region comprises one, two or three CDRs independently selected from SEQ ID NOs: 29, 30, 40, 41 and 60, for example wherein CDR H1 is SEQ ID NO: 29 or 30, CDR H2 is SEQ ID NO: 40 or 41 and CDR H3 is SEQ ID NO: 60.

Thus one embodiment CDR H1 is SEQ ID NO: 29 or 30 and CDR H2 is SEQ ID NO: 40 or 41; or CDR H1 is SEQ ID NO: 29 or 30 and CDR H3 is SEQ ID NO: 60: or CDR H2 is SEQ ID NO: 40 or 41 and CDR H3 is SEQ ID NO: 60.

Thus one embodiment CDR H1 is SEQ ID NO: 29 and CDR H2 is SEQ ID NO: 40; or CDR H1 is SEQ ID NO: 29 and CDR H3 is SEQ ID NO: 60: or CDR H2 is SEQ ID NO: 40 and CDR H3 is SEQ ID NO: 60.

In another embodiment CDR H1 is SEQ ID NO: 30 and CDR H2 is SEQ ID NO: 41, or CDR H1 is SEQ ID NO: 30 and CDR H3 is SEQ ID NO: 60, or CDR H2 is SEQ ID NO: 41 and CDR H3 is SEQ ID NO: 60.

In another embodiment CDR H1 is SEQ ID NO: 29 and CDR H2 is SEQ ID NO: 41.

In one example there is provided an anti-CD22 an antibody molecule of the present disclosure (for example antibody or binding fragment thereof) comprising a heavy chain or heavy chain fragment having a variable region, wherein said variable region comprises one, two or three CDRs independently selected from SEQ ID NOs: 31, 32, 42, 43, 61 and 62, for example wherein CDR H1 is SEQ ID NO: 31 or 32, CDR H2 is SEQ ID NO: 42 or 43 and CDR H3 is SEQ ID NO: 61 or 62.

Thus one embodiment CDR H1 is SEQ ID NO: 31 or 32 and CDR H2 is SEQ ID NO: 42 or 43; or CDR H1 is SEQ ID NO: 31 or 32 and CDR H3 is SEQ ID NO: 61 or 62; or CDR H2 is SEQ ID NO: 42 or 43 and CDR H3 is SEQ ID NO: 61 or 62. Thus one embodiment CDR H1 is SEQ ID NO: 31 and CDR H2 is SEQ ID NO: 42, or CDR H1 is SEQ ID NO: 31 and CDR H3 is SEQ ID NO: 61, or CDR H2 is SEQ ID NO: 42 and CDR H3 is SEQ ID NO: 61. In one embodiment CDR H1 is SEQ ID NO: 31 and CDR H2 is SEQ ID NO: 43, or CDR H1 is SEQ ID NO: 31 and CDR H3 is SEQ ID NO: 62, or CDR H2 is SEQ ID NO: 43 and CDR H3 is SEQ ID NO: 61. In another embodiment CDR H1 is SEQ ID NO: 32 and CDR H2 is SEQ ID NO: 42, or CDR H1 is SEQ ID NO: 32 and CDR H3 is SEQ ID NO: 61, or CDR H2 is SEQ ID NO: 42 and CDR H3 is SEQ ID NO: 61. In another embodiment CDR H1 is SEQ ID NO: 32 and CDR H2 is SEQ ID NO: 43, or CDR H1 is SEQ ID NO: 32 and CDR H3 is SEQ ID NO: 62, or CDR H2 is SEQ ID NO: 43 and CDR H3 is SEQ ID NO: 62.

In one example there is provided an anti-CD22 antibody molecule of the present disclosure, (for example antibody or binding fragment thereof) comprising a heavy chain or heavy chain fragment having a variable region, wherein said variable region comprises one, two or three CDRs independently selected from SEQ ID NOs: 33, 34, 44, 45, and 63, for example wherein CDR H1 is SEQ ID NO: 33, CDR H2 is SEQ ID NO: 44 and CDR H3 is SEQ ID NO: 63.

Thus one embodiment CDR H1 is SEQ ID NO: 33 or 34 and CDR H2 is SEQ ID NO: 44 or 45, or CDR H1 is SEQ ID NO: 33 or 34 and CDR H3 is SEQ ID NO: 63, or CDR H2 is SEQ ID NO: 44 or 45 and CDR H3 is SEQ ID NO: 63. Thus one embodiment CDR H1 is SEQ ID NO: 33 and CDR H2 is SEQ ID NO: 44, or CDR H1 is SEQ ID NO: 33 and CDR H3 is SEQ ID NO: 63, or CDR H2 is SEQ ID NO: 44 and CDR H3 is SEQ ID NO: 63. In one embodiment CDR H1 is SEQ ID NO: 33 and CDR H2 is SEQ ID NO: 45, or CDR H1 is SEQ ID NO: 34 and CDR H3 is SEQ ID NO: 63, or CDR H2 is SEQ ID NO: 45 and CDR H3 is SEQ ID NO: 63.

In another embodiment CDR H1 is SEQ ID NO: 34 and CDR H2 is SEQ ID NO: 44, or CDR H1 is SEQ ID NO: 34 and CDR H3 is SEQ ID NO: 63. In one embodiment CDR H1 is SEQ ID NO: 34 and CDR H2 is SEQ ID NO: 45.

In one example there is provided an anti-CD22 antibody molecule according to the present disclosure (for example antibody or binding fragment thereof) comprising a heavy chain or heavy chain fragment having a variable region, wherein said variable region comprises one, two or three CDRs independently selected from SEQ ID NOs: 35, 36, 46, 47 and 64, for example wherein CDR H1 is SEQ ID NO: 35 or 36, CDR H2 is SEQ ID NO: 46 or 47 and CDR H3 is SEQ ID NO: 64.

Thus one embodiment CDR H1 is SEQ ID NO: 35 or 36 and CDR H2 is SEQ ID NO: 46 or 47, or CDR H1 is SEQ ID NO: 35 or 36 and CDR H3 is SEQ ID NO: 64, or CDR H2 is SEQ ID NO: 46 or 47 and CDR H3 is SEQ ID NO: 64. Thus one embodiment CDR H1 is SEQ ID NO: 35 and CDR H2 is SEQ ID NO: 46, or CDR H1 is SEQ ID NO: 35 and CDR H3 is SEQ ID NO: 64, or CDR H2 is SEQ ID NO: 46 and CDR H3 is SEQ ID NO: 64.

In one embodiment CDR H1 is SEQ ID NO: 35 and CDR H2 is SEQ ID NO: 47, or CDR H1 is SEQ ID NO: 36 and CDR H3 is SEQ ID NO: 64, or CDR H2 is SEQ ID NO: 47 and CDR H3 is SEQ ID NO: 64. In another embodiment CDR H1 is SEQ ID NO: 36 and CDR H2 is SEQ ID NO: 46, or CDR H1 is SEQ ID NO: 36 and CDR H2 is SEQ ID NO: 47.

In one example there is provided an anti-CD22 antibody molecule according to the present disclosure, (for example antibody or binding fragment thereof) comprising a heavy chain or heavy chain fragment having a variable region, wherein said variable region comprises one, two or three CDRs independently selected from SEQ ID NOs: 37, 48, 49, 50, 51, 52, 53, 65, 66 and 67, for example wherein CDR H1 is SEQ ID NO: 37, CDR H2 is SEQ ID NO: 48, 49, 50, 51, 52 or 53, and CDR H3 is SEQ ID NO: 65, 66 or 67.

In one embodiment CDR H1 is SEQ ID NO: 37, CDR H2 is SEQ ID NO: 48, 49, 50, 51, 52 or 53 and CDR H3 is SEQ ID NO: 65, 66 or 67.

Thus one embodiment:

```
CDRH1 is SEQ ID NO: 37
and

CDR H2 is SEQ ID NO: 48, 49, 50, 51, 52, 53,
or

CDRH1 is SEQ ID NO: 37
and

CDR H2 is SEQ ID NO: 48,
or

CDRH1 is SEQ ID NO: 37
and

CDR H2 is SEQ ID NO: 49,
or

CDRH1 is SEQ ID NO: 37
and

CDR H2 is SEQ ID NO: 50,
or

CDRH1 is SEQ ID NO: 37
and

CDR H2 is SEQ ID NO: 51,
or

CDRH1 is SEQ ID NO: 37
and

CDR H2 is SEQ ID NO: 52,
or

CDRH1 is SEQ ID NO: 37
and

CDR H2 is SEQ ID NO: 53,
or

CDRH1 is SEQ ID NO: 37
and

CDR H3 is SEQ ID NO: 65,
or

CDRH1 is SEQ ID NO: 37
and

CDR H3 is SEQ ID NO; 66,
or

CDRH1 is SEQ ID NO: 37
and

CDR H3 is SEQ ID NO: 67.
```

In one embodiment CDR H2 is SEQ ID NO: 48, 49, 50, 51, 52, 53 and CDR H3 is SEQ ID NO: 65.

Thus one embodiment:

```
CDRH2 is SEQ ID NO: 48
and

CDR H3 is SEQ ID NO: 65,
or

CDRH2 is SEQ ID NO: 48
and

CDR H3 is SEQ ID NO: 66,
or

CDRH2 is SEQ ID NO: 48
and

CDR H3 is SEQ ID NO: 67.
```

In one embodiment:

```
CDRH2 is SEQ ID NO: 49
and

CDR H3 is SEQ ID NO: 65,
or

CDRH2 is SEQ ID NO: 49
and

CDR H3 is SEQ ID NO: 66,
or

CDRH2 is SEQ ID NO: 49
and

CDR H3 is SEQ ID NO: 67.
```

In another embodiment:

```
CDRH2 is SEQ ID NO: 50
and

CDR H3 is SEQ ID NO: 65,
or

CDRH2 is SEQ ID NO: 50
and

CDR H3 is SEQ ID NO: 66,
or

CDRH2 is SEQ ID NO: 50
and

CDR H3 is SEQ ID NO: 67
```

In another embodiment:

```
CDRH2 is SEQ ID NO: 51
and

CDR H3 is SEQ ID NO: 65,
or

CDRH2 is SEQ ID NO: 51
and

CDR H3 is SEQ ID NO: 66,
or

CDRH2 is SEQ ID NO: 51
and

CDR H3 is SEQ ID NO: 67.
```

In another embodiment:

```
CDRH2 is SEQ ID NO: 52
and

CDR H3 is SEQ ID NO: 65,
or
```

```
-continued
CDRH2 is SEQ ID NO: 52
and

CDR H3 is SEQ ID NO: 66,
or

CDRH2 is SEQ ID NO: 52
and

CDR H3 is SEQ ID NO: 67.
```

In another embodiment:

```
CDRH2 is SEQ ID NO: 53
and

CDR H3 is SEQ ID NO: 65,
or

CDRH2 is SEQ ID NO: 53
and

CDR H3 is SEQ ID NO: 66,
or

CDRH2 is SEQ ID NO: 53
and

CDR H3 is SEQ ID NO: 67.
```

In one embodiment CDR H1 is SEQ ID NO: 37, CDR H2 is SEQ ID NO: 48 and CDR H3 is SEQ ID NO: 65.
In one embodiment CDR H1 is SEQ ID NO: 37, CDR H2 is SEQ ID NO: 49 and CDR H3 is SEQ ID NO: 65.
In one embodiment CDR H1 is SEQ ID NO: 37, CDR H2 is SEQ ID NO: 50 and CDR H3 is SEQ ID NO: 65.
In one embodiment CDR H1 is SEQ ID NO: 37, CDR H2 is SEQ ID NO: 51 and CDR H3 is SEQ ID NO: 65.
In one embodiment CDR H1 is SEQ ID NO: 37, CDR H2 is SEQ ID NO: 52 and CDR H3 is SEQ ID NO: 65.
In one embodiment CDR H1 is SEQ ID NO: 37, CDR H2 is SEQ ID NO: 53 and CDR H3 is SEQ ID NO: 65.
In one embodiment CDR H1 is SEQ ID NO: 37, CDR H2 is SEQ ID NO: 48 and CDR H3 is SEQ ID NO: 66.
In one embodiment CDR H1 is SEQ ID NO: 37, CDR H2 is SEQ ID NO: 49 and CDR H3 is SEQ ID NO: 66.
In one embodiment CDR H1 is SEQ ID NO: 37, CDR H2 is SEQ ID NO: 50 and CDR H3 is SEQ ID NO: 66.
In one embodiment CDR H1 is SEQ ID NO: 37, CDR H2 is SEQ ID NO: 51 and CDR H3 is SEQ ID NO: 66.
In one embodiment CDR H1 is SEQ ID NO: 37, CDR H2 is SEQ ID NO: 52 and CDR H3 is SEQ ID NO: 66.
In one embodiment CDR H1 is SEQ ID NO: 37, CDR H2 is SEQ ID NO: 53 and CDR H3 is SEQ ID NO: 66.
In one embodiment CDR H1 is SEQ ID NO: 37, CDR H2 is SEQ ID NO: 48 and CDR H3 is SEQ ID NO: 67.
In one embodiment CDR H1 is SEQ ID NO: 37, CDR H2 is SEQ ID NO: 49 and CDR H3 is SEQ ID NO: 67.
In one embodiment CDR H1 is SEQ ID NO: 37, CDR H2 is SEQ ID NO: 50 and CDR H3 is SEQ ID NO: 67.
In one embodiment CDR H1 is SEQ ID NO: 37, CDR H2 is SEQ ID NO: 51 and CDR H3 is SEQ ID NO: 67.
In one embodiment CDR H1 is SEQ ID NO: 37, CDR H2 is SEQ ID NO: 52 and CDR H3 is SEQ ID NO: 67.
In one embodiment CDR H1 is SEQ ID NO: 37, CDR H2 is SEQ ID NO: 53 and CDR H3 is SEQ ID NO: 67.

In one example there is provided an anti-CD22 an antibody molecule of the present disclosure, (for example an antibody or binding fragment) thereof comprising a heavy chain or heavy chain fragment having a variable region, wherein said variable region comprises one, two or three CDRs independently selected from SEQ ID NOs: 38, 39, 54, 55, 56, 57, 58, 59 and 68, for example wherein CDR H1 is SEQ ID NO: 38 or 39, CDR H2 is SEQ ID NO: 54, 55, 56, 57, 58 or 59 and CDR H3 is SEQ ID NO: 68.

In one embodiment CDR H1 is SEQ ID NO: 38 or 39 and CDR H2 is SEQ ID NO: 54, 55, 56, 57, 58, 59 or CDR H1 is SEQ ID NO: 38 or 39 and CDR H3 is SEQ ID NO: 68, or CDR H2 is SEQ ID NO: 54, 55, 56, 57, 58, 59, and CDR H3 is SEQ ID NO: 68.

In one embodiment:

```
CDRH1 is SEQ ID NO: 38
and

CDR H2 is SEQ ID NO: 54,
or

CDRH1 is SEQ ID NO: 38
and

CDR H2 is SEQ ID NO: 55,
or

CDRH1 is SEQ ID NO: 38
and

CDR H2 is SEQ ID NO: 56,
or

CDRH1 is SEQ ID NO: 38
and

CDR H2 is SEQ ID NO: 57,
or

CDRH1 is SEQ ID NO: 38
and

CDR H2 is SEQ ID NO: 58,
or

CDRH1 is SEQ ID NO: 38
and

CDR H2 is SEQ ID NO: 59.
```

In one embodiment:

```
CDRH1 is SEQ ID NO: 39
and

CDR H2 is SEQ ID NO: 68.

CDRH1 is SEQ ID NO: 39
and

CDR H2 is SEQ ID NO: 54,
or

CDRH1 is SEQ ID NO: 39
and

CDR H2 is SEQ ID NO: 55,
or

CDRH1 is SEQ ID NO: 39
and

CDR H2 is SEQ ID NO: 56,
or

CDRH1 is SEQ ID NO: 39
and

CDR H2 is SEQ ID NO: 57,
or
```

-continued

CDRH1 is SEQ ID NO: 39
and

CDR H2 is SEQ ID NO: 58,
or

CDRH1 is SEQ ID NO: 39
and

CDR H2 is SEQ ID NO: 59.

In one embodiment:

CDRH1 is SEQ ID NO: 39
and

CDR H2 is SEQ ID NO: 68

In one embodiment:

CDR H2 is SEQ ID NO: 54
and

CDR H3 is SEQ ID NO: 68,
or

CDR H2 is SEQ ID NO: 55
and

CDR H3 is SEQ ID NO: 68,
or

CDR H2 is SEQ ID NO: 56
and

CDR H3 is SEQ ID NO: 68,
or

CDR H2 is SEQ ID NO: 57
and

CDR H3 is SEQ ID NO: 68,
or

CDR H2 is SEQ ID NO: 58
and

CDR H3 is SEQ ID NO: 68,
or

CDR H2 is SEQ ID NO: 59
and

CDR H3 is SEQ ID NO: 68.

In one embodiment:

CDR H1 is SEQ ID NO: 38
and

CDR H2 is SEQ ID NO: 54,
and

CDR H3 is SEQ ID NO: 68

CDR H1 is SEQ ID NO: 38
and

CDR H2 is SEQ ID NO: 55,
and

CDR H3 is SEQ ID NO: 68

CDR H1 is SEQ ID NO: 38
and

CDR H2 is SEQ ID NO: 56,
and

CDR H3 is SEQ ID NO: 68

CDR H1 is SEQ ID NO: 38
and

CDR H2 is SEQ ID NO: 57,
and

CDR H3 is SEQ ID NO: 68

CDR H1 is SEQ ID NO: 38
and

CDR H2 is SEQ ID NO: 58,
and

CDR H3 is SEQ ID NO: 68

CDR H1 is SEQ ID NO: 38
and

CDR H2 is SEQ ID NO: 59
and

CDR H3 is SEQ ID NO: 68.

In one embodiment a heavy chain variable region listed above is employed in combination with a light chain variable region listed herein.

In one example the antibody molecule according to the present disclosure further comprises a light chain or light chain fragment having a variable region, for example comprising one, two or three CDRs independently selected from SEQ ID NOs: 69 to 101, in particular wherein CDR L1 has the sequence independently selected from SEQ ID NOs: 69 to 74, CDR L2 has the sequence independently selected from SEQ ID NOs: 75 to 80 and CDR L3 has the sequence independently selected from SEQ ID NOs: 81 to 101.

In one example the antibody molecule according to the present disclosure comprises a light chain or light chain fragment having a variable region, for example comprising one, two or three CDRs independently selected from SEQ ID NO: 69, 75 and 81, in particular wherein CDR L1 has the sequence given in SEQ ID NO: 69, CDR L2 has the sequence given in SEQ ID NO: 75 and CDR L3 has the sequence given in SEQ ID NO: 81.

Thus in one embodiment CDR L1 is SEQ ID NO: 69 and CDR L2 is SEQ ID NO: 75, or CDR L1 is SEQ ID NO: 69 and CDR L3 is SEQ ID NO: 81; or CDR L2 is SEQ ID NO: 75 and CDR L3 is SEQ ID NO: 81.

In one example the antibody molecule according to the present disclosure comprises a light chain or light chain fragment having a variable region, for example comprising one, two or three CDRs independently selected from SEQ ID NO: 70, 76 and 82, in particular wherein CDR L1 has the sequence given in SEQ ID NO: 70, CDR L2 has the sequence given in SEQ ID NO: 76 and CDR L3 has the sequence given in SEQ ID NO: 82.

Thus in one embodiment CDR L1 is SEQ ID NO: 70 and CDR L2 is SEQ ID NO: 76; or CDR L1 is SEQ ID NO: 70 and CDR L3 is SEQ ID NO: 82; or CDR L2 is SEQ ID NO: 76 and CDR L3 is SEQ ID NO: 82.

In one example the antibody molecule according to the present disclosure comprises a light chain or light chain fragment having a variable region, for example comprising one, two or three CDRs independently selected from SEQ ID NO: 71, 77, 83, 84, 85, 86, 87, 88, 89, 90, 91, 92, 93, 94, 95, 96, 97 and 98, in particular wherein CDR L1 has the sequence given in SEQ ID NO: 71, CDR L2 has the sequence given in SEQ ID NO: 77 and CDR L3 has the sequence given in SEQ ID NO: 83, 84, 85, 86, 87, 88, 89, 90, 91, 92, 93, 94, 95, 96, 97 and 98.

Thus in one embodiment CDR L1 is SEQ ID NO: 71 and CDR L2 is SEQ ID NO: 77; or CDR L1 is SEQ ID NO: 71 and CDR L3 is SEQ ID NO: 83, 84, 85, 86, 87, 88, 89, 90, 91, 92, 93, 94, 95, 96, 97 or 98; or CDR L2 is SEQ ID NO: 77 and CDR L3 is SEQ ID NO: 83, 84, 85, 86, 87, 88, 89, 90, 91, 92, 93, 94, 95, 96, 97 or 98.

In one embodiment:

```
CDR L1 is SEQ ID NO: 71
and
CDR L3 is SEQ ID NO: 83,
or
CDR L1 is SEQ ID NO: 71
and
CDR L3 is SEQ ID NO: 84,
or
CDR L1 is SEQ ID NO: 71
and
CDR L3 is SEQ ID NO: 85,
or
CDR L1 is SEQ ID NO: 71
and
CDR L3 is SEQ ID NO: 86,
or
CDR L1 is SEQ ID NO: 71
and
CDR L3 is SEQ ID NO: 87,
or
CDR L1 is SEQ ID NO: 71
and
CDR L3 is SEQ ID NO: 88,
or
CDR L1 is SEQ ID NO: 71
and
CDR L3 is SEQ ID NO: 89,
or
CDR L1 is SEQ ID NO: 71
and
CDR L3 is SEQ ID NO: 90,
or
CDR L1 is SEQ ID NO: 71
and
CDR L3 is SEQ ID NO: 91,
or
CDR L1 is SEQ ID NO: 71
and
CDR L3 is SEQ ID NO: 92,
or
CDR L1 is SEQ ID NO: 71
and
CDR L3 is SEQ ID NO: 93,
or
```
-continued
```
CDR L1 is SEQ ID NO: 71
and
CDR L3 is SEQ ID NO: 94,
or
CDR L1 is SEQ ID NO: 71
and
CDR L3 is SEQ ID NO: 95,
or
CDR L1 is SEQ ID NO: 71
and
CDR L3 is SEQ ID NO: 96,
or
CDR L1 is SEQ ID NO: 71
and
CDR L3 is SEQ ID NO: 97,
or
CDR L1 is SEQ ID NO: 71
and
CDR L3 is SEQ ID NO: 98.
```

In one embodiment:

```
CDR H2 is SEQ ID NO: 77
and
CDR L3 is SEQ ID NO: 83,
or
CDR H2 is SEQ ID NO: 77
and
CDR L3 is SEQ ID NO: 84,
or
CDR H2 is SEQ ID NO: 77
and
CDR L3 is SEQ ID NO: 85,
or
CDR H2 is SEQ ID NO: 77
and
CDR L3 is SEQ ID NO: 86,
or
CDR H2 is SEQ ID NO: 77
and
CDR L3 is SEQ ID NO: 87,
or
CDR H2 is SEQ ID NO: 77
and
CDR L3 is SEQ ID NO: 88,
or
CDR H2 is SEQ ID NO: 77
and
CDR L3 is SEQ ID NO: 89,
or
CDR H2 is SEQ ID NO: 77
and
CDR L3 is SEQ ID NO: 90,
or
```

CDR H2 is SEQ ID NO: 77 and

CDR L3 is SEQ ID NO: 91,
or

CDR H2 is SEQ ID NO: 77 and

CDR L3 is SEQ ID NO: 92,
or

CDR H2 is SEQ ID NO: 77 and

CDR L3 is SEQ ID NO: 93,
or

CDR H2 is SEQ ID NO: 77 and

CDR L3 is SEQ ID NO: 94,
or

CDR H2 is SEQ ID NO: 77 and

CDR L3 is SEQ ID NO: 95,
or

CDR H2 is SEQ ID NO: 77 and

CDR L3 is SEQ ID NO: 96,
or

CDR H2 is SEQ ID NO: 77 and

CDR L3 is SEQ ID NO: 97,
or

CDR H2 is SEQ ID NO: 77 and

CDR L3 is SEQ ID NO: 98.

In one embodiment:

CDR L1 is SEQ ID NO: 71, CDR H2 is SEQ ID NO: 77 and

CDR L3 is SEQ ID NO: 83,
or

CDR L1 is SEQ ID NO: 71, CDR H2 is SEQ ID NO: 77 and

CDR L3 is SEQ ID NO: 84,
or

CDR L1 is SEQ ID NO: 71, CDR H2 is SEQ ID NO: 77 and

CDR L3 is SEQ ID NO: 85,
or

CDR L1 is SEQ ID NO: 71, CDR H2 is SEQ ID NO: 77 and

CDR L3 is SEQ ID NO: 86,
or

CDR L1 is SEQ ID NO: 71, CDR H2 is SEQ ID NO: 77 and

CDR L3 is SEQ ID NO: 87,
or

CDR L1 is SEQ ID NO: 71, CDR H2 is SEQ ID NO: 77 and

CDR L3 is SEQ ID NO: 88,
or

CDR L1 is SEQ ID NO: 71, CDR H2 is SEQ ID NO: 77 and

CDR L3 is SEQ ID NO: 89,
or

CDR L1 is SEQ ID NO: 71, CDR H2 is SEQ ID NO: 77 and

CDR L3 is SEQ ID NO: 90,
or

CDR L1 is SEQ ID NO: 71, CDR H2 is SEQ ID NO: 77 and

CDR L3 is SEQ ID NO: 91,
or

CDR L1 is SEQ ID NO: 71, CDR H2 is SEQ ID NO: 77 and

CDR L3 is SEQ ID NO: 92,
or

CDR L1 is SEQ ID NO: 71, CDR H2 is SEQ ID NO: 77 and

CDR L3 is SEQ ID NO: 93,
or

CDR L1 is SEQ ID NO: 71, CDR H2 is SEQ ID NO: 77 and

CDR L3 is SEQ ID NO: 94,
or

CDR L1 is SEQ ID NO: 71, CDR H2 is SEQ ID NO: 77 and

CDR L3 is SEQ ID NO: 95,
or

CDR L1 is SEQ ID NO: 71, CDR H2 is SEQ ID NO: 77 and

CDR L3 is SEQ ID NO: 96,
or

CDR L1 is SEQ ID NO: 71, CDR H2 is SEQ ID NO: 77 and

CDR L3 is SEQ ID NO: 97,
or

CDR L1 is SEQ ID NO: 71, CDR H2 is SEQ ID NO: 77 and

CDR L3 is SEQ ID NO: 98.

In one example the antibody molecule according to the present disclosure comprises a light chain or light chain fragment having a variable region, for example comprising one, two or three CDRs independently selected from SEQ ID NO: 72, 78 and 99, in particular wherein CDR L1 has the sequence given in SEQ ID NO: 72, CDR L2 has the sequence given in SEQ ID NO: 78 and CDR L3 has the sequence given in SEQ ID NO: 99.

Thus in one embodiment CDR L1 is SEQ ID NO: 72 and CDR L2 is SEQ ID NO: 78; or CDR L1 is SEQ ID NO: 72 and CDR L3 is SEQ ID NO: 99; or CDR L2 is SEQ ID NO: 78 and CDR L3 is SEQ ID NO: 99.

In one example the antibody molecule according to the present disclosure comprises a light chain or light chain fragment having a variable region, for example comprising one, two or three CDRs independently selected from SEQ ID NO: 73, 79 and 100, in particular wherein CDR L1 has the sequence given in SEQ ID NO: 73, CDR L2 has the sequence given in SEQ ID NO: 79 and CDR L3 has the sequence given in SEQ ID NO: 100.

Thus in one embodiment CDR L1 is SEQ ID NO: 73 and CDR L2 is SEQ ID NO: 79; or CDR L1 is SEQ ID NO: 73 and CDR L3 is SEQ ID NO: 100 or CDR L2 is SEQ ID NO: 79 and CDR L3 is SEQ ID NO: 100.

In one example the antibody molecule according to the present disclosure comprises a light chain or light chain fragment having a variable region, for example comprising one, two or three CDRs independently selected from SEQ ID NO: 74, 80 and 101, in particular wherein CDR L1 has the sequence given in SEQ ID NO: 74, CDR L2 has the sequence given in SEQ ID NO: 80 and CDR L3 has the sequence given in SEQ ID NO: 101.

Thus in one embodiment CDR L1 is SEQ ID NO: 74 and CDR L2 is SEQ ID NO: 80 or CDR L1 is SEQ ID NO: 74 and CDR L3 is SEQ ID NO: 101 or CDR L2 is SEQ ID NO: 80 and CDR L3 is SEQ ID NO: 101.

In one example the antibody molecules according to the present disclosure (such as antibodies or binding fragments) comprise CDR sequences selected from SEQ ID NOs: 29 to 101, for example wherein CDR H1 is independently selected from SEQ ID NOs: 29 to 39, CDR H2 is independently selected from SEQ ID NOs: 40 to 59, CDR H3 is independently selected from SEQ ID NOs: 60 to 68, CDR L1 is independently selected from SEQ ID NOs: 69 to 74, CDR L2 is independently selected from SEQ ID NOs: 75 to 80 and CDR L3 is independently selected from SEQ ID NOs: 81 to 101.

In one embodiment CDR H1 is SEQ ID NO: 29 or 30, CDR H2 is SEQ ID NO: 40 or 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 29, CDR H2 is SEQ ID NO: 40 or 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 30, CDR H2 is SEQ ID NO: 40 or 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 29 or 30, CDR H2 is SEQ ID NO: 40, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 29 or 30, CDR H2 is SEQ ID NO: 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 29, CDR H2 is SEQ ID NO: 40, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 29, CDR H2 is SEQ ID NO: 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 30, CDR H2 is SEQ ID NO: 40, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 30, CDR H2 is SEQ ID NO: 41, CDR H3 is SEQ ID NO: 60, CDR L1 is SEQ ID NO: 69, CDR L2 is SEQ ID NO: 75 and CDR L3 is SEQ ID NO: 81.

In one embodiment CDR H1 is SEQ ID NO: 31 or 32, CDR H2 is SEQ ID NO: 42 or 43, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42 or 43, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 43 or, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42 or 43, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42 or 43 CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 43, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 42, CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 31, CDR H2 is SEQ ID NO: 43, CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42 or 43, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 43 or, CDR H3 is SEQ ID NO: 61 or 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42 or 43, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42 or 43 CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 43, CDR H3 is SEQ ID NO: 61, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 42, CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 32, CDR H2 is SEQ ID NO: 43, CDR H3 is SEQ ID NO: 62, CDR L1 is SEQ ID NO: 70, CDR L2 is SEQ ID NO: 76 and CDR L3 is SEQ ID NO: 82.

In one embodiment CDR H1 is SEQ ID NO: 33 or 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 83, 84, 85, 86, 87, 88, 89, 90, 91, 92, 93, 94, 95, 96, 97 or 98.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 83.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 83.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 83.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 83.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 83.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 84.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 84.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 84.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 84.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 84.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 85.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 85.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 85.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 85.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 85.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 86.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 86.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 86.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 86.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 86.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 87.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 87.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 87.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 87.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 87.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 88.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 88.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 88.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 88.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 88.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 89.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 89.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 89.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 89.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 89.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 90.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 90.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 90.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 90.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 90.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 91.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 91.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 91.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 91.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 91.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 92.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 92.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 92.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 92.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 92.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 93.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 93.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 93.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 93.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 93.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 94.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 94.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 94.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 94.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 94.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 95.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 95.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 95.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 95.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 95.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 96.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 96.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 96.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 96.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 96.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 97.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 97.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 97.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 97.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 97.

In one embodiment CDR H1 is SEQ ID NO: 33, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 98.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 98.

In one embodiment CDR H1 is SEQ ID NO: 34, CDR H2 is SEQ ID NO: 44 or 45, CDR H3 is SEQ ID NO: 63, CDR L1 is SEQ ID NO: 71, CDR L2 is SEQ ID NO: 77 and CDR L3 is SEQ ID NOs: 98.

In one embodiment CDR H1 is SEQ ID NO: 33 or 34, CDR H2 is SEQ ID NO: 44, CDR H3 is SEQ ID NO: 63, CDR L1 is SEQ ID NO: 71, CDR L2 is SEQ ID NO: 77 and CDR L3 is SEQ ID NOs: 98.

In one embodiment CDR H1 is SEQ ID NO: 33 or 34, CDR H2 is SEQ ID NO: 45, CDR H3 is SEQ ID NO: 63, CDR L1 is SEQ ID NO: 71, CDR L2 is SEQ ID NO: 77 and CDR L3 is SEQ ID NOs: 98.

In one embodiment CDR H1 is SEQ ID NO: 35 or 36, CDR H2 is SEQ ID NO: 46 or 47, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 35, CDR H2 is SEQ ID NO: 46 or 47, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 36, CDR H2 is SEQ ID NO: 46 or 47, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 35 or 36, CDR H2 is SEQ ID NO: 46, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 35 or 36, CDR H2 is SEQ ID NO: 47, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 35, CDR H2 is SEQ ID NO: 46, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 36, CDR H2 is SEQ ID NO: 46, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 36, CDR H2 is SEQ ID NO: 47, CDR H3 is SEQ ID NO: 64, CDR L1 is SEQ ID NO: 72, CDR L2 is SEQ ID NO: 78 and CDR L3 is SEQ ID NO: 99.

In one embodiment CDR H1 is SEQ ID NO: 37, CDR H2 is SEQ ID NO: 48, 49, 50, 51, 52 or 53, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 48, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 49, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 50, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 51, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 52, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 53, CDR H3 is SEQ ID NO: 65, 66 or 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 48, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 49, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 50, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 51, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 52, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 53, CDR H3 is SEQ ID NO: 65, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 48, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 49, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 50, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 51, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 52, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 53, CDR H3 is SEQ ID NO: 66, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 48, CDR H3 is SEQ ID NO: 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 49, CDR H3 is SEQ ID NO: 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 50, CDR H3 is SEQ ID NO: 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 51, CDR H3 is SEQ ID NO: 675, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 52, CDR H3 is SEQ ID NO: 67, CDR L1 is SEQ ID NO: 73, CDR L2 is SEQ ID NO: 79 and CDR L3 is SEQ ID NO: 100.

In one embodiment CDR H1 is SEQ ID NO: 37, CDR H2 is SEQ ID NO: 53, CDR H3 is SEQ ID NO: 67, CDR L1 is SEQ ID NO: 73, CDR L2 is SEQ ID NO: 79 and CDR L3 is SEQ ID NO: 100.

In one embodiment CDR H1 is SEQ ID NO: 38 or 39, CDR H2 is SEQ ID NO: 54, 55, 56, 57, 58, or 59, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 54, 55, 56, 57, 58, or 59, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 54, 55, 56, 57, 58, or 59, CDR H3 is SEQ ID NO: 68, CDR L1 is SEQ ID NO: 74, CDR L2 is SEQ ID NO: 80 and CDR L3 is SEQ ID NO: 101. In one embodiment CDR H1 is SEQ ID NO: 38, CDR H2 is SEQ ID NO: 54, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 54, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 55, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 55, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 56, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 56, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 57, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 57, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 58, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 58, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 38, CDR H2 is SEQ ID NO: 59, CDR H3 is SEQ ID NO: 68, CDR L1 is SEQ ID NO: 74, CDR L2 is SEQ ID NO: 80 and CDR L3 is SEQ ID NO: 101.

In one embodiment CDR H1 is SEQ ID NO: 39, CDR H2 is SEQ ID NO: 59, CDR H3 is SEQ ID NO: 68, CDR L1 is SEQ ID NO: 74, CDR L2 is SEQ ID NO: 80 and CDR L3 is SEQ ID NO: 101.

In one independent aspect the present disclosure provides a variable heavy domain comprising the sequence of SEQ ID NO: 62, 71, 80, 90 and a sequence at least 95% identical or similar (such as 96, 97, 98, 99% identical or similar) to any one of the same.

In one independent aspect there is provided a variable light region comprising a sequence of SEQ ID NO: 102, 111, 122, 131, 140 and a sequence at least 95% identical or similar (such as 96, 97, 98, 99% identical or similar) to any one of the same.

In one independent aspect the present disclosure provides a variable heavy domain comprising the sequence of SEQ ID NO: 104, 113, 124, 133, 142 a sequence at least 95% identical or similar (such as 96, 97, 98, 99% identical or similar) to any one of the same, and a variable light region comprising a sequence of SEQ ID NO: 60, 69, 78, 88 and a sequence at least 95% identical or similar (such as 96, 97, 98, 99% identical or similar) to any one of the same.

In one embodiment the VH and VL pairs are selected from:
  SEQ ID NO: 102 or a sequence at least 95% identical or similar to the same and SEQ ID NO: 104 or a sequence at least 95% identical or similar to the same,
  SEQ ID NO:111 or a sequence at least 95% identical or similar to the same and SEQ ID NO: 113 or a sequence at least 95% identical or similar to the same,
  SEQ ID NO: 122 or a sequence at least 95% identical or similar to the same and SEQ ID NO: 124 or a sequence at least 95% identical or similar to the same, and
  SEQ ID NO: 131 or a sequence at least 95% identical or similar to the same and SEQ ID NO: 133 or a sequence at least 95% identical or similar to the same.
  SEQ ID NO: 140 or a sequence at least 95% identical or similar to the same and SEQ ID NO: 142 or a sequence at least 95% identical or similar to the same.

In one embodiment there is provided a humanised version of a non-human variable domain disclosed herein.

Kabat numbering is employed herein unless the context indicates otherwise.

In one embodiment an antibody molecule according to the present disclosure is humanised and incorporates one or more of the CDRs described herein or variants thereof.

In one embodiment the heavy chain variable region human framework employed in the construct such as an antibody molecule of the present disclosure is selected from the group comprising IGHV3-7, IGHV3-9, IGHV3-21, IGHV3-33, IGHV3-66, IGHV4-38-2, IGHV4-4, IGHV4-59, and a variant of any one of the same wherein one, two, three, four, five, six, seven, eight, nine, ten or more amino acids are substituted with an amino acid other than cysteine, for example substituted with a donor residue in the corresponding location in the original lagomorph donor antibody. See for example the rabbit donor antibody sequences provided herein.

In one embodiment an antibody molecule according to the present disclosure is humanised.

Typically the human framework further comprises a suitable J region sequence such as the JH4 or JH2 J region.

In one embodiment a human VH framework employed in an antibody molecule of the present disclosure comprises an amino acid substitution in at least one position selected from the group comprising 11, 23, 24, 37, 47, 48, 49, 67, 71, 73, 76, 78 and 94 for example wherein the original amino acid in the human framework is substituted for another amino acid other than cysteine, in particular substituted for a residue in the corresponding location in the framework of the donor antibody.

In one embodiment substitutions are made at at least positions 73 and 76.

In one embodiment substitutions are made at at least positions 73, 76 and 78.

In one embodiment substitutions are made at at least positions 67, 73, 76 and 78.

In one embodiment substations are made at at least positions 48, 67, 73, 76 and 78.

In one embodiment substations are made at at least positions 24, 48, 67, 73, 76 and 78.

In one embodiment when the VH framework is type IGHV3 then substitutions may be made in at least one position, at least two positions, at least three positions or at least four positions (usually five or six positions) selected from 11, 23, 24, 47, 48, 49, 67, 71, 73, 76, 78 and 94 such as 71, 73, 76 and 78 (in particular suitable for IGHV3-7), or 47, 48, 49, 71, 73, 76, 78, and 94 (in particular suitable for IGHV3-9), or 48, 49, 71, 73, 76 and 78 (in particular suitable for IGHV3-21), or 11, (optionally 23 and 24) 48, 71, 73, 76 and 78 (in particular suitable for IGHV3-33), or 48, 49, 67, 71, 73, 76 and 78 (in particular suitable for IGHV3-66).

In one embodiment when the VH framework is a type IGHV4 then substitutions may be made in at least one position, at least two positions, at least three positions, at least four positions, five or more positions, such as at 6 positions selected from 23, 24, 37, 47, 48, 49, 67, 71, 73, 76 and 78, such as 24, 37, (optionally 47), (optionally 49), 67, 71, 73, 76 and 78 (in particular suitable for IGHV4-38-2), or 24, (optionally 48), (optionally 49), (optionally 67), 71, 73, 76, and 78 (in particular suitable for IGHV4-4), or 23, 24, 37, 49, 67, 71, 73, 76 and 78 (in particular suitable for IGHV4-59).

In one embodiment after substitution position 11 is leucine.

In one embodiment after substitution position 23 is lysine.

In one embodiment after substitution position 24 is alanine or glycine.

In one embodiment after substitution position 37 is valine.

In one embodiment after substitution position 47 is leucine.

In one embodiment after substitution position 48 is isoleucine, valine or serine.

In one embodiment after substitution position 49 is alanine or glycine.

In one embodiment after substitution position 67 is phenylalanine or valine.

In one embodiment after substitution position 71 is lysine or asparagine.

In one embodiment after substitution position 73 is serine.

In one embodiment after substitution 76 is threonine.

In one embodiment after substitution 78 is valine.

In one embodiment after substitution 94 is arginine.

In one embodiment wherein the human VH framework is glutamine at position 1 of the human framework, the glutamine is replaced with glutamic acid (E1) to afford the expression and purification of a homogeneous product: conversion of glutamine to pyroglutamate at the N-terminus of antibodies and antibody fragments is widely reported.

It will be appreciated that one or more of these substitutions may be combined to generate a humanised VH region for use in an antibody molecule of the invention.

In one independent aspect of the invention there is provided a humanised VH variable domain comprises any suitable sequence disclosed herein, for example comprising a sequence independently selected from SEQ ID NO: 107, 108, 109, 110, 116, 117, 118, 119, 120, 121, 127, 128, 129, 130, 136, 137, 138, 139, 145, 146, 147, 148, 154, 155, 156, 157 and a sequence at least 80%, 85%, 90%, 95% identical or similar to the same (such as 96, 97, 98 or 99% similar or identical).

In one embodiment the humanised VH variable domain comprises any suitable sequence disclosed herein, for example comprising a sequence independently selected from SEQ ID NO: 107, 108, 109, 110, 116, 117, 118, 119, 120, 121, 127, 128, 129, 130, 136, 137, 138, 139, 145, 146, 147, 148, 154, 155, 156 and 157.

In one embodiment the light chain variable region human framework employed in the humanised antibody molecule of the present disclosure is selected from the group comprising IGKV1-5, IGKV1-9, IGKV1D-13 and a variant of any one of the same wherein one, two, three, four or five amino acids are substituted with an amino acid other than cysteine, for example substituted with a donor residue in the corresponding location in the original lagomorph donor antibody. See for example the donor rabbit antibody sequences provided herein. Typically the human framework further comprises a suitable J region such as a JK4 J region.

In one embodiment a human VL framework employed in an antibody molecule of the present disclosure comprises an amino acid substitution in at least one position selected from the group comprising 1, 2, 3, 36, 63, 65, 66, 70 and 71, for example wherein the original amino acid in the framework is substituted for another amino acid other than cysteine, in particular substituted for a residue in the corresponding location in the framework of the donor antibody.

In one embodiment substitutions are made at at least positions 3 and 70.

In one embodiment substitutions are made at at least positions 3 and 71.

In one embodiment substitutions are made at at least positions 2, 3 and 70.

In one embodiment substitutions are made at at least positions 1, 3 and 71.

In one embodiment substitutions are made at at least positions 1, 3, 70 and 71.

In one embodiment when an IGKV1-5 human framework is employed one or more substitutions may be made at position 1, 3, 36, 63, 65, 66, 70 and 71, for example 3 and 70, or 3 and 71, or 1, 3 and 70 or 3, 36, 63, 65, 66 and 71.

In one embodiment when an IGKV1-9 human framework is employed one or more, two or more or three substitutions may be made at positions independently selected from 1, 2 and 3.

In one embodiment when an IGKV1D-13 human framework is employed one or two or three substitutions made at positions independently selected from 2 and 3.

In one embodiment after substitution in the VL framework position 1 is alanine.

In one embodiment after substitution in the VL framework position 2 is phenylalanine or alanine.

In one embodiment after substitution in the VL framework position 3 is valine or glutamic acid.

In one embodiment after substitution in the VL framework position 36 is phenylalanine In one embodiment after substitution in the VL framework position 63 is lysine.

In one embodiment after substitution in the VL framework position 65 is aspartic acid.

In one embodiment after substitution in the VL framework position 66 is arginine.

In one embodiment after substitution in the VL framework position 70 is glutamine.

In one embodiment after substitution in the VL framework position 71 is tyrosine.

It will be appreciated that one or more of these substitutions may be combined to generate a humanised VL region for use in an antibody molecule of the invention.

In one independent aspect there is provided a humanised VL variable domain comprises a sequence independently selected from SEQ ID NO: 106, 115, 126, 135, 144, 153 and a sequence at least 80%, 85%, 90%, 95% identical or similar to the same (such as 96, 97, 98 or 99% similar or identical).

In one embodiment the humanised VL variable domain comprises a sequence independently selected from SEQ ID NO: 106, 115, 126, 135, 144 and 153.

In one embodiment there is provided an antibody molecule comprising a VH independently selected from SEQ ID NO: 107, 108, 109, 110 and VL with a sequence shown in SEQ ID NO: 106.

In one embodiment there is provided an antibody molecule comprising a VH independently selected from SEQ ID NO: 116, 117, 118, 119, 120 121 and a VL with a sequence shown in SEQ ID NO: 115.

In one embodiment there is provided an antibody molecule comprising a VH independently selected from SEQ ID NO: 127, 128, 129, 130 and a VL with a sequence shown in SEQ ID NO: 126.

In one embodiment there is provided an antibody molecule comprising a VH independently selected from SEQ ID NO: 136, 137, 138, 139 and a VL with a sequence shown in SEQ ID NO: 135.

In one embodiment there is provided an antibody molecule comprising a VH independently selected from SEQ ID NO: 145, 146, 147, 148 and a VL with a sequence shown in SEQ ID NO: 144.

In one embodiment there is provided an antibody molecule comprising a VH independently selected from SEQ ID NO: 154, 155, 156, 157 and a VL with a sequence shown in SEQ ID NO: 153.

In one embodiment the antibody molecule of the present disclosure is a full length antibody.

In one embodiment the antibody molecule of the present disclosure is a Fab or Fab' fragment.

In one embodiment the antibody molecule of the present disclosure is a scFv.

In one embodiment the antibody molecule of the present disclosure is multispecific, for example bispecific or trispecific.

In one embodiment the multispecific antibody molecule (such as a bispecific antibody molecule) of the disclosure in a addition to a binding domain specific to CD22 comprises a binding domain specific to CD79, for example comprising 1, 2, 3, 4, 5 or 6 anti-CD79 CDRs disclosed herein or variants thereof, such as a variable domain or a variable domain pair, in particular a humanised variable domain or pair of variable domains disclosed herein.

The combination according to the present disclosure in a multispecific (such as a bispecific) format shows interesting biological activity in functional in vitro assays, for example inhibition of B cell signalling as measured by any one of the following: inhibition of phosphorylation of Akt S473, inhibition of phosphorylation of P38 and PLCγ2 Y759 inhibition of IkB, in addition to the inhibition of expression of CD86, CD71 and/or CD40 on B cells. The same level of activity is not apparent for individual components alone or the components provided in admixture. However, the activity is apparent when a bispecific construct with specificity for CD22 and CD79 is provided.

The inhibition of certain B cell functions observed in these assays is indicative that a multispecific molecule of the invention, comprising a binding domain specific to CD22 and a binding domain specific to CD79, may be used to alter B cell function and, for example to provide a therapeutic alternative to depletion of B cells.

In one embodiment the binding domain or binding domains of the multispecific molecules of the present invention each independently comprise one or two (such as two) antibody variable domains specific to a relevant antigen (such as at least one binding domain specific to CD22 and a further binding domain specific CD79 or a further antigen if the molecule is at least trispecific).

In one embodiment the antibody molecule of the present disclosure is specific to CD22.

In one embodiment an antibody or binding fragment thereof employed in the molecules of the present disclosure is specific to CD79a.

In one embodiment an antibody or binding fragment thereof employed in the molecules of the present disclosure is specific to CD79b.

In one embodiment an antibody or binding fragment thereof employed in the molecules of the present disclosure is specific to CD79 complex, i.e. it recognises an epitope present in the complex and is specific thereto, for example an epitope comprising an interaction between CD79a and CD79b.

In one embodiment even where the binding domain is specific to CD79a or CD79b it will be appreciated that the binding domain will still bind to CD79a or CD79b when in the complex form.

Where there are two variable regions in a binding domain or in each binding domain then the two variable regions will generally work co-operatively to provide specificity for the relevant antigen, for example they are a cognate pair or affinity matured to provide adequate affinity such that the domain is specific to a particular antigen. Typically they are a heavy and light chain variable region pair (VH/VL pair).

In one embodiment the molecule of the present disclosure is bispecific.

In one embodiment the molecule of the present disclosure is trispecific, for example where the third binding domain is specific to serum albumin, for example human serum albumin.

In one embodiment the molecule of the present disclosure is monospecific for CD79 and CD22 i.e. the molecule only comprises one binding domain which binds CD79 and one binding domain which binds CD22.

In one embodiment the multispecific molecule of the present disclosure is a single chain.

In one embodiment the multispecific molecule of the present disclosure comprises a heavy chain and also a light chain. In one example, as employed herein a heavy and light chain pairing is not referred to as a dimer, particularly where in one embodiment the molecule of the present disclosure does not comprise multimers, such as dimers of the antibody, unit/fragment or components.

In one embodiment the molecule comprises no more than one binding site for CD22 and no more than one binding site for CD79.

Also provided is an antibody or binding fragment that binds the same epitope as an antibody or binding fragment explicitly disclosed herein.

In one embodiment there is provided an antibody or binding fragment that cross-blocks an antibody molecule of the present disclosure antibody or binding fragment explicitly disclosed herein to human CD22, or is cross-blocked from binding human CD22 by said antibody.

The disclosure also extends to pharmaceutical compositions comprising antibody molecules of the present disclosure.

The present disclosure also provides novel CD22 antibodies, employed in any antibody format including in a multispecific molecule, for use in therapy.

The present disclosure also provides a method of treating a patient comprising administering a therapeutically effective amount of antibody molecule or pharmaceutical formulation comprising the same.

The disclosure also extends to use of antibody molecule or a pharmaceutical formulation comprising the same according to the present disclosure for the manufacture of a medicament for the treatment of disorder disclosed herein.

The present disclosure also extends to novel frameworks disclosed herein, which are suitable for grafting non-human CDRs into. That is frameworks with amino acid changes without the corresponding CDRs.

DESCRIPTION OF DRAWINGS

FIG. 10 is a table showing the data for the antigen grid cross specificities. Antigen 2=CD79b and antigen 3=CD22. Values are percentage inhibition (negative value for activation) of phosphorylation of Syk & represent the mean of multiple V region combinations evaluated.

FIG. 11 is a table showing the data for the antigen grid cross specificities. Antigen 2=CD79b and antigen 3=CD22. Values are percentage inhibition (negative value for activation) of phosphorylation of PLCγ2 & represent the mean of multiple V-region combinations evaluated.

FIG. 12 is a table showing the data for the antigen grid cross specificities. Antigen 2=CD79b and antigen 3=CD22. Values are percentage inhibition (negative value for activation) of phosphorylation of AKT & represent the mean of multiple V region combinations evaluated.

FIG. 13 is a graph showing the percentage inhibition of the phosphorylation of Syk, PLCγ2 & AKT for each V-region combination for CD79b specificity in Fab-X combined with CD22 specificity in Fab-Y

FIG. 27 shows the inhibition of tetanus toxoid IgG production from PBMCs cultured with VR4447/VR4126 BYbe, VR4447/VR4127 BYbe and VR4447/VR4130 BYbe. Data represents pooled data from 3 donors.

FIG. 28 shows the inhibition of tetanus toxoid IgG production from purified B cells cultured with VR4447/VR4126 BYbe, VR4447/VR4127 BYbe and VR4447/VR4130 BYbe. Data represents pooled data from 2 donors. shows the inhibition of tetanus toxoid IgG production from either PBMC or FIG. 29 purified B cells cultured with VR4447/VR4126 BYbe, VR4447/VR4127 BYbe, VR4447/VR4130 BYbe, VR4447/VR4126/VR645 BYbe/Albumin and VR4447/VR4130/VR645 BYbe/Albumin. Data shown from a single donor.

FIG. 31 shows the effect of CD79b+CD22 specific VR4447/VR4130 BYbe on anti-IgM induced B-cell NFkB phosphorylation, from 12 Healthy Volunteer (HV) and 12 SLE Donors.

FIG. 32 shows the effect of CD79b+CD22 specific VR4447/VR4130 BYbe on anti-IgM induced B-cell Akt phosphorylation, from 12 Healthy Volunteer (HV) and 12 SLE Donors.

FIG. 33 shows the effect of CD79b+CD22 specific VR4447/VR4130 BYbe on anti-IgM induced B-cell Syk phosphorylation, from 12 Healthy Volunteer (HV) and 12 SLE Donors.

FIG. 34 shows the effect of CD79b+CD22 specific VR4447/VR4130 BYbe on anti-IgM induced B-cell Erk 1 & 2 phosphorylation, from 12 Healthy Volunteer (HV) and 12 SLE Donors.

FIG. 35 Sequences of the present disclosure

DETAILED DESCRIPTION OF THE DISCLOSURE

Figure 1:
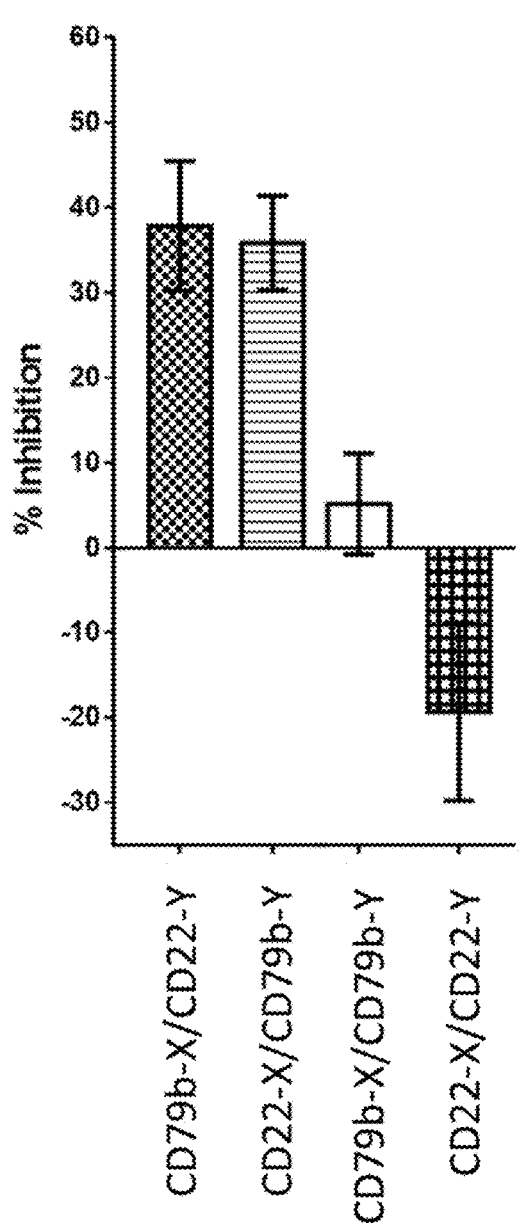
FIG. 1 is a bar chart of the relative potency of inhibition of phosphorylated Akt for bispecific and bivalent combinations of antibodies with specificity for CD22 and CD79b.

B cell receptor signalling is a critical function of the B cell and a requirement for antigen specific activation of B cells. BcR signalling is vital from early stages of B cell development through to the activation and development of memory B cell responses. The B cell receptor is composed of a surface immunoglobulin (Ig) molecule which associates with heterodimeric complex of CD79a and CD79b. When surface Ig recognises antigen it is thought that this results in a clustering of the CD79a/b complex which results in downstream activation of the immediate signalling cascade which includes Src family kinases as well as Syk and Btk tyrosine kinases. This signalling complex then can recruit adaptor proteins such as CD19 and BLNK and results in activation of PLCγ2 and PI3K which in turn can activate further downstream pathways such as those that control B cell growth, survival and differentiation. This signalling complex can be further regulated by other second signals via signalling through BAFF-R, IL-21R and CD40 and can also be regulated by other signalling molecules such as CD19, CD21, CD83, CD22, CD32b and CD45 amongst others. Upon recognition of antigen by the BcR one of the first responses activated is the upregulation of surface receptors such as the co-stimulatory molecules CD80 and CD86. These molecules bind to corresponding receptors on T cells which deliver further survival and activation signals that allow survival and expansion of T cells that recognise antigen in the context of MHC class II. This response is further amplified by the ability of B cells to present antigen in the context of MHC class II back to the T cell, which releases factors such as IL-2 and IL-21. These cytokines in turn expand B cell number greatly. Thus down regulation of CD86 on the surface of cells may be indicative of inhibition of B cell signalling.

Furthermore, inhibition of B cell receptor signalling can lead to inhibition of downstream functions. One such outcome would be the inhibition of co-stimulatory molecules such as CD86 (or reduced expression of the same) which will lead to the inhibition of T cell function, survival and differentiation.

Thus inhibition of B cell receptor signalling can be beneficial in controlling aberrant B cell functions associated with autoimmunity and cancer. B cell receptor signalling is required for B cell proliferation, differentiation, antigen presentation and cytokine release in autoimmune disease. Thus inhibiting BcR activity can regulate B cell functions such as immunoglobulin secretion, T cell activation and control inappropriate B cell activity associated with, for example autoimmune conditions. In addition there are some B cell leukaemias and lymphomas that require B cell receptor signalling for survival and growth which may be controlled by inhibitors of B cell receptor activation.

CD22 (also known as cluster of differentiation-22) is a known protein. CD22 is an inhibitory co-receptor of the B-cell receptor (BCR), and plays a critical role in establishing signalling thresholds for B-cell activation. The human sequence is available in UniProt entry number P20273 (SEQ ID NO: 244 and without signal peptide, amino acids 20-847 of SEQ ID NO:244). The murine version in UniProt entry P35329. The present disclosure relates to all forms of CD22 from any species, in particular human and natural variants thereof. In one embodiment CD22 refers to the human form of the protein.

In one embodiment the affinity of the binding domain for CD22 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger. In one embodiment an antibody or binding fragment thereof employed in the molecules of the present disclosure is specific to CD22.

CD79 as used herein refers to the complex composed of CD79a and CD79b. Accordingly, antibodies or binding domains which bind CD79 may bind to CD79a and/or CD79b. Binds to CD79a and/or CD79b as employed herein refers to specific to CD79a, specific to CD79b, specific to both CD79a and CD79b (i.e. recognises an epitope on CD79a and the same antibody or binding domain also recognises an epitope on CD79b i.e. pan specific) or is specific to the complex of CD79a and CD79b (i.e. recognises an epitope formed from the interaction of CD79a and CD79b in the complex form and this is capable of distinguishing the complex from the individual components).

In one embodiment an antibody or binding fragment thereof employed in the molecules of the present disclosure is specific to CD79a.

In one embodiment an antibody or binding fragment thereof employed in the molecules of the present disclosure is specific to CD79b.

In one embodiment an antibody or binding fragment thereof employed in the molecules of the present disclosure is specific to CD79 complex, i.e. it recognises an epitope present in the complex and is specific thereto, for example an epitope comprising an interaction between CD79a and CD79b.

In one embodiment even where the binding domain is specific to CD79a or CD79b it will be appreciated that the binding domain will preferably still bind to CD79a or CD79b when in the complex form, as the two protein are naturally co-expressed on the cell surface.

In one embodiment there is provided a construct comprising a binding domain of the specific disclosure.

Construct comprising a binding domain as employed herein includes any structure capable of providing the binding domain such that is can bind the antigen to which it is specific. Example of a construct include, but are not limited, to a chimeric antigen receptor, a modified T cell receptor, an antibody molecule, an aptamer and the like.

It will be appreciated that the antibody molecules of the present invention, may be incorporated into other molecular formats or constructs, wherein the binding domains provided by the present invention bind to and thereby target CD22. For example, binding regions of the present invention, for example fragments such as a Fab or scFv may be used to re-direct cells in vivo, for example via the transduction of T cells with chimeric antigen receptors (CAR-T cells) and then transferring these cells into the patient (Nat. Revs. Drug Disc. 2015. 14. 499-509). Accordingly, the present invention also provides a chimeric antigen receptor comprising one or more binding domains as described herein.

Where there are two variable regions in a binding domain and/or in each binding domain, then the two variable regions will generally work co-operatively to provide specificity for the relevant antigen, for example they are a cognate pair or affinity matured to provide adequate affinity such that the domain is specific to a particular antigen. Typically they are a heavy and light chain variable region pair (VH/VL pair).

"Multispecific molecule" as employed herein refers to a molecule with the ability to specifically bind at least two distinct antigens, for example different antigens. In one embodiment the multispecific molecule is a bispecific, trispecific or tetraspecific molecule, in particular a bispecific or trispecific molecule.

In one embodiment the molecule of the present disclosure is bispecific.

In one embodiment the molecule of the present disclosure is trispecific.

In one embodiment the multispecific antibody molecule (such as a bispecific antibody molecule) of the disclosure in addition to a binding domain specific to CD22 comprises a binding domain specific to another antigen.

In one embodiment the molecule of the present disclosure is monospecific for CD79 and monospecific for CD22 i.e. the molecule only comprises one binding domain which binds CD79 and one binding domain which binds CD22.

In one embodiment the multispecific molecule of the present disclosure is a single chain.

In one embodiment the multispecific molecule of the present disclosure comprises a heavy chain and also a light chain. In one example, as employed herein a heavy and light chain pairing is not referred to as a dimer, particularly where in one embodiment the molecule of the present disclosure does not comprise multimers, such as dimers of the antibody, unit/fragment or components.

Thus in one aspect the disclosure extends to a molecule of a suitable format specific to at least CD22 and CD79a and to use of antibodies/fragments or combinations thereof specific to CD22 and CD79a in a multispecific molecule, such as a bispecific format or trispecific format.

In one aspect the disclosure extends to a molecule of a suitable format specific to at least CD22 and CD79b and to use of antibodies/fragments or combinations thereof specific to CD22 and CD79b in a multispecific molecule, such as a bispecific format or trispecific format.

In one aspect the disclosure extends to a molecule of a suitable format specific to at least CD22 and CD79a/b complex and to use of antibodies/fragments or combinations thereof specific to CD22 and CD79a/b complex in a multispecific molecule, such as a bispecific format or trispecific format.

In one embodiment the molecule of the present disclosure is trispecific, for example where the third binding domain is capable of extending the half-life of the molecule, for example by binding a serum carrier protein.

A variety of proteins exist in plasma and include thyroxine-binding protein, transthyretin, α1-acid glycoprotein, transferrin, fibrinogen and albumin, or a fragment of any thereof (Bartalena & Robbins, 1993, Clinics in Lab. Med. 13:583-598; Bree et al., 1986, Clin. Pharmacokin. 11:336-342; Gitlin et al. 1964, J. Clin. Invest. 10:1938-1951; Peters, 1985, Adv Protein Chem. 37:161-245; Waldeman & Strober, 1969, Progr. Allergy, 13:1-110. In on example the third binding domain is specific to serum albumin, for example human serum albumin.

Multispecific Molecule Formats

Examples of suitable multispecific molecules for use in the present invention are known in the art, for example as disclosed in the review "The coming of Age of Engineered Multivalent Antibodies, Nunez-Prado et al Drug Discovery Today Vol 20 Number 5 Mar. 2015, page 588-594, D. Holmes, Nature Rev Drug Disc November 2011:10; 798, Chan and Carter, Nature Reviews Immunology vol 10, May 2010, 301 incorporated herein by reference.

In one embodiment multispecific formats include those known in the art and those described herein, such as wherein the molecule format is selected from the group comprising or consisting of:

tandem sdAb, tandem sdAb-sdAb (three sdAbs);
(scFv)$_2$ (also referred to as tandem scFv), scFv-dsFv, dsscFv-dsFv (dsFv)$_2$;
diabody, dsdiabody, didsdiabody,
scdiabody, dsscdiabody, didsscdiabody;
Dart antibody i.e., VL$_1$ linker VH$_2$ linker and VH$_1$ linker VL$_2$ wherein the C-terminus of VH$_1$ and VH$_2$ are joined by a disulfide bond;
BiTE®, dsBiTE, didsBiTE;
Di-diabody (see Nunez-Prado et al in particular molecule number 25 in FIG. 1 therein), dsdi-diabody, didsdi-diabody;
triabody, dstriabody, didstriabody, tridstriabody;
tetrabodies, dstetrabody, didstetrabody, tridstetrabody, tetradstetrabody;
tandab (see Nunez-Prado et al in particular molecule number 22 in FIG. 1 therein); dstandab, didstandab, tridstandab, tetradstandab;
[sc(Fv)$_2$]$_2$, (see Nunez-Prado et al in particular molecule number 22 in FIG. 1 therein), ds[sc(Fv)$_2$]$_2$, dids [sc(Fv)$_2$]$_2$, trids[sc(Fv)$_2$]$_2$, tetrads [sc(Fv)$_2$]$_2$,
Pentabody (see Nunez-Prado et al in particular molecule number 27 in FIG. 1 therein);
Fab-scFv (also referred to as a bibody), Fab'scFv, FabdsscFv (or BYbe), Fab'dsscFv;
tribody, dstribody, didstribody (also referred to as Fab-didsscFv or TrYbe or Fab-(dsscFv)$_2$), Fab'didsscFv;
Fabdab, FabFv, Fab'dab, Fab'Fv;
Fab single linker Fv (also referred to herein as FabdsFv as disclosed in WO2014/096390), Fab' single linker Fv (also referred to herein as Fab'dsFv);
FabscFv single linker Fv, Fab'scFv single linker Fv;
FabdsscFv single linker Fv, Fab'dsscFv single linker Fv;
FvFabFv, FvFab'Fv, dsFvFabFv, dsFvFab'Fv, FvFabdsFv, FvFab'dsFv, dsFvFabdsFv, dsFvFab'dsFv,
FabFvFv, Fab'FvFv, FabdsFvFv, Fab'dsFvFv, FabFvdsFv, Fab'FvdsFv, FabdsFvdsFv, Fab'dsFvdsFv,
diFab, diFab' including a chemically conjugated diFab', (FabscFv)$_2$, (Fab)$_2$scFvdsFv, (Fab)$_2$dsscFvdsFv, (FabdscFv)$_2$,
(Fab'scFv)$_2$, (Fab')$_2$scFvdsFv, (Fab')$_2$dsscFvdsFv, (Fab'dscFv)$_2$,
V$_H$HCκ (see Nunez-Prado et al in particular molecule number 6 in FIG. 1 therein);
minibody, dsminibody, didsminibody,
a miniantibody (ZIP) [see Nunez-Prado et al in particular molecule number 7 in FIG. 1 therein], dsminiantibody (ZIP) and didsminiantibody (ZIP);
tribi-minibody [see Nunez-Prado et al in particular molecule number 15 in FIG. 1 therein] dstribi-minibody, didstribi-minibody, tridstribi-minibody;
diabody-CH$_3$, dsdiabody-CH$_3$, didsdiabody-CH$_3$, scdiabody-CH$_3$, dsscdiabody-CH$_3$, didsscdiabody-CH$_3$,
tandemscFv-CH$_3$, tandemdsscFv-CH$_3$, tandemdidsscFv-CH$_3$, tandemtridsscFv-CH$_3$, tandemtetradsscFv-CH$_3$,
scFv-Fc (also referred to herein as a (scFvCH$_2$CH$_3$)$_2$), as described in WO2008/012543 and a single chain version thereof, dsscFvscFv-Fc, dsscFv-Fc (also referred to herein as (dsscFvCH$_2$CH$_3$)$_2$), scFv-dsFv-Fc, dsscFv-dsFv-Fc, dsFv-Fc (also referred to herein a (dsFvCH$_2$CH$_3$)$_2$),
scorpion molecule (Trubion) i.e. a binding domain, linker —CH$_2$CH$_3$ binding domain as described in U.S. Pat. No. 8,409,577;
SMIP (Trubion) i.e. (scFv-CH$_2$CH$_3$)$_2$;
(dsFvCH$_2$CH$_3$)$_2$, tandem scFv-Fc, tandem dsscFvscFv-Fc, tandem dsscFv-Fc,
scFv-Fc-scFv, dsscFv-Fc-scFv, scFv-Fc-dsscFv,
diabody-Fc, dsdiabody-Fc, didsdiabody-Fc, triabody-Fc, dstriabody-Fc, didstriabody-Fc, tridstriabody-Fc, tetrabody-Fc, dstetrabody-Fc, didstetrabody-Fc, tridstetrabody-Fc, tetradstetrabody-Fc, dstetrabody-Fc, didstetrabody-Fc, tridstetrabody-Fc, tetradstetrabody-Fc, scdiabody-Fc, dsscdiabody-Fc, didsscdiabody-Fc;
bi or trifunctional antibody, for example with different heavy chain variable regions and common light chains for example Merus bispecific antibody format (Biclonics®) with common light chains of a fixed sequence and different heavy chains (including different CDRs) and engineered CH$_3$ domain to drive the dimerization o the different heavy chains,
Duobody (i.e. wherein one full length chain in the antibody has different specificity to the other full length chain in the antibody);

a full-length antibody wherein Fab arm exchange has been employed to create a bispecific format;

bi or tri functional antibody wherein a full-length antibody has common heavy chain and different light chains also referred to as kappa/lambda body' or 'κ/λ-body see WO2012/023053;

Ig-scFv one, two, three or four from the C terminus of heavy or light chain, scFv-Ig one, two, three or four from the N terminus of heavy or light chain, single linker Ig-Fv, Ig-dsscFv one, two, three or four from the C terminus of heavy or light chain (with one, two, three or four disulfide bonds);

Ig-dsscFv one, two, three or four from the N terminus of heavy or light chain (with one, two, three or four disulfide bonds), Ig single linker Fv (see PCT/EP2015/064450), Ig-dab, dab-Ig, scFv-Ig, V-Ig, Ig-V, scFabFvFc, scFabdsFvFc (single linker version scFavFv), (FabFvFc)$_2$, (FabdsFvFc)$_2$, scFab'FvFc, scFab'dsFvFc, (Fab'FvFc)$_2$, (Fab' dsFvFc)$_2$ and DVDIg, which are discussed in more detail below.

In one embodiment multispecific molecule formats include those known in the art and those described herein, such as wherein the molecule format is selected from the group comprising or consisting of: diabody, scdiabody, triabody, tribody, tetrabodies, tandem scFv, FabFv, Fab'Fv, FabdsFv, Fab-scFv, Fab-dsscFv, Fab-(dsscFv)$_2$, diFab, diFab', tandem scFv-Fc, scFv-Fc-scFv, scdiabody-Fc, scdiabody-CH3, Ig-scFv, scFv-Ig, V-Ig, Ig-V, Duobody and DVDIg, which are discussed in more detail below.

In one embodiment the multispecific antibody molecule of the present disclosure does not comprise an Fc domain i.e. does not comprise a CH$_2$ and a CH$_3$ domain, for example the molecule is selected from the group comprising a tandem scFv, scFv-dsFv, dsscFv-dsFv didsFv, diabody, dsdiabody, didsdiabody, scdiabody (also referred to as an (scFv)$_2$), dsscdiabody, triabody, dstriabody, didstriabody, tridstriabody, tetrabodies, dstetrabody, didstetrabody, tridstetrabody, tetradstetrabody, tribody, dstribody, didstribody, Fabdab, FabFv, Fab'dab, Fab'Fv, Fab single linker Fv (as disclosed in WO2014/096390), Fab' single linker Fv, FabdsFv, Fab'dsFv, Fab-scFv (also referred to as a bibody), Fab'scFv, FabdsscFv, Fab'dsscFv, FabdidsscFv, Fab'didsscFv, FabscFv single linker Fv, Fab'scFv single linker Fv, FabdsscFvs single linker Fv, Fab'dsscFv single linker Fv, FvFabFv, FvFab'Fv, dsFvFabFv, dsFvFab'Fv, FvFabdsFv, FvFab'dsFv, dsFvFabdsFv, dsFvFab'dsFv, FabFvFv, Fab'FvFv, FabdsFvFv, Fab'dsFvFv, FabFvdsFv, Fab'FvdsFv, FabdsFvdsFv, Fab' dsFvdsFv, diFab, diFab' including a chemically conjugated diFab', (FabscFv)$_2$, (Fab)$_2$scFvdsFv, (Fab)$_2$dsscFvdsFv, (FabdscFv)$_2$, minibody, dsminibody, didsminibody, diabody-CH$_3$, dsdiabody-CH$_3$, didsdiabody-CH$_3$, scdiabody-CH$_3$, dsscdiabody-CH$_3$, didsscdiabody-CH$_3$, tandemscFv-CH$_3$, tandemdsscFv-CH$_3$, tandemdidsscFv-CH$_3$, tandemtridsscFv-CH$_3$ and tandemtetradsscFv-CH$_3$.

In one embodiment the molecule of the present disclosure does not comprise an Fc domain.

In one embodiment the molecule of the present disclosure comprises an altered Fc domain as described herein below.

Fc domain as employed herein generally refers to —(CH$_2$CH$_3$)$_2$, unless the context clearly indicates otherwise.

In one embodiment the molecule of the present disclosure does not comprise a —CH$_2$CH$_3$ fragment.

In one embodiment the molecule of the present disclosure does not comprise a CH$_2$ domain.

In one embodiment the molecule of the present disclosure does not comprise a CH$_3$ domain.

Molecule as employed herein is used in the biochemistry sense to refer to a group of atoms that form an organic, in particular proteinaceous mass, which includes a complex suitable for handling as a single entity under appropriate conditions once the complex has been formed, for example a complex formed by two or more polypeptide chains.

Molecule and construct are used interchangeably herein, unless the context indicates otherwise. Although, construct may be employed more often to refer to a polynucleotide molecule and molecule may be employed more often to refer an entity primarily comprising an amino acid sequence.

Specificity (or specific) as employed herein refers to where the partners in the interaction only recognise each other or have significantly higher affinity for each other in comparison to non-partners, for example at least 2, 3, 4, 5, 6, 7, 8, 9, 10 times higher affinity, than for example a background level of binding or binding to another unrelated protein.

A 'binding domain' as employed herein refers to a binding region, typically a polypeptide, capable of binding a target antigen, for example with sufficient affinity to characterise the domain as specific for the antigen. In one embodiment the binding domain contains at least one variable domain or a derivative thereof, for example a pair of variable domains or derivatives thereof, such as a cognate pair of variable domains or a derivative thereof. Typically this is a VH/VL pair.

Any suitable binding domains may be used in the multispecific molecules of the present invention. These may be derived from any suitable source.

In one embodiment a biocompatible framework structure is used in a binding domain of the molecules of the present disclosure and such structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See for example, Nygren and Uhlen, 1997, Current Opinion in Structural Biology, 7, 463-469).

The term 'multi-specific molecules' as used herein may also include binding agents based on biological scaffolds including Adnectins, Affibodies, Darpins, Phylomers, Avimers, Aptamers, Anticalins, Tetranectins, Microbodies, Affilins and Kunitz domains.

The multispecific molecule of the present invention is typically a multispecific antibody molecule, ie. at least one or more of the binding domains of the multispecific molecule are derived from an antibody or fragment thereof.

Where the binding domain is derived from an antibody, a "binding domain or site" as employed herein is the part of the antibody that contacts the antigen. In one embodiment the binding domain contains at least one variable domain or a derivative thereof, for example a pair of variable domains or derivatives thereof, such as a cognate pair of variable domains or a derivative thereof. Typically this is a VH/VL pair.

Variable regions (also referred to herein as variable domains) generally comprise 3 CDRs and a suitable framework. In one embodiment the binding domain comprises two variable regions, a light chain variable region and a heavy chain variable region and together these elements contribute to the specificity of the binding interaction of the antibody or binding fragment.

In one embodiment the variable domains in a binding domain in an antibody molecule of the present disclosure are cognate pair.

A "cognate pair" as employed herein refers to a heavy and light chain pair of variable domains (or a derivative thereof, such as a humanised version thereof) isolated from a host as a pre-formed couple. This definition does not include variable domains isolated from a library, wherein the original pairing from a host is not retained. Cognate pairs may be advantageous because they are often affinity matured in the host and therefore may have higher affinity for the antigen to which they are specific, than a combination of variable domain pairs selected from a library, such as phage library.

In one embodiment a binding domain in an antibody molecule of the present disclosure is a derivative of a naturally occurring binding domain.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, GPI anchors, or solvent exposed lysines. These modifications can be achieved by replacing the relevant amino acid residues with a conservative amino acid substitution.

Modification in the CDRs may, for example include replacing one or more cysteines with, for example a serine residue. Asn can be the substrate for deamination and this propensity can be reduced by replacing Asn and/or a neighbouring amino acid with an alternative amino acid, such as a conservative substitution. The amino acid Asp in the CDRs may be subject to isomerization. The latter can be minimized by replacing Asp or a neighbouring amino acid with an alternative amino acid, for example a conservative substitution.

Humanised versions of a variable region are also a derivative thereof, in the context of the present specification. Humanisation may include the replacement of a non-human framework for a human framework and optionally the back-mutation of one or more residues to "donor residues". Donor residues as employed herein refers to residues found in the original variable region isolated from the host, in particular replacing a given amino acid in the human framework with the amino acid in the corresponding location in the donor framework.

In one embodiment, the binding domain or each binding domain is part of (included or incorporated in) an antibody or an antibody fragment.

In one embodiment the binding domains in the molecules of the present disclosure are in immunoglobulin/antibody molecules.

As used herein "antibody molecule" includes antibodies and binding fragments thereof.

In one embodiment the term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site or binding domain herein), located in the variable region of the immunoglobulin molecule.

"Antibody fragments" as employed herein refer to antibody binding fragments including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217).

A "binding fragment" as employed herein refers to a fragment capable of binding a target peptide or antigen with sufficient affinity to characterise the fragment as specific for the peptide or antigen.

The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in WO05/003169, WO05/003170 and WO05/003171. Multi-valent antibodies may comprise multiple specificities e.g. bispecific or may be monospecific (see for example WO92/22853, WO05/113605, WO2009/040562 and WO2010/035012).

Constructs comprising an antibody or antibody fragment include chimeric antigen receptors (which are membrane anchored antibodies/fragments contected to a signalling domain) and modified T cell receptors (also membrane anchored proteins).

The term "Fab fragment" as used herein refers to an antibody fragment comprising a light chain fragment comprising a $V_L$ (variable light) domain and a constant domain of a light chain ($C_L$), and a $V_H$ (variable heavy) domain and a first constant domain ($CH_1$) of a heavy chain.

The Fv refers to two variable domains, for example co-operative variable domains, such as a cognate pair or affinity matured variable domains, i.e. a $V_H$ and $V_L$ pair.

Co-operative variable domains as employed herein are variable domains that complement each other and/or both contribute to antigen binding to render the Fv ($V_H/V_L$ pair) specific for the antigen in question.

The following is a list of example antibody formats that may be employed in an antibody molecule of the present disclosure.

"Single domain antibody" (also referred to herein as a dab and sdAb) as used herein refers to an antibody fragment consisting of a single monomeric variable antibody domain. Examples of single domain antibodies include $V_H$ or $V_L$ or $V_H H$.

Tandem-sdAb as employed herein refers to two domain antibodies connected by a linker, for example a peptide linker, in particular where the domain antibodies have specificity for different antigens.

Tandem-sdAb-sdAb as employed herein refers to three domain antibodies connected in series by two linkers, for example peptide linkers, in particular where the domain antibodies have specificity for different antigens.

dsFv as employed herein refers to an Fv with an intra-variable disulfide bond. The dsFv may be a component of a larger molecule, for example the one of the variable domains may be linked, for example via an amino acid linker to another antibody fragment/component.

$(dsFv)_2$ as employed herein refers to a dsFv with one domain linked, for example via a peptide linker or a disulfide bond (for example between, the C-terminus of two $V_H$'s) to a domain in a second dsFv, the format resembles a $(scFv)_2$ described below but each pair of variable regions comprise a intra-variable region disulfide bond.

Component as employed herein refers to a building block or portion of a multispecific molecule of the present disclosure, in particular where the component is an antibody fragment such as scFv, Fab or other fragment, in particular as described herein.

Single-chain Fv or abbreviated as "scFv", as used herein refers to an antibody fragment that comprises $V_H$ and $V_L$ antibody domains linked (for example by a peptide linker) to form a single polypeptide chain. The constant regions of the heavy and light chain are omitted in this format.

dsscFv as employed herein refers to scFv with an intra-variable region disulfide bond.

Figure 9:
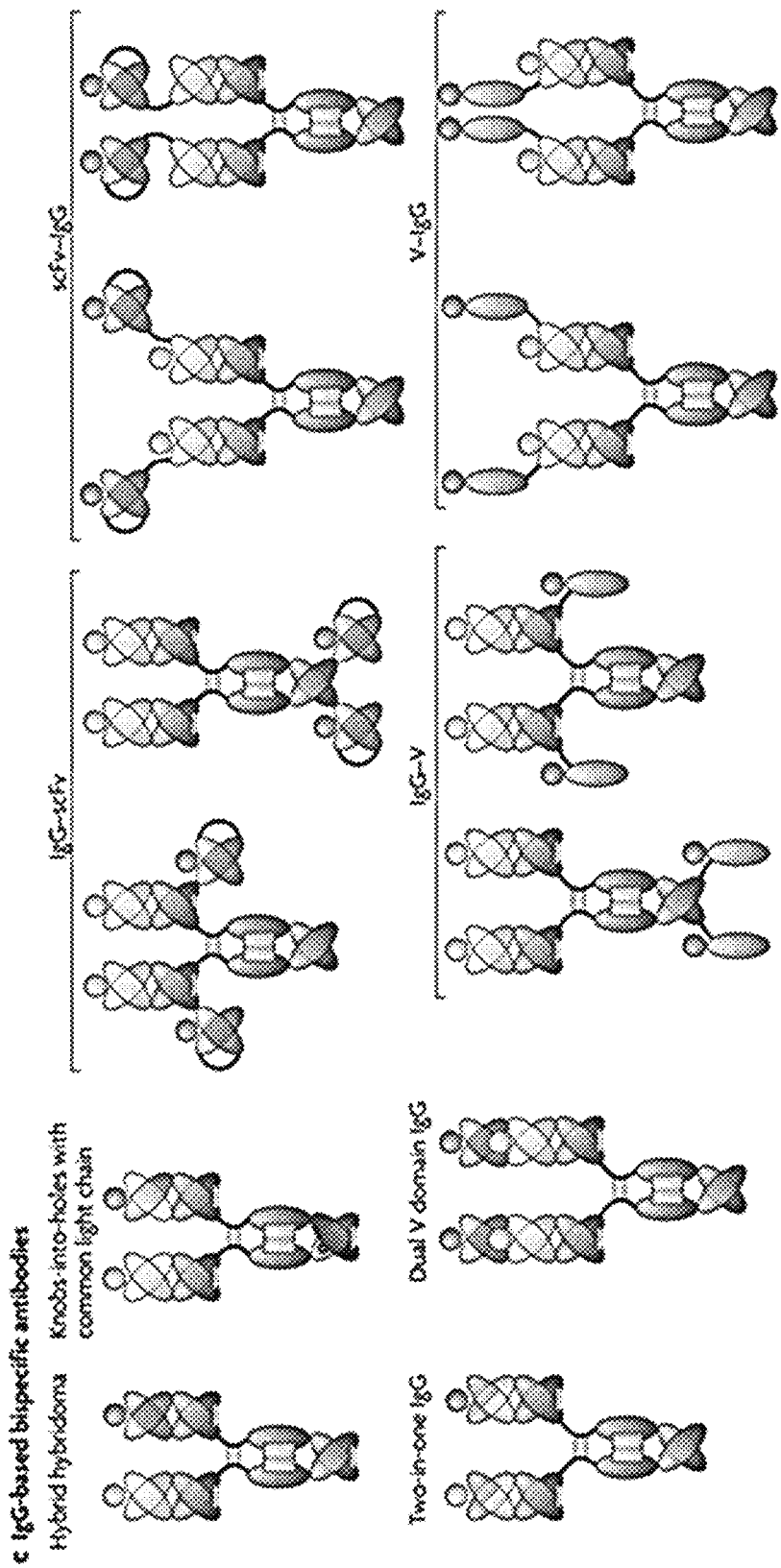
FIG. 9 is an extract from Chan and Carter, Nature Reviews Immunology vol 10, May 2010, 301 showing certain antibody formats

Tandem scFv (also referred to herein as a discFv or (scFv)$_2$) as employed herein refers to two scFvs linked via a single linker such that there is a single inter-Fv linker, for example as shown in FIG. 9b.

Tandem dsscFv (also referred to herein as a scFvdsscFv or dsscFvscFv) as employed herein refers to two scFvs linked via a single linker such that there is a single inter-Fv linker, for example as shown in FIG. 9b, and wherein one of the scFv has an intravariable region disulfide bond.

Tandem didsscFv (also referred to herein as a didsscFv) as employed herein refers to two scFvs linked via a single linker such that there is a single inter-Fv linker, for example as shown in FIG. 9b, and wherein each scFv comprises an intravariable region disulfide bond.

scFv-dsFv as employed herein is a scFv linked, for example by a peptide linker, to an Fv domain which is comprised of two variable domains linked via a disulfide bond to form a dsFv. In this format the VH or VL of the scFv may be linked to the VH or VL of the dsFv.

dsscFv-dsFv as employed herein is a dsscFv linked, for example by a peptide linker, to an Fv domain which is comprised of two variable domains linked via a disulfide bond to form a dsFv. In this format the VH or VL of the dsscFv may be linked to the VH or VL of the dsFv.

Diabody as employed herein refers to two Fv pairs $V_H/V_L$ which have two inter-Fv linkers, such that the $V_H$ of a first Fv is linked to the $V_L$ of the second Fv and the $V_L$ of the first Fv is linked to the $V_H$ of the second Fv.

dsDiabody as employed herein refers to a diabody comprising an intra-variable region disulfide bond.

didsDiabody as employed herein refers to a diabody comprising two intra-variable region disulfide bonds, i.e. one ds between each pair of variable regions.

Sc-diabody as employed herein refers a diabody comprising an intra-Fv linker, such that the molecule comprises three linkers and forms two normal scFvs, for example VH$_1$linkerVL$_1$ linker VH$_2$ linker VL$_2$.

dssc-diabody as employed herein refers to a sc-diabody with an intra-variable region disulfide bond.

didssc-diabody as employed herein refers to a sc-diabody with an intra-variable region disulfide bond between each pair of variable regions.

Dart as employed herein refers to VL$_1$ linker VH$_2$ linker and VH$_1$ linker VL$_2$ wherein the C-terminus of VH$_1$ and VH$_2$ are joined by a disulfide bond Paul A. Moore et al *Blood*, 2011; 117(17):4542-4551.

Bite® as employed herein refers to a molecule comprising two pairs of variable domains in the following format; a domain from pair 1 (eg VH$_1$) connected via a linker to a domain from pair 2 (eg VH$_2$ or VL$_2$) said second domain connected by a linker to the further domain from pair 1 (eg VL$_1$) in turn connected to the remaining domain from pair two (i.e VL$_2$ or VH$_2$).

Di-diabody see Nunez-Prado et al in particular molecule number 25 in FIG. 1 therein.

Dsdi-diabody as employed herein refers to a di-diabody with an intra-variable region disulfide bond.

Didsdi-diabody as employed herein is a di-diabody with an intra-variable region disulfide bond between each pair of variable regions.

Triabody as employed herein refers to a format similar to the diabody comprising three Fvs and three inter-Fv linkers.

dstriabody as employed herein refers to a triabody comprising an intra-variable region disulfide bond between one of the variable domain pairs.

Didstriabody as employed herein refers to a triabody comprising two intra-variable region disulfide bonds, i.e. one ds between each of two variable domain pairs.

Tridstriabody as employed herein refers to a triabody comprising three intra-variable region disulfide bonds i.e. one ds between each pair of variable regions.

Tetrabody as employed herein refers to a format similar to the diabody comprising four Fvs and four inter-Fv linkers.

dstetrabody as employed herein refers to a tetrabody comprising an intra-variable region disulfide bond between one of the variable domain pairs.

Didstetrabody as employed herein refers to a tetrabody comprising two intra-variable region disulfide bonds, i.e. one ds between each of two variable domain pairs.

Tridstetrabody as employed herein refers to a tetrabody comprising three intra-variable region disulfide bonds i.e. one ds between each of three pairs of variable regions.

Tetradstetrabody as employed herein refers to a tetrabody comprising four intra-variable region disulfide bonds i.e. one ds between each variable domain.

Tribody (also referred to a Fab(scFv)$_2$) as employed herein refers to a Fab fragment with a first scFv appended to the C-terminal of the light chain and a second scFv appended to the C-terminal of the heavy the chain.

dstribody as employed herein refers to a tribody comprising a dsscFv in one of the two positions.

didstribody or TrYbe as employed herein refers to a tribody comprising two dsscFvs.

dsFab as employed herein refers to a Fab with an intra-variable region disulfide bond.

dsFab' as employed herein referst to a Fab' with an intra-variable region disulfide bond.

scFab is a single chain Fab fragment.

scFab' is a single chain Fab' fragment.

dsscFab is a dsFab as a single chain.

dsscFab' is a dsFab' as a single chain.

Fabdab as employed herein refers to a Fab fragment with a domain antibody appended to the heavy or light chain thereof, optionally via a linker.

Fab' dab as employed herein refers to a Fab' fragment with a domain antibody appended to the heavy or light chain thereof, optionally via a linker.

FabFv as employed herein refers to a Fab fragment with an additional variable region appended to the C-terminal of each of the following, the CH$_1$ of the heavy chain and CL of the light chain see for example WO2009/040562. The format may be provided as a PEGylated version thereof see for example WO2011/061492, Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions, see for example WO2010/035012. The format may be provided as a PEGylated version thereof.

Fab single linker Fv and Fab' single linker as employed herein refers to a Fab or Fab' fragment linked to a variable domain, for example by a peptide linker, and said variable domain is linked to a second variable domain via an intra-variable domain disulfide bond thereby forming a dsFv, see for example WO2014/096390.

Fab-scFv (also referred to as a bibody) as employed herein is a Fab molecule with a scFv appended on the C-terminal of the light or heavy chain, optionally via a linker.

Fab'-scFv as employed herein is a Fab' molecule with a scFv appended on the C-terminal of the light or heavy chain, optionally via a linker.

FabdsscFv or BYbe as employed herein is a Fab-scFv with a disulfide bond between the variable regions of the single chain Fv.

Fab'dsscFv as employed herein is a Fab'scFv with a disulfide bond between the variable regions of the single chain Fv.

FabscFv-dab as employed herein refers to a Fab with a scFv appended to the C-terminal of one chain and domain antibody appended to the C-terminal of the other chain.

Fab'scFv-dab as employed herein refers to a Fab' with a scFv appended to the C-terminal of one chain and domain antibody appended to the C-terminal of the other chain.

FabdsscFv-dab as employed herein refers to a Fab with a dsscFv appended to the C-terminal of one chain and domain antibody appended to the C-terminal of the other chain.

Fab'dsscFv-dab as employed herein refers to a Fab' with a dsscFv appended to the C-terminal of one chain and domain antibody appended to the C-terminal of the other chain.

FabscFv single linker Fv as employed herein refers to a Fab single linker Fv wherein a domain of the Fv is linked to the heavy or light chain of the Fab and a scFv is linked to the other Fab chain and the domains of the Fv are connected by an intra-variable region disulfide.

FabdsscFv single linker Fv as employed herein refers to a FabscFv single linker Fv wherein the scFv comprises an intra-variable region disulfide bond.

Fab'scFv single linker Fv as employed herein refers to a Fab' single linker Fv wherein a domain of the Fv is linked to the heavy or light chain of the Fab and a scFv is linked to the other Fab chain and the domains of the Fv are connected by an intra-variable region disulfide.

Fab'dsscFv single linker Fv as employed herein refers to a Fab'scFv single linker Fv wherein the scFv comprises an intra-variable region disulfide bond.

FvFabFv as employed herein refers to a Fab with the domains of a first Fv appended to the N-terminus of the heavy and light chain of the Fab and the domains of a second Fv appended to the C-terminus of the heavy and light chain.

FvFab'Fv as employed herein refers to a Fab' with the domains of a first Fv appended to the N-terminus of the heavy and light chain of the Fab' and the domains of a second Fv appended to the C-terminus of the heavy and light chain.

dsFvFabFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain.

FvFabdsFv as employed herein refers to a Fab with the domains of a first Fv appended to the N-terminus of the heavy and light chain of the Fab and the domains of a second Fv appended to the C-terminus of the heavy and light chain and wherein the second Fv comprises an intra-variable region disulfide bond.

dsFvFab'Fv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain.

FvFab'dsFv as employed herein refers to a Fab' with the domains of a first Fv appended to the N-terminus of the heavy and light chain and the domains of a second Fv appended to the C-terminus of the heavy and light chain of the Fab' and wherein the second Fv comprises an intra-variable region disulfide bond.

dsFvFabdsFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain and wherein the second Fv also comprises an intra-variable region disulfide bond.

dsFvFab'dsFv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain and wherein the second Fv also comprises an intra-variable region disulfide bond.

FabFvFv as employed herein refers to a Fab fragment with two pairs of Fvs appended in series to the C-terminal of the heavy and light chain, see for example WO2011/086091.

Fab'FvFv as employed herein refers to a Fab' fragment with two pairs of Fvs appended in series to the C-terminal of the heavy and light chain, see for example WO2011/086091.

FabdsFvFv as employed herein refers to a Fab fragment with two pairs of Fvs appended in series to the C-terminal of the heavy and light chain, see for example WO2011/086091, wherein the first Fv pair attached directly to the C-terminal comprise an intra-variable region disulfide bond.

Fab'dsFvFv as employed herein refers to a Fab' fragment with two pairs of Fvs appended in series to the C-terminal of the heavy and light chain, see for example WO2011/086091, wherein the first Fv pair attached directly to the C-terminal comprise an intra-variable region disulfide bond.

FabFvdsFv as employed herein refers to a Fab fragment with two pairs of Fvs appended in series to the C-terminal of the heavy and light chain, wherein the second Fv pair at the "C"-terminal of the molecule comprise an intra-variable region disulfide bond.

Fab'FvdsFv as employed herein refers to a Fab' fragment with two pairs of Fvs appended in series to the C-terminal of the heavy and light chain, wherein the second Fv pair at the "C"-terminal of the molecule comprise an intra-variable region disulfide bond.

FabdsFvdsFv as employed herein refers to a Fab fragment with two pairs of Fvs appended in series to the C-terminal of the heavy and light chain, wherein the first and second Fv pair comprise an intra-variable region disulfide bond.

Fab'dsFvdsFv as employed herein refers to a Fab' fragment with two pairs of Fvs appended in series to the C-terminal of the heavy and light chain, wherein the first and second Fv comprise an intra-variable region disulfide bond.

DiFab as employed herein refers to two Fab molecules linked via their C-terminus of the heavy chains.

DiFab' as employed herein refers to two Fab' molecules linked via one or more disulfide bonds in the hinge region thereof.

DiFab and DiFab' molecules include chemically conjugated forms thereof.

(FabscFv)$_2$ as employed herein refers to a diFab molecule with two scFvs appended thereto, for example appended to the C-terminal of the heavy or light chain, such as the heavy chain.

(Fab'scFv)$_2$ as employed herein refers to a diFab' molecule with two scFvs appended thereto, for example appended to the C-terminal of the heavy or light chain, such as the heavy chain.

(Fab)$_2$scFvdsFv as employed herein refers to a diFab with a scFv and dsFv appended, for example one from each of the heavy chain C-terminal.

(Fab')$_2$scFvdsFv as employed herein refers to a diFab' with a scFv and dsFv appended, for example one from each of the heavy chain C-terminal.

(Fab)$_2$dsscFvdsFv, as employed herein refers to a diFab with a dsscFv and dsFv appended, for example from the heavy chain C-terminal.

(Fab')$_2$dsscFvdsFv as employed herein refers to the a diFab' with a dsscFv and dsFv appended, for example from the heavy chain C-terminal.

Minibody as employed herein refers to (VL/VH-CH$_3$)$_2$.

dsminibody as employed herein refers to (VL/VH-CH$_3$)$_2$ wherein one VL/VH comprises an intra-variable region disulfide bond.

didsminibody as employed herein refers to a (dsFv-CH$_3$)$_2$ kappa/lambda body' or 'κ/λ-body is in the format of a normal IgG with two heavy chains and two light chains, wherein the two light chains are different to each other, one is a lambda light chain (VL-CL) and the other is a kappa light chain (VK-CK). The heavy chain is identical, even at the CDRs, as described in WO2012/023053.

scFv-Fc as employed herein refers to a scFv appended to the N-terminus of a CH$_2$ domain, for example via a hinge, of constant region fragment —(CH$_2$CH$_3$), such that the molecule has 2 binding domains.

dsscFv-Fc as employed herein refers to a dsscFv appended to the N-terminus of a CH$_2$ domain and a scFv appended to the N-terminus of a second CH$_2$ domain, for example via a hinge, of constant region fragment —(CH$_2$CH$_3$)$_2$, such that the molecule has 2 binding domains.

didsscFv-Fc as employed herein refers to a scFv appended to the N-terminus of a CH$_2$ domain, for example via a hinge, of constant region fragment —(CH$_2$CH$_3$)$_2$, such that the molecule has 2 binding domains Tandem scFv-Fc as employed herein refers to two tandem scFvs, wherein each one is appended in series to the N-terminus of a CH$_2$ domain, for example via a hinge, of constant region fragment —(CH$_2$CH$_3$), such that the molecule has 4 binding domains.

Scdiabody-Fc as employed herein is two scdiabodies, wherein each one is appended to the N-terminus of a CH$_2$ domain, for example via a hinge, of constant region fragment —CH$_2$CH$_3$.

ScFv-Fc-scFv as employed herein refers to four scFvs, wherein one of each is appended to the N-terminus and the C-terminus of both the heavy and light chain of a —CH$_2$CH$_3$ fragment.

Scdiabody-CH$_3$ as employed herein refers to two scdiabody molecules each linked, for example via a hinge to a CH$_3$ domain.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

Duobody or 'Fab-arm exchange' as employed herein is a bispecific IgG format antibody where matched and complementary engineered amino acid changes in the constant domains (typically CH3) of two different monoclonal antibodies lead, upon mixing, to the formation of heterodimers. A heavy:light chain pair from the first antibody will, as a result of the residue engineering, prefer to associate with a heavy:light chain pair of a second antibody. See for example WO2008/119353, WO2011/131746 and WO2013/060867.

In one embodiment an antibody molecule according to the present disclosure is a bispecific protein complex having the formula A-X:Y-B wherein:
A-X is a first fusion protein;
Y-B is a second fusion protein;
X:Y is a heterodimeric-tether;
: is a binding interaction between X and Y;
A is a first protein component of the bispecific selected from a Fab or Fab' fragment;
B is a second protein component of the bispecific selected from a Fab or Fab';
X is a first binding partner of a binding pair independently selected from an antigen or an antibody or binding fragment thereof; and
Y is a second binding partner of the binding pair independently selected from an antigen or an antibody or a binding fragment thereof;
with the proviso that when X is an antigen Y is an antibody or binding fragment thereof specific to the antigen represented by X and when Y is an antigen X is an antibody or binding fragment thereof specific to the antigen represented by Y.

In one aspect, there is provided a multi-specific antibody molecule comprising or consisting of:
a) a polypeptide chain of formula (I):

$$V_H—CH_1—X—(V_1)_p;$$

b) a polypeptide chain of formula (II):

$$V_L—C_L—Y—(V_2)_q;$$

wherein:
$V_H$ represents a heavy chain variable domain;
$CH_1$ represents a domain of a heavy chain constant region, for example domain 1 thereof;
X represents a bond or linker, for example an amino acid linker;
Y represents a bond or linker, for example an amino acid linker;
$V_1$ represents a dab, scFv, dsscFv or dsFv;
$V_L$ represents a variable domain, for example a light chain variable domain;

$C_L$ represents a domain from a constant region, for example a light chain constant region domain, such as Ckappa;

$V_2$ represents a dab, scFv, dsscFv or dsFv;

p is 0 or 1;

q is 0 or 1; and when p is 1 q is 0 or 1 and when q is 1 p is 0 or 1 i.e. p and q do not both represent 0

In one embodiment the multispecific antibody molecule comprises no more than one binding domain for CD22 and no more than one binding domain for CD79.

In one embodiment q is 0 and p is 1.

In one embodiment q is 1 and p is 1.

In one embodiment $V_1$ is a dab and $V_2$ is a dab and together they form a single binding domain of a co-operative pair of variable regions, such as a cognate $V_H/V_L$ pair, which are optionally linked by a disulphide bond.

In one embodiment $V_H$ and $V_L$ are specific to, CD79, for example CD79a or CD79b.

In one embodiment the $V_1$ is specific to, CD79, for example CD79a or CD79b.

In one embodiment the $V_2$ is specific to, CD79, for example CD79a or CD79b.

In one embodiment the $V_1$ and $V_2$ together (eg as binding domain) are specific to, CD79, for example CD79a or CD79b and $V_H$ and $V_L$ are specific to, CD22.

In one embodiment the $V_1$ is specific to, CD22.

In one embodiment the $V_2$ is specific to, CD22.

In one embodiment the $V_1$ and $V_2$ together (eg as one binding domain) are specific to, CD22 and $V_H$ and $V_L$ are specific to CD79.

In one embodiment the $V_1$ is specific to CD22, $V_2$ is specific to albumin and $V_H$ and $V_L$ are specific to CD79.

In one embodiment the $V_1$ is specific to albumin, $V_2$ is specific to CD22 and $V_H$ and $V_L$ are specific to CD79.

In one embodiment the $V_1$ is specific to CD79, $V_2$ is specific to albumin and $V_H$ and $V_L$ are specific to CD22.

In one embodiment the $V_1$ is specific to albumin, $V_2$ is specific to CD79 and $V_H$ and $V_L$ are specific to CD22.

In one embodiment the $V_1$ is a dsscFv specific to CD22, $V_2$ is a dsscFv specific to albumin and $V_H$ and $V_L$ are specific to CD79.

In one embodiment the $V_1$ is a dsscFv specific to albumin, $V_2$ is a dscFv specific to CD22 and $V_H$ and $V_L$ are specific to CD79.

In one embodiment the $V_1$ is a dsscFv specific to CD79, $V_2$ is a dsscFv specific to albumin and $V_H$ and $V_L$ are specific to CD22.

In one embodiment the $V_1$ is a dsscFv specific to albumin, $V_2$ is a dsscFv specific to CD79 and $V_H$ and $V_L$ are specific to CD22.

$V_1$, $V_2$, VH and VL in the constructs above may each represent a binding domain and incorporate any of the sequences provided herein.

X and Y represent any suitable linker, for example X and Y may be independently SGGGGSGGGGS (SEQ ID NO:271) or SGGGGTGGGGS (SEQ ID NO: 272).

In one embodiment, when $V_1$ and/or $V_2$ are a dab, dsFv or a dsscFv, the disulfide bond between the variable domains $V_H$ and $V_L$ of $V_1$ and/or $V_2$ is formed between positions $V_H44$ and $V_L100$.

Where one or more pairs of variable regions in a multispecific antibody molecule comprise a disulphide bond between VH and VL this may be in any suitable position such as between two of the residues listed below (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990); $V_H100b+V_L49$;

$V_H98+V_L46$ see for example Protein Science 6, 781-788 Zhu et al (1997); $V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995) and a position corresponding thereto in variable region pair located in the molecule.

In one embodiment, the disulphide bond is formed between positions $V_H44$ and $V_L100$.

"Monospecific" as employed herein refers to the ability to bind a target antigen only once.

Thus is one embodiment the multispecific molecules of the present invention are monospecific for each antigen.

Thus in one embodiment the binding domains of the multispecific molecules according to the present disclosure are monospecific. This is advantageous in some therapeutic applications because the molecules of the disclosure are not able to cross-link antigen via binding the target antigen more than once. Thus in one embodiment bispecific or multispecific molecules of the present-disclosure are not able to cross-link by binding the same target twice in two different locations, for example on the same cell or on two different cells.

Cross-linking, in particular in relation to CD79b on the same cell or different cells can generate signals in vivo, for example which stimulate the activity of the target antigen.

In one example the multispecific molecules of the present invention contain no more than one binding domain for CD22 and no more than one binding domain for CD79. Each binding domain is monospecific.

In one example therefore the multispecific molecule is monovalent for CD22 and monovalent for CD79.

In one embodiment, each antibody or antibody fragment employed in the multi-specific molecules of the present disclosure is monovalent.

Thus in one embodiment the binding domains of the multispecific molecules of the present disclosure are monovalent.

Thus in one embodiment the binding domains of the multispecific molecules of the present disclosure are monovalent and monospecific.

In one embodiment the multispecific molecule of the present disclosure is comprised of two or more monospecific, monovalent binding domains such as Fab, Fab', scFV, VH, VL, VHH, Fv, dsFv, combined or linked in any suitable way to construct a multispecific molecule, for example as described herein above.

In another embodiment, for example where the molecules of the disclosure comprise at least three binding domains then two or three binding domains (for example antibodies, fragments or a combination of an antibody and a fragment) may have different antigen specificities, for example binding to three different target antigens.

Constant Regions

The antibody constant region domains of an antibody of the present disclosure, if present, for example in a full length antibody or a multispecific molecule, may be selected having regard to the proposed function of the multispecific antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

In one embodiment, the antibody heavy chain comprises a $CH_1$ domain and the antibody light chain comprises a CL domain, either kappa or lambda.

In one embodiment, the antibody heavy chain comprises a $CH_1$ domain, a $CH_2$ domain and a $CH_3$ domain and the antibody light chain comprises a CL domain, either kappa or lambda. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns P. et al., 2009. Specificity and affinity of human Fcgamma receptors and their polymorphic variants for human IgG subclasses. Blood. 113(16):3716-25), see also Jeffrey B. Stavenhagen, et al. Cancer Research 2007 Sep. 15; 67(18):8882-90.

Binding of IgG to the FcγRs or C1q depends on residues located in the hinge region and the $CH_2$ domain. Two regions of the $CH_2$ domain are critical for FcγRs and C1q binding, and have unique sequences in IgG2 and IgG4. Substitutions into human IgG1 of IgG2 residues at positions 233-236 and IgG4 residues at positions 327, 330 and 331 have been shown to greatly reduce ADCC and CDC (Armour K L. et al., 1999. Recombinant human IgG molecules lacking Fcgamma receptor I binding and monocyte triggering activities. Eur J Immunol. 29(8):2613-24 and Shields R L. et al., 2001. High resolution mapping of the binding site on human IgG1 for Fc gamma RI, Fc gamma RII, Fc gamma RIII, and FcRn and design of IgG1 variants with improved binding to the Fc gamma R. J Biol Chem. 276(9):6591-604). Furthermore, Idusogie et al. demonstrated that alanine substitution at different positions, including K322, significantly reduced complement activation (Idusogie E E. et al., 2000. Mapping of the C1q binding site on rituxan, a chimeric antibody with a human IgG1 Fc. J Immunol. 164(8):4178-84). Similarly, mutations in the CH2 domain of murine IgG2A were shown to reduce the binding to FcγRI, and C1q (Steurer W. et al., 1995. Ex vivo coating of islet cell allografts with murine CTLA4/Fc promotes graft tolerance. J Immunol. 155(3): 1165-74).

In one embodiment the Fc region employed is mutated, in particular a mutation described herein. In one embodiment the mutation is to remove binding and/or effector function.

In one embodiment the Fc mutation is selected from the group comprising a mutation to remove binding of the Fc region, a mutation to increase or remove an effector function, a mutation to increase half-life and a combination of the same.

Some antibodies that selectively bind FcRn at pH 6.0, but not pH 7.4, exhibit a higher half-life in a variety of animal models. Several mutations located at the interface between the CH2 and CH3 domains, such as T250Q/M428L (Hinton P R. et al., 2004. Engineered human IgG antibodies with longer serum half-lives in primates. J Biol Chem. 279(8): 6213-6) and M252Y/S254T/T256E+H433K/N434F (Vaccaro C. et al., 2005. Engineering the Fc region of immunoglobulin G to modulate in vivo antibody levels. Nat Biotechnol. 23(10):1283-8), have been shown to increase the binding affinity to FcRn and the half-life of IgG1 in vivo.

However, there is not always a direct relationship between increased FcRn binding and improved half-life (Datta-Mannan A. et al., 2007. Humanized IgG1 Variants with Differential Binding Properties to the Neonatal Fc Receptor: Relationship to Pharmacokinetics in Mice and Primates. Drug Metab. Dispos. 35: 86-94).

IgG4 subclass show reduced Fc receptor (FcγRIIIa) binding, antibodies of other IgG subclasses generally show strong binding. Reduced receptor binding in these other IgG subtypes can be effected by altering, for example replacing one or more amino acids selected from the group comprising Pro238, Aps265, Asp270, Asn270 (loss of Fc carbohydrate), Pro329, Leu234, Leu235, Gly236, Gly237, Ile253, Ser254, Lys288, Thr307, Gln311, Asn434 and His435.

In one embodiment a molecule according to the present disclosure has an Fc of IgG subclass, for example IgG1, IgG2 or IgG3 wherein the Fc is mutated in one, two or all following positions S228, L234 and/or D265.

In one embodiment the mutations in the Fc region are independently selected from S228P, L234A, L235A, L235A, L235E and combinations thereof.

It may be desired to either reduce or increase the effector function of an Fc region. Antibodies that target cell-surface molecules, especially those on immune cells, abrogating effector functions is required. In some embodiments, for example for the treatment of autoimmunity, enhanced Fc binding on immune cells by increasing negative Fc receptor binding (FcgRIIb or CD32b) may be desirable see Stavenhagen J B, et al *Advances in Enzyme Regulation* 2007 Dec. 3 and Veri M C, et al. *Arthritis Rheum*, 2010 Mar. 30; 62(7):1933-43. Conversely, for antibodies intended for oncology use, increasing effector functions may improve the therapeutic activity.

Numerous mutations have been made in the CH2 domain of human IgG1 and their effect on ADCC and CDC tested in vitro (Idusogie E E. et al., 2001. Engineered antibodies with increased activity to recruit complement. J Immunol. 166 (4):2571-5). Notably, alanine substitution at position 333 was reported to increase both ADCC and CDC. Lazar et al. described a triple mutant (S239D/I332E/A330L) with a higher affinity for FcγRIIIa and a lower affinity for FcγRIIb resulting in enhanced ADCC (Lazar G A. et al., 2006. Engineered antibody Fc variants with enhanced effector function. PNAS 103(11): 4005-4010). The same mutations were used to generate an antibody with increased ADCC (Ryan M C. et al., 2007. Antibody targeting of B-cell maturation antigen on malignant plasma cells. Mol. Cancer Ther., 6: 3009-3018). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards J O et al 2008. Optimization of antibody binding to Fcgamma RIIa enhances macrophage phagocytosis of tumor cells. Mol Cancer Ther. 7(8):2517-27).

Due to their lack of effector functions, IgG4 antibodies represent a suitable IgG subclass for receptor blocking without cell depletion. IgG4 molecules can exchange halfmolecules in a dynamic process termed Fab-arm exchange. This phenomenon can occur between therapeutic antibodies and endogenous IgG4. The S228P mutation has been shown to prevent this recombination process allowing the design of less unpredictable therapeutic IgG4 antibodies (Labrijn A F. et al., 2009. Therapeutic IgG4 antibodies engage in Fab-arm exchange with endogenous human IgG4 in vivo. Nat Biotechnol. 27(8):767-71). This technology may be employed to create bispecific antibody molecules.

It will also be understood by one skilled in the art that antibodies may undergo a variety of post-translational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

Affinity

The antibody molecules of the present disclosure comprise at least one binding domain which is specific to CD22.

The multispecific molecules of the present invention comprise a binding domain specific to the antigen CD22 and a binding domain specific to the antigen CD79a and/or CD79b.

In one embodiment a binding domain employed in the molecules of the present disclosure is specific to CD22.

In one embodiment a binding domain employed in the molecules of the present disclosure is specific to CD79a.

In one embodiment a binding domain employed in the molecules of the present disclosure is specific to CD79b.

In one embodiment a binding domain employed in the molecules of the present disclosure is specific to CD79 complex, i.e. it recognises an epitope present in the complex and specific thereto, for example an epitope comprising an interaction between CD79a and CD79b.

The binding domain for CD79 may bind to CD79a and/or CD79b.

CD79a (also known as immunoglobulin alpha and B-cell antigen receptor complex-associated protein alpha chain) is a known protein. Expression of CD79a is restricted to B lymphocytes. The human sequence is available in UniProt under entry P11912 (SEQ ID NO: 162 and without signal sequence amino acids 33-226 of SEQ ID NO:162). The murine version is available in UniProt under entry 11911. The present disclosure relates to all forms of CD79a from any species, in particular human and any natural variants thereof. In one embodiment CD79a refers to the human form of the protein.

CD79b (also known as immunoglobulin associated beta and cluster differentiation 79B) is a known protein. Expression of CD79b is restricted to B lymphocytes. The human sequence is available in UniProt under entry P40259 (SEQ ID NO:163 and without signal sequence amino acids 29-229 of SEQ ID NO:163). The murine version in UniProt under entry P15530. The present disclosure relates to all forms of CD79b, from any species, in particular human and any natural variants thereof. In one embodiment CD79b refers to the human form of the protein.

In one embodiment the binding domain specific to CD79 binds CD79a.

In one embodiment the binding domain specific to CD79 binds CD79b.

In one embodiment the binding domain specific to CD79 binds a complex of CD79a and CD79b.

In one embodiment the affinity of the binding domain for CD79 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79a in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79b in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

It will be appreciated that the affinity of the binding domain for CD22 may be the same or different from the affinity of the binding domain for CD79.

In one embodiment, the multi-specific antibody molecules of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al J. Mol. Biol., 250, 359-368, 1996), DNA shuffling (Patten et al Curr. Opin. Biotechnol., 8, 724-733, 1997), phage display (Thompson et al., J. Mol. Biol., 256, 77-88, 1996) and sexual PCR (Crameri et al Nature, 391, 288-291, 1998). Vaughan et al (supra) discusses these methods of affinity maturation.

Antibodies & Generation of Same

Binding domains for use in the present invention may be generated by any suitable method known in the art, for example CDRs may be taken from non-human antibodies including commercially available antibodies and grafted into human frameworks or alternatively chimeric antibodies can be prepared with non-human variable regions and human constant regions etc.

Typically the binding domains for use in the present invention are binding domains derived from antibodies which bind the selected antigen, such as antibodies which bind CD22, or CD79a and/or CD79b.

Examples of CD22, and CD79 antibodies are known in the art and these may be employed directly in the molecules of the present invention or screened for suitability using the methods described herein, and subsequently modified if necessary, for example humanised, using the methods described herein. Examples of CD22 antibodies in the clinic include epratuzumab and inotuzumab. Other therapeutic antibodies have been described in the art, for example anti-CD22 antibodies disclosed in US2003202975 and WO14/011520, anti-CD79b antibodies disclosed in WO14011521 and WO15021089. Non-human anti-CD22 antibodies include rabbit monoclonal antibody LS-C2210357 (LSBio) from clone SP104, mouse monoclonal LS-C174778 from clone 4C3, mouse monoclonal LS-C4802, mouse monoclonal LS-B9996 from clone 1B1, mouse monoclonal LS-C340404 from clone 2E6, mouse monoclonal LS-C312263, mouse monoclonal LS-C152867, mouse monoclonal LS-C87523, mouse monoclonal LS-C134333 from clone FRB4, mouse monoclonal LS-C134336, mouse monoclonal LS-C40961 from clone HIB22, mouse monoclonal LS-C134332, the following antibodies from Santa Cruz Biotechnology sc-271579, sc-377304, sc-7032, sc-18909, sc-7932, sc-7323, sc-7307, sc-7031, sc-20053, sc-189000, sc-136440, sc-136507, sc-53031, sc-73363, sc-53032, Abcam rabbit monoclonal Ab33859 (EP498Y), mouse monoclonal antibody AA 1-687 catalog number ABIN1999423, mouse monoclonal from Biolegend workshop number V CD22.14 from clone HIB22.

Commercially available anti-CD79a antibodies include mouse monoclonal LS-B4504 (LSBio) from clone HM57, mouse monoclonal LS-B8330, mouse monoclonal LS-C44954, rabbit monoclonal LS-B9093, mouse monoclonal LS-B8513 from clone JCB117, rabbit monoclonal LS-C210607 from clone SP18, mouse monoclonal LS-C175441 from clone 5E2, mouse monoclonal LS-C338670 from clone 3D3, mouse monoclonal LS-C88120 from clone HM47/A9, mouse monoclonal LS-C191714, mouse monoclonal LS-C87592, mouse monoclonal LS-C44955, mouse monoclonal LS-C95934, mouse monoclonal LS-C121584, mouse monoclonal LS-C121585, mouse monoclonal LS-C204347, mouse monoclonal LS-C88122, Abcam mouse monoclonal ab3121 [HM47/A9], rabbit monoclonal ab79414, and rabbit monoclonal ab133483.

Commercially available CD79b antibodies include mouse monoclonal Abcam antibody ab33295, rat monoclonal ab23826, mouse monoclonal ab103422, rabbit monoclonal ab134103, rabbit monoclonal ab134147, and rabbit monoclonal ab183343.

Such commercially available antibodies may be useful tools in the discovery of further therapeutic antibodies.

The skilled person may generate antibodies for use in the multi-specific molecules of the invention using any suitable method known in the art.

Antigen polypeptides, for use in generating antibodies for example for use to immunize a host or for use in panning, such as in phage display, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The antigen polypeptide may in some instances be part of a larger protein such as a fusion protein for example fused to an affinity tag or similar. In one embodiment the host may be immunised with a cell, such as a fibroblast, transfected with the relevant protein or polypeptide, for example co-transfected with CD79a and CD79b.

Antibodies generated against an antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al 1983, Immunology Today, 4:72) and the EBV-hybridoma technique (Cole et al Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al 1996, Proc. Natl. Acad. Sci. USA 93(15):7843-78481; WO92/02551; WO2004/051268 and WO2004/106377.

The antibodies for use in the present disclosure can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; 5,969,108, and WO20011/30305.

In one example the multi-specific molecules of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

In one example the binding domains of the multi-specific molecules according to the disclosure are humanised.

Humanised (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term "humanised antibody molecule" refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Examples of human frameworks which can be used in the present disclosure are KOL, NEWM, REI, EU, TUR, TEI, LAY and POM (Kabat et al supra). For example, KOL and NEWM can be used for the heavy chain, REI can be used for the light chain and EU, LAY and POM can be used for both the heavy chain and the light chain. Alternatively, human germline sequences may be used; these are available at: http://www2.mrc-lmb.cam.ax.uk/vbase/list2.php.

In a humanised antibody molecule of the present disclosure, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al 1998, Nature, 332, 323-324). Such changes should be kept to the minimum necessary to recover the affinity of the donor antibody. A protocol for selecting residues in the acceptor framework regions which may need to be changed is set forth in WO91/09967.

Derivatives of frameworks may have 1, 2, 3, 4, 5, 6, 7, 8, 9 or 10 amino acids replaced with an alternative amino acid, for example with a donor residue.

Donor residues are residues from the donor antibody, i.e. the antibody from which the CDRs were originally derived, in particular the residue in a corresponding location from the donor sequence is adopted. Donor residues may be replaced by a suitable residue derived from a human receptor framework (acceptor residues).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one example there is provided a binding domain, for example in an antibody molecule of the present disclosure comprising a heavy chain variable region (for example, VH), specific for CD79 which comprises three CDRs, wherein CDR H1 has the sequence given in SEQ ID NO: 158, CDR H2 has the sequence given in SEQ ID NO: 159, and CDR H3 has the sequence given in SEQ ID NO: 160.

In one embodiment there is provided a binding domain, for example in an antibody molecule of the present disclosure comprising a heavy chain variable region (for example, VH), specific for CD79 comprising 3 heavy chain CDRs SEQ ID NO: 175 for CDRH1, SEQ ID NO: 176 for CDRH2 and SEQ ID NO: 177 for CDRH3.

In one embodiment there is provided a binding domain, for example in an antibody molecule of the present disclosure comprising a light chain variable region (for example VL) specific for CD79 comprising 3 light chain CDRs SEQ ID NO: 161 for CDRL1, SEQ ID NO: 162 for CDRL2 and SEQ ID NO: 163, 164, 165 or 166 for CDRL3.

In one embodiment there is provided binding domain, for example in an antibody molecule of the present disclosure comprising a light chain variable region (for example VL) specific for CD79 comprising 3 light chain CDRs SEQ ID NO: 178 for CDRL1, SEQ ID NO: 179 for CDRL2 and SEQ ID NO: 180, 181, 182 or 183 for CDRL3.

In one example there is provided a binding domain, for example in an antibody molecule of the present disclosure comprising a heavy chain variable region (VH), specific for CD79 which comprises three CDRs, wherein CDR H1 has the sequence given in SEQ ID NO: 158, CDR H2 has the sequence given in SEQ ID NO: 159, and CDR H3 has the sequence given in SEQ ID NO: 160 and a light chain variable region (VL) which comprises three CDRs, wherein CDR L1 has the sequence given in SEQ ID NO: 161, CDR L2 has the sequence given in SEQ ID NO: 162 and CDR L3 has the sequence given in SEQ ID NO: 163, 164, 165 or 166.

In one example there is provided a binding domain, for example in an antibody molecule of the present disclosure comprising a heavy chain variable region (VH), specific for CD79 which comprises three CDRs, wherein CDR H1 has the sequence given in SEQ ID NO: 175, CDR H2 has the sequence given in SEQ ID NO: 176, and CDR H3 has the sequence given in SEQ ID NO: 177 and a light chain variable region (VL) which comprises three CDRs, wherein CDR L1 has the sequence given in SEQ ID NO: 178, CDR L2 has the sequence given in SEQ ID NO: 179 and CDR L3 has the sequence given in SEQ ID NO: 180, 181, 182 or 183.

In one embodiment there is provided an antibody molecule comprising a VH and VL specific to CD79b selected from SEQ ID NO: 171 and 173, 171 and 174, 172 and 173, 172 and 174, 188 and 189, and 188 and 190.

The sequences of these anti-CD79 antibodies (antibody 4447 and antibody 4450), including VH, VL and CDR sequences are provided herein in FIG. 35. The sequences of the anti-CD22 antibodies (antibodies 4120, 4126, 4127, 4128, 4130, 4132) including VH, VL and CDR sequences are provided herein in FIG. 35, these may be combined as binding domains in molecules of the present invention.

In one embodiment there is provided a variable domain or a binding domain comprising a pair of variable domains with a sequence disclosed herein or variant thereof.

In one example there is provided a binding domain specific to albumin comprising a heavy chain variable region (VH) having the sequence given in SEQ ID NO: 240 and a light chain variable region (VL) having the sequence given in SEQ ID NO: 242.

In one embodiment a binding domain or domains are humanised.

In one example one or more CDRs provided herein may be modified to remove undesirable residues or sites, such as cysteine residues or aspartic acid (D) isomerisation sites or asparagine (N) deamidation sites.

For example one or more cysteine residues in any one of the CDRs may be substituted with another amino acid, such as serine.

In one example an Asparagine deamidation site may be removed from one or more CDRs by mutating the asparagine residue (N) and/or a neighbouring residue to any other suitable amino acid. In one example an asparagine deamidation site such as NG or NS may be mutated, for example to NA or NT.

In one example an Aspartic acid isomerisation site may be removed from one or more CDRs by mutating the aspartic acid residue (D) and/or a neighbouring residue to any other suitable amino acid. In one example an aspartic acid isomerisation site such as DG or DS may be mutated, for example to EG, DA or DT.

In one example an N-glycosylation site such as NLS may be removed by mutating the asparagine residue (N) to any other suitable amino acid, for example to SLS or QLS. In one example an N-glycosylation site such as NLS may be removed by mutating the serine residue (S) to any other residue with the exception of threonine (T).

The skilled person is able to test variants of CDRs or humanised sequences in any suitable assay such as those described herein to confirm activity is maintained.

Specific binding to antigen may be tested using any suitable assay including for example ELISA or surface plasmon resonance methods such as BIAcore where binding to antigen (CD22 or CD79) may be measured. Such assays may use isolated natural or recombinant CD22 or CD79 (a and/or b) or a suitable fusion protein/polypeptide. In one example binding is measured using recombinant CD22 (such as the sequence provided in SEQ ID NO: 244 or amino acids 20-847 of SEQ ID NO: 244) or CD79 (such as the sequence provided in SEQ ID NO: 245 and SEQ ID NO:246 and amino acids 33-226 of SEQ ID NO:245 and amino acids 29-229 of SEQ ID NO: 246) by for example surface plasmon resonance, such as BIAcore. Alternatively the proteins may be expressed on a cell, such as a HEK cell and affinity measured employing a flow cytometry based affinity determination.

Antibodies which cross-block the binding of an antibody molecule according to the present invention to CD22 in particular, an antibody molecule comprising the heavy chain sequence given in SEQ ID NO: 107, 108, 109 or 110 and the light chain sequence given in SEQ ID NO: 106; or an antibody molecule comprising the heavy chain sequence given in SEQ ID NO: 116, 117, 118, 119, 120 or 121 and the light chain sequence given in SEQ ID NO: 115; or an antibody molecule comprising the heavy chain sequence given in SEQ ID NO: 127, 128, 129 or 130 and the light chain sequence given in SEQ ID NO: 126; or an antibody molecule comprising the heavy chain sequence given in SEQ ID NO: 136, 137, 138 or 139 and the light chain sequence given in SEQ ID NO: 135; or an antibody molecule comprising the heavy chain sequence given in SEQ ID NO: 145, 146, 147 or 148 and the light chain sequence given in SEQ ID NO: 144; or an antibody molecule comprising the heavy chain sequence given in SEQ ID NO: 154, 155, 156 or 157 and the light chain sequence given in SEQ ID NO: 153 may be similarly useful in binding CD22 and therefore similarly useful in the antibody molecules, such as the multispecific molecules of the present invention. Accordingly, the present invention also provides an antibody molecule such as a multi-specific molecule comprising a binding domain specific to the antigen CD22 and a binding domain specific to the antigen CD79b wherein the binding domain for CD22 cross-blocks the binding of any one of the antibody molecules described herein above to CD22 and/or is cross-blocked from binding CD22 by any one of those antibodies. In one embodiment, such an antibody binds to the same epitope as an antibody described herein above. In another embodiment the cross-blocking antibody binds to an epitope which borders and/or overlaps with the epitope bound by an antibody described herein above.

In another embodiment the cross-blocking neutralising antibody binds to an epitope which borders and/or overlaps with the epitope bound by an antibody described herein above.

Cross-blocking antibodies can be identified using any suitable method in the art, for example by using competition ELISA or BIAcore assays where binding of the cross blocking antibody to antigen (CD22 and/or CD79) prevents the binding of an antibody of the present invention or vice versa. Such cross blocking assays may use, cell expressed, isolated natural or recombinant CD22 or CD79 (a and/or b) or a suitable fusion protein/polypeptide. In one example binding and cross-blocking is measured using recombinant CD22 or a suitable fragment or natural variant thereof (such as the sequence provided in SEQ ID NO: 244 or the sequence provided in amino acids 20-847 of SEQ ID NO: 244) or CD79 such as the sequence provided in SEQ ID NO:245 or the sequence provided in amino acids 33-226 of SEQ ID NO: 245 (CD79a) and/or the sequence provided in SEQ ID NO:246 or the sequence provided in amino acids 29-229 of SEQ ID NO: 246, for example by 85% or greater, such as 90% or greater, in particular by 95% or greater.

Such cross blocking antibodies may have comparable activity in one or more functional assays as the multi-specific antibodies molecules described herein.

The present disclosure also extends to novel polypeptide sequences disclosed herein and sequences at least 80% similar or identical thereto, for example 85% or greater, such 90% or greater, in particular 95%, 96%, 97%, 98% or 99% or greater similarity or identity.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

Linkers

The teaching herein of linkers in one context can equally be applied to linkers in different contexts where a linker is employed, such as in any multispecific molecule of the present invention.

In one embodiment, the linker employed in a molecule of the disclosure is an amino acid linker 50 residues or less in length, for example selected from a sequence shown in sequence 251 to 314.

TABLE 1

Hinge linker sequences

| SEQ ID NO: | SEQUENCE |
|---|---|
| 208 | DKTHTCAA |
| 209 | DKTHTCPPCPA |
| 210 | DKTHTCPPCPATCPPCPA |
| 211 | DKTHTCPPCPATCPPCPATCPPCPA |
| 212 | DKTHTCPPCPAGKPTLYNSLVMSDTAGTCY |
| 213 | DKTHTCPPCPAGKPTHVNVSVVMAEVDGTCY |
| 214 | DKTHTCCVECPPCPA |
| 215 | DKTHTCPRCPEPKSCDTPPPCPRCPA |
| 216 | DKTHTCPSCPA |

TABLE 2

Flexible linker sequences

| SEQ ID NO: | SEQUENCE |
|---|---|
| 217 | SGGGGSE |
| 218 | DKTHTS |
| 219 | (S)GGGGS |
| 220 | (S)GGGGSGGGGS |
| 221 | (S)GGGGSGGGGSGGGGS |
| 222 | (S)GGGGSGGGGSGGGGSGGGGS |
| 223 | (S)GGGGSGGGGSGGGGSGGGGSGGGGS |
| 224 | AAAGSG-GASAS |
| 225 | AAAGSG-XGGGS-GASAS |
| 226 | AAAGSG-XGGGSXGGGS-GASAS |
| 227 | AAAGSG-XGGGSXGGGSXGGGS-GASAS |
| 228 | AAAGSG-XGGGSXGGGSXGGGSXGGGS-GASAS |
| 229 | AAAGSG-XS-GASAS |
| 230 | PGGNRGTTTTRRPATTTGSSPGPTQSHY |
| 231 | ATTTGSSPGPT |
| 232 | ATTTGS GS |
| 233 | EPSGPISTINSPPSKESHKSP |
| 234 | GTVAAPSVFIFPPSD |
| 235 | GGGGIAPSMVGGGGS |
| 236 | GGGGKVEGAGGGGS |
| 237 | GGGGSMKSHDGGGGS |
| 238 | GGGGNLITIVGGGGS |
| 239 | GGGGVVPSLPGGGGS |
| 240 | GGEKSIPGGGGS |
| 241 | RPLSYRPPFPFGFPSVRP |
| 242 | YPRSIYIRRRHPSPSLTT |
| 243 | TPSHLSHILPSFGLPTFN |
| 244 | RPVSPFTFPRLSNSWLPA |
| 245 | SPAAHFPRSIPRPGPIRT |
| 246 | APGPSAPSHRSLPSRAFG |
| 247 | PRNSIHFLHPLLVAPLGA |
| 248 | MPSLSGVLQVRYLSPPDL |
| 249 | SPQYPSPLTLTLPPHPSL |
| 250 | NPSLNPPSYLHRAPSRIS |
| 251 | LPWRTSLLPSLPLRRRP |
| 252 | PPLFAKGPVGLLSRSFPP |
| 253 | VPPAPVVSLRSAHARPPY |

TABLE 2-continued

Flexible linker sequences

| SEQ ID NO: | SEQUENCE |
|---|---|
| 254 | LRPTPPRVRSYTCCPTP- |
| 255 | PNVAHVLPLLTVPWDNLR |
| 256 | CNPLLPLCARSPAVRTFP |

(S) is optional in sequences 219-223

Examples of rigid linkers include the peptide sequences GAPAPAAPAPA (SEQ ID NO: 273), PPPP (SEQ ID NO: 274) and PPP.

Other linkers are shown in Table 3:

| SEQ ID NO: | SEQUENCE |
|---|---|
| 257 | DLCLRDWGCLW |
| 258 | DICLPRWGCLW |
| 259 | MEDICLPRWGCLWGD |
| 260 | QRLMEDICLPRWGCLWEDDE |
| 261 | QGL1GDICLPRWGCLWGRSV |
| 262 | QGL1GDICLPRWGCLWGRSVK |
| 263 | EDICLPRWGCLWEDD |
| 264 | RLMEDICLPRWGCLWEDD |
| 265 | MEDICLPRWGCLWEDD |
| 266 | MEDICLPRWGCLWED |
| 267 | RLMEDICLARWGCLWEDD |
| 268 | EVRSFCTRWPAEKSCKPLRG |
| 269 | RAPESFVCYWETICFERSEQ |
| 270 | EMCYFPGICWM |

Effector Molecules

If desired a multispecific molecule for use in the present invention may be conjugated to one or more effector molecule(s). It will be appreciated that the effector molecule may comprise a single effector molecule or two or more such molecules so linked as to form a single moiety that can be attached to the multispecific molecules of the present invention. Where it is desired to obtain an antibody or multispecific molecule according to the present disclosure linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

In one embodiment the multispecific molecules of the present disclosure may comprise an effector molecule.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) as such methoxypoly(ethyleneglycol) or derivatives thereof Functional Assays Typically suitable binding domains for use in the present invention can be identified by testing one or more binding domain pairs in a functional assay. For example an anti-CD22 antibody molecule such as a multi specific molecule comprising a binding domain specific to the antigen CD22 and a binding domain specific to the antigen CD79a and/or CD79b may be tested in one or more functional assays.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays.

The efficacy of multispecific antibodies according to the present disclosure can be compared to individual antibodies or mixtures of antibodies (or fragments) in such models by methods generally known to one of ordinary skill in the art.

The functional assays may be repeated a number of times as necessary to enhance the reliability of the results. Various statistical tests known to the skilled person can be employed to identify statistically significant results and thus identify multispecific molecules with biological functions.

Examples of suitable functional assays are described in the Examples herein and include measuring the ability of a multispecific molecule of the present invention to inhibit B cell activation following stimulation with anti-IgM, as measured by detecting the inhibition of markers of B cell activation such as phosphorylated Akt expression, phosphorylated P38 expression, PLCγ signalling, CD40 expression, CD71 expression and/or CD86 expression.

In one example an antibody molecule, such as a multispecific antibody, of the present invention has an IC50 of less than 5 nM for inhibition of CD86 expression in anti-IgM stimulated B cells.

In one embodiment in vivo assays, such as animal models, including mouse tumor models, models of auto-immune disease, virus-infected or bacteria-infected rodent or primate models, and the like, may be employed to test molecules of the present disclosure.

"Fusion proteins" as employed herein comprise a protein component, for example A or B fused to another entity, for example a binding partner X or Y (as appropriate). In embodiment the fusion protein is a translational protein expressed by a recombinant techniques from a genetic construct, for example expressed in a host from a DNA construct.

The function of the tether X:Y is to retain the proteins A and B in proximity to each other so that synergistic function of A and B can be realised.

"heterodimeric-tether" as used herein refers to a tether comprising two different binding partners X and Y which form a interaction (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein. In one embodiment "unsuitable for forming homodimers" as employed herein refers to formation of the heterodimers of X-Y are more preferable, for example stable, such as thermodynamically stable and/or physically stable (for example evidenced by lack of aggregation), once formed.

In one embodiment the X-Y interaction is more favourable than the X-X or Y-Y interaction. This reduces the formation of homodimers X-X or Y-Y when the fusion proteins A-X and B-Y are mixed. This also renders removal of homodimers relatively simple, for example, one purification step, such as column chromatography provides substantially pure fusion proteins and/or bispecific protein complexes according to the present disclosure.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer, for example one of the binding partners is a peptide and the other binding partner is a Vim specific to said peptide.

In one embodiment a scFv employed in the molecules of the present disclosure is incapable of forming a homodimer.

Incapable of forming homodimers as employed herein, refers to a low or zero propensity to form homodimers. Low as employed herein refers to 5% or less, such as 4, 3, 2, 1, 0.5% or less aggregate.

In one embodiment: is a binding interaction, for example based on attractive forces such as Van der Waals forces, such as hydrogen bonding and electrostatic interactions, for example, based on antibody specificity for an antigen, such as a peptide.

In one embodiment: is not a covalent bond.

"Form the complex" as employed herein refers to an interaction, including a binding interactions or a chemical reaction, which is sufficiently specific and strong when the fusion protein components A-X and B-Y are brought into contact under appropriate conditions that the complex is assembled and the fusion proteins are retained together.

"Retained together" as employed herein refers to the holding of the components (the fusion proteins) in the proximity of each other, such that after binding the complex can be handled as if it were one molecule, and in many instances behaves and acts like a single molecule. In one embodiment the retention renders the complex suitable for use in the method disclosed herein, i.e. suitable for use in at least one functional screen.

In one embodiment the binding interaction is reversible.

Specificity when in relation to X and Y as employed herein refers where the binding partners X and Y in the interaction only recognise each other or have significantly higher affinity for each other in comparison to non-partners, for example at least 2, 3, 4, 5, 6, 7, 8, 9, 10 times higher affinity.

In one embodiment, the binding interaction between X and Y has a low dissociation constant.

Examples of a low dissociation constant include $1\text{-}9\times10^{-2}$ $s^{-1}$ or less, for example $1\text{-}9\times10^{-3}$ $s^{-1}$, $1\text{-}9\times10^{-4}$ $s^{-1}$, $1\text{-}9\times10^{-5}$ $s^{-1}$, $1\text{-}9\times10^{-6}$ $s^{-1}$ or $1\text{-}9\times10^{-7}$ $s^{-1}$. Particularly suitable dissociation constants include $1\times10^{-4}$ $s^{-1}$ or less, for example $1\times10^{-5}$ $s^{-1}$, $1\times10^{-6}$ $s^{-1}$ or $1\times10^{-7}$ $s^{-1}$.

Whilst not wishing to be bound by theory it is thought that the low dissociation constant (also referred to as off rate) allows the molecules to be sufficiently stable to render the bispecific protein complex useful, in particular in functional screening assays.

In one embodiment, the affinity of X and Y for each other is 5 nM or stronger, for example 4 nM, 3 nM, 2 nM, 1 nM or stronger.

In one embodiment, the affinity of X and Y for each other is 900 pM or stronger, such as 800, 700, 600, 500, 400, 300, 200, 100 or 50 pM or stronger.

In another embodiment, the affinity of X and Y for each other is 10 pM or stronger, for example 9, 8, 7, 6 or 5 pM.

Affinity is a value calculated from the on and off rate of an interaction. The term "affinity" as used herein refers to the strength of the sum total of non-covalent interactions between a single binding site of a molecule (e.g. an antibody) and its binding partner (e.g. a peptide). The affinity of a molecule for its binding partner can generally be represented by the equilibrium dissociation constant (KD). Affinity can be measured by common methods known in the art, including those described herein, such as surface plasmon resonance methods, in particular BIAcore.

In one embodiment, multiple bispecific protein complexes according to the present disclosure are tested in parallel or essentially simultaneously.

Simultaneously as employed herein refers to the where the samples/molecules/complexes are analysed in the same analysis, for example in the same "run".

In one embodiment simultaneously refers to concomitant analysis where the signal output is analysed by the instrument at essentially the same time. This signal may require deconvolution to interpret the results obtained.

Advantageously, testing multiple bispecific protein complexes allows for more efficient screening of a large number of bispecific protein complexes and the identification of new and interesting relationships. Clearly different variable regions to the target antigens of interesting CD22 and CD79 can give access to subtle nuances in biological function.

In one embodiment, the multiple bispecific protein complexes are tested by using a multiplex as defined above and subjecting the same to one or more functional assays.

The term "biological function" as used herein refers to an activity that is natural to or the purpose of the biological entity being tested, for example a natural activity of a cell, protein or similar. Ideally the presence of the function can be tested using an in vitro functional assay, including assays utilizing living mammalian cells. Natural function as employed herein includes aberrant function, such as functions associated with cancers.

In one embodiment a multispecific antibody molecule according to the present disclosure has a novel or synergistic function.

The term "synergistic function" as used herein refers to biological activity that is not observed or higher than observed when the first and second proteins of a bispecific protein complex of the present disclosure are not employed together, for example activity which is only observed in a bispecific form. Therefore, "synergistic" includes novel biological function.

Novel biological function as employed herein refers to function which is not apparent or absent until the two or more synergistic entities [protein A and protein B] are brought together (as a bispecific or otherwise) or a previously unidentified function.

Higher as employed herein refers to an increase in activity including an increase from zero i.e. some activity in the bispecific where the individual uncomplexed bispecific component or components has/have no activity in the relevant functional assay, also referred to herein as new activity or novel biological function. Higher as employed herein also includes a greater than additive function in the bispecific in a relevant functional assay in comparison to the individual uncomplexed bispecific components or bivalent binding domains, for example 10, 20, 30, 40, 50, 60, 70, 80, 90, 100, 200, 300% or more increase in a relevant activity.

In one embodiment the novel synergistic function is a higher inhibitory activity.

In one embodiment the multispecific antibody molecule of the present invention has a higher inhibitory activity than the sum of the activity of a bivalent binding domain to CD22 and a bivalent binding domain to CD79a provided alone or in admixture.

In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number P05412 and P05627 respectively), human influenza hemagglutinin (HA), polyhistidine (His), green fluorescent protein (GFP) and FLAG. Other peptides are also contemplated as suitable for use in the present disclosure and particularly suitable peptides are affinity tags for protein purification because such peptides have a tendency to bind with high affinity to their respective binding partners.

The term "peptide" as used herein refers to a short polymer of amino acids linked by peptide bonds, wherein the peptide contains in the range of 2 to 100 amino acids, for example 5 to 99, such as 6 to 98, 7 to 97 or 8 to 96. In one embodiment a peptide employed in the present disclosure is an amino acid sequence of 50 amino acid residues or less, for example 40, 30, 10 or less. The peptides used in the present disclosure are of a sufficient length to be fit for purpose, for example if the peptide is a linker, it needs to be suitably long to allow the fragment which it links to perform its biological function; alternatively if the peptide is a binding partner, it must be capable of binding specifically to another entity such as an antibody.

In one embodiment, the other binding partner of the binding pair (the alternative first or second binding partner) is a protein.

Protein as employed herein refers to an amino acid sequence of 100 amino acids or more. In one embodiment a "protein" as employed herein refers to an amino acid sequence with a secondary or tertiary structure.

In one embodiment, the first protein, A, and/or second protein, B, of the bispecific protein complex is an antibody or antibody fragment. Such a bispecific protein complex may be referred to as a bispecific antibody complex.

In one embodiment each antibody or fragment employed in the bispecific antibody complex of the disclosure comprises one binding site.

The full length antibody or antibody fragment employed in the fusion proteins (A-X or B-Y) may be monospecific, multivalent or bispecific.

Advantageously, the use of two bispecific antibody or antibody fragments allows the molecules of the present disclosure, such as the bispecific antibody complex described herein to potentially be specific for up to 4 different antigens (i.e. the complex may be tetraspecific). This allows avidity type effects to be investigated.

In one embodiment, the antibody or antibody fragment employed in the molecules of the present disclosure or components thereof, such as the first fusion protein A-X is a monospecific antibody or antibody fragment, for example a Fab, Fab', scFv or similar, and in particular is specific to CD22.

In one embodiment, the antibody or antibody fragment employed in the molecules of the present disclosure or components thereof, such as the second fusion protein B-Y is a monospecific antibody or antibody fragment, for example a Fab, Fab', scFv or similar, and in particular is specific to CD79a and/or CD79b.

In one embodiment, the antibody or antibody fragment employed in the molecules of the present disclosure or components thereof, such as the second fusion protein B-Y is multivalent, that is has two or more binding domains.

In one embodiment, the antibody or antibody fragment employed in the molecules of the present disclosure or components thereof, such as the first fusion protein A-X is monovalent and the antibody or antibody fragment employed in the molecules of the present disclosure or components thereof, such as the second fusion protein B-X is monovalent.

Thus in one embodiment the binding domains of the multispecific molecules of the present disclosure are monovalent.

Thus in one embodiment the binding domains of the multispecific molecules of the present disclosure are monovalent and monospecific.

In one embodiment, the antibody or antibody fragment employed in the molecules of the present disclosure or components thereof, such as the first fusion protein A-X is monovalent and the antibody or antibody fragment employed in the molecules of the present disclosure or components thereof, such as the second fusion protein B-Y is multivalent.

In one embodiment, the antibody or antibody fragment employed in the molecules of the present disclosure or components thereof, such as the first fusion protein A-X is multivalent and the antibody or antibody fragment employed in the molecules of the present disclosure or components thereof, such as the second fusion protein B-Y is monovalent.

In one embodiment, the antibody or antibody fragment employed in the molecules of the present disclosure or components thereof, such as the first fusion protein A-X is multivalent and the antibody or antibody fragment employed in the molecules of the present disclosure or components thereof, such as the second fusion protein B-Y is multivalent.

In one embodiment, a first antibody, a second antibody or both the first and second antibody of a the molecules of the present disclosure or components thereof, such as a bispecific antibody complex may be an IgG format, for example an anti-CD22 and/or anti-CD79 antibody may be provided in an IgG format.

In one embodiment, an antibody fragment is selected from the group consisting of: a fragment antigen (Fab) fragment, a single chain variable fragment (scFv) and a single domain antibody (sdAb), such as a scFv, is employed in the first (A-X) or second fusion protein (B-Y). Advantageously, the small size of a scFv may facilitate the correct folding of the bispecific antibody complexes.

In one embodiment, the first (A), second antibody/fragment (B) or both the first and second antibody/fragment of the bispecific antibody complex of the present disclosure may be a Fab.

In one embodiment, the first, second antibody/fragment or both the first and second antibody/fragment of the bispecific antibody complex of the present disclosure is/are a Vim.

"Fusion protein" as employed in the context of a bispecific complex of the present disclosure refers to a protein, for example an antibody or antibody fragment attached to a binding partner.

For convenience bispecific protein complexes of the present disclosure are referred to herein as A-X:Y-B. However, this nomenclature is not intended to limit how the fusion protein A-X and B-Y are designed because our experiments indicate that binding partners X and Y can be reversed i.e. A-Y and B-X without adversely impacting on the method. Thus A and B and X and Y are nominal labels referred to for assisting the explanation of the present technology.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair.

In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

In one embodiment, the first binding partner (X) is selected from the group comprising: a full length antibody, a Fab, a Fab', a scFv, a peptide and a sdAb, wherein examples of a sdAb include VH or VL or $V_H H$.

In one embodiment, the second partner (Y) is selected from the group comprising: a full length antibody, a Fab, a Fab', a scFv, a peptide and a sdAb, wherein examples of a sdAb include VH or VL or $V_H H$.

In one embodiment, where A is an antibody or fragment thereof the first binding partner (X) is attached to the C-terminal of the heavy or light chain of the first antibody or antibody fragment, for example, the first binding partner is attached to the C-terminal of the heavy chain of the first antibody or antibody fragment.

In another embodiment, where B is an antibody or fragment thereof the second binding partner (Y) is attached to the C-terminal of the heavy or light chain of the second antibody or antibody fragment, for example the second binding partner is attached to the C-terminal of the heavy chain of the second antibody or antibody fragment.

In one embodiment X is attached to the C-terminal of the heavy chain of the antibody or fragment (protein A) and Y is attached to the C-terminal of the antibody or fragment (protein B).

In one embodiment X is attached via a linker (such as ASGGGG or ASGGGGSG) to the C-terminal of the heavy chain of the antibody or fragment (protein A) and Y is attached via a linker (such as ASGGGG or ASGGGGSG) to the C-terminal of the antibody or fragment (protein B).

In one embodiment, the first or second binding partner (X or Y) is a peptide.

Examples of a suitable binding pair may include GCN4 (SEQ ID NO: 247) or a variant thereof and 52SR4 (SEQ ID NO: 249) or a variant thereof, which is a scFv specific for GCN4.

In a one embodiment, the first binding partner (nominally X) is GCN4 (for example as shown in SEQ ID NO: 247) or a variant thereof (for example without the His tag) and the second binding partner (nominally Y) is a scFv specific for GCN4 (for example as shown in SEQ ID NO: 249 or a variant thereof.

In a one embodiment, the first binding partner (nominally X) is a sFv specific for GCN4 (for example as shown in SEQ ID NO: 249) or a variant thereof and the second binding partner (nominally Y) is GCN4 (for example as shown in SEQ ID NO: 247) or a variant thereof.

GCN4 variants include an amino acid sequence with at least 80%, 85%, 90%, 91%, 92%, 93%, 94% 95%, 96%, 97% or 98%, or 99% identity to SEQ ID NO: 247. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO: 248, or a nucleotide sequence which hybridises to SEQ ID NO: 145 under stringent conditions.

A suitable scFv specific to GCN4 is 52SR4 (SEQ ID NO: 146) or a variant thereof. Variants of 52SR4 include an amino acid sequence with at least 80%, or 85%, or 90%, or 95%, or 98%, or 99% identity to SEQ ID NO: 250. 52SR4 variants also include an amino acid sequence having at least at least 80%, or 85%, or 90%, or 95%, or 98%, or 99% to a sequence encoded by a nucleotide sequence SEQ ID NO: 146, or a nucleotide sequence which hybridises to SEQ ID NO: 248 under stringent conditions.

The present inventors have found that the single chain antibody 52SR4 and peptide GCN4, are a binding pair suitable for use in the bispecific protein complexes of the present disclosure.

Alternatively, any suitable antibody/fragment and antigen (such as a peptide) may be employed as X and Y.

In one embodiment, the first binding partner (X) and the second binding partner(Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, N.J., 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In one embodiment, the first or second binding partner (X or Y) is a protein or peptide.

In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker.

The term "peptide linker" as used herein refers to a peptide with amino acid sequences. A range of suitable peptide linkers will be known to the person of skill in the art.

In one embodiment, the peptide linker may be of synthetic origin, i.e. prepared by synthetic chemistry techniques.

In one embodiment, the binding partners of the bispecific protein complexes are joined to their respective proteins via peptide linkers.

In one embodiment the fusion proteins is a translational fusion, that is a fusion protein expressed in a host cells comprising a genetic construct from which the fusion protein is expressed.

In one embodiment the fusion protein is prepared by conjugating the A to X or B to Y optionally via a peptide linker.

In one embodiment, the peptide linker is 50 amino acids in length or less, for example 20 amino acids of less.

Generally it will be more efficient to express the fusion protein recombinantly and therefore a direct peptide bond or a peptide linker that can be expressed by a host cell may be advantageous.

In one embodiment the complexes formed require no further purification steps. In one embodiment the complexes formed require one purification step, for example column chromatography.

In one embodiment the method further comprises at least one purification step, for example after expression of a fusion protein according to the present disclosure.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays, In one embodiment in vivo assays, such as animal models, including mouse tumor models, models of auto-immune disease, virus-infected or bacteria-infected rodent or primate models, and the like, may be employed to test molecules of the present disclosure.

In the context of bispecific antibody complexes, the efficacy of bispecific antibody complexes according to the present disclosure can be compared to individual antibodies or mixtures of antibodies (or fragments) in such models by methods generally known to one of ordinary skill in the art.

The functional assays may be repeated a number of times as necessary with or without different samples of a particular bispecific antibody complex to enhance the reliability of the results. Various statistical tests known to the skilled person can be employed to identify statistically significant results and thus identify bispecific antibody complexes with biological functions, and in particular to identify optimal variable region pairs for use in multispecific molecule of the present invention.

Compositions and Medical Uses

In one aspect there is provided a molecule according to the present disclosure or a component, such as a fusion protein, a heterodimerically-tethered bispecific protein complex, a composition comprising a molecule of the invention, including a fusion protein or said bispecific protein complex, a multiplex, array, library as defined herein.

In one embodiment the molecules of the present disclosure, for example an antibody described herein, a multispecific molecule and a bispecific protein complex are suitable for therapeutic applications and may provide novel therapies for treating diseases. Thus in a further aspect, there is provided an antibody molecule of the present disclosure, for example a bispecific protein complex as described above, for use in therapy. The molecules of the present disclosure including the bispecific protein complexes described herein are suitable for treating a range of diseases, such as cancer.

The molecules of the present disclosure, including the multispecific molecules and bispecific protein complexes described herein are also particularly suited for inhibiting B cell function in order to control immune and autoimmune reactions in various autoimmune diseases.

Thus, the present disclosure extends to a method of treating a disease in a patient, comprising the administration of a therapeutically effect amount of a molecule of the present disclosure, for example a multispecific molecule or bispecific protein complex of the present disclosure.

In one aspect, there is provided a pharmaceutical composition comprising one or more molecules of the present disclosure, for example a multispecific molecule of the present disclosure.

Various different components can be included in the composition, including pharmaceutically acceptable carriers, excipients and/or diluents. The composition may, optionally, comprise further molecules capable of altering the characteristics of the population of multispecific molecules of the invention thereby, for example, reducing, stabilizing, delaying, modulating and/or activating the function of the antibodies. The composition may be in solid, or liquid form and may be, inter alia, be in the form of a powder, a tablet, a solution or an aerosol.

The present invention also provides a pharmaceutical or diagnostic composition comprising an antibody molecule or a multispecific molecule of the present invention in combination with one or more of a pharmaceutically acceptable excipient, diluent or carrier. Accordingly, provided is the use of a multispecific molecule of the invention for use in the treatment and for the manufacture of a medicament for the treatment of a pathological condition or disorder.

Pathological Conditions

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In one embodiment the disorder is cancer, for example leukemia, including lyphocytic leukemia, such as acute lymphoblastic leukemia or chronic lymphocytic leukemia; or myelogenus leukemia, such as acture myelogenous leukemia or chronic myelogenous leukemia.

In one embodiment autoimmune disease includes:— Acute disseminated encephalomyelitis (adem), acute necrotizing hemorrhagic leukoencephalitis, Addison's disease, adrenal insufficiency, hypocortisolism, alopecia areata, amyloidosis, ankylosing spondylitis, spondyloarthritis, Strumpell-marie disease, anti-GBM/anti-TBM nephritis, antiphospholipid syndrome (aps), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), Canale-Smith syndrome, autoimmune myocarditis, autoimmune oophoritis, autoimmune pancreatitis (AIP), autoimmune polyglandular syndromes(types I, II & III), autoimmune retinopathy (AR), autoimmune thrombocytopenic purpura (ATP), autoimmune thyroid disease, autoimmune urticaria, axonal/neuronal neuropathies, balo disease, Behcet's disease, bullous pemphigoid, cardiomyopathy, Castleman disease, coeliac disease, chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid (CP), Crohn's disease, inflammatory bowel disease, colitis, enteritis, ileitis, Cogans syndrome, cold agglutinin disease, congenital heart block, Coxsackie myocarditis, crest disease, cryoglobulinemia, demyelinating neuropathies, dermatitis herpetiformis, Duhring's disease, dermatomyositis, diabetes, type I, discoid lupus erythematosus (DLE), Dressler's syndrome, endometriosis, epidermolysis bullosa (EB) and eb acquisita (EBA), eosinophilic gastroenteritis, esophagitis, eosinophilic fasciitis, schulman's syndrome, erythema nodosum, experimental allergic encephalomyelitis, Evans syndrome, fibrosing alveolitis, giant cell arteritis (temporal arteritis), giant cell myocarditis, glomerulonephritis (non-proliferative: focal segmental glomerulosclerosis and membranous glomerulonephritis. proliferative: IgA nephropathy), goodpasture's syndrome, granulomatosis with polyangiitis (GPA) (formerly called Wegener's granulomatosis), Graves' disease, Guillain-Barré syndrome, Miller Fisher syndrome, acute motor axonal neuropathy, acute motor sensory axonal neuropathy, acute panautonomic neuropathy, Bickerstaff s brainstem encephalitis, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy (IGAN), berger's syndrome, synpharyngitic glomerulonephritis, IgA pemphigus, IgG4-related sclerosing disease, immune-regulated infertility, inclusion body myositis, insulin-dependent diabetes mellitus, interstitial cystitis, Isaac's syndrome, neuromyotonia, juvenile arthritis, juvenile myositis, Kawasaki syndrome, Lambert-Eaton syndrome, leukocytoclastic vasculitis, lichen planus, lichen sclerosus, ligneous conjunctivitis, linear IgA dermatosis (LAD), pemphigoid, lupus (SLE), lyme disease, Meniere's disease, microscopic polyangiitis (MPA), mixed connective tissue disease (MCTD), monoclonal gammaopathy, Mooren's ulcer, Mucha-Habermann disease, multiple sclerosis, myasthenia gravis, myositis, narcolepsy, neuromyelitis optica (device's), neuromyotonia, Isaac's syndrome (acquired, paraneoplastic, hereditary), neutropenia, ocular cicatricial pemphigoid, optic neuritis, oophoritis, opsoclonus-myoclonus syndrome, orchitis, palindromic rheumatism, pandas (pediatric autoimmune neuropsychiatric disorders associated with *streptococcus*), paraneoplastic autoimmune multiorgan syndrome (PAMS), paraneoplastic cerebellar degeneration, paraneoplastic pemphigus (PNP), paroxysmal nocturnal hemoglobinuria (PNH), Parry Romberg syndrome, Parsonnage-Turner syndrome, pars planitis (peripheral uveitis), pempgigoid gestationis (PG), pemphigus vulgaris (PV), pemphigus folliaceus (PF), peripheral neuropathy, perivenous encephalomyelitis, pernicious anemia, Poems syndrome, polyarteritis nodosa (PAN), polymyalgia rheumatic, polymyositis, postmyocardial infarction syndrome, postpericardiotomy syndrome, progesterone dermatitis primary biliary cirrhosis, Hanot syndrome, primary sclerosing cholangitis (PSC), sclerosong cholangitis, psoriasis, psoriatic arthritis, pyoderma gangrenosum, pure red cell aplasia, Rasmussen's encephalitis, chronic focal encephalitis (CFE), Raynauds phenomenon, reactive arthritis, Reiter's syndrome, recoverin-associated retinopathy (RAR), reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, systemic sclerosis, sjogren's syndrome, sperm & testicular autoimmunity, stiff person/man syndrome, subacute bacterial endocarditis (SBE), Susac's syndrome, sympathetic ophthalmia, Takayasu's arteritis, temporal arteritis/giant cell arteritis, thromboangiitis obliterans, Buerger's disease, thrombocytopenic purpura (TTP), Tolosa-Hunt syndrome, transverse myelitis, ulcerative colitis, undifferentiated connective tissue disease (UCTD), uveitis, polymyalgia rheumatica, Takayasu's arteritis, temporal arteritis, Buerger's disease, cutaneous vasculitis, Kawasaki disease, polyarteritis nodosa, Behçet's syndrome, Churg-Strauss syndrome, cutaneous vasculitis, Henoch-Schonlein purpura, microscopic polyangiitis, Wegener's granulomatosis, golfer's vasculitis, vesiculobullous dermatosis, Vitiligowegener's granulomatosis (now termed granulomatosis with polyangiitis (GPA).

In one embodiment the autoimmune disease is selected from the group comprising or consisting of:—ANCA vasculitis, IgA nephropathy (Berger's), pemphigus vulgaris/bullous pemphigoid, ITP, primary biliary cirrhosis, autoimmune thyroiditis (Grave's disease), hashimoto's disease, lupus nephritis, membranous glomerulonephritis (or membranous nephropathy), APS, myasthenia gravis, neuromyelitis optica, primary Sjogren's, autoimmune neutropaenia, autoimmune pancreatitis, dermatosmyositis, autoimmune uveitis, autoimmune retinopathy, Behçet's disease, IPF, systemic sclerosis, liver fibrosis, autoimmune hepatitis, primary sclerosing cholangitis, vitiligo, goodpasture's syndrome, pulmonary alveolar proteinosis, chronic autoimmune urticarial, psoriasis, rheumatoid arthritis, psoriatic arthritis, axial spodyloarthritis, transplantation (including GvHD), asthma, COPD, giant cell arteritis, refractory autoimmune cytopaenias, Evans syndrome (autoimmune haemolytic anaemia), type I diabetes, sarcoidosis, polymyositis, ulcerative colitis, Crohn's disease, coeliac disease, Waldenstrom's macroglobulinaemia, focal segmental glomerulosclerosis, chronic Lyme disease (Lyme borreliosis), lichen planus, Stiff person syndrome, dilated cardiomyopathy, autoimmune (lymphocytic) oophoritis, epidermolysis bullosa acquisita, autoimmune atrophic gastritis, pernicious anaemia, atopic dermatitis, atherosclerosis, multiple sclerosis, Rasmussen's encephalitis, Guillain-Barré syndrome, acquired neuromyotonia, stroke.

In one embodiment the disorder is cancer, for example Leukemia, for example lyphocytic leukemia, such as acute lymphoblastic leukemia or chronic lymphocytic leukemia; or myelogenus leukemia, such as acture myelogenous leukemia or chronic myelogenous leukemia; or lymphoma, such as diffuse large B cell lymphoma or Hodgkin's or non-Hodkin's lymphoma.

The present invention also provides a pharmaceutical or diagnostic composition comprising a molecule of the present disclosure, such as a multispecific molecule described herein in combination with one or more of a pharmaceutically acceptable excipient, diluent or carrier. Accordingly, provided is the use of a molecule of the present disclosure, such as a multispecific molecule as described herein for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the multispecific molecule of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragees, capsules, liquids, gels, syrups, slurries and suspensions, for ingestion by the patient.

The molecules of the disclosure such as a multispecific molecule described herein can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the multispecific molecule of the present disclosure is administered depends on the nature of the condition to be treated, the extent of the inflammation present and on whether the antibody molecule is being used prophylactically or to treat an existing condition.

The frequency of dose will depend on the half-life of the multispecific molecule and the duration of its effect. If the multispecific molecule has a short half-life (e.g. 2 to 10 hours) it may be necessary to give one or more doses per day. Alternatively, if the multispecific molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the multispecific molecule, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

Where the product is for injection or infusion, it may take the form of a suspension, solution or emulsion in an oily or aqueous vehicle and it may contain formulatory agents, such as suspending, preservative, stabilising and/or dispersing agents. Alternatively, the multispecific molecule may be in dry form, for reconstitution before use with an appropriate sterile liquid. If the composition is to be administered by a route using the gastrointestinal tract, the composition will need to contain agents which protect the antibody from degradation but which release the bispecific protein complex once it has been absorbed from the gastrointestinal tract.

A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

In one embodiment the construct of the present disclosure is at least trispecific. In this situation the further specificity may be directed to any antigen of interest, for example antigens to extend half-life such as albumin or Fc neonatal receptor (FcRn); antigens for effector function such as activating or inhibiting Fc receptors or costimulatory molecules; tissue or cell targeting antigens; or antigens to aid blood/brain barrier (BBB) transfer such as transferrin receptor or LRP1.

The disclosure also extends to compositions, such as pharmaceutical compositions comprising said novel formats with the particular antigen specificity.

In a further aspect the disclosure includes use of the formats and the compositions in treatment.

The present invention also provides a process for preparation of a pharmaceutical or diagnostic composition comprising adding and mixing the antibody molecule or multispecific molecule of the present invention together with one or more of a pharmaceutically acceptable excipient, diluent or carrier.

The antibody molecule or multispecific molecule may be the sole active ingredient in the pharmaceutical or diagnostic composition or may be accompanied by other active ingredients including other antibody ingredients or non-antibody ingredients such as steroids or other drug molecules.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

Agents as employed herein refers to an entity which when administered has a physiological affect.

Drug as employed herein refers to a chemical entity which at a therapeutic dose has an appropriate physiological affect.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) and/or long lasting pharmacodynamics (PD) profile it may only be necessary to give a dosage once per day, once per week or even once every 1 or 2 months.

In one embodiment the dose is delivered bi-weekly, i.e. twice a month.

In one embodiment doses are spaced to allow anti-drug (in this case anti-antibody) responses to waine before administration of further dose.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the μl of the protein is in the range 8-9 or above then a formulation pH of 7 may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example a nebulizer connected to a compressor (e.g., the Pari LC-Jet Plus® nebulizer connected to a Pari Master® compressor manufactured by Pari Respiratory Equipment, Inc., Richmond, Va.).

The antibody or multispecific molecule of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

In one embodiment, the molecule of the present disclosure, such as an antibody molecule described herein may be used to functionally alter the activity of the antigen or antigens of interest. For example, the antibody molecule of the disclosure may neutralize, antagonize or agonise the activity of said antigen or antigens, directly or indirectly.

In one embodiment, molecules of the present disclosure including fusion proteins, bispecific proteins complexes or compositions comprising same are provided for use as a laboratory reagent.

The present disclosure also extends to a kit, comprising a molecule of the present disclosure or a component thereof. In one embodiment the kit comprises:
a) one or more fusion proteins (A-X) comprising a first antibody or antibody fragment (A) specific to CD22 or CD79a and/or CD79b attached to a first binding partner of a binding pair (X); and
b) one or more fusion proteins (B-Y) comprising a second antibody or antibody fragment (B) specific to CD22 or CD79a and/or CD79b attached to a second binding partner of the binding pair (Y), wherein the latter is specific for the first binding partner; for example wherein the first binding partner (X) is a peptide or polypeptide and the second binding (Y) partner is an antibody or antibody fragment specific thereto;
wherein Y the second binding partner is specific to the first binding partner X and the second binding partner is, for example an antibody or antibody fragment specific thereto; and the specific interaction (such as a binding interaction) of the two binding partners forms a heterodimer-tether which physically brings the two fusion proteins from a) and b) together to form a bispecific protein complex; and
wherein at least one of A or B is specific to CD22 and the other is specific to CD79a and/or CD79b, and the fusion protein(s) is/are in a complexed or a non-complexed form.

Advantageously, the kit may comprise bispecific protein complexes of the present disclosure, or may comprise fusion proteins which are in a complexed or non-complexed form. In the former case, the bispecific protein complexes are ready for use "out of the box" which provides convenience and ease of use, whereas in the latter case, the bispecific protein complexes can be assembled according to the user's requirements by using combining different fusion proteins.

In another embodiment, the kit further comprises instructions for use.

In yet another embodiment, the kit further comprises one or more reagents for performing one or more functional assays.

In one embodiment, molecules of the present disclosure including fusion proteins, bispecific proteins complexes or compositions comprising same are provided for use as a laboratory reagent.

FURTHER ASPECTS

In a further aspect, there is provided a nucleotide sequence, for example a DNA sequence encoding a construct as described herein including a multispecific molecule or a fusion protein as defined above.

In one embodiment, there is provided a nucleotide sequence, for example a DNA sequence encoding a construct as described herein including a multispecific molecule or a bispecific protein complex or an antibody according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example E. coli, and other microbial systems may be used or eukaryotic, for example mammalian, host cell expression systems may also be used. Suitable mammalian host cells include CHO, myeloma or hybridoma cells.

The present disclosure also provides a process for the production of a molecule according to the present disclosure or a component thereof comprising culturing a host cell containing a vector of the present disclosure under conditions suitable for leading to expression of protein from DNA encoding the molecule of the present disclosure, and isolating the molecule.

The molecules of the present disclosure including the bispecific protein complexes described herein may be used in diagnosis/detection kits. The kits may, for example comprise bispecific antibody complexes that are specific for two antigens, both of which are present on the same cell type, and wherein a positive diagnosis can only be made if both antigens are successfully detected. By using a molecule of the present disclosure such as a bispecific antibody complexes described herein rather than two separate antibodies or antibody fragments in a non-complexed form, the specificity of the detection can be greatly enhanced.

In one embodiment, the molecules of the present disclosure such as the bispecific antibody complexes are fixed on a solid surface. The solid surface may for example be a chip, or an ELISA plate.

Further provided is the use of a molecule according to the present disclosure, for example a bispecific protein complex described herein for detecting in a sample the presence of a first and a second peptide, whereby the said molecules are used as detection agents.

The molecules of the present disclosure such as the bispecific antibody complexes described herein may for example be conjugated to a fluorescent marker which facilitates the detection of bound antibody-antigen complexes. Such bispecific antibody complexes can be used for immunofluorescence microscopy. Alternatively, the bispecific antibody complexes may also be used for western blotting or ELISA.

In one embodiment, there is provided a process for purifying a molecule according to the present disclosure or a component thereof In one embodiment, there is provided a process for purifying a molecule according the present disclosure or a component thereof comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements. Positively recited embodiments may be employed herein as a basis for a disclaimer.

All references referred to herein are specifically incorporated by reference.

The sub-headings herein are employed to assist in structuring the specification and are not intended to be used to contruct the meaning of technical terms herein.

Sequences of the disclosure are provided in FIG. 35.

In the context of this specification "comprising" is to be interpreted as "including".

Aspects of the disclosure comprising certain elements are also intended to extend to alternative embodiments "consisting" or "consisting essentially" of the relevant elements. Positively recited embodiments may be employed herein as a basis for a disclaimer.

All references referred to herein are specifically incorporated by reference.

Paragraphs

1. An antibody molecule comprising a binding domain specific to CD22 wherein the binding domain comprises a heavy chain variable domain (VH) comprising a: CDRH1 of formula (I):

(SEQ ID NO: 1)
$GX_1X_2FSX_3X_4X_5X_6X_7X_8$ wherein $X_1$ is F, I or L (such as F), $X_2$ is S or D, $X_3$ is S, N or G (such as S), $X_4$ is S, Y, L or G, $X_5$ is Y or absent, $X_6$ is W, Y or D (such as W or Y, particularly Y), $X_7$ is M or I and $X_8$ is C or S (particularly S);

CDRH2 of formula (II):

(SEQ ID NO: 2)
$X_9LX_{10}X_{11}X_{12}X_{13}X_{14}X_{15}X_{16}TX_{17}YAX_{18}WAKG$ wherein $X_9$ is C or S, $X_{10}$ is Y, D, V or N, $X_{11}$ is T, P, I, G, S or A, $X_{12}$ is G, S or A (particularly G), $X_{13}$ is S, I or T, $X_{14}$ is S, N or absent, $X_{15}$ is G, D, S, A or T, $X_{16}$ is D, T, S, N, V or G, $X_{17}$ is Y, D or A and $X_{18}$ is T or S (particularly S);

CDHR3 of formula (III):

(SEQ ID NO: 3)
$X_{19}X_{20}X_{21}X_{22}X_{23}X_{24}X_{25}X_{26}X_{27}X_{28}X_{29}X_{30}X_{31}X_{32}X_{33}L$ wherein $X_{19}$ is A or absent, $X_{20}$ is G, Y, or absent, $X_{21}$ is P, G or absent, $X_{22}$ is Y, S, D, E or absent, $X_{23}$ is V, G or W, $X_{24}$ is G, S, Y or V, $X_{25}$ is Y, S, G or N, $X_{26}$ is G, A, S or T, $X_{27}$ is Y, A, G or D, $X_{28}$ is W, D, I, Y or H, $X_{29}$ is L, G, S, Y or K, $X_{30}$ is V, Q, C, S, G, T or D, $X_{31}$ is Y, A or R, $X_{32}$ is L or F, $X_{33}$ is N, Y or D (particularly D), and a light chain variable domain (VL).

2. An antibody molecule comprising a binding domain specific to CD22 wherein the binding domain comprises a light chain variable domain (VL) comprising a: CDRL1 of formula (IV):

(SEQ ID NO: 4)
$QX_{34}SX_{35}X_{36}X_{37}X_{38}X_{39}X_{40}X_{41}X_{42}LX_{43}$ wherein $X_{34}$ is A or S (particularly A), $X_{35}$ is Q or E (particularly Q), $X_{36}$ is S, N or T (particularly S), $X_{37}$ is I or V, $X_{38}$ is S, Y or G (such as S or Y), $X_{39}$ is T, S, G or N (such as S or N), $X_{40}$ is A, G, N, Y, T or R, $X_{41}$ is absent, N or K (particularly absent), $X_{42}$ is absent, E or D (particularly absent) and $X_{43}$ is A or S (particularly A);

CDRL2 of formula (V):

(SEQ ID NO: 5)
$X_{44}X_{45}SX_{46}LX_{47}S$ wherein $X_{44}$ is G, Y, L, A or S, $X_{45}$ is A, S or T (particularly A), $X_{46}$ is T, R or K (particularly T) and $X_{47}$ is A or S (particularly A);

CDRL3 has a formula (VI):

(SEQ ID NO: 6)
$AGYKSX_{48}X_{49}DX_{50}X_{51}TT$ wherein $X_{48}$ is D or E (particularly D), $X_{49}$ is S, A or T, $X_{50}$ is D or E (particularly D) and $X_{51}$ is G, A or S; or CDRL3 of formula (VII):

(SEQ ID NO: 7)
$QX_{52}X_{53}X_{54}X_{55}X_{56}SX_{57}X_{58}X_{59}X_{60}X_{61}X_{62}X_{63}X_{64}$ wherein $X_{52}$ is S, I or G (such as S or G), $X_{53}$ is Y, H or G (particularly Y), $X_{54}$ is Y, D or F (particularly Y), $X_{55}$ is G, S or Y (such as S or Y), $X_{56}$ is T, A or S (particularly S), $X_{57}$ is S, G, V or D, $X_{58}$ is G, S, L or absent, $X_{59}$ is G, R, S or N, $X_{60}$ is S, D or V (such as S or D), $X_{61}$ is W, Y or absent (such as W or Y), $X_{62}$ is A, T, G or absent, $X_{63}$ is N or absent (particularly absent), $X_{64}$ is A or absent (particularly absent), and a heavy chain variable domain (VH).

3. An antibody molecule comprising a binding domain specific to CD22 wherein the binding domain comprises a heavy chain variable domain (VH) comprising:

CDRH1 of formula (I):

(SEQ ID NO: 1)
$GX_1X_2FSX_3X_4X_5X_6X_7X_8$ wherein $X_1$ is F, I or L (such as F), $X_2$ is S or D, $X_3$ is S, N or G (such as S), $X_4$ is S, Y, L or G, $X_5$ is Y or absent, $X_6$ is W, Y or D (such as W or Y, particularly Y), $X_7$ is M or I and $X_8$ is C or S (particularly S);

CDRH2 of formula (II):

(SEQ ID NO: 2)
$X_9LX_{10}X_{11}X_{12}X_{13}X_{14}X_{15}X_{16}TX_{17}YAX_{18}WAKG$ wherein $X_9$ is C or S, $X_{10}$ is Y, D, V or N, $X_{11}$ is T, P, I, G, S or A, $X_{12}$ is G, S or A (particularly G), $X_{13}$ is S, I or T, $X_{14}$ is S, N or absent, $X_{15}$ is G, D, S, A or T, $X_{16}$ is D, T, S, N, V or G, $X_{17}$ is Y, D or A and $X_{18}$ is T or S (particularly S);

CDHR3 of formula (III):

(SEQ ID NO: 3)
$X_{19}X_{20}X_{21}X_{22}X_{23}X_{24}X_{25}X_{26}X_{27}X_{28}X_{29}X_{30}X_{31}X_{32}X_{33}L$ wherein $X_{19}$ is A or absent, $X_{20}$ is absent, G or Y, $X_{21}$ is absent, P or G, $X_{22}$ is absent, Y, S, D or E, $X_{23}$ is V, G, Y or W, $X_{24}$ is G, Y, S or V, $X_{25}$ is Y, S, G or N, $X_{26}$ is G, A, S or T, $X_{27}$ is Y, G or D, $X_{28}$ is D, I, Y, W or H, $X_{29}$ is L, G, S, Y or K, $X_{30}$ is V, Q, C, S, G, T or D, $X_{31}$ is Y, A or R, $X_{32}$ is L or F, $X_{33}$ is N, Y or D (particularly D), and a light chain variable domain (VL) comprising CDRL1 of formula (IV):

(SEQ ID NO: 4)
$QX_{34}SX_{35}X_{36}X_{37}X_{38}X_{39}X_{40}X_{41}X_{42}LX_{43}$ wherein $X_{34}$ is A or S (particularly A), $X_{35}$ is Q or E (particularly Q), $X_{36}$ is S, N or T (particularly S), $X_{37}$ is I or V, $X_{38}$ is S, Y or G (such as S or Y), $X_{39}$ is T, S, G or N (such as S or N), $X_{40}$ is A, G, N, Y, T or R, $X_{41}$ is absent, N or K (particularly absent), $X_{42}$ is absent, E or D (particularly absent) and $X_{43}$ is A or S (particularly A);

CDRL2 of formula (V):

(SEQ ID NO: 5)
$X_{44}X_{45}SX_{46}LX_{47}S$ wherein $X_{44}$ is G, Y, L, A or S, $X_{45}$ is A, S or T (particularly A), $X_{46}$ is T, R or K (particularly T) and $X_{47}$ is A or S (particularly A);

CDRL3 has a formula (VI):

(SEQ ID NO: 6)
$AGYKSX_{48}X_{49}DX_{50}X_{51}TT$ wherein $X_{48}$ is D or E (particularly D), $X_{49}$ is S, A or T, $X_{50}$ is D or E (particularly D) and $X_{51}$ is G, A or S; or CDRL3 of formula (VII):

(SEQ ID NO: 7)
$QX_{52}X_{53}X_{54}X_{55}X_{56}SX_{57}X_{58}X_{59}X_{60}X_{61}X_{62}X_{63}X_{64}$ wherein $X_{19}$ is A or absent, $X_{20}$ is G, Y or absent, $X_{21}$ is P, D, G or absent, $X_{22}$ is Y, S, D, E or absent, $X_{23}$ is V, G or W, $X_{24}$ is G, S, Y or V, $X_{25}$ is Y, S, G or N, $X_{26}$ is G, A, S or T, $X_{27}$ is Y, A, G or D, $X_{28}$ is W, D, I, Y or H, $X_{29}$ is L, G, S, Y or K, $X_{30}$ is V, Q, C, S, G, T or D, $X_{31}$ is Y, A or R, $X_{32}$ is L or F, $X_{33}$ is N, Y or D (particularly D), and a light chain variable domain (VL) comprising.

4. An antibody molecule according to any one of paragraphs 1 to 3, wherein CDRH1 is formula (Ia):

(SEQ ID NO: 8)
$GX_1X_2FSX_3X_4XSYX_7X_8$ wherein $X_1$, $X_2$, $X_3$, $X_4$, $X_5$, $X_7$ and $X_8$ are defined above for formula (I).

5. An antibody molecule according to paragraph 4, wherein CDRH1 has a formula (Ib):

(SEQ ID NO: 9)
$GX_1X_2FSX_3X_4X_5YX_7S$ wherein $X_1$, $X_2$, $X_3$, $X_4$, $X_5$ and $X_7$ are as defined above for formula I.

6. An antibody molecule according to any one of the paragraphs 1 to 5, wherein CDRH2 has a formula (IIa):

(SEQ ID NO: 10)
$X_9LX_{10}X_{11}GX_{13}X_{14}X_{15}X_{16}TX_{17}YAX_{18}WAKG$ wherein $X_9, X_{10}, X_{11}, X_{13}, X_{14}, X_{15}, X_{16}, X_{17}$ and $X_{18}$ are as defined above for formula II.

7. An antibody molecule according to paragraph 6, wherein CDRH2 has a formula (IIb):

(SEQ ID NO: 11)
$X_9LX_{10}X_{11}X_{12}X_{13}X_{14}X_{15}X_{16}TX_{17}YASWAKG$ wherein $X_9, X_{10}, X_{11}, X_{12}, X_{13}, X_{14}, X_{15}, X_{16}$ and $X_{17}$ are as defined above for formula II, in particular a sequence of formula (IIb) wherein $X_{12}$ is G.

8. An antibody molecule according to any one of paragraphs 1 to 7, wherein CDRH3 has a formula (IIIa):

(SEQ ID NO: 12)
$X_{19}X_{20}X_{21}X_{22}X_{23}X_{24}X_{25}X_{26}X_{27}X_{28}X_{29}X_{30}X_{31}X_{32}DL$ wherein $X_{19}, X_{20}, X_{21}, X_{22}, X_{23}, X_{24}, X_{25}, X_{26}, X_{27}, X_{28}, X_{29}, X_{30}, X_{31}$ and $X_{32}$ are as defined above for formula III.

9. An antibody molecule according to any one of paragraphs 1 to 8, wherein CDRL1 has a formula (IVa):

(SEQ ID NO: 13)
$QASX_{35}X_{36}X_{37}X_{38}X_{39}X_{40}X_{41}X_{42}LX_{43}$ wherein $X_{35}, X_{36}, X_{37}, X_{38}, X_{39}, X_{40}, X_{41}, X_{42}$ and $X_{43}$ are as defined above for formula IV.

10. An antibody molecule according to paragraph 9, wherein CDRL1 has a formula (IVb):

(SEQ ID NO: 14)
$QASQX_{36}X_{37}X_{38}X_{39}X_{40}X_{41}X_{42}LX_{43}$ wherein $X_{36}, X_{37}, X_{38}, X_{39}, X_{40}, X_{41}, X_{42}$ and $X_{43}$ are as defined above for formula IV.

11. An antibody molecule according to paragraph 9 or 10, wherein CDRL1 has a formula (IVc):

(SEQ ID NO: 15)
$QASQSX_{37}X_{38}X_{39}X_{40}X_{41}X_{42}LX_{43}$ wherein $X_{37}, X_{38}, X_{39}, X_{40}, X_{41}, X_{42}$ and $X_{43}$ are as defined above for formula IV.

12. An antibody molecule according to any one of paragraphs 9 to 11, wherein CDRL1 has a formula (IIId):

(SEQ ID NO: 16)
$QASQSX_{37}X_{38}X_{39}X_{40}X_{42}LX_{43}$ wherein $X_{37}, X_{38}, X_{39}, X_{40}, X_{42}$ and $X_{43}$ are as defined above for formula IV.

13. An antibody molecule according to any one of paragraphs 9 to 11, wherein CDRL1 has a formula (IVe):

(SEQ ID NO: 17)
$QASQSX_{37}X_{38}X_{39}X_{40}LX_{43}$ wherein $X_{37}, X_{38}, X_{39}, X_{40}$, and $X_{43}$ are as defined above for formula IV.

14. An antibody molecule according to any one of paragraphs 9 to 13, wherein CDRL1 has a formula (IVf):

(SEQ ID NO: 18)
$QASQSX_{37}X_{38}X_{39}X_{40}LA$ wherein $X_{37}, X_{38}, X_{39}$ and $X_{40}$ are as defined above for formula IV.

15. An antibody molecule according to any one of paragraphs 1 to 14, wherein CDRL2 has a formula (Va):

(SEQ ID NO: 19)
$X_{44}ASX_{46}LX_{47}S$ wherein $X_{44}, X_{46}$ and $X_{47}$ are as defined above for formula V.

16. An antibody molecule according to paragraph 15, wherein CDRL2 has a formula (Vb):

(SEQ ID NO: 20)
$X_{44}ASX_{46}LAS$ wherein $X_{44}$ and $X_{46}$ are as defined above for formula V.

17. An antibody molecule according to claim 16, wherein CDRL2 has a formula (Vc):

(SEQ ID NO: 21)
$X_{44}ASTLAS$ wherein $X_{44}$ is as defined above for formula V.

18. An antibody molecule according to any one of paragraphs 1 to 17, wherein CDRL3 has a formula (VIa):

(SEQ ID NO: 22)
$AGYKSX_{48}X_{49}DX_{50}X_{51}TT$ wherein $X_{49}, X_{50}$ and $X_{51}$ are as defined above for formula V.

19. An antibody molecule according to paragraph 18, wherein CDRL3 has a formula (VIb):

(SEQ ID NO: 23)
$AGYKSDX_{49}DDX_{51}TT$ wherein $X_{49}$ and $X_{51}$ are as defined above for formula VI.

20. An antibody molecule according to any one of paragraphs 1 to 17, wherein CDRL3 has a formula (VIIa):

(SEQ ID NO: 24)
$QX_{52}YX_{54}X_{55}X_{56}SX_{57}X_{58}X_{59}X_{60}X_{61}X_{62}X_{63}X_{64}$ wherein $X_{52}, X_{54}, X_{55}, X_{56}, X_{57}, X_{58}, X_{59}, X_{60}, X_{61}, X_{62}, X_{63}$ and $X_{64}$ are as defined above for formula VII.

21. An antibody molecule according to paragraph 20, wherein CDRL3 has a formula (VIIb):

$$QX_{52}YYX_{55}X_{56}SX_{57}X_{58}X_{59}X_{60}X_{61}X_{62}X_{63}X_{64}$$ (SEQ ID NO: 25)

wherein $X_{52}$, $X_{55}$, $X_{57}$, $X_{58}$, $X_{59}$, $X_{60}$, $X_{61}$, $X_{62}$, $X_{63}$ and $X_{64}$ are as defined above for formula VII.

22. An antibody molecule according to paragraph 21, wherein CDRL3 has a formula (VIIc):

$$QX_{52}YYX_{55}SSX_{57}X_{58}X_{59}X_{60}X_{61}X_{62}X_{63}X_{64}$$ (SEQ ID NO: 26)

wherein $X_{52}$, $X_{55}$, $X_{56}$, $X_{57}$, $X_{58}$, $X_{59}$, $X_{60}$, $X_{61}$, $X_{62}$, $X_{63}$ and $X_{64}$ are as defined above for formula VII.

23. An antibody molecule according to paragraph 21 or 22, wherein CDRL3 has a formula (VIId):

$$QX_{52}YYX_{55}SSX_{57}X_{58}X_{59}X_{60}X_{61}X_{62}X_{64}$$ (SEQ ID NO: 27)

wherein $X_{52}$, $X_{55}$, $X_{57}$, $X_{58}$, $X_{59}$, $X_{60}$, $X_{61}$, $X_{62}$ and $X_{64}$ are as defined above for formula VII.

24. An antibody molecule according to paragraph 21 or 22, wherein CDRL3 has a formula (VIIe):

$$QX_{52}YYX_{55}SSX_{57}X_{58}X_{59}X_{60}X_{61}X_{62}$$ (SEQ ID NO: 28)

wherein $X_{52}$, $X_{55}$, $X_{57}$, $X_{58}$, $X_{59}$, $X_{60}$, $X_{61}$, $X_{62}$ are as defined above for formula VII.

25. An antibody molecule according to any one of paragraphs 1 to 3, wherein CDRH1 is independently selected from SEQ ID NOs: 29 to 39, CDRH2 is independently selected from SEQ ID NOs: 40 to 59, and CDRH3 is independently selected from SEQ ID NOs: 60 to 68.

26. An antibody molecule according to any one of paragraphs 1 to 3 and 25, wherein CDR H1 is SEQ ID NO: 29 or 30, CDR H2 is SEQ ID NO: 40 or 41 and CDR H3 is SEQ ID NO: 60.

27. An antibody molecule according to any one of paragraphs 1 to 3 and 25, wherein CDR H1 is SEQ ID NO: 31 or 32, CDR H2 is SEQ ID NO: 42 or 43 and CDR H3 is SEQ ID NO: 61 or 62.

28. An antibody molecule according to any one of paragraphs 1 to 3 or 25, wherein CDR H1 is SEQ ID NO: 33 or 34, CDR H2 is SEQ ID NO: 44 or 45 and CDR H3 is SEQ ID NO: 63.

29. An antibody molecule according to any one of paragraphs 1 to 3 or 25, wherein CDR H1 is SEQ ID NO: 35 or 36, CDR H2 is SEQ ID NO: 46 or 47 and CDR H3 is SEQ ID NO: 64.

30. An antibody molecule according to any one of paragraphs 1 to 3 or 25, wherein CDR H1 is SEQ ID NO: 37, CDR H2 is SEQ ID NO: 48, 49, 50, 51, 52 or 53 and CDR H3 is SEQ ID NO: 65, 66 or 67.

31. An antibody molecule according to any one of paragraphs 1 to 3 or 25, wherein CDR H1 is SEQ ID NO: 38 or 39, CDR H2 is SEQ ID NO: 54, 55, 56, 57, 58 or 59 and CDR H3 is SEQ ID NO: 68.

32. An antibody molecule according to any one of paragraphs 1 to 3 and 25 to 31, wherein CDRL1 is independently selected from SEQ ID NOs: 69 to 74, CDRL2 is independently selected from SEQ ID NO: 75 to 80, and CDRL3 is independently selected from SEQ ID NO: 81 to 101.

33. An antibody molecule according to any one of paragraphs 1 to 3 and 25 to 32, wherein CDR L1 is SEQ ID NO: 69, CDR L2 is SEQ ID NO: 75 and CDR L3 is SEQ ID NO: 81.

34. An antibody molecule according to paragraph 32, wherein CDR L1 is SEQ ID NO: 70, CDR L2 is SEQ ID NO: 76 and CDR L3 is SEQ ID NO: 82.

35. An antibody molecule according to any one of paragraphs 1 to 3 and 25 to 32, wherein CDR L1 is SEQ ID NO: 71, CDR L2 is SEQ ID NO: 77 and CDR L3 is SEQ ID NO: 83, 84, 85, 86, 87, 88, 89, 90, 91, 92, 93, 94, 95, 96, 97 or 98.

36. An antibody molecule according to any one of paragraphs 1 to 3 and 25 to 32, wherein CDR L1 is SEQ ID NO: 72, CDR L2 is SEQ ID NO: 78 and CDR L3 is SEQ ID NO: 99.

37. An antibody molecule according to paragraph 32, wherein CDR L1 is SEQ ID NO: 73, CDR L2 is SEQ ID NO: 79 and CDR L3 is SEQ ID NO: 100.

38. An antibody molecule according to any one of paragraphs 1 to 3 and 25 to 32, wherein CDR L1 is SEQ ID NO: 74, CDR L2 is SEQ ID NO: 80 and CDR L3 is SEQ ID NO: 101.

39. An antibody molecule according to any one of claims to any one of paragraphs 1 to 3 and 25 to 38, wherein CDR H1 has the sequence given in SEQ ID NO: 29 or 30, CDR H2 has the sequence given in SEQ ID NO: 40 or 41, and CDR H3 has the sequence given in SEQ ID NO: 60; and wherein CDR L1 has the sequence given in SEQ ID NO: 69, CDR L2 has the sequence given in SEQ ID NO: 75 and CDR L3 has the sequence given in SEQ ID NO: 81.

40. An antibody molecule according to any one of paragraphs 1 to 3 and 25 to 38, wherein CDR H1 has the sequence given in SEQ ID NO: 31 or 32, CDR H2 has the sequence given in SEQ ID NO: 42 or 43, and CDR H3 has the sequence given in SEQ ID NO: 61 or 62; and wherein CDR L1 has the sequence given in SEQ ID NO: 70, CDR L2 has the sequence given in SEQ ID NO: 76 and CDR L3 has the sequence given in SEQ ID NO: 82.

41. An antibody molecule according to any one of paragraphs 1 to 3 and 25 to 38, wherein CDR H1 has the sequence given in SEQ ID NO: 33 or 34, CDR H2 has the sequence given in SEQ ID NO: 44 or 45, and CDR H3 has the sequence given in SEQ ID NO: 63; and wherein CDR L1 has the sequence given in SEQ ID NO: 71, CDR L2 has the sequence given in SEQ ID NO: 77 and CDR L3 has the sequence given in SEQ ID NO: 83, 84, 85, 86, 87, 88, 89, 90, 91, 92, 93, 94, 95, 96, 97 or 98.

42. An antibody molecule according to any one of paragraphs 1 to 3 and 25 to 38, wherein CDR H1 has the sequence given in SEQ ID NO: 35 or 36, CDR H2 has the sequence given in SEQ ID NO: 46 or 47, and CDR H3 has the sequence given in SEQ ID NO: 64; and wherein CDR L1 has the sequence given in SEQ ID NO: 72, CDR L2 has the sequence given in SEQ ID NO: 78 and CDR L3 has the sequence given in SEQ ID NO: 99.

43. An antibody molecule according to any one of paragraphs 1 to 3 and 25 to 38, wherein CDR H1 has the sequence given in SEQ ID NO: 37, CDR H2 has the sequence given in SEQ ID NO: 48, 49, 50, 51, 52 or 53 and CDR H3 has the sequence given in SEQ ID NO: 65, 66 or 67; and wherein CDR L1 has the sequence given in SEQ ID NO: 73, CDR L2 has the sequence given in SEQ ID NO: 79 and CDR L3 has the sequence given in SEQ ID NO: 100.

44. An antibody molecule according to any one of paragraphs 1 to 3 and 25 to 38, wherein CDR H1 has the sequence given in SEQ ID NO: 38 or 39, CDR H2 has the sequence given in SEQ ID NO: 54, 55, 56, 57, 58 or 59, and CDR H3 has the sequence given in SEQ ID NO: 68; and wherein CDR L1 has the sequence given in SEQ ID NO: 74, CDR L2 has the sequence given in SEQ ID NO: 80 and CDR L3 has the sequence given in SEQ ID NO: 101.

45. An antibody molecule according to any one of paragraphs 1 to 44 wherein VH and VL are humanised.

46. An antibody molecule according to paragraph 45 wherein the variable domain of the heavy chain (VH) comprises a human framework region wherein the residue at at least one of positions 11, 23, 24, 37, 47, 48, 49, 67, 71, 73, 76, 78 and 94 is a donor residue and the variable domain of the light chain (VL) comprises a human framework region wherein the residue at at least one of positions 1, 2, 3, 36, 63, 65, 66, 70 and 71, is a donor residue.

47. An antibody molecule according to any one of paragraphs 1 to 3 or paragraph 45 or 46, comprising a VH independently selected from SEQ ID NO: 107, 108, 109, 110, 116, 117, 118, 119, 120, 121, 127, 128, 129, 130, 136, 137, 138, 139, 145, 146, 147, 148, 154, 155, 156 and 157.

48. An antibody molecule according to any one of paragraphs 1 to 3 and 47, comprising a VL variable domain comprising a sequence independently selected from SEQ ID NO: 106, 115, 126, 135, 144 and 153.

49. An antibody molecule according to any one of paragraphs 1 to 3 and 47 or 48, comprising a VH independently selected from SEQ ID NO: 107, 108, 109 and 110 and a VL with a sequence shown in SEQ ID NO: 106.

50. An antibody molecule according to any one of paragraphs 1 to 3 and 47 or 48, comprising a VH independently selected from SEQ ID NO: 116, 117, 118, 119, 120 and 121 and a VL with a sequence shown in SEQ ID NO: 115.

51. An antibody molecule according to any one of paragraphs 1 to 3 and 47 or 48, wherein comprising a VH independently selected from SEQ ID NO: 127, 128, 129 and 130 and a VL with a sequence shown in SEQ ID NO: 126.

52. An antibody molecule according to any one of paragraphs 1 to 3 and 47 or 48, wherein comprising a VH independently selected from SEQ ID NO: 136, 137, 138 and 139 and a VL with a sequence shown in SEQ ID NO: 135.

53. An antibody molecule according to any one of paragraphs 1 to 3 and 47 or 48, wherein comprising a VH independently selected from SEQ ID NO: 145, 146, 147 and 148 and a VL with a sequence shown in SEQ ID NO: 144.

54. An antibody molecule according to any one of paragraphs 1 to 3 and 47 or 48, wherein comprising a VH independently selected from SEQ ID NO: 154, 155, 156 and 157 and a VL with a sequence shown in SEQ ID NO: 153.

55. An antibody molecule according to any one of paragraphs 1 to 54, wherein each binding domain comprises two antibody variable domains.

56. An antibody molecule according to paragraph 55, wherein the two antibody variable domains are a VH/VL pair.

57. An antibody molecule according to any one of paragraphs 1 to 45 wherein the variable domain of the light chain comprises a sequence having at least 80% identity or similarity to the light chain variable domain of SEQ ID NO: 106, 115, 126, 135, 144 and 153 and wherein the variable domain of the heavy chain comprises a sequence having at least 80% identity or similarity to the heavy chain variable domain of SEQ ID NO: 107, 108, 109, 110, 116, 117, 118, 119, 120, 121, 127, 128, 129, 130, 136, 137, 138, 139, 145, 146, 147, 148, 154, 155, 156 and 157.

58. An antibody molecule according to any one of paragraphs 1-57 wherein the antibody is a full length antibody.

59. An antibody molecule according to any one of paragraphs 1-57 wherein the antibody is a scFv, Fv, Fab or Fab' fragment.

60. An antibody molecule according to any one of paragraphs 1 to 57 wherein the molecule is a multispecific protein, such as a bispecific or trispecific.

61. An antibody molecule according to paragraph 60, wherein the multispecific molecule comprises one binding domain which is specific to CD22 and one binding domain which is specific to CD79a and/or CD79b.

62. An antibody molecule according to any one of paragraphs 1 to 61, wherein the molecule format is selected from a diabody, scdiabody, triabody, tandem scFv, FabFv, Fab'Fv, FabdsFv, Fab-scFv, Fab-dsscFv, Fab-(dsscFv)$_2$ diFab, diFab', tribody, tandem scFv-Fc, scFv-Fc-scFv, scdiabody-Fc, scdiabody-CH3, Ig-scFv, scFv-Ig, V-Ig, Ig-V, Duobody and DVD-Ig.

63. An antibody molecule according to any one of paragraphs 1 to 62, which comprises a binding domain specific to serum albumin, such as human serum albumin.

64. An antibody molecule according to any one of paragraphs 1 to 63 in which the binding domain or domains are humanised.

65. An antibody molecule according to any one of paragraphs 1 to 64 in which one amino acid in one or more CDRs have been substituted with another amino acid.

66. A composition comprising one or more antibody molecules as defined in any one of paragraphs 1 to 65.

67. A nucleotide sequence encoding an antibody molecule as defined in any one of paragraphs 1 to 65.

68. A vector comprising a nucleotide sequence defined in paragraph 67.

69. An antibody molecule according to any one of paragraphs 1 to 65 or a composition according to paragraph 66, for use in therapy.

70. Use of an antibody molecule according to any one of paragraphs 1 to 65 or a composition according to paragraph 66, for the manufacture of a medicament for use in therapy, in particular for the treatment of a condition or disorder described herein.

71. A method of treating a patient, comprising the administration of a therapeutically effective amount of an antibody molecule according to any one of paragraphs 1 to 65 or a composition according to paragraph 66.

REFERENCES

1. Ribosome display efficiently selects and evolves high-affinity antibodies in vitro from immune libraries. Hanes J, Jermutus L, Weber-Bornhauser S, Bosshard H R, Plückthun A. (1998) Proc. Natl. Acad. Sci. U.S.A. 95, 14130-14135

2. Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877
3. Antigen recognition by conformational selection. Berger C, Weber-Bornhauser S, Eggenberger Y, Hanes J, Pluckthun A, Bosshard H. R. (1999) F.E.B.S. Letters 450, 149-153

EXAMPLES

The term Fab-Kd-Fab as used in the Examples describes the bispecific protein complex having the formula A-X:Y-B wherein:

A-X is a first fusion protein;
Y-B is a second fusion protein;
X:Y is a heterodimeric-tether;
A comprises a Fab fragment specific to an antigen such as CD22 or CD79;
B comprises a Fab fragment specific to an antigen such as CD22 or CD79;
X is a first binding partner of a binding pair such as a scFv;
Y is a second binding partner of the binding pair such as a peptide; and
: is an interaction (such as a binding interaction) between X and Y.

Example 1—Production of Fab'-A (Fab-scFv [A-X]) and Fab'-B (Fab-Peptide [B-Y]) for Functional Assays Cloning Strategy Antibody variable region DNA was generated by PCR or gene synthesis flanking restriction enzyme sites DNA sequence. These sites were HindIII and XhoI for variable heavy chains and HindIII and BsiWI for variable light chains. This makes the heavy variable region amenable to ligating into the two heavy chain vectors (pNAFH with FabB-Y and pNAFH with FabA-Xds [disulphide stabilised]) as they have complementary restriction sites. This ligates the variable region upstream (or 5') to the murine constant regions and peptide Y (GCN4) or scFv X (52SR4) creating a whole reading frame. The light chains were cloned into standard in house murine constant kappa vectors (pMmCK or pMmCK S171C) which again use the same complimentary restriction sites. The pMmCK S171C vector is used if the variable region is isolated from a rabbit. The cloning events were confirmed by sequencing using primers which flank the whole open reading frame.

Cultivating CHO-S

Suspension CHOS cells were pre-adapted to CDCHO media (Invitrogen) supplemented with 2 mM (100×) glutamx. Cells were maintained in logarithmic growth phase agitated at 140 rpm on a shaker incubator (Kuner A G, Birsfelden, Switzerland) and cultured at 37° C. supplemented with 8% $CO_2$.

Electroporation Transfection

Prior to transfection, the cell numbers and viability were determined using CEDEX cell counter (Innovatis AG. Bielefeld, Germany) and required amount of cells ($2\times10^8$ cells/ml) were transferred into centrifuge conical tubes and were spun at 1400 rpm for 10 minutes. The Pelleted cells were re-suspended in sterile Earls Balanced Salts Solution and spun at 1400 rpm for further minutes. Supernatant was discarded and pellets were re-suspended to desired cell density.

Vector DNA at a final concentration of 400 ug for $2\times10^8$ cells/ml mix and 800 µl was pipetted into Cuvettes (Biorad) and electroporated using in-house electroporation system.

Transfected cells were transferred directly into 1×3 L Erlenmeyer Flasks contained ProCHO 5 media enriched with 2 mM glutamx and antibiotic antimitotic (100×) solution (1 in 500) and Cells were cultured in Kuhner shaker incubator set at 37° C., 5% $CO_2$ and 140 rpm shaking.

Feed supplement 2 g/L ASF (AJINOMOTO) was added at 24 hr post transfection and temperature dropped to 37° C. for further 13 days culture. At day four 3 mM Sodium buryate (n-BUTRIC ACID Sodium Salt, Sigma B-5887) was added to the culture.

On day 14, cultures were transferred to tubes and supernatant separated from the cells after centrifugation for 30 minutes at 4000 rpm. Retained supernatants were further filtered through 0.22 um SARTO BRAN P Millipore followed by 0.22 µm Gamma gold filters. Final expression levels were determined by Protein G-HPLC.

Large Scale (LOL) Purification

The Fab-A and Fab-B were purified by affinity capture using the AKTA Xpress systems and HisTrap Excel prepacked nickel columns (GE Healthcare). The culture supernatants were 0.22 µm sterile filtered and pH adjusted to neutral, if necessary, with weak acid or base before loading onto the columns. A secondary wash step, containing 15-25 mM Imidazole, was used to displace any weakly bound host cell proteins/non-specific His binders from the nickel resin. Elution was performed with 10 mM sodium phosphate, pH7.4+1M NaCl+250 mM Imidazole and 2 ml fractions collected. One column volume into the elution the system was paused for 10 minutes to tighten the elution peak, and consequently decrease the total elution volume. The cleanest fractions were pooled and buffer exchanged into PBS (Sigma), pH7.4 and 0.22 µm filtered. Final pools were assayed by A280 Scan, SE-HPLC (G3000 method), SDS-PAGE (reduced & non-reduced) and for endotoxin using the PTS Endosafe system.

Example 2—Use of Fab'-A (Fab-scFv [A-X]) and Fab'-b (Fab-Peptide [B-Y]) in Heterodimerically-Tether Bispecific Protein Complex Format to Demonstrate that CD79/CD22 Bispecific but not Bivalent Combinations Inhibit Akt Signaling Human PBMC derived from platelet apheresis cones were banked as frozen aliquots. Prior to an assay being performed, cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-A (Fab-scFv) and Fab'-B (Fab-peptide) with antigen specificity for the cell surface proteins CD22 and CD79b in DMEM containing 10% calf serum and 2 mM glutamine. This grid is shown in Table 4.

TABLE 4

Possible grid of bispecific and bivalent combinations of
antibodies with specificity for CD22 and CD79b.

| (A-X) | (B-Y) Fab B | |
|---|---|---|
| Fab A | CD22-Y | CD79b-Y |
| CD22-X | CD22-X:Y-CD22 | CD22-X:Y-CD79b |
| CD79b-X | CD79b-X:Y-CD22 | CD79b-X:Y-CD79b | where X is a scFv (52SR4) and Y is a peptide (GCN4)

Fab'A-X and Fab'B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for minutes before centrifugation at 500 g for 5 minutes. Excess supernatant was discarded from the cell pellet which was resuspended in flow buffer (PBS+1% BSA+0.01% $NaN_3$) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25 µl of flow buffer. Cellular expression of CD20 and Akt was measured using an Intellicyt HTFC™ flow cytometer.

Using the data analysis software package Forecyt™ (Intellicyt) B cells were identified as distinct from other cell populations and the geometric mean of Akt levels was calculated for each well. All data was then expressed as the percentage inhibition of the maximal response (anti-IgM only) minus the background (cells only). The relative effect of the combinations of CD22 and CD79b is shown in Table 5 (↓=inhibition, ↑=stimulation and ⇔=no overall effect).

TABLE 5

Table of the relative potency of inhibition of phosphorylated
Akt for bispecific and bivalent combinations of antibodies
with specificity for CD22 and CD79b.

| (A-X) | (B-Y) Fab B | |
|---|---|---|
| Fab A | CD22-Y | CD79b-Y |
| CD22-X | ↑↑ | ↓↓↓ |
| CD79b-X | ↓↓↓ | ⇔ | where X is a scFv (52SR4) and Y is a peptide (GCN4).

This data is also shown in the form of a bar chart (FIG. 1): the data represents mean values and the error bars are 95% confidence intervals. The data shows that the combinations of CD22 with CD79b can inhibit phospho-Akt expression in B cells stimulated with anti-IgM. In contrast, the combination of CD22 with CD22 exhibited elevated levels of phosho-Akt expression.

Example 3 Use of Fab'-A (Fab-scFv [A-X]) and Fab'-b (Fab-Peptide [B-Y]) in Heterodimerically-Tether Bispecific Protein Complex Format to Demonstrate that CD79/CD22 Bispecific but not Bivalent Combinations Inhibit PLCγ2 Signalling Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-a (Fab-scFv [A-X]) and Fab'-B (Fab-peptide [B-Y]) with antigen specificity for the cell surface proteins CD22 and CD79b in DMEM containing 10% calf serum and 2 mM glutamine. This grid is shown in Table 4.

Fab'A-X and Fab'B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat $F(ab')_2$ anti-human IgM (Southern Biotechnology) for 8 minutes at 37° C. The signalling reaction was then halted by adding an equal volume of Cytofix buffer (BD Biosciences). Plates were then left at room temperature for minutes before centrifugation at 500 g for 5 minutes. Excess supernatant was discarded from the cell pellet which was resuspended in flow buffer and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and a fluorescently labelled anti-phospho PLCγ2 antibody that recognises a modified tyrosine residue at position 759 on the protein. Plates were then resuspended and incubated for 1 hour at room temperature in the dark. After this time plates were washed a further two times and resuspended in 25 µl of flow buffer. Cellular expression of CD20 and PLCγ2 was measured using an Intellicyt HTFC™ flow cytometer.

Using the data analysis software package Forecyt™ (Intellicyt) B cells were identified as distinct from other cell populations and the geometric mean of PLCγ2 levels was calculated for each well. All data was then expressed as the percentage inhibition of the maximal response (anti-IgM only) minus the background (cells only). The relative effect of the combinations of CD22 and CD79b is shown in Table 6 (↓=inhibition, ↑=stimulation and ⇔=no overall effect).

TABLE 6

Table of the relative potency of inhibition of phosphorylated
PLCg2 for bispecific and bivalent combinations of
antibodies with specificity for CD22 and CD79b.

| (A-X) | (B-Y) Fab B | |
|---|---|---|
| Fab A | CD22-Y | CD79b-Y |
| CD22-X | ↑ | ↓↓↓ |
| CD79b-X | ↓↓↓ | ⇔ | where X is a scFv and Y is a peptide

Figure 2:
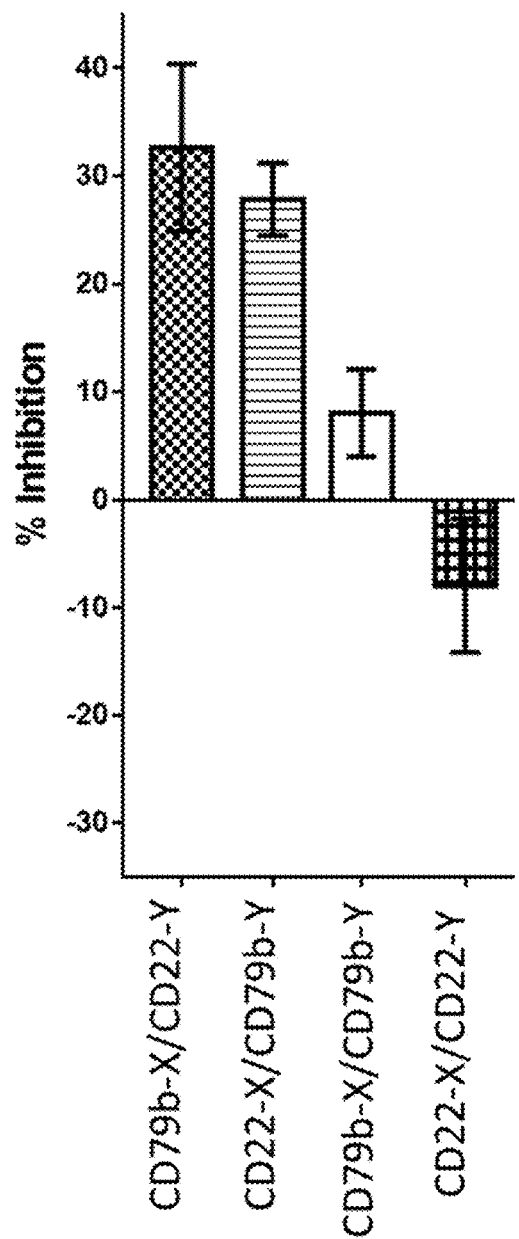
FIG. 2 is a bar chart of the relative potency of inhibition of phosphorylated PLCγ2 for bispecific and bivalent combinations of antibodies with specificity for CD22 and CD79b.

This data can also be expressed as a bar chart (FIG. 2), the data represents mean values and the error bars are 95% confidence intervals. The data shows that the combinations of CD22 with CD79b and CD79b with CD79b can all inhibit phospho-PLCγ2 expression in B cells stimulated with anti- IgM. In contrast, the combination of CD22 with CD22, exhibited elevated levels of phosho-PLCγ2 expression.

Example 4—Use of Fab'-A (Fab-scFv [A-X]) and Fab'-b (Fab-Peptide [B-Y]) in Heterodimerically-Tether Bispecific Protein Complex Format to Demonstrate that CD79/CD22 Bispecific Combinations Inhibit CD86 Expression Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-X (Fab-scFv) and Fab'-Y (Fab-peptide) with antigen specificity for the cell surface proteins CD22 and CD79b in DMEM containing 10% calf serum and 2 mM glutamine. This grid is shown in Table 4. Fab'A-X and Fab'B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 24 hours at 37° C. After this time plates were placed on ice and washed once in ice cold flow buffer (PBS+1% BSA+0.01% $NaN_3$). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 µl of flow buffer. Cellular expression of CD19 and CD86 was measured using an Intellicyt HTFC™ flow cytometer.

Using the data analysis software package Forecyt™ (Intellicyt) B cells were identified as distinct from other cell populations and the geometric mean of CD86 levels was calculated for each well. All data was then expressed as the percentage inhibition of the maximal response (anti-IgM only) minus the background (cells only). The relative effect of the combinations of CD22 and CD79b is shown in table 7 (↓=inhibition, ↑=stimulation and ↔=no overall effect).

TABLE 7

Table of the relative potency of inhibition of B Cell CD86 expression for bispecific and bivalent combinations of antibodies with specificity for CD22 and CD79b.

| (A-X) | (B-Y) Fab B | |
|---|---|---|
| Fab A | CD22-Y | CD79b-Y |
| CD22-X | ↑ | ↓↓↓ |
| CD79b-X | ↓↓ | ↓↓ | where X is a scFv (52SR4) and Y is a peptide (GCN4)

Figure 3:
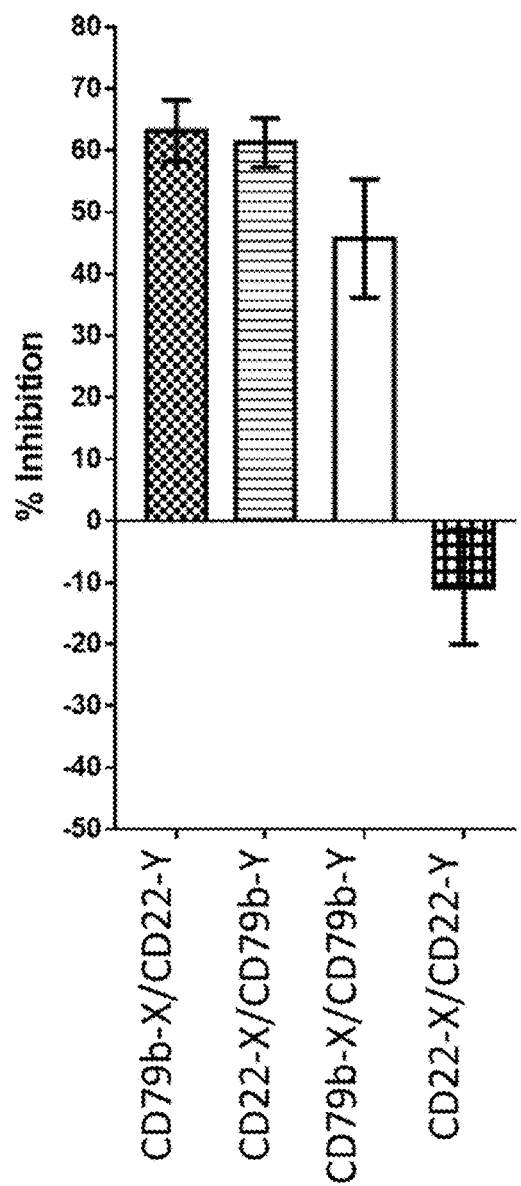
FIG. 3 is a bar chart of the relative potency of inhibition of CD86 expression for bispecific and bivalent combinations of antibodies with specificity for CD22 and CD79b.

This data is also shown in the form of a bar chart (FIG. 3), the data represents mean values and the error bars are 95% confidence intervals. The data shows that the combinations of CD22 with CD79b and CD79b with CD79b can all inhibit CD86 expression on B cells stimulated with anti-IgM. In contrast the combination of CD22 with CD22 exhibited elevated levels of CD86 expression.

Example 5—the Inhibitory Effect of CD22 and CD79b can Only be Reproduced when the Antibodies are Arranged in a Bispecific Orientation Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period combinations of bispecific, bivalent or mixtures of antibodies were created by diluting equimolar (200 nM) quantities of Fab'-X (Fab-scFv) and/or Fab'-Y (Fab-peptide) with antigen specificity for the cell surface proteins CD22 and CD79b in DMEM containing 10% calf serum and 2 mM glutamine. These combinations are shown in Table 8. For the titration curve experiment these combinations were then diluted in 8 stepwise 1 in 2.5 dilutions to create a dose titration for this combination.

TABLE 8

Grid of bispecific, bivalent or mixtures with specificity for CD22 and CD79b.

| (A-X) | (B-Y) Fab B | | |
|---|---|---|---|
| Fab A | CD22-Y | CD79b-Y | CD79b-X |
| CD22-X | CD22-X:Y-CD22 | CD22-X:Y-CD79b | CD22-X X-CD79 |
| CD79b-X | CD79b-X:Y-CD22 | CD79b-X:Y-CD79b | — |
| CD22-Y | — | CD22-Y Y-CD79b | — | where X is a scFv (52SR4) and Y is a peptide (GCN4)

Fab'A-X and/or Fab'B-Y were incubated together for 90 minutes (in a 37° C./5% $CO_2$ environment) before mixing with $2.5 \times 10^5$ PBMC in V bottomed 96 well plates. PBMC plus Fab'A-X and/or Fab'B-Y combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+1% BSA+0.01% $NaN_3$) and washed once more. Cells were then resuspended in ice cold Perm Buffer III (BD Biosciences) for 30 minutes before being washed twice in flow buffer.

Figure 4:
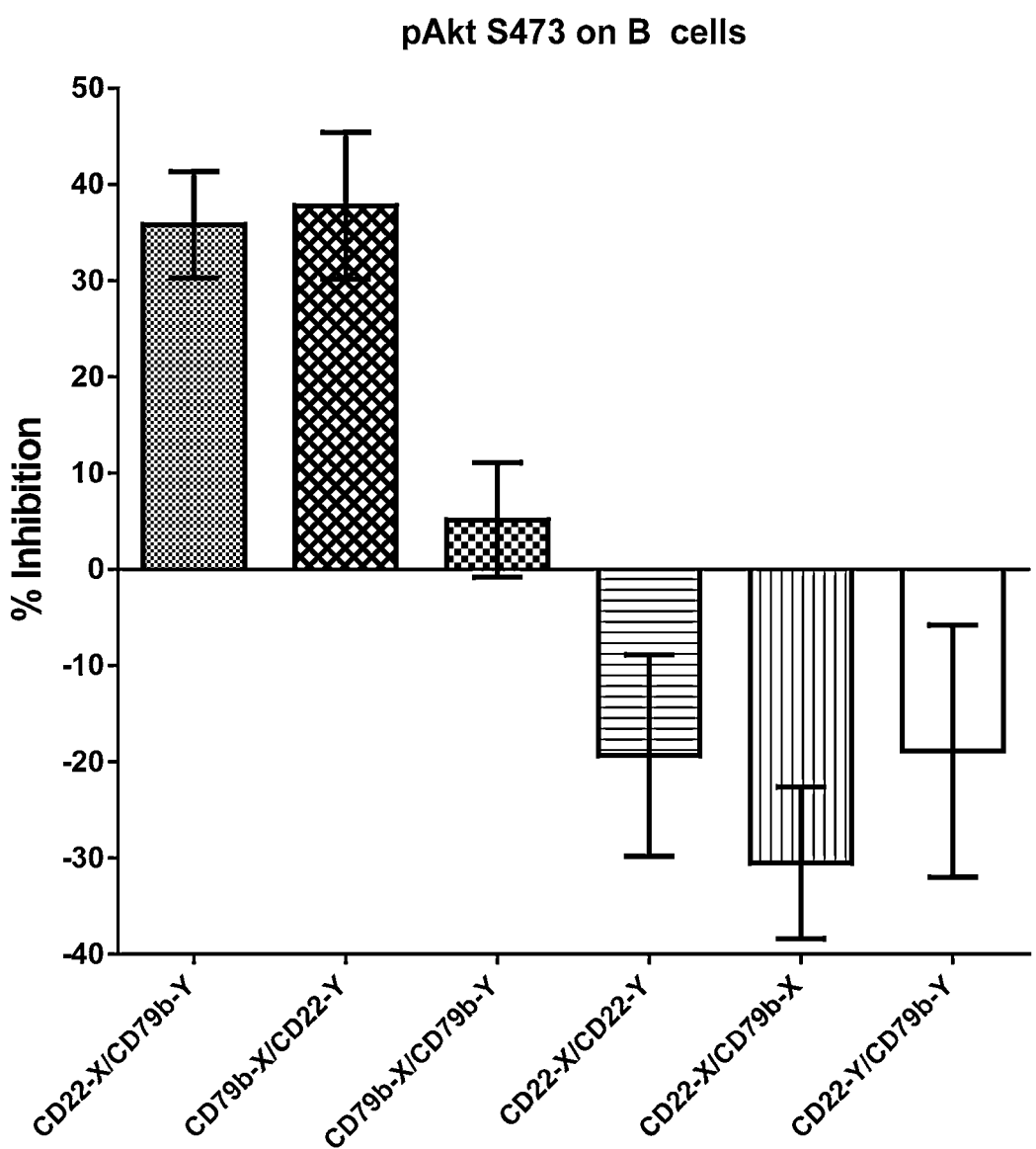
FIG. 4 is a bar chart of the relative potency of inhibition of phosphorylated Akt for bispecific, bivalent or mixtures of antibodies with specificity for CD22 and CD79b.
Figure 5:
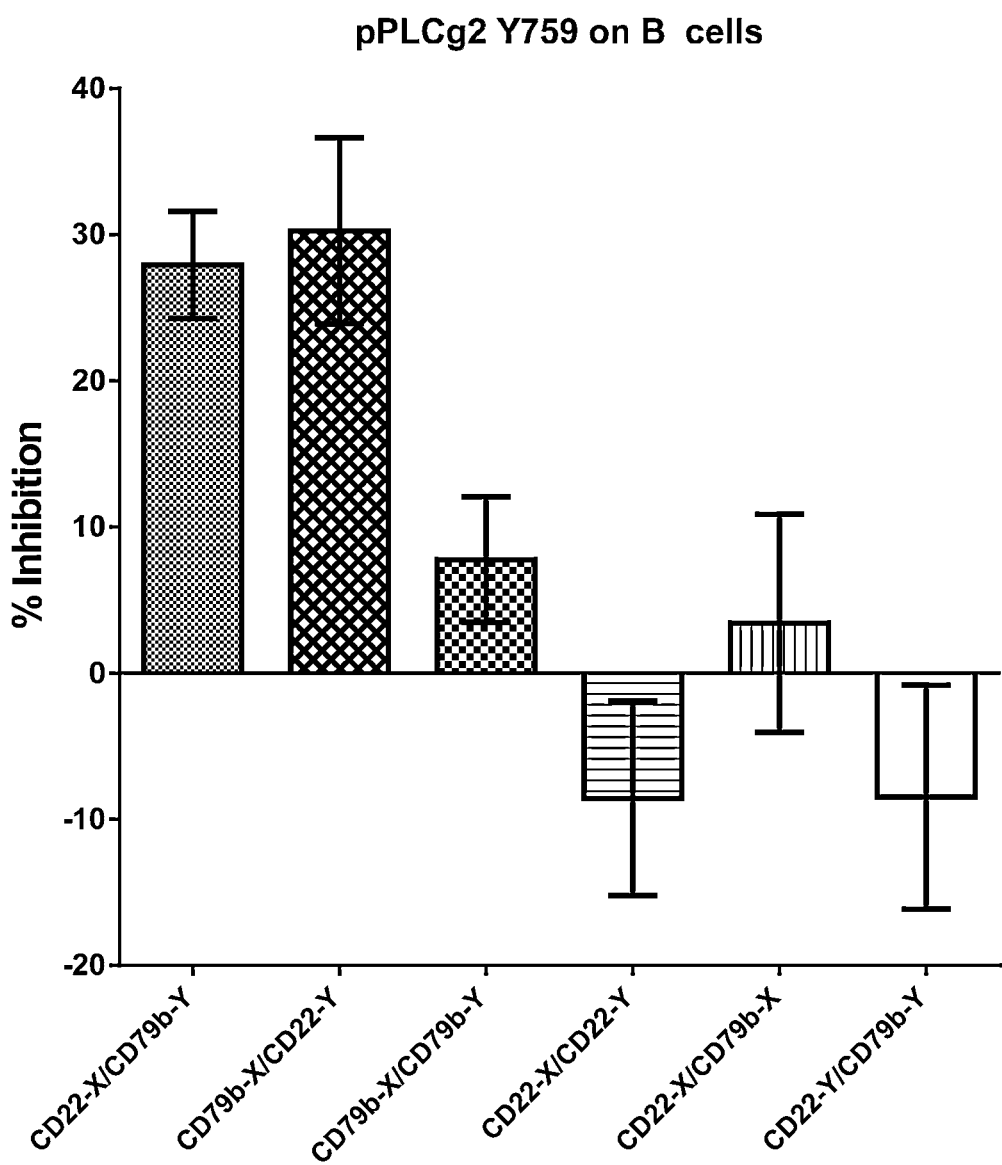
FIG. 5 is a bar chart of the relative potency of inhibition of phosphorylated PLCγ2 for bispecific, bivalent or mixtures of antibodies with specificity for CD22 and CD79b.

Cells were then stained with a fluorescently labelled anti-CD20 antibody (BD Biosciences), anti-phospho Akt antibody that recognises a modified serine residue at position 473 and an anti-phospho PLCγ2 antibody that recognises a modified tyrosine residue at position 759. Plates were then resuspended and incubated for 1 hour at room temperature in the dark. After this time plates were washed a further two times and resuspended in 25 µl of flow buffer. Cellular expression of CD20, Akt and PLCγ2 was measured using an Intellicyt HTFC™ flow cytometer. Using the data analysis software package Forecyt™ (Intellicyt) B cells were identified as distinct from other cell populations and the geometric mean of Akt and PLCγ2 levels were calculated for each well. All data was then expressed as the percentage inhibition of the maximal response (anti-IgM only) minus the background (cells only). FIGS. 4 and 5 show that only the bispecific combination of CD22 and CD79b but not the mixtures of CD22 and CD79b antibodies inhibited phosphorylated Akt and PLCγ2 expression (the data represents mean values and the error bars are 95% confidence intervals).

In order to validate the inhibition seen with the bispecific combination of CD22 and CD79b this combination along with a mixture of CD22 and CD79b antibodies was titrated and inhibition of total intracellular IkB (signalling readout) and CD86 (activation marker after 24 hours) was measured in B cells.

Figure 6:
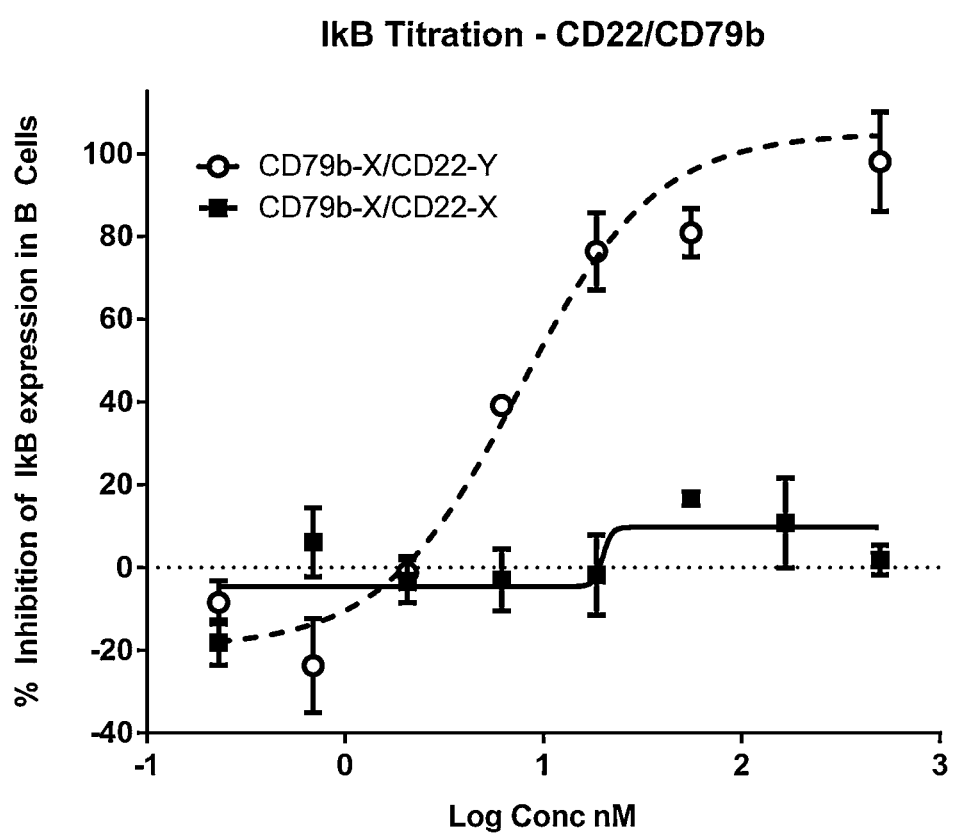
FIG. 6 is a graph showing the titration of the effect of the bispecific combination of CD22 and CD79b on total IkB levels in anti-IgM stimulated B cells.

As can be seen in FIG. 6, a combination of CD22-X/CD79b-Y but not the combination of CD22-X/CD79b-X was able to inhibit NF-kB signal activation after anti-IgM stimulation as measured by the level of total IkB protein. The IC50, as extrapolated using a 4 parameter logistic curve fit using Graphpad Prism 6, was 7.5 nM (the data represents mean values and the error bars are standard deviations). Additionally a titration of the combination of CD22-X/CD79b-Y but not the combination of CD22-X/CD79b-X was able to inhibit anti-IgM induced CD86 expression on B cells after 24 hours (see FIG. 7).

Figure 7:
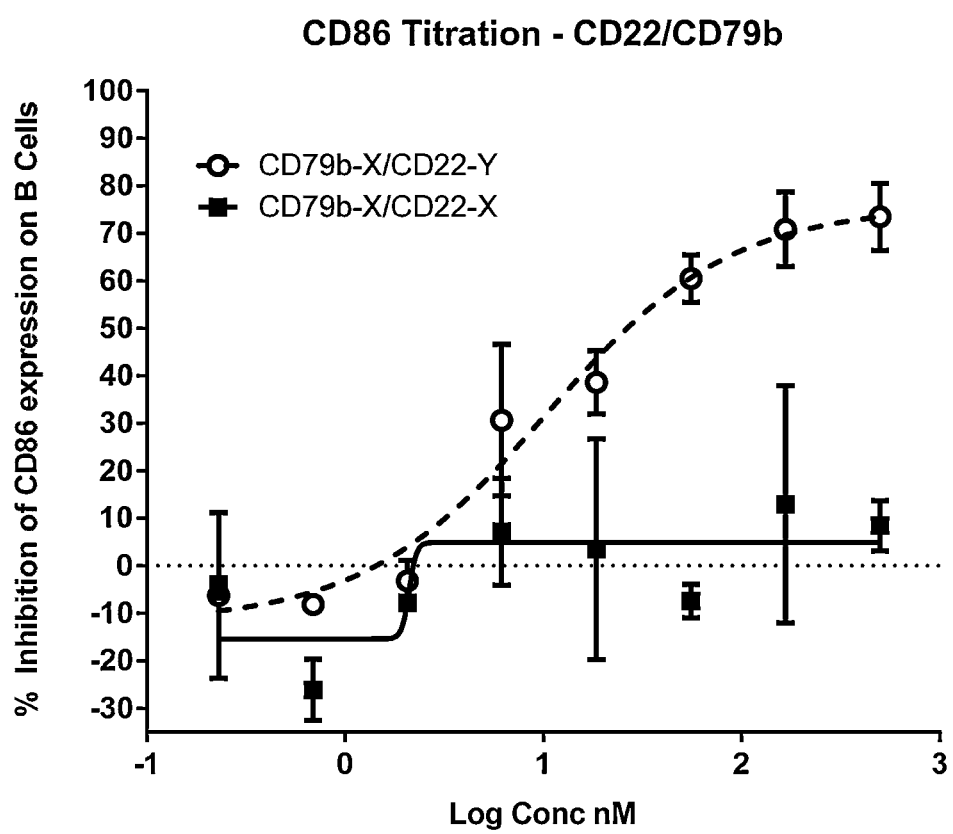
FIG. 7 is a graph showing the titration of the effect of the bispecific combination of CD22 and CD79b on CD86 expression on anti-IgM stimulated B cells.

Human PBMC derived from platelet apheresis cones were banked as frozen aliquots. Prior to an assay being performed cells were thawed, washed in DMEM (Life Technologies) and allowed to acclimatise to a 37 degree C./5% $CO_2$ environment. During this period bispecific combinations were created by diluting equimolar (500 nM) quantities of Fab'-X (Fab-scFv) and Fab'-Y (Fab-peptide) with antigen specificity for the cell surface proteins CD22 and CD79b in DMEM containing 10% calf serum and 2 mM glutamine. These combinations were then diluted in 8 stepwise 1 in 2.5 dilutions to create a dose titration for this combination. Fab'-X and Fab'-Y were incubated together for 90 minutes (in a 37 degree C./5% $CO_2$ environment) before adding 2.5×105 PBMC to V bottomed 96 well plates. PBMC were then added to Fab'-X and Fab'-Y combinations and incubated together for a further 90 minutes. After this time B cells were activated by the addition of 200 nM of goat F(ab')2 anti-human IgM (Southern Biotechnology) for 24 hours at 37 degrees C. To enable detection of cell surface activation markers plates were placed on ice and washed once in ice cold flow buffer (PBS+1% BSA+0.01% NaN3). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 ul of flow buffer. Cellular expression of CD19 and CD86 was measured using an Intellicyt HTFC™ flow cytometer. Using the data analysis software package Forecyt™ (Intellicyt) B cells were identified as distinct from other cell populations and the geometric mean of CD86 levels was calculated for each well. All data was then expressed as the percentage inhibition of the maximal response (anti-IgM only) minus the background (cells only). As can be seen in FIG. 7 a titration of the combination of CD22-X/CD79b-Y was able to inhibit anti-IgM induced CD86 expression on B cells after 24 hours. The IC50, as extrapolated using a 4 parameter logistic curve fit using Graphpad Prism 6, was 10.3 nM (the data represents mean values and the error bars are standard deviations).

Example 6—the Inhibitory Effect of CD22 and CD79b Bispecific Protein can be Reproduced with Different Antibody V Regions Immunisation: DNA encoding selected antigens was obtained by gene synthesis or commercial sources & cloned into an expression vector with a strong constitutive promoter. Plasmid DNA was then transfected into Rab-9 rabbit fibroblast cells (ATCC® CRL-1414™) using an in-house electroporation system. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody discovery: B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 µl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$.

The presence of antigen-specific antibodies in B cell culture supernatants was determined using a homogeneous fluorescence-based binding assay using HEK293 cells co-transfected with the antigens that the rabbits were immunized with. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with antigens separately and Superavidin™ beads (Bangs Laboratories) coated with recombinant protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1).

Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and Superavidin™ beads (Bangs Laboratories) coated with recombinant protein or antigen transfected HEK cells. This was done to confirm the specificity of the cloned antibodies.

Production of Small Scale Fab A-X and Fab B-Y (Small Scale (50 mL) Expi293 Transfection)

The Expi293 cells were routinely sub-cultured in Expi293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed Expi293™ Expression Medium for each 50 mL transfection.

To prepare the lipid-DNA complexes for each transfection a total of 50 µg of heavy chain and light chain plasmid DNAs were diluted in Opti-MEM® I medium (LifeTechnologies) to a total volume of 2.5 mL and 135 µL of ExpiFectamine™ 293 Reagent (LifeTechnologies) was diluted in Opti-MEM® I medium to a total volume of 2.5 mL. All dilutions were mixed gently and incubate for no longer than 5 minutes at room temperature before each DNA solution was added to the respective diluted ExpiFectamine™ 293 Reagent to obtain a total volume of 5 mL. The DNA-ExpiFectamine™ 293 Reagent mixtures were mixed gently and incubated for 20-30 minutes at room temperature to allow the DNA-ExpiFectamine™ 293 Reagent complexes to form.

After the DNA-ExpiFectamine™ 293 reagent complex incubation was completed, the 5 mL of DNA-ExpiFectamine™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 µL of ExpiFectamine™ 293 Transfection Enhancer 1 (LifeTechnologies) and 2.5 mL of ExpiFectamine™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification: Both Fab-X and Fab-Y were purified separately by affinity capture using a small scale vacuum based purification system. Briefly, the 50 ml of culture supernatants were 0.22 µm sterile filtered before 500 µl of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+ 1M NaCl. The eluted fractions buffer exchanged into PBS (Sigma), pH7.4 and 0.22 µm filtered. Final pools were assayed by A280 scan, SE-UPLC (BEH200 method), SDS-PAGE (reduced & non-reduced) and for endotoxin using the PTS Endosafe system.

Human PBMC derived from platelet apheresis cones were banked as frozen aliquots. Prior to an assay being performed cells were thawed, washed in RPMI 1640 (Life Technologies) and allowed to acclimatise to a 37° C./5% $CO_2$ environment. During this period combinations of bispecific, bivalent or mixtures of antibodies were created by diluting equimolar (200 nM) quantities of Fab'-X (Fab-scFv) and/or Fab'-Y (Fab-peptide) with antigen specificity for the cell surface proteins CD22 and CD79b in RPMI 1640 containing 10% fetal bovine serum, 50 units/mL Penicillin, 50 µg/mL Streptomycin and 2 mM glutamine. These combinations of 3 different CD79b Fab-Ys and 3 different CD22 Fab-Xs are shown in Table 9.

TABLE 9

| Grid of bispecific proteins with specificity for CD22 and CD79b. | | | |
|---|---|---|---|
| (A-X) Fab A | (B-Y) Fab B CD79-Y VR4447 | CD79-Y VR4450 | CD79b-y VR4246 |
| CD22-X VR0982 | CD22-X:Y-CD79b | CD22-X:Y-CD79b | CD22-X:Y-CD79b |
| CD22-X VR4126 | CD22-X:Y-CD79b | CD22-X:Y-CD79b | CD22-X:Y-CD79b |
| CD22-X VR4130 | CD22-X:Y-CD79b | CD22-X:Y-CD79b | CD22-X:Y-CD79b | where X is a scFv (52SR4) and Y is a peptide (GCN4)

Fab'A-X and Fab'B-Y were incubated together for 60 minutes (in a 37° C./5% $CO_2$ environment) before mixing with $2.5 \times 10^5$ PBMC in V bottomed 96 well plates. PBMC plus Fab'A-X and/or Fab'B-Y combinations were then incubated together for a further 90 minutes. After this time B cells were activated by the addition of 12.5 µg/mL of goat F(ab')2 anti-human IgM (Southern Biotechnology) for 10 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+1% BSA+0.1% $NaN_3$+2 mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences), and an anti-phospho PLCγ2 antibody that recognises a modified tyrosine residue at position 759.

Plates were then resuspended and incubated for 1 hour at room temperature in the dark. After this time plates were washed a further two times and resuspended in 40 µl of flow buffer.

Cellular expression of CD20 and PLCγ2 was measured using an Intellicyt HTFC™ flow cytometer.

Using the data analysis software package Forecyt™ (Intellicyt) B cells were identified as distinct from other cell populations and the geometric mean of PLCγ2 levels were calculated for each well. All data was then expressed as the percentage inhibition of the maximal response (anti-IgM only) minus the background (cells only).

Figure 8:
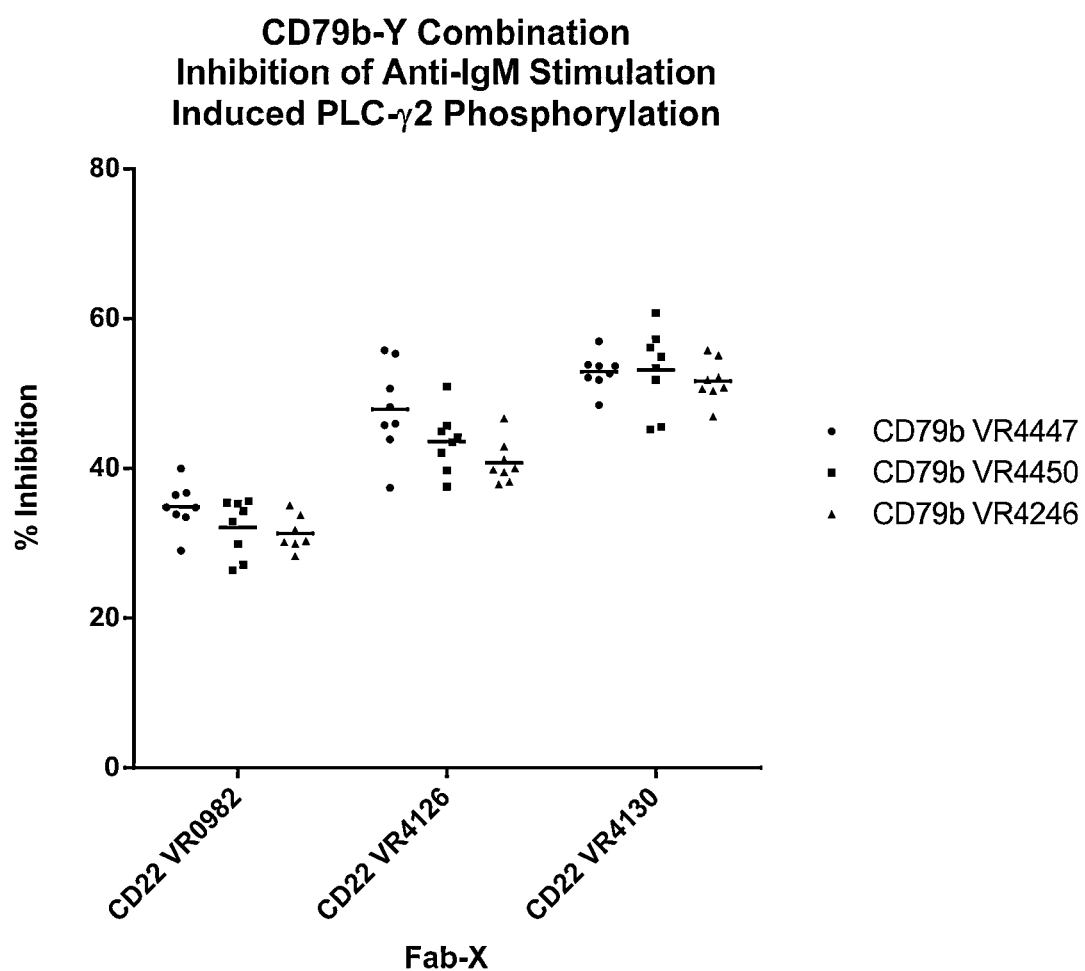
FIG. 8 is a graph of inhibition of phosphorylated PLCγ2 for bispecific proteins with specificity for CD22 and CD79b with different V regions.

As can be seen in FIG. 8 the data shows that the combination of CD22 with CD79b using all the different antibody V regions can inhibit phospho-PLCγ2 expression in B cells stimulated with anti-IgM.

Example 7: Grid Screening of Large Panels of Heterodimerically Tethered Protein Complexes to Identify Novel Bispecific Antibody Targets Introduction: Following the successful validation of the bispecific format and screening method in the earlier examples the screening was expanded to a larger number of antigen pairs. A panel of antibody variable (V) region pairs to 23 different antigens expressed on B cells was generated. Using the Fab-Kd-Fab [i.e. A-X:Y-B wherein A and B are Fab fragments] format a grid of heterodimerically tethered protein complexes was formed representing multiple V region combinations of each of 315 different antigen pair combinations. These combinations were screened for their ability to modulate BCR (B cell receptor) signalling in a high through-put flow cytometry assay to select novel target pairs for intervention with a bispecific antibody.

Antibodies were Isolated as Described in Example 6.

Screening Assays

Donor PBMCs were rapidly thawed using a water bath set to 37° C., and carefully transferred to a 50 ml Falcon tube. They were then diluted dropwise to 5 ml in assay media to minimise the osmotic shock. The cells were then diluted to 20 ml carefully before adding the final media diluent to make the volume 50 ml. The cells were then spun at 500 g for 5 minutes before removing the supernatant and resuspending the cells in 1 ml media. The cells were then counted and diluted to $1.66 \times 10^6$ cells/ml before dispensing 30 μl per well into a V-bottom TC plate giving a final assay concentration of $5.0 \times 10^4$ cells/well. The cell plate was then stored covered in a 37° C., 5% $CO_2$ incubator until they were required, giving them a minimum of 1 hour to rest.

Fab-X and Fab-Y reagents were mixed in an equimolar ratio at 5× the final assay concentration in assay media and incubated for 90 min at 37° C., 5% $CO_2$. Samples were prepared in a 96-well U-bottom polypropylene plate and covered during the incubation.

10 μl of 5×Fab-KD-Fab mixture was added to the appropriate test wells containing cells and mixed by shaking at 1000 rpm for 30 sec prior to being incubated for 90 min at 37° C., 5% $CO_2$.

The cells were then stimulated with 10 μl of anti-human IgM. The final assay concentration of stimulus varied depending on the assay panel readouts, the three antibody cocktails A, B and C (detailed below) were stimulated at a final assay concentration of either 50 μg/ml (cocktail A & C) or 25 μg/ml (cocktail B). The assay plates were then gently mixed at 1000 rpm for 30 sec prior to incubation at 37° C., 5% $CO_2$ for 5 min (antibody cocktail A & C) or 2 min (antibody cocktail B). The assay was stopped by adding 150 μl ice-cold BD CytoFix to all wells and incubated for 15 min at RT. The fixed cells were then spun at 500 g for 5 min to pellet the cells and allow removal of the supernatant using a BioTek ELx405 plate washer. The pellet was re-suspended by vortexing the plate at 2400 rpm for 30 sec. The cells were then permeabilised at 4° C. by adding 100 μl ice-cold BD Cell Permeabilisation Buffer III for 30 min. The cells were then washed in 100 μl FACS buffer and spun at 500 g for 5 min. Supernatant was again removed by the ELx405 before using it to rapidly dispense 200 μl FACS Buffer to wash away any residual permeabilisation buffer. Cells were again spun at 500 g and the supernatant removed by inversion. During the preceding spin step the antibody cocktail was prepared in FACS Buffer and kept shielded from the light. The cells were then re-suspended by vortexing (2400 RPM, 30 sec) before 20 μl of antibody cocktail was added to all wells and the plate shaken for 30 sec at 1000 rpm. The cells were then incubated for 60 min at RT in the dark.

The cells were then washed twice in 200 μl FACS buffer with a 500 g spin and supernatant removed after each step. Finally the cells were re-suspended by vortexing for 30 sec at 2400 rpm before adding a final 20 μl FACS buffer. The plate(s) were then read on the Intellicyt HTFC/iQue instrument.

FACS Buffer=PBS+1% BSA+0.05% $NaN_3$+2 mM EDTA

Antibody Cocktail A=1:2 CD20 PerCp-Cy5.5 (BD Biosciences)+1:5 PLCγ2 AF88+1:10 Akt AF647+1:50 ERK1/2 PE (diluted in FACS buffer).

Antibody Cocktail B=1:2 CD20 PerCp-Cy5.5 (BD Biosciences)+1:5 Syk PE+1:5 BLNK AF647 (diluted in FACS buffer)

Antibody Cocktail C=1:5 CD20 PerCp-Cy5.5 (Biolegend)+1:5 PLCγ2 AF488+1:10 Akt AF647+1:5 Syk PE (diluted in FACS buffer)

| Reagent | Supplier | Catalogue number |
|---|---|---|
| Anti-human IgM | Southern Biotech | 2022-14 |
| CytoFix | BD Biosciences | 554655 |
| Perm Buffer III | BD Biosciences | 558050 |
| Anti Akt (pS473) AF647 | BD Biosciences | 561670 |
| Anti SYK (pY348) PE | BD Biosciences | 558529 |
| Anti PLCγ2 (pY759) AF488 | BD Biosciences | 558507 |
| Anti-BLNK(pY84) AF647 | BD Biosciences | 558443 |
| Anti ERK1/2 (pT202/pY204) PE | BD Biosciences | 561991 |
| Anti-human CD20 PerCp-Cy5.5 | BD Biosciences | 558021 |
| Anti-human CD20 AF488 | BD Biosciences | 558056 |
| Anti-human CD20 PerCp-Cy5.5 | Biolegend | 340508 |
| Phosphate Buffer Saline (PBS) | Fisher Scientific | 10562765 |
| RPMI 1640 | Life Technologies | 31870 |
| Foetal Calf Serum (FCS) | Life Technologies | 16140 |
| Glutamax | Life Technologies | 35050 |
| Penicillin/Streptomycin (P/S) | Life Technologies | 15070 |
| EDTA | Sigma | 03690 |
| Sodium Azide (NaN3) | Sigma | S2002 |
| Bovine Serum Albumin (BSA) | Sigma | A1470 |

Fab-X+Fab-Y combinations were screened with either antibody cocktail A and B or C alone. All screens were conducted on cone cells from 2 different blood donors. Data was captured and evaluated using commercially available software tools. A total of 2500 Fab-X+Fab-Y combinations were screened to 315 different antigen combinations.

Results

The percentage inhibition of the induction of phosphorylation of BCR signalling cascade proteins by each Fab-Kd-Fab [i.e. A-X:Y-B where A and B are Fab fragments] combination was calculated, in this example looking for new combinations of antigens that inhibit B cell function, the criteria for a positive combination was set as at least 30% inhibition of at least two phospho-readouts by at least one combination of V regions. According to this threshold 11 new antigen pair combinations out of 315 examined met the required criteria. This represents a 3.5% hit rate demonstrating the importance of screening large numbers of combinations to find those of desired activity and how rare the activity of the combination of CC79b and CD22 is.

FIGS. 10-12 show the data for the antigen grid cross specificities. Values are percentage inhibition (negative value for activation) of phosphorlylation of Syk, PLCγ2 & AKT respectively and represent the mean of multiple V-region combinations evaluated. 315 different antigen combinations were tested and as can be seen the effect on BCR signalling by different combinations of antibody varied significantly from strong inhibition e.g. antigen 2 (CD79b) on Fab-X combined with antigen 3 (CD22) on Fab-Y (69.66% inhibition of phospho Syk) and antigen 2 (CD79b) on Fab-Y combined with antigen 3 (CD22) on Fab-X (52.32% inhibition of phospho Syk) shown in FIG. 11) to activation e.g antigen 6 on X and antigen 11 on Y (minus 118.10% phospho Syk FIG. 11).

Figure 14:
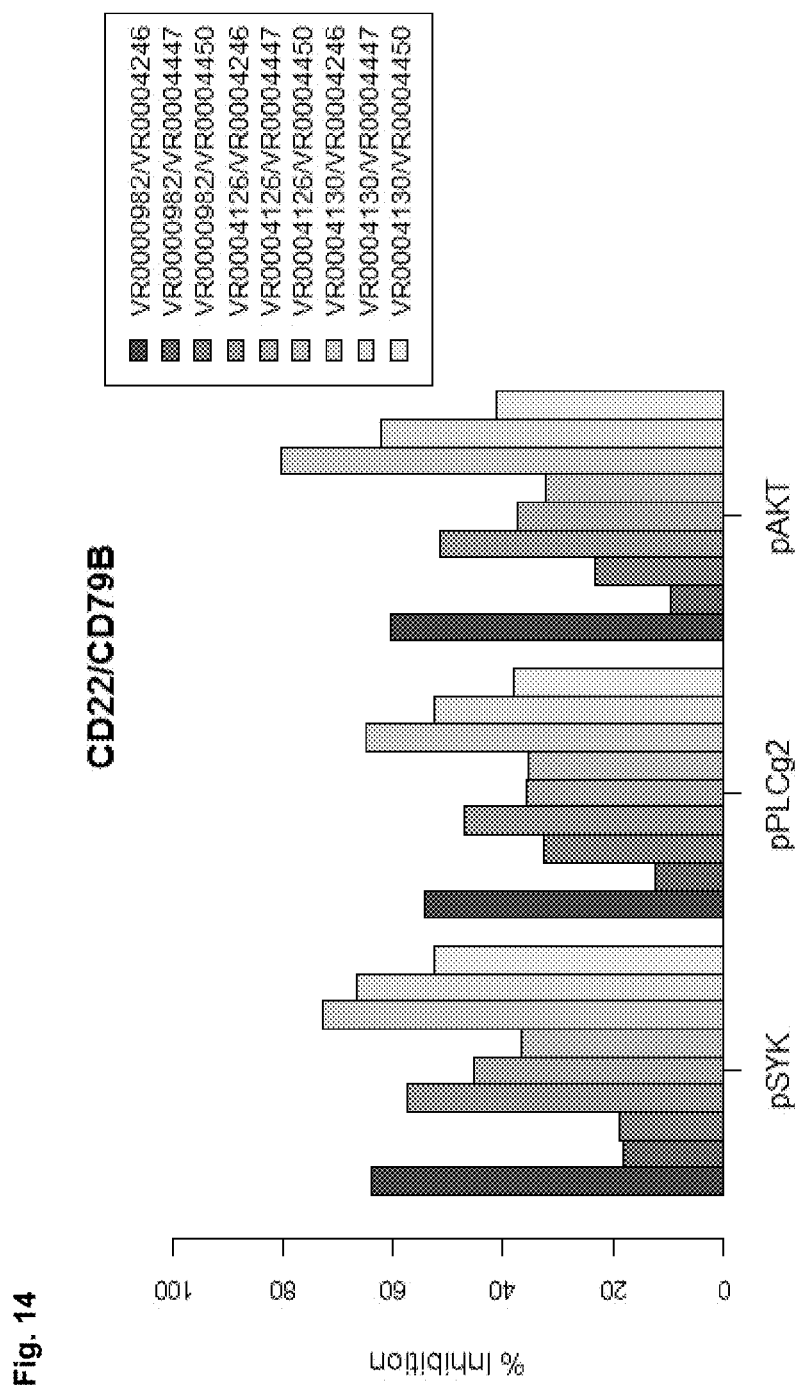
FIG. 14 is a graph showing the percentage inhibition of the phosphorylation of Syk, PLCγ2 & AKT of the phosphorylation of Syk, PLCγ2 & AKT for each V-region combination for CD22 specificity in Fab-X combined with CD79b specificity in Fab-Y.

Each data point representing the mean % values represented in FIGS. 10-12 is shown for antigen 2 (CD79b) on Fab-X and antigen 3 (CD22) on Fab-Y in FIG. 13. In this case, 23 different combinations of different antibody V regions were evaluated. The same antigen combination but in alternative orientation, i.e. antigen 2 (CD79b) on Fab-Y and antigen 3 (CD22) on Fab-X is shown in FIG. 14. In this case, 9 different combinations of different antibody V-regions were evaluated. All V regions show inhibition but advantageously this method can also be used in the selection of optimal V-region combinations.

Example 8 Comparison of the Activity of Antigen CD79b Plus Antigen CD22 Co-Targeting in Fab-Kd-Fab Screening Format to a Molecularly Linked Bispecific BYbe Format Introduction: To check that CD79b/CD22 target pair activity identified in the Fab-Kd-Fab heterodimerically tethered screening complex could translate to similar desired activity in an alternative therapeutic molecularly linked format, Antigen CD79b specificity (VR4447) and antigen CD22 specificity (VR4130) were generated in a BYbe format. This BYbe format consists of the anti-Antigen CD22 V regions (VR4130) as a disulphide stabilised (ds) single chain (sc)-Fv fused to the heavy chain of the anti-Antigen CD79b Fab (VR4447) via a linker SGGGGSGGGGS (SEQ ID NO:17).

Methods:
The purification of BYbes for functional screening was performed as follows:

The functional screening BYbe (Fab-dsscFv [scFv off C-terminus of Fab heavy chain]) formats were purified as follows. Clarified cell culture supernatants from standard expiHEK or CHO expression were 0.22 µm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH2.7. The elution was followed by absorbance at 280 nm, the elution peak collected, and then neutralised with ½5$^{th}$ volume of 2M Tris/HCl pH8.5. The neutralised samples were concentrated using Amicon Ultra-15 concentrators with a 10 kDa (BYbes) molecular weight cut off membrane and centrifugation at 4000×g in a swing out rotor. Concentrated samples were applied to either a XK16/60 or XK26/60 Superdex200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 µm, 7.8×300 mm column developed with an isocratic gradient of 0.2M phosphate, pH7.0 at 1 ml/min, with detection by absorbance at 280 nm. Selected monomer fractions were pooled and concentrated to >1 mg/ml using an Amicon Ultra-15 concentrator with a 10 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 µm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's EndoSafe® Portable Test System with Limulus Amebocyte Lysate (LAL) test cartridges.

Functional Assays

Activation Marker Assay: Antigen CD79b-specific Fab'-Y and Antigen CD22-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen CD79b and CD22-specific BYbe was also titrated from a starting molarity of 100 nM, in 1:4 serial dilutions. In V-bottomed 96 well plates, 1.5×10$^5$ PBMC were added to wells, to which were added titrated Fab'-X and Fab'-Y combinations or titrated BYbe. The Fab'-X and Fab'-Y combinations or BYbe were incubated with cells for a further 90 minutes. After this time B cells were activated by the addition of 25 µg/mL of goat F(ab')2 anti-human IgM (Southern Biotechnology) for 24 hours at 37° C. plus 5% $CO_2$.

To the wells were added 100 µL, ice-cold FACS buffer (PBS+1% BSA+0.1% NaN3+2 mM EDTA), the plates were sealed and covered with wet-ice for approximately 15 minutes, before centrifuging at 500×g for 5 minutes at 4° C. Excess supernatant was discarded from the cell pellets and the plates shaken at 2000 rpm for 30 seconds.

Cells were then stained with a cocktail of fluorescently labelled anti-CD19, anti-CD20 and anti-CD71, anti-CD40 and anti-CD86 antibodies (BD Biosciences). Plates were shaken briefly and incubated for 1 hour on wet-ice in the dark. After this time plates were washed twice and resuspended in 20 µL of FACS buffer. Cellular expression of CD19, CD20 and CD71, CD40 and CD86 was measured using an Intellicyt iQUE® Screener flow cytometer.

Using the data analysis software package Forecyt™ (Intellicyt) B cells were identified as distinct from other cell populations and the geometric mean of CD71, CD40 and CD86 levels were calculated for each well. All data was then expressed as the percentage inhibition of the maximal response (anti-IgM only) minus the background (cells only).

PhosFlow Assay: Antigen CD79b-specific Fab'-Y and Antigen CD22-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen CD79b and Antigen CD22-specific BYbe was also titrated from a starting molarity of 100 nM, in 1:4 serial dilutions. In V-bottomed 96 well plates, 5.0×10$^4$ PBMC were added to wells, to which were added titrated Fab'-X and Fab'-Y combinations or titrated BYbe.

The Fab'-X and Fab'-Y combinations or BYbe were incubated with cells for a further 90 minutes. After this time B cells were activated by the addition of 25 µg/mL of goat F(ab')2 anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes.

Excess supernatant was discarded from the cell pellet which was resuspended in FACS buffer (PBS+1% BSA+ 0.01% NaN3+2 mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and anti-phosphorylated PLCγ2, anti-phosphorylated Akt and anti-phosphorylated p38 antibodies (BD Biosciences). Plates were then resuspended and incubated for 1 hour at room temperature in the dark. After this time plates were washed a further two times and resuspended in 20 μL of FACS buffer. Cellular expression of CD20 and phospho-PLCγ2, phospho-Akt and phospho-p38 were measured using an Intellicyt iQUE® flow cytometer.

Using the data analysis software package Forecyt™ (Intellicyt) B cells were identified as distinct from other cell populations and the geometric mean of PLCγ2, Akt and p38 levels were calculated for each well. All data was then expressed as the percentage inhibition of the maximal response (anti-IgM only) minus the background (cells only).

Results

Figure 15:
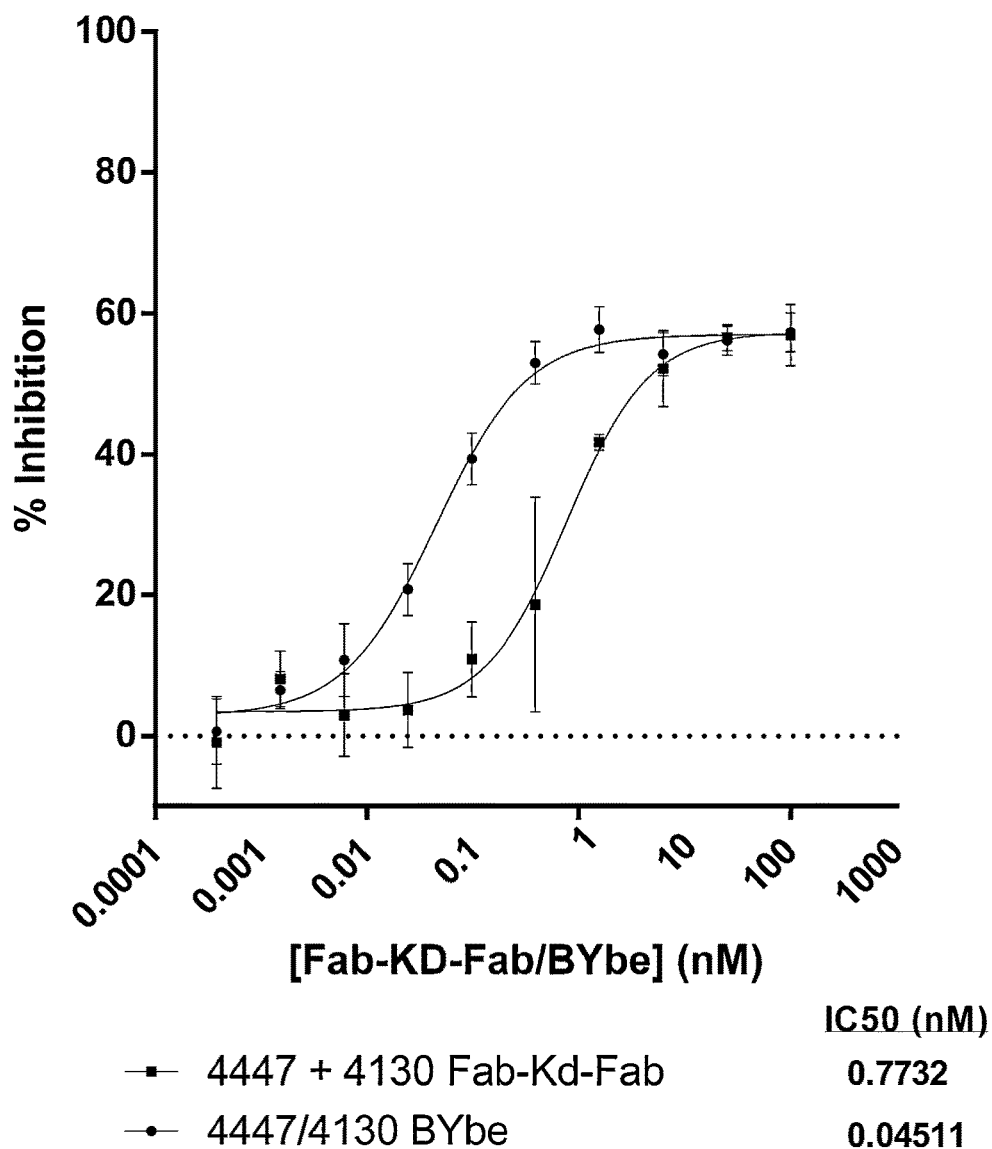
FIG. 15 shows data for the percentage inhibition of anti-IgM induced phosphorylated PLCγ2 in B-cells by CD79b and CD22 specific Fab-Kd-Fab or BYbe
Figure 16:
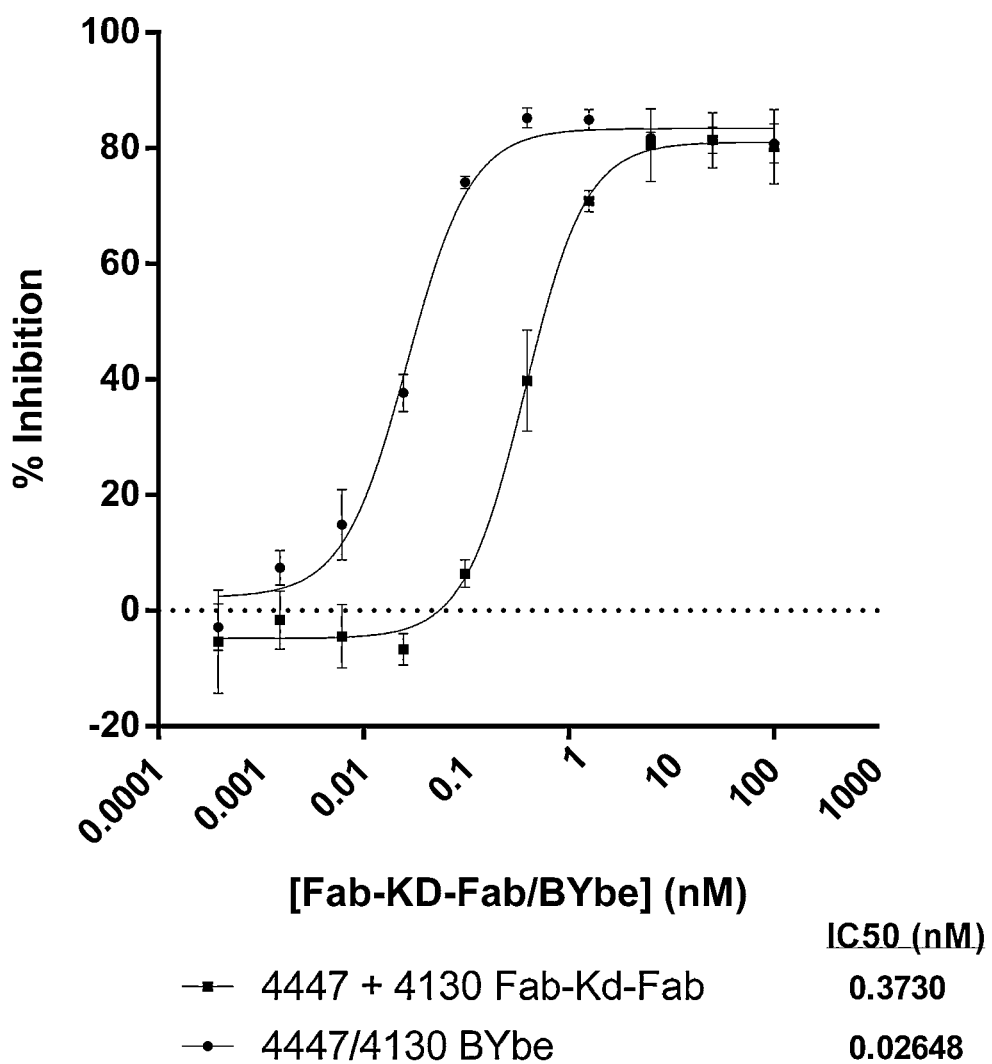
FIG. 16 shows data for the percentage inhibition of anti-IgM induced phosphorylated P38 in B-cells by CD79b and CD22 specific Fab-Kd-Fab or BYbe
Figure 17:
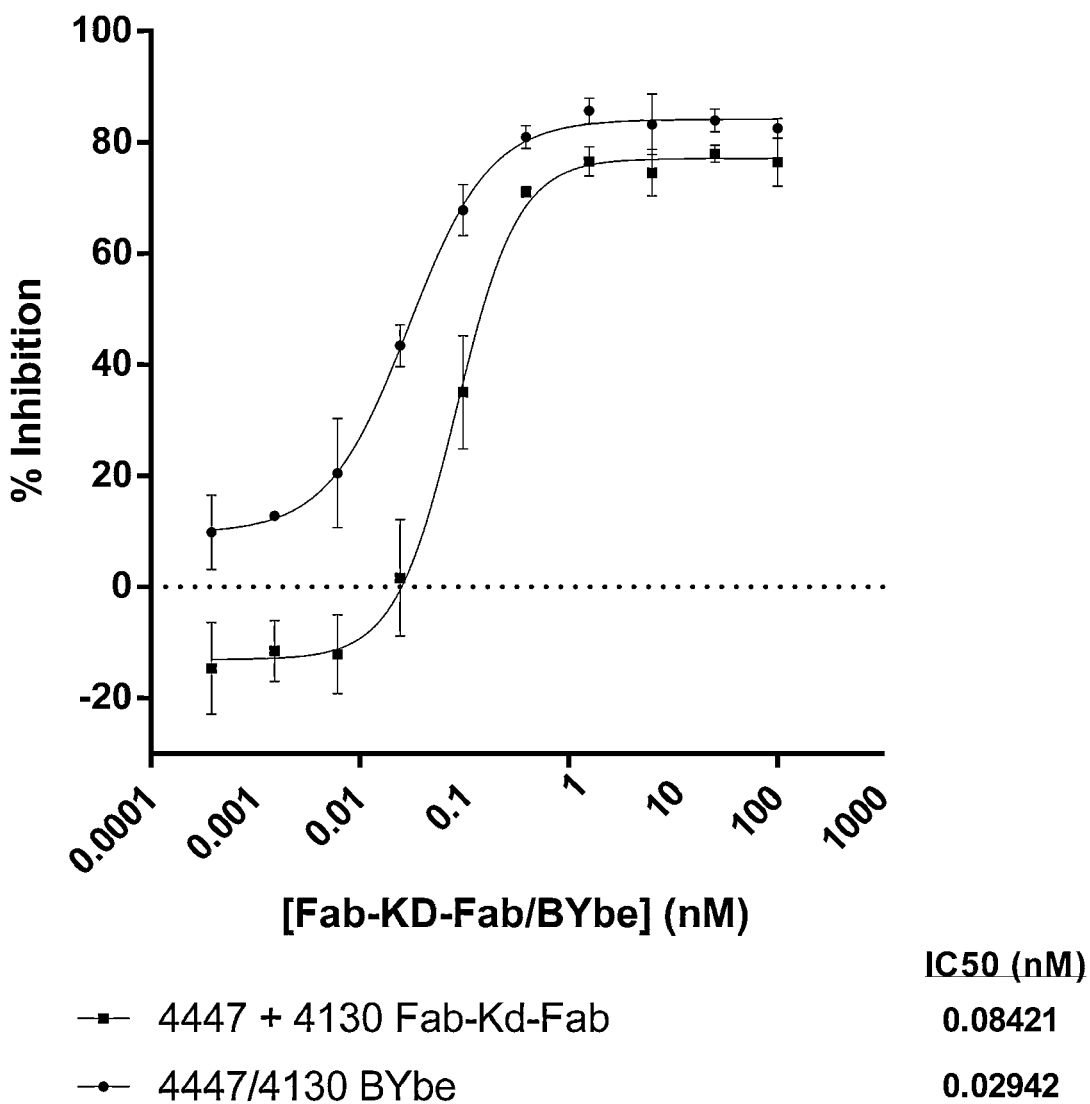
FIG. 17 shows data for the percentage inhibition of anti-IgM induced phosphorylated Akt in B-cells by CD79b and CD22 specific Fab-Kd-Fab or BYbe

PhosFlow Assay: The data in FIG. 15 show that targeting antigen CD79b and antigen CD22 either in the Fab-Kd-Fab or BYbe format can inhibit phosphorylated PLCγ2 in B-cells stimulated with anti-IgM. The data in FIG. 16 show that targeting antigen CD79b and antigen CD22 either in the Fab-Kd-Fab or BYbe format can inhibit phosphorylated P38 in B-cells stimulated with anti-IgM. The data in FIG. 17 show that targeting antigen CD79b and antigen CD22 either in the Fab-Kd-Fab or BYbe format can inhibit phosphorylated Akt in B-cells stimulated with anti-IgM.

Figure 18:
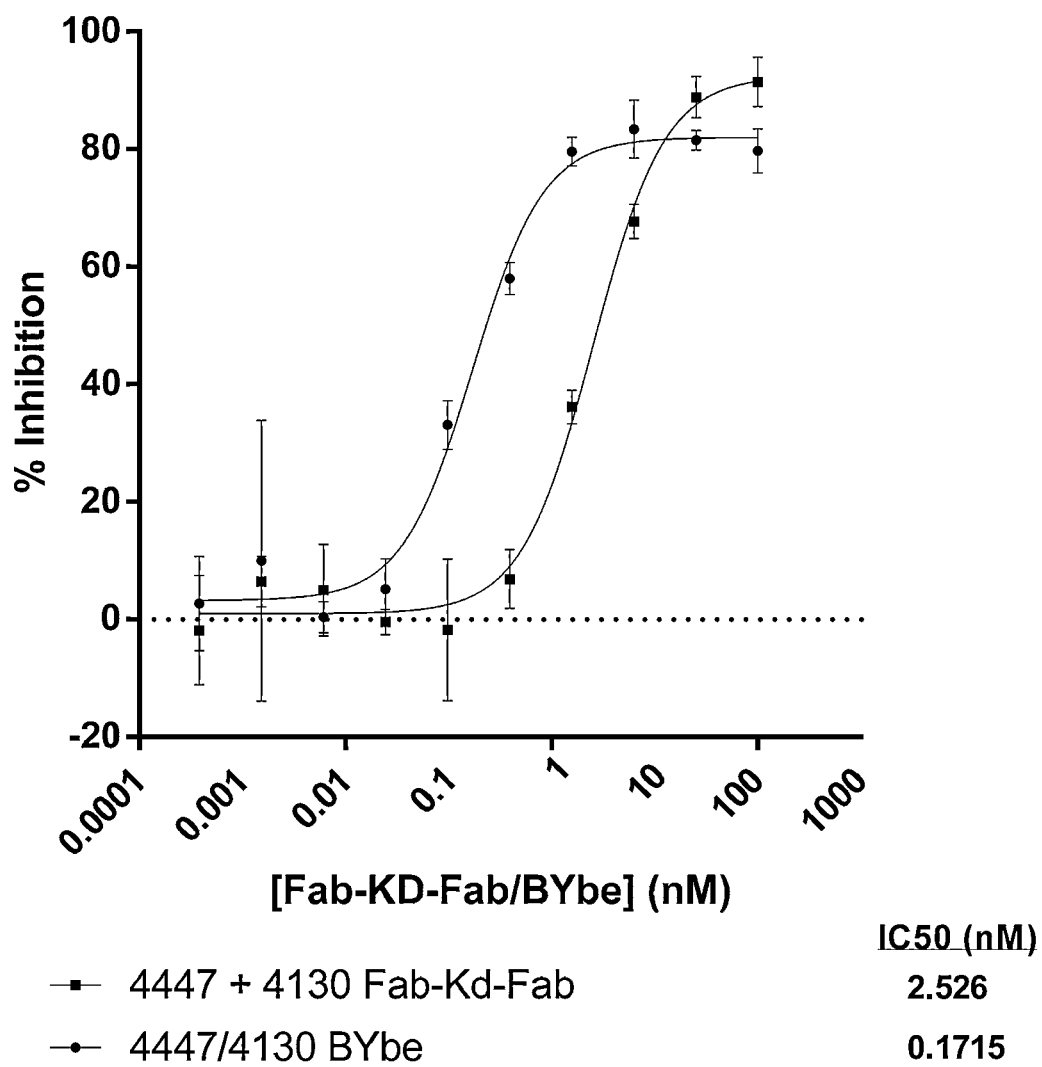
FIG. 18 shows data for the percentage inhibition of anti-IgM induced CD71 expression on B-cells by CD79b and CD22 specific Fab-Kd-Fab or BYbe
Figure 19:
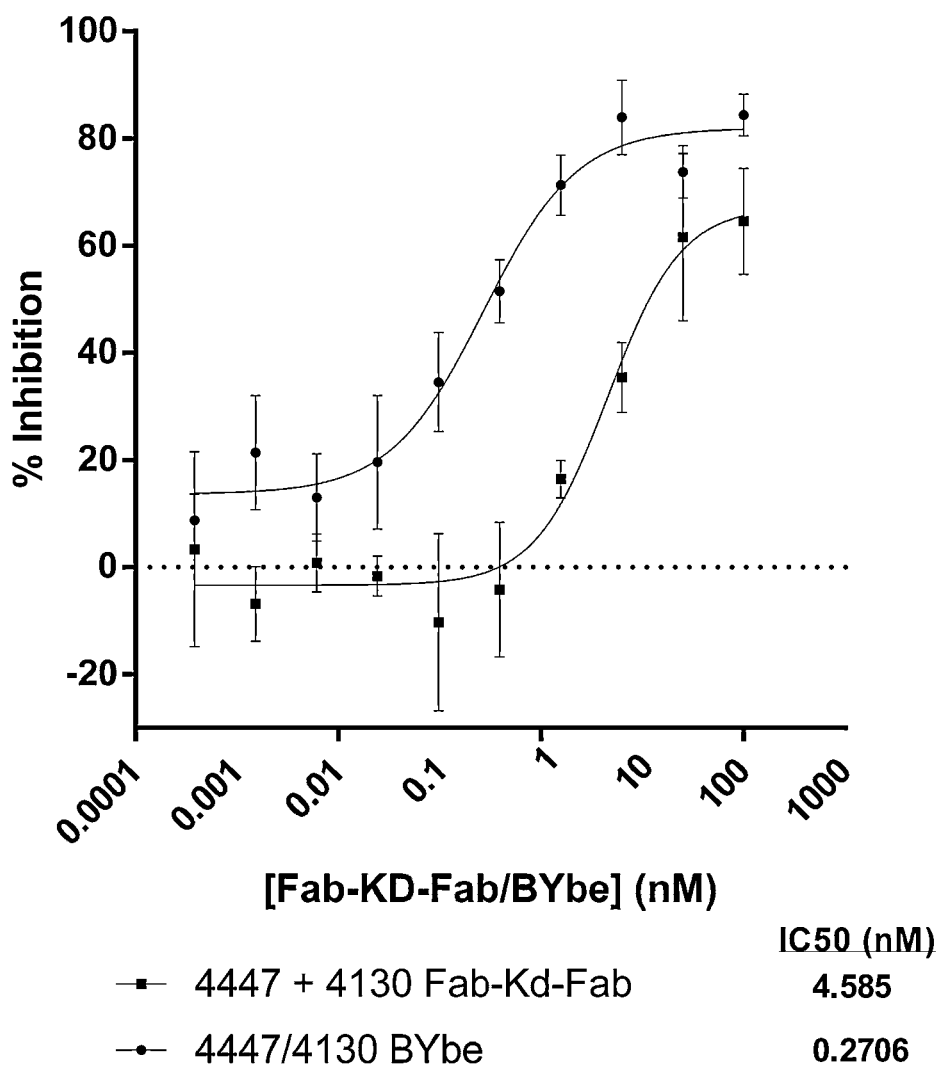
FIG. 19 shows data for the percentage inhibition of anti-IgM induced CD40 expression on B-cells, by CD79b and CD22 specific Fab-Kd-Fab or BYbe.
Figure 20:
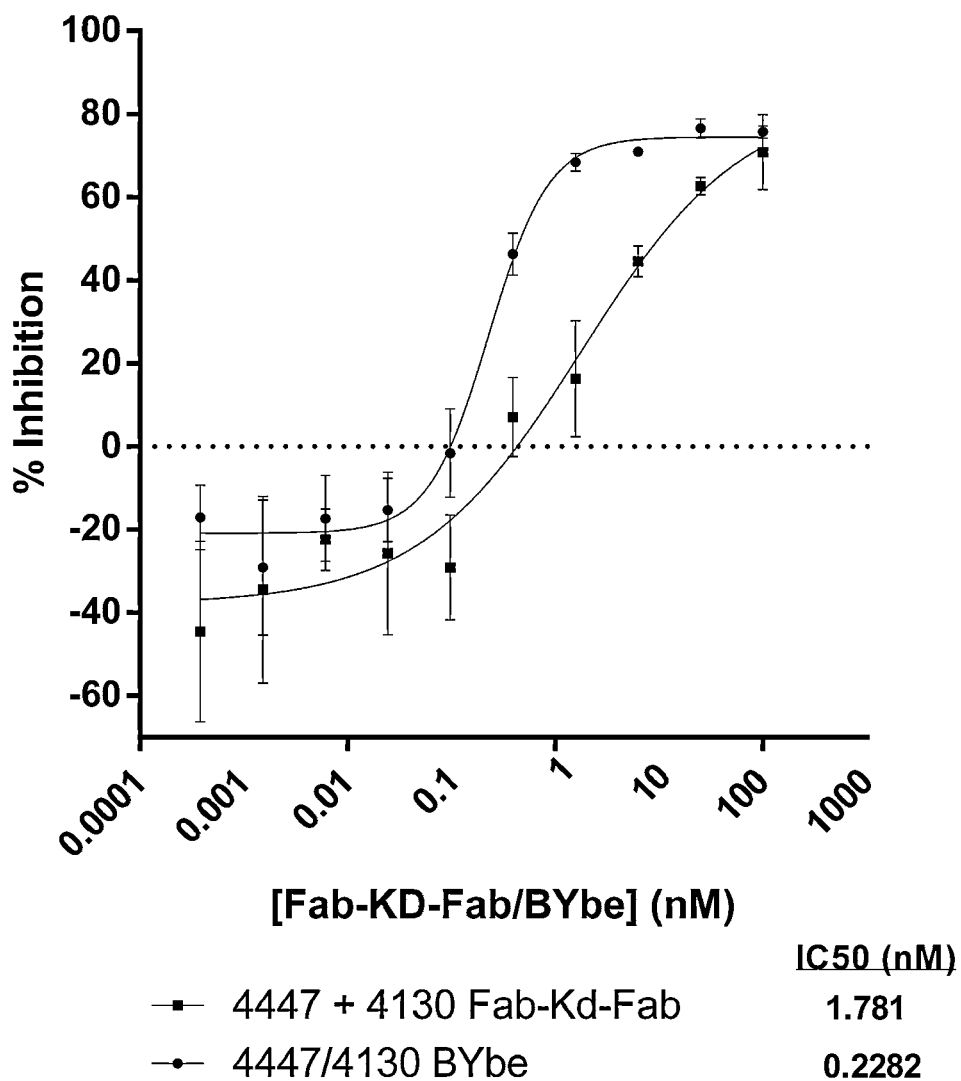
FIG. 20 shows data for the percentage inhibition of anti-IgM induced CD86 expression on B-cells by CD79b and CD22 specific Fab-Kd-Fab or BYbe

Activation Marker Assay: As can be seen in FIG. 18, the data show that targeting antigen CD79b and antigen CD22 either in the Fab-Kd-Fab or BYbe format can inhibit CD71 expression on B-cells stimulated with anti-IgM. The data in FIG. 19 show that targeting antigen CD79b and antigen CD22 either in the Fab-Kd-Fab or BYbe format can inhibit CD40 expression on B-cells stimulated with anti-IgM. The data in FIG. 20 show that targeting antigen CD79b and antigen CD22 either in the Fab-Kd-Fab or BYbe format can inhibit CD86 expression on B-cells stimulated with anti-IgM Example 9—Comparison of the Activity of Antigen CD79b Plus Antigen CD22 Co-Targeting in a Molecularly Linked Bispecific Bybe Format with the Further Addition of an Anti-Albumin Binding Domain for Extention of In Vivo Half-Life Introduction: To check that the CD79b/CD22 target pair activity identified in the Fab-Kd-Fab heterodimerically tethered screening complex could translate to similar desired activity in a potential therapeutic molecularly linked format with an anti-albumin targeted in vivo half-life extension, an anti-albumin antibody fragment was fused to the light chain of the antigen CD22 Fab of the BYbe format described in Example 8 via a linker having the sequence SGGGGSGGGGS (SEQ ID NO:17). Antigen CD79b specificity (VR4447) and antigen CD22 specificity (VR4130 and VR4126) were generated in a Bybe format with and without addition of an anti-albumin fragment (VR0645).

Description of constructs used in this experiment.

| Construct Name | Fab Specificity | Heavy Chain scFv | Light Chain scFv |
|---|---|---|---|
| VR4447/VR4126 BYbe | Antigen CD79b | Antigen CD22 | None |
| VR4447/VR4126/VR645) BYbe/Albumin | Antigen CD79b | Antigen CD22 | Albumin |
| VR4447/VR4130 BYbe | Antigen CD79b | Antigen CD22 | None |
| VR4447/VR4130/VR645) BYbe/Albumin | Antigen CD79b | Antigen CD22 | Albumin |

Methods

Purification of BYbes with/without Anti-Albumin Additional Specificity

The BYbe (Fab-dsscFv [scFv off C-terminus of Fab heavy chain]) and BYbe with anti-albumin (Fab-2×dsscFv [scFvs off C-terminus of Fab heavy chain and light chain]) formats were purified as follows. Clarified cell culture supernatants from standard expiHEK or CHO expression were 0.22 μm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH 2.7. The elution was followed by absorbance at 280 nm, the elution peak collected, and then neutralised with $\frac{1}{25}^{th}$ volume of 2 M Tris/HCl pH8.5. The neutralised samples were concentrated using Amicon Ultra-15 concentrators with either a 10 kDa or 30 kDa molecular weight cut off membrane and centrifugation at 4000×g in a swing out rotor. Concentrated samples were applied to either a XK16/60 or XK26/60 Superdex 200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 μm, 7.8×300 mm column developed with an isocratic gradient of 0.2 M phosphate, pH 7.0 at 1 ml/min, with detection by absorbance at 280 nm. Selected monomer fractions were pooled and concentrated to >1 mg/ml using an Amicon Ultra-15 concentrator with a 10 kDa or 30 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 μm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's EndoSafe® Portable Test System with Limulus Amebocyte Lysate (LAL) test cartridges.

100 nM of each construct purified protein were pre-incubated with human PBMC derived from five separate donors for 60 min at 37 degree C./5% CO₂ in RMPI 1640 media plus 10% foetal bovine serum and 2 mM Glutamax (R10 media). After 60 min cells were stimulated with 25 ug/ml of a goat anti-IgM antibody designed to stimulate B cells only. 24 hours later plates were placed on ice to halt any further cell activation before washing once with ice cold flow cytometry buffer (PBS+1% BSA+0.01% NaN3). All supernatant was removed and cell pellets resuspended. Cells were placed on ice and a cocktail of anti-CD19, -CD20, -CD27, -CD71 and CD86 antibodies added. Cells were incubated for 60 min before washing twice in flow cytometry buffer. Data on the binding of anti-CD27, -CD71 and CD86 to CD19/CD20 positive B cells was generated using an iQUE high throughput flow cytometer. Forecyt software was used to generate histograms and derive geometric mean intensity readings for the binding of anti-CD27, -CD71 and CD86 antibodies to B cells. This data was imported into Excel and percentage inhibition values generated for each combination. The data was then imported into Graphpad Prism and box and whisker charts generated for each combination with the mean indicated by a '+'.

Figure 21:
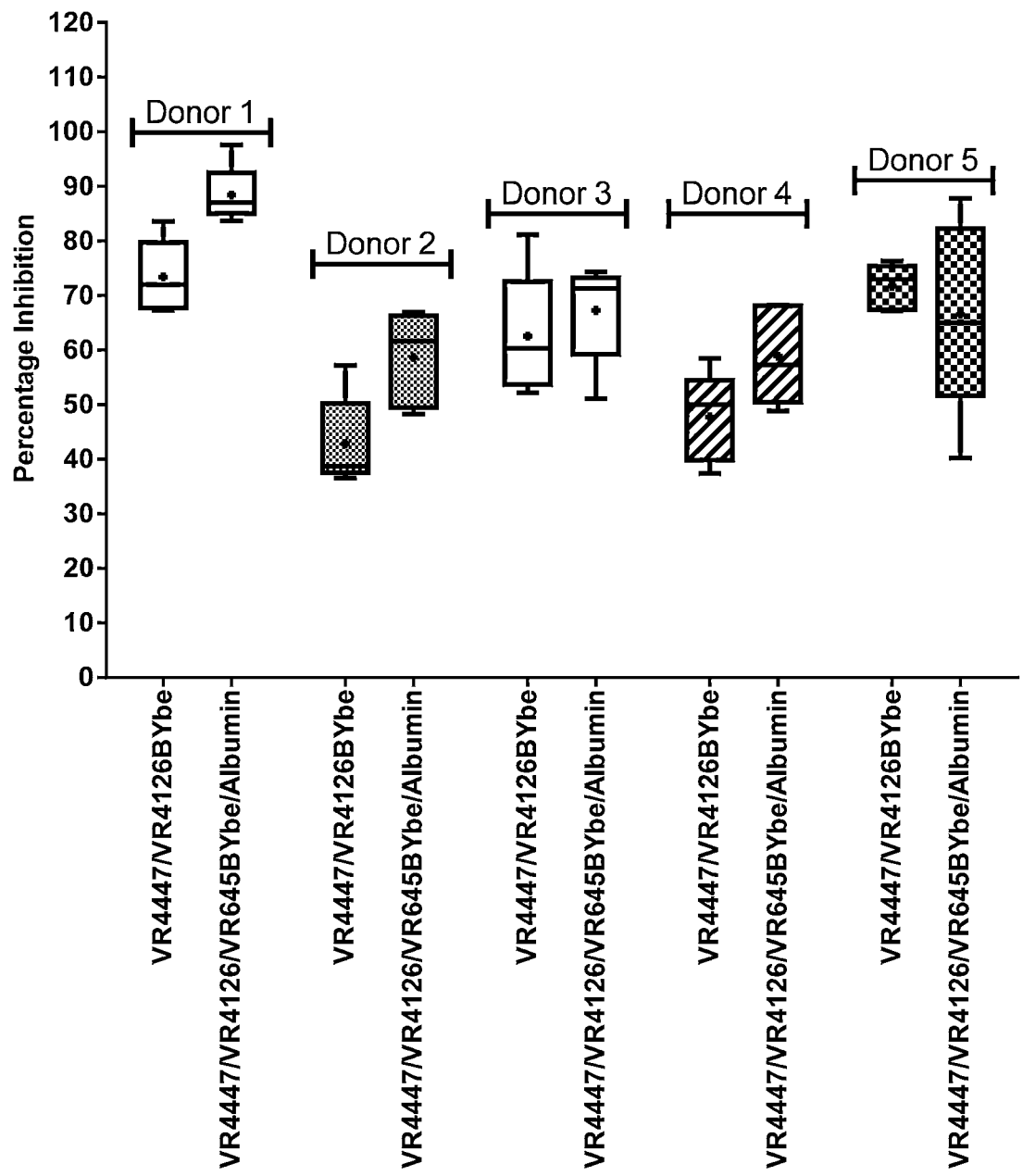
FIG. 21 shows the inhibition of CD27 expression on B cells by CD79b and CD22 specific VR4447/VR4126 BYbe and VR4447/VR4126/VR645 BYbe/Albumin
Figure 22:
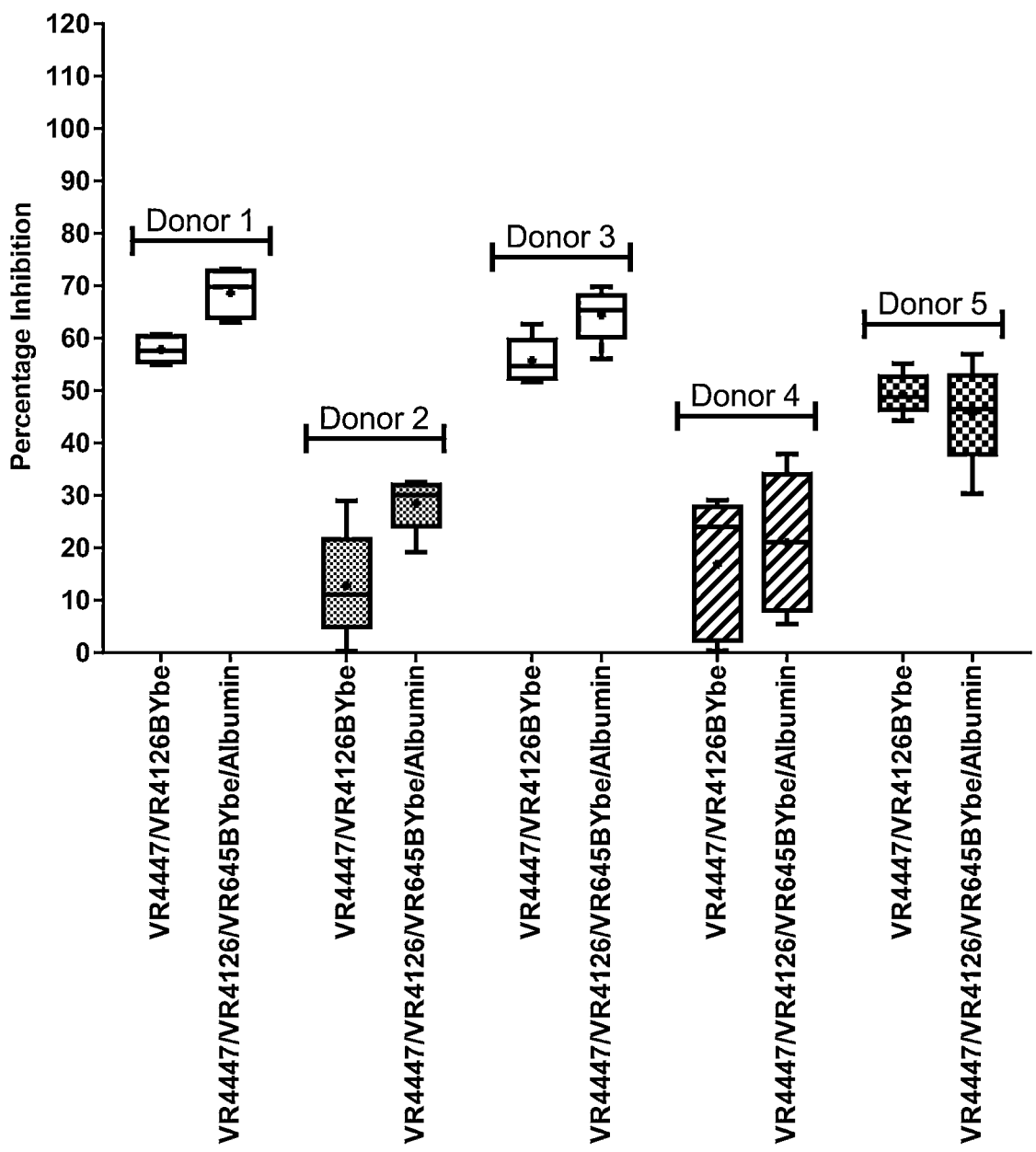
FIG. 22 shows the inhibition of CD71 expression on B cells by CD79b and CD22 specific VR4447/VR4126 BYbe and VR4447/VR4126/VR645 BYbe/Albumin
Figure 23:
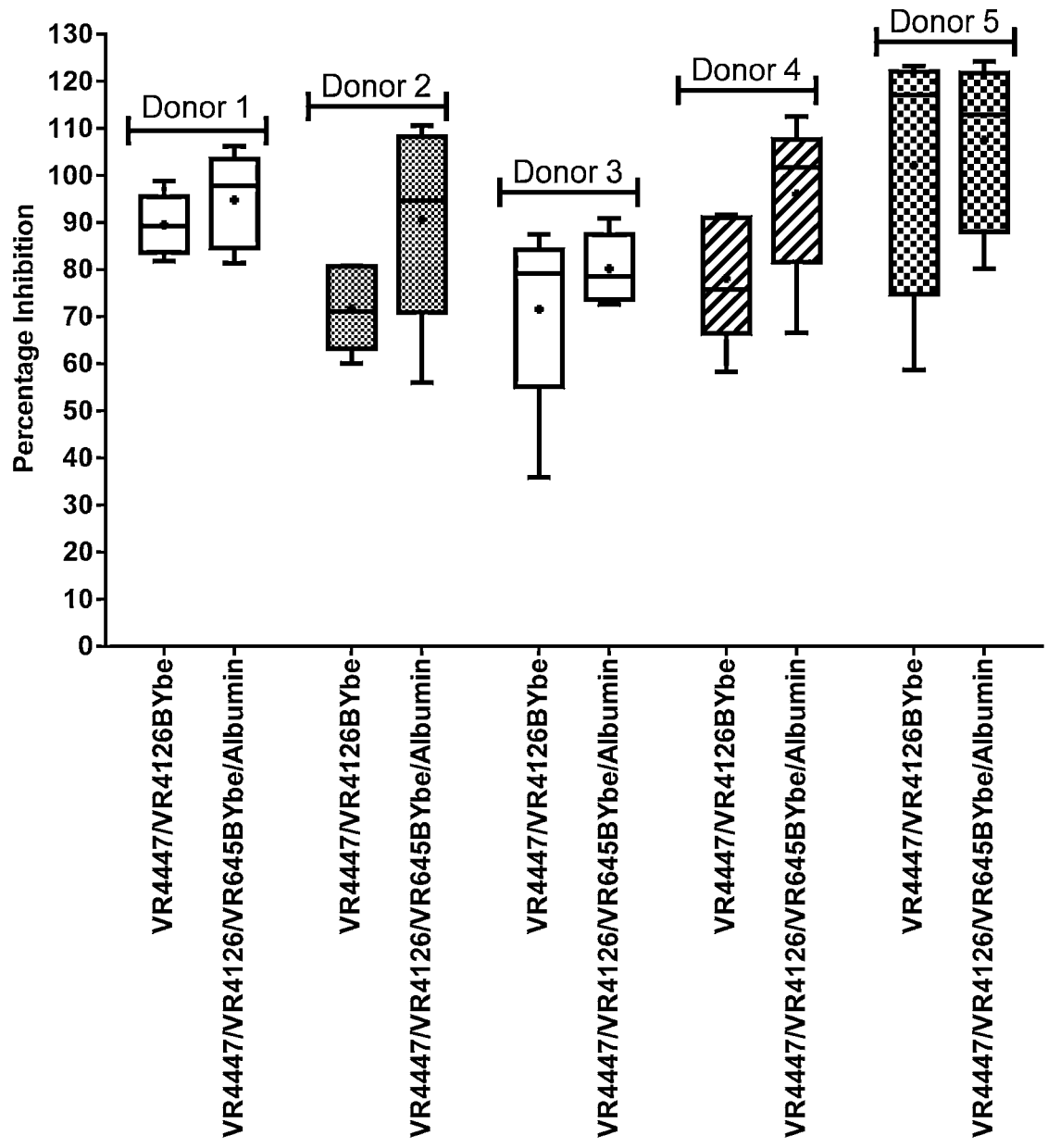
FIG. 23 shows the inhibition of CD86 expression on B cells by CD79b and CD22 specific VR4447/VR4126 BYbe and VR4447/VR4126/VR645 BYbe/Albumin

FIG. 21 shows the inhibition of CD27 expression on B cells induced by VR4447/VR4126 BYbe and VR4447/VR4126/VR645 BYbe/Albumin. Across the five donors tested both showed consistently similar levels of inhibition of anti-IgM induced CD27. FIG. 22 shows the inhibition of CD71 expression on B cells induced by VR4447/VR4126 BYbe and VR4447/VR4126/VR645 BYbe/Albumin. Across the five donors both showed consistently similar levels of inhibition of anti-IgM induced CD71. FIG. 23 shows the inhibition of CD86 expression on B cells induced by VR4447/VR4126 BYbe and VR4447/VR4126/VR645 BYbe/Albumin. Across the five donors both showed consistently similar levels of inhibition of anti-IgM induced CD86.

Figure 24:
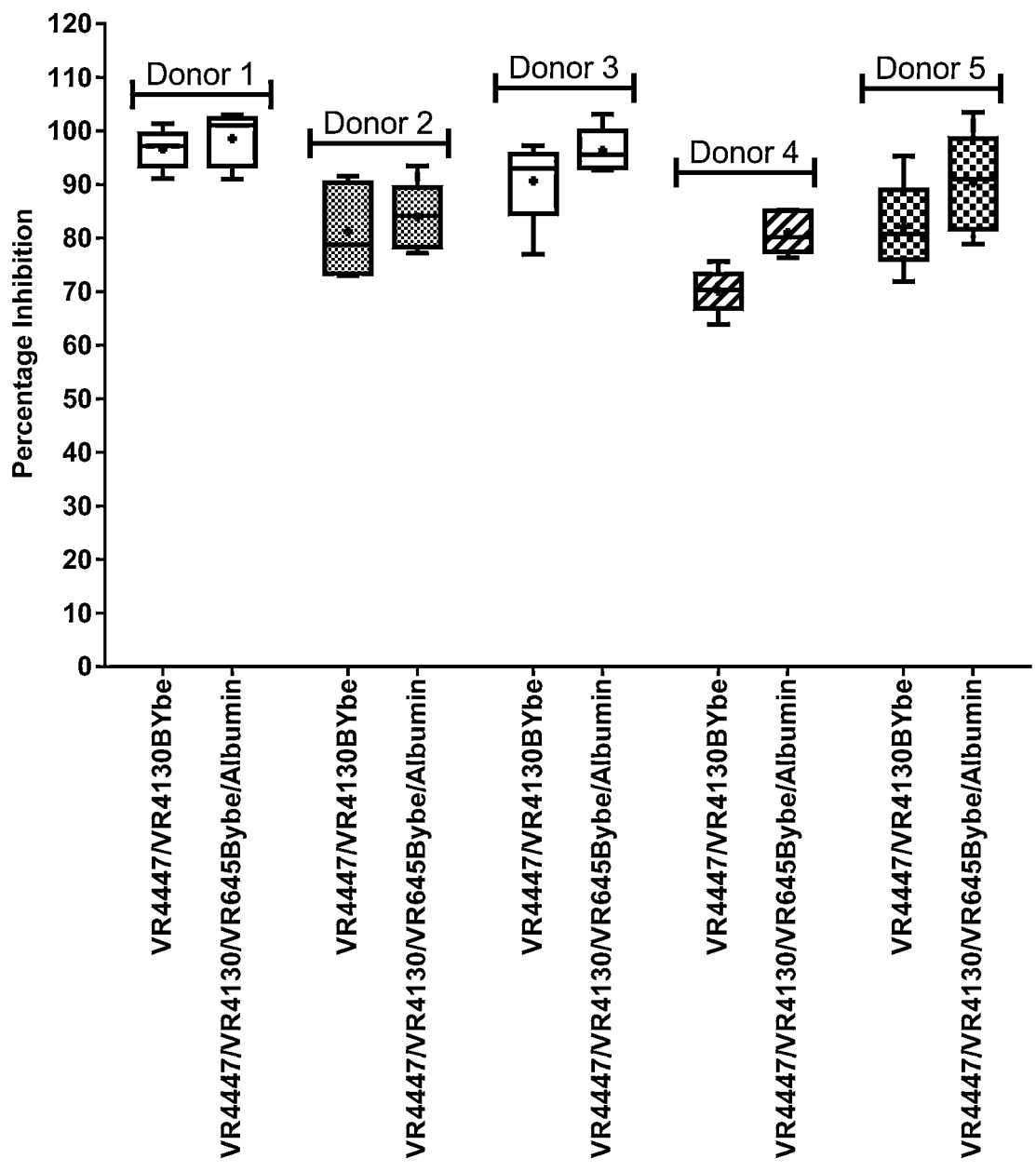
FIG. 24 shows the inhibition of CD27 expression on B cells by CD79b and CD22 specific VR4447/VR4130 BYbe and VR4447/VR4130/VR645 BYbe/Albumin
Figure 25:
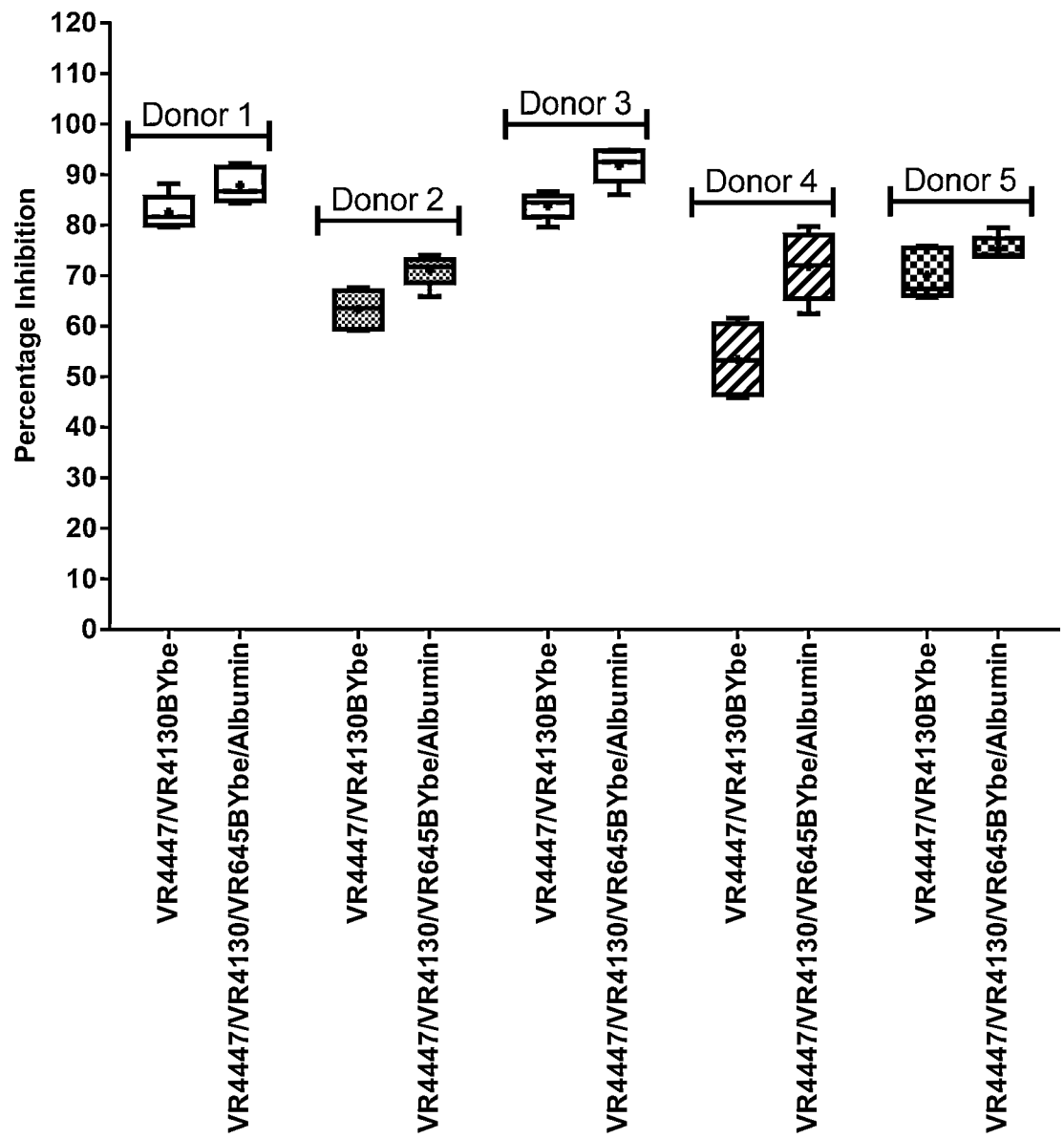
FIG. 25 shows the inhibition of CD71 expression on B cells by CD79b and CD22 specific VR4447/VR4130 BYbe and VR4447/VR4130/VR645 BYbe/Albumin
Figure 26:
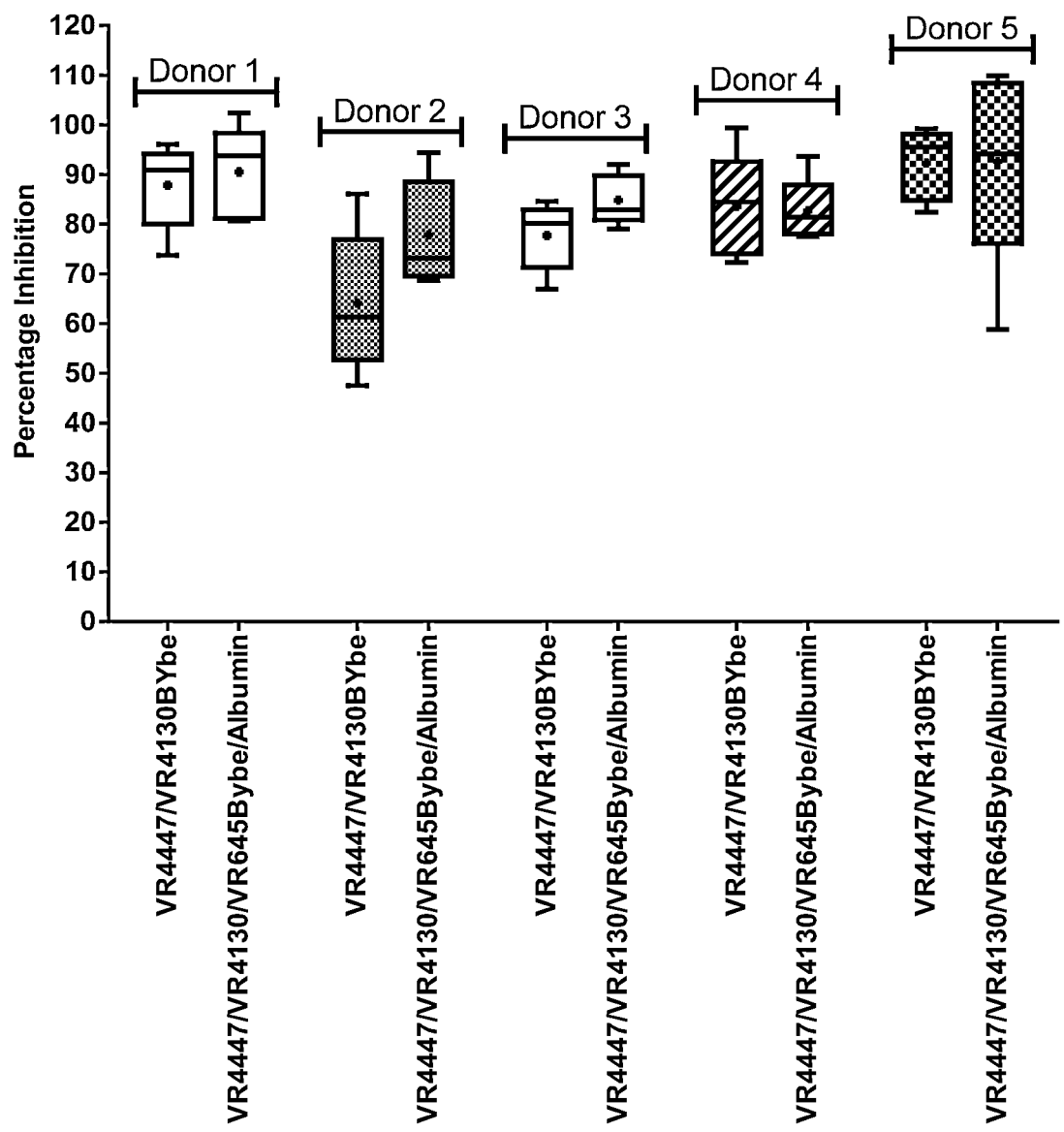
FIG. 26 shows the inhibition of CD86 expression on B cells by CD79b and CD22 specific VR4447/VR4130 BYbe and VR4447/VR4130/VR645 BYbe/Albumin.

FIG. 24 shows the inhibition of CD27 expression on B cells induced by VR4447/VR4130 BYbe and VR4447/VR4130/VR645 BYbe/Albumin. Across the five donors tested both showed consistently similar levels of inhibition of anti-IgM induced CD27. FIG. 25 shows the inhibition of CD71 expression on B cells induced by VR4447/VR4130 BYbe and VR4447/VR4130/VR645 BYbe/Albumin. Across the five donors both showed consistently similar levels of inhibition of anti-IgM induced CD71. FIG. 26 shows the inhibition of CD86 expression on B cells induced by VR4447/VR4130 BYbe and VR4447/VR4130/VR645 BYbe/Albumin. Across the five donors both showed consistently similar levels of inhibition of anti-IgM induced CD86.

Example 10—Effect of Co-Targeting the Antigen CD79b Plus Antigen CD22 on Memory B Cell Function Using Molecularly Linked Bispecific Bybes with or without Further Addition of an Anti-Albumin Introduction: To evaluate whether targeting CD79b/CD22 has a functional effect on B cells in long term culture, IgG production from B cells cultured in isolation or in a mixed PBMC culture was measured. The measurement of specific antibodies to the recall antigen tetanus toxoid provides a read out of memory B cell function.

Antigen CD79b specificity (VR4447) and antigen CD22 specificity (VR4126, VR4127 and VR4130) were generated in a BYbe format with or without addition of an anti-albumin fragment (VR0645). The anti-albumin antibody fragment was fused to the light chain of the antigen CD22 Fab of the BYbe format as described in Example 8 via a linker having the sequence SGGGGSGGGGS (SEQ ID NO:17).

Description of constructs used in this experiment.

| Construct Name | Fab Specificity | Heavy Chain scFv | Light Chain scFv |
|---|---|---|---|
| VR4447/VR4126 BYbe | Antigen CD79b | Antigen CD22 | None |
| VR4447/VR4126/VR645 BYbe/Albumin | Antigen CD79b | Antigen CD22 | Albumin |
| VR4447/VR4127 BYbe | Antigen CD79b | Antigen CD22 | None |
| VR4447/VR4130 BYbe | Antigen CD79b | Antigen CD22 | None |
| VR4447/VR4130/VR645 BYbe/Albumin | Antigen CD79b | Antigen CD22 | Albumin |

Methods

Purification of BYbes with/without Anti-Albumin Additional Specificity

The BYbe (Fab-dsscFv [scFv off C-terminus of Fab heavy chain]) and BYbe with anti-albumin (Fab-2×dsscFv [scFvs off C-terminus of Fab heavy chain and light chain]) formats were purified as described in example 9.

Activation of B Cells and Measurement of Tetanus Toxoid Specific IgG

Human PBMC or purified B cells derived from up to 3 separate donors were stimulated with 500 ng/ml CD40L, 1 ug/ml CpG and 50 ng/ml IL-21 in 1640 media plus 10% foetal bovine serum and 2 mM Glutamax (R10 medium) for 6 days. Constructs of purified protein were added at a final concentration of 100 nM at day 0 and remained in the culture medium for the duration of the assay. After 6 days the supernatants were harvested and the amount of tetanus toxoid specific IgG was detected by ELISA. Briefly, Maxisorp half-well ELISA plates (Nunc) were coated with 10 ug/ml tetanus toxoid in PBS overnight at 4° C. The plates were then blocked in 5% Milk-in PBS containing 0.05% Tween20 for 2 hours. The supernatants were diluted and then added for 2 hours at room temperature. The plates were washed with PBS-0.05% Tween20 and tetanus bound antibody was detected using a peroxidase-goat anti-human IgG(H+L) diluted to 1 ug/ml in 5% milk-PBS-0.05% Tween20. Plates were developed using TMB substrate solution (KPL) and absorbance was measured at 450 nM using a Synergy 2 micro-plate reader (Biotek). Data was exported to Excel and percentage inhibition was calculated relative to cells cultured without test antibodies. The data was then imported into Graphpad Prism® and plotted as bar charts.

FIG. 27 shows the inhibition of tetanus toxoid IgG production from PBMCs cultured with VR4447/VR4126 BYbe, VR4447/VR4127 BYbe and VR4447/VR4130 BYbe. Data represents pooled data from 3 donors.

FIG. 28 shows the inhibition of tetanus toxoid IgG production from purified B cells cultured with VR4447/VR4126 BYbe, VR4447/VR4127 BYbe and VR4447/VR4130 BYbe. Data represents pooled data from 2 donors.

Figure 29:
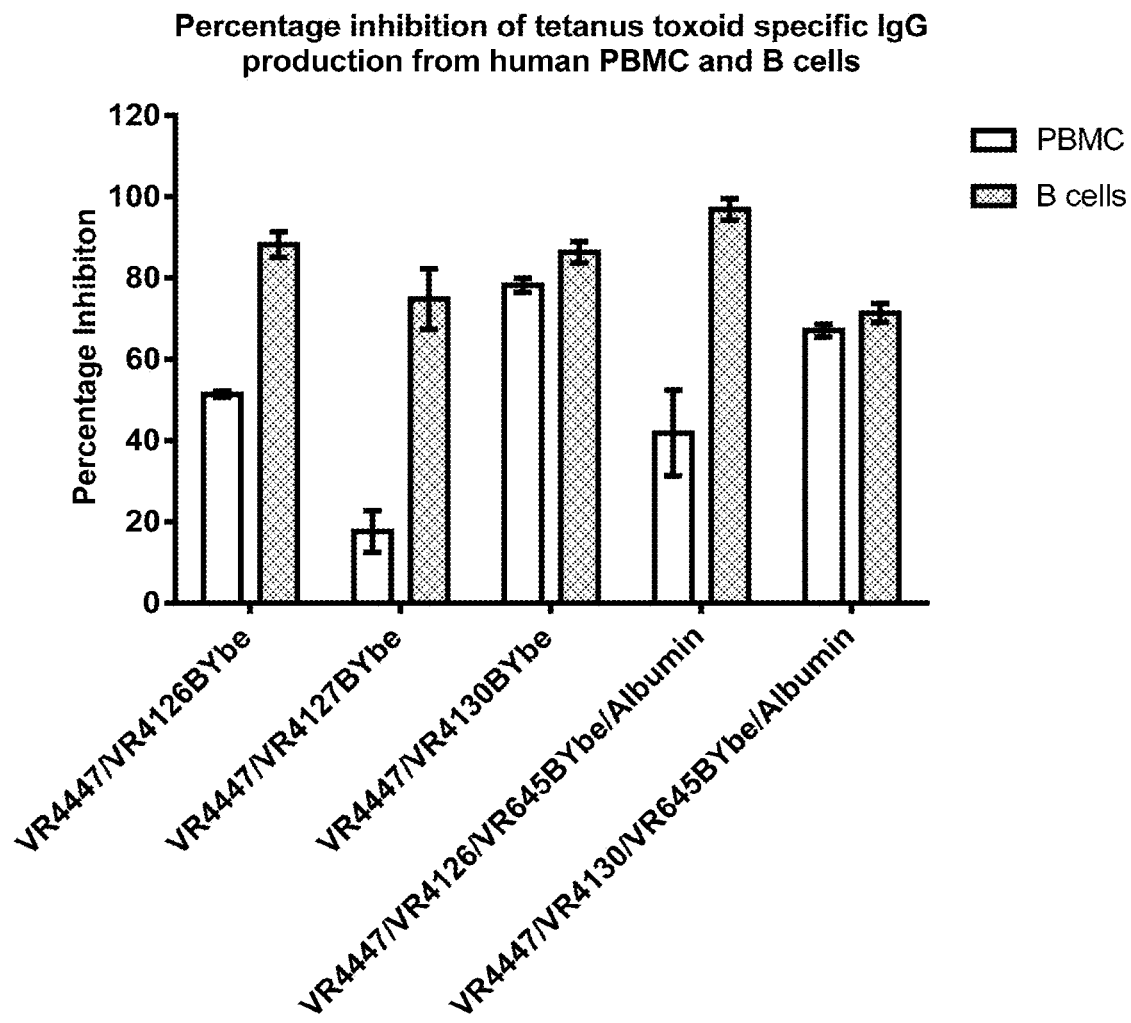

FIG. 29 shows the inhibition of tetanus toxoid IgG production from either PBMC or purified B cells cultured with VR4447/VR4126 BYbe, VR4447/VR4127 BYbe, VR4447/VR4130 BYbe, VR4447/VR4126/VR645 BYbe/Albumin and VR4447/VR4130/VR645 BYbe/Albumin. Data shown from a single donor.

Example 11—Dis-Regulation of BCR Signalling in SLE Patient B Cells & the Effect of Co-Targeting the Antigen CD79b Plus Antigen CD22 on SLE B Cell Function Introduction: In order to evaluate if the combination of CD79b/CD22 could be used to treat people with autoimmune diseases we used B cells from patients with systemic lupus erythematosus (SLE) as a model system. The impact of the CD79b/CD22 combination (VR4447/VR4130) was tested on the activation status of signalling proteins known to be involved in B cell function but dysregulated in SLE patients compared to healthy volunteers. In this experiment B cells from 12 SLE patients and 12 healthy volunteers were compared for the effect that co-targeting CD79b and CD22 had on their activation status.

Methods:

PhosFlow Assay: All assays were performed using $2\times10^5$ PBMC per well.

In treated samples antigen CD79b and antigen CD22-specific BYbe was tested at a concentration of 100 nM. PBMC from both healthy volunteers and patients with SLE were preincubated with BYbe for 90 minutes at 37° C. In the untreated samples, the BYbe was simply omitted during this incubation period. After this time cells were activated with 25 µg/mL of goat F(ab')$_2$ anti-human IgM (Southern Biotechnology) for 10 minutes at 37° C. plus 5% $CO_2$ and the reaction stopped by the addition of fixative (Cytofix—BD Biosciences). In the unstimulated samples, the anti-human IgM was simply omitted during this incubation period. After 15 minutes at room temperature cells were pelleted (500×g for 5 min) and then resupended in ice cold perm buffer III (BD Biosciences) before being washed twice in flow buffer (PBS+1% BSA+0.01% NaN3+2 mM EDTA). Cells were then stained with anti-CD20, anti-phosphorylated (p) NF-κB, anti-pSyk, anti-pAtk and anti-pErk1&2 and incubated at room temperature in the dark for one hour. Finally plates were washed twice in flow buffer before being measured on an iQUE flow cytometer (Intellicyt). The geometric mean (mean fluorescence intensity, MFI) of pNF-κB, pSyk, pAkt and pErk1&2 expression in B cells was then calculated and expressed in graphical form.

Figure 30:
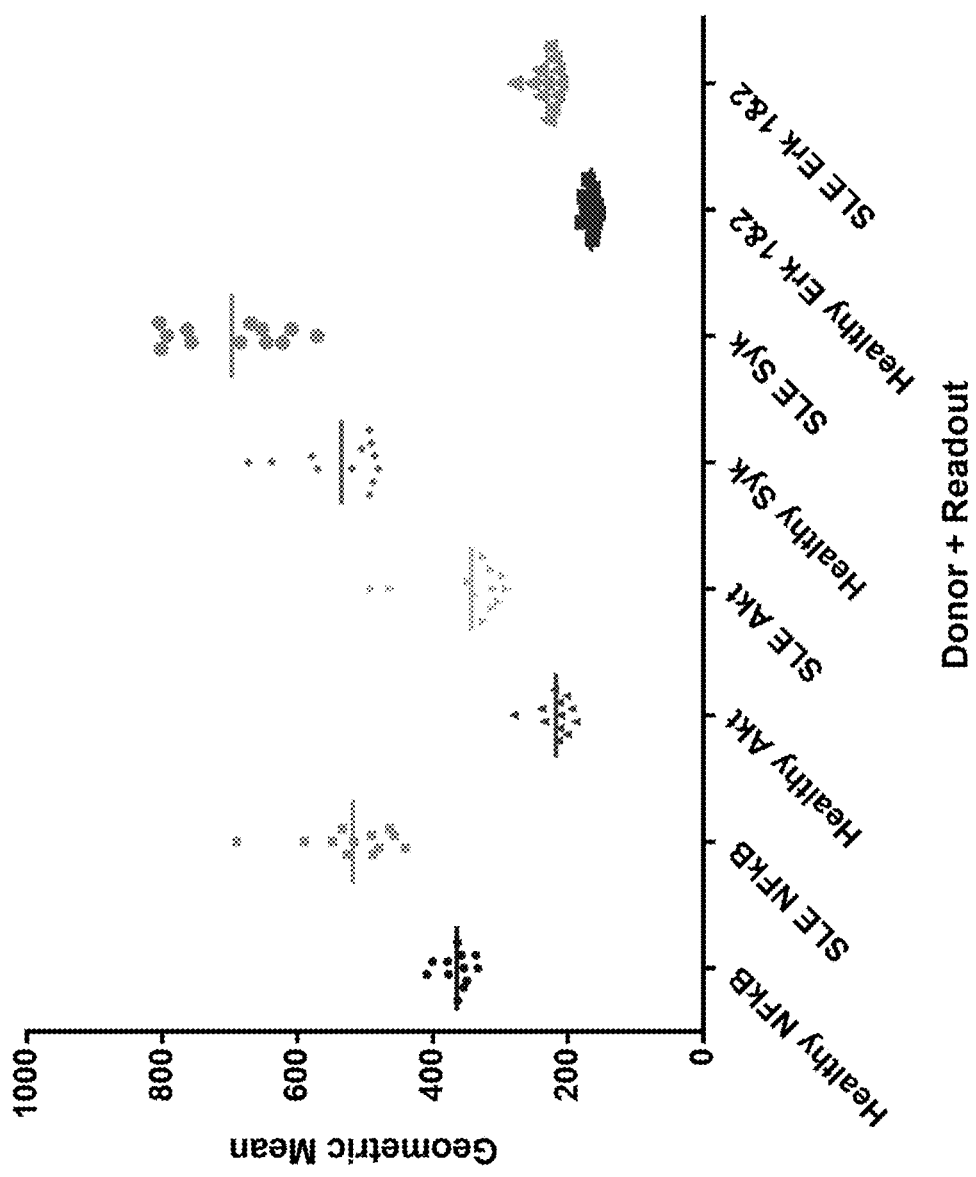
FIG. 30 shows the baseline levels of phosphorylation in unstimulated B-cells from 12 Healthy and 12 SLE Patient Samples.

Results:

FIG. 30 shows that the base-line phosphorylation of NF-κB, Syk, Akt and Erk1&2 (unstimulated & untreated) is elevated in SLE patient B cells as compared to those from healthy volunteers.

FIGS. 31 to 34 shows that the CD79/CD22 BYbe can equally inhibit pNF-κB, pSyk, pAkt and pErk1&2 in healthy volunteers and SLE patients.

Conclusions:

This data shows that B cells from SLE patients are activated before any in vitro stimulation when compared with healthy volunteers. Upon stimulation of the cells via the B cell receptor both healthy volunteers and SLE patients show an enhanced levels of activation compared to the background signal. In both healthy volunteers and SLE patients this signal is substantially blocked by the CD79b/CD22 combination. This data indicates that the CD79b/CD22 combination can inhibit B cell from both healthy volunteers as well as people with an underlying autoimmune disease indicating that this pathway is of fundamental importance to B cell activation.

Example 12 Humanisation Method

Humanised versions of the rabbit antibodies obtained in the previous examples and provided in FIG. 35 were designed by grafting the CDRs from the rabbit antibody V-regions onto human germline antibody V-region frameworks. In order to improve the likelihood of recovering the activity of the antibody, a number of framework residues from the rabbit V-regions were also retained in the designed humanised sequences. These residues were selected using the protocol outlined by Adair et al. (1991) (Humanised antibodies. WO91/09967). The CDRs grafted from the donor to the acceptor sequence are as defined by Kabat (Kabat et al., 1987), with the exception of CDRH1 where the combined Chothia/Kabat definition is used (see Adair et al., 1991 Humanised antibodies. WO91/09967). Commonly the VH genes of rabbit antibodies are shorter than the selected human VH acceptor genes. When aligned with the human acceptor sequences, framework 1 of the VH regions of rabbit antibodies typically lack the N-terminal residue, which is retained in the humanised antibody. Framework 3 of the rabbit antibody VH regions also typically lack one or two residues (75, or 75 and 76) in the loop between beta sheet strands D and E: in the humanised antibodies the gap is filled with the corresponding residues from the selected human acceptor sequence.

The humanised sequences are provided in FIG. 35 and donor residues indicated in bold and underlined. Variant CDR sequences are also provided.

CD79 Antibody Ab 4447

Human V-region IGKV1D-13 plus JK4 J-region (IMGT, http://www.imgt.org/) was chosen as the acceptor for antibody 4447 light chain CDRs. In addition to the CDRs, one or more of the following framework residues from the 4447 VK gene (donor residues) may be retained at positions 2, 3, 36, 46, 49 and 70 (Kabat numbering): Glutamine (Q2), Valine (V3), Leucine (L36), Glutamine (Q46), Histidine (H49) and Glutamine (Q70), respectively.

Human V-region IGHV3-48 plus JH4 J-region (IMGT, http://www.imgt.org/) was chosen as an acceptor for the heavy chain CDRs of antibody 4447. In addition to the CDRs, one or more of the following framework residues from the 4447 VH gene (donor residues) may be retained at positions 24, 48, 49, 71, 73, and 78 (Kabat numbering): Valine (V24), Isoleucine (I48), Glycine (G49), Lysine (K71), Serine (S73) and Valine (V78), respectively.

Human V-region IGHV4-59 plus J1-14 J-region (IMGT, http://www.imgt.org/) was chosen as an alternative acceptor for the heavy chain CDRs of antibody 4447. In addition to the CDRs, one or more of the following framework residues from the 4447 VH gene (donor residues) may be retained at positions 37, 67, 71, 73 and 78 (Kabat numbering): Valine (V37), Phenylalanine (F67), Lysine (K71), Serine (S73) and Valine (V78), respectively. The Glutamine residue at position 1 of the human framework was replaced with Glutamic acid (E1) to afford the expression and purification of a homogeneous product: the conversion of Glutamine to pyro-Glutamate at the N-terminus of antibodies and antibody fragments is widely reported. In some cases, CDRL3 may be mutated to remove a pair of Cysteine residues (CDRL3 variant).

CD79 AntibodyAb 4450

Human V-region IGKV1-6 plus JK4 J-region (IMGT, http://www.imgt.org/) was chosen as the acceptor for antibody 4450 light chain CDRs. In addition to the CDRs, one or more of the following framework residues from the 4450 VK gene (donor residues) may be retained at positions 3 and 70 (Kabat numbering): Aspartic acid (D3) and Glutamine (Q70), respectively. In some cases, CDRL3 may be mutated to modify a potential aspartate isomerisation site (CDRL3 variants 1-3).

Human V-region IGHV3-66 plus JH4 J-region (IMGT, was chosen as an acceptor for the heavy chain CDRs of antibody 4450. In addition to the CDRs, one or more of the following framework residues from the 4450 VH gene (donor residues) may be retained at positions 24, 48, 49, 73 and 78 (Kabat numbering): Valine (V24), Isoleucine (I48), Glycine (G49), Serine (S73) and Valine (V78), respectively.

Human V-region IGHV4-59 plus JH4 J-region (IMGT, http://www.imgt.org/) was chosen as an alternative acceptor for the heavy chain CDRs of antibody 4450. In addition to the CDRs, one or more of the following framework residues from the 4450 VH gene (donor residues) may be retained at positions 37, 67, 71, 73 and 78 (Kabat numbering): Valine (V37), Phenylalanine (F67), Arginine (R71), Serine (S73) and Valine (V78), respectively. The Glutamine residue at position 1 of the human framework was replaced with Glutamic acid (E1) to afford the expression and purification of a homogeneous product.

CD22 Antibody Ab 4120

Human V-region IGKV1D-13 plus JK4 J-region (IMGT, http://www.imgt.org/) was chosen as the acceptor for antibody 4120 light chain CDRs. In addition to the CDRs, one or more of the following framework residues from the 4120 VK gene (donor residues) may be retained at positions 2 and 3 (Kabat numbering): Phenylalanine (F2) and Glutamic acid (E3), respectively. Human V-region IGHV3-33 plus JH4 J-region (IMGT, http://www.imgt.org/) was chosen as an acceptor for the heavy chain CDRs of antibody 4120. In addition to the CDRs, one or more of the following framework residues from the 4120 VH gene (donor residues) may be retained at positions 11, 48, 71, 73, 76 and 78 (Kabat numbering): Leucine (L11), Isoleucine (I48), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

Human V-region IGHV4-38-2 plus JH4 J-region (IMGT, http://www.imgt.org/) was chosen as an alternative acceptor for the heavy chain CDRs of antibody 4120. In addition to the CDRs, one or more of the following framework residues from the 4120 VH gene (donor residues) may be retained at positions 24, 37, 49, 67, 71, 73, 76 and 78 (Kabat numbering): Alanine (A24), Valine (V37), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD22 Antibody Ab 4126

Human V-region IGKV1-5 plus JK4 J-region (IMGT, http://www.imgt.org/) was chosen as the acceptor for antibody 4126 light chain CDRs. In addition to the CDRs, one or more of the following framework residues from the 4126 VK gene (donor residues) may be retained at positions 3 and 70 (Kabat numbering): Valine (V3) and Glutamine (Q70), respectively.

Human V-region IGHV3-7 plus JH4 J-region (IMGT, http://www.imgt.org/) was chosen as an acceptor for the heavy chain CDRs of antibody 4126. In addition to the CDRs, one or more of the following framework residues from the 4126 VH gene (donor residues) may be retained at positions 71, 73, 76 and 78 (Kabat numbering): Lysine (K71), Serine (S73), Threonine (T76) and Valine (V78), respectively. In some cases, CDRH1, CDRH2 and CDRH3 may be mutated to remove Cysteine residues (CDRH1 variant, CDRH2 and CDRH3 variant, respectively).

Human V-region IGHV4-4 plus JH4 J-region (IMGT, http://www.imgt.org/) was chosen as an alternative acceptor for the heavy chain CDRs of antibody 4126. In addition to the CDRs, one or more of the following framework residues from the 4126 VH gene (donor residues) may be retained at positions 24, 48, 49, 67, 71, 73, 76 and 78 (Kabat numbering): Alanine (A24), Valine (V48), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1, CDRH2 and CDRH3 may be mutated to remove Cysteine residues (CDRH1 variant, CDRH2 and CDRH3 variant, respectively).

CD22 Antibody Ab 4127

Human V-region IGKV1-5 plus JK4 J-region (IMGT, http://www.imgt.org/) was chosen as the acceptor for antibody 4127 light chain CDRs. In addition to the CDRs, one or more of the following framework residues from the 4127 VK gene (donor residues) may be retained at positions 1, 3 and 70 (Kabat numbering): Alanine (A1), Valine (V3) and Glutamine (Q70), respectively. In some cases, CDRL3 may be mutated to modify potential Aspartic acid isomerisation sites (CDRL3 variants 1-15).

Human V-region IGHV3-9 plus JH-4 J-region (IMGT, http://www.imgt.org) was chosen as an acceptor for the heavy chain CDRs of antibody 4127. In addition to the CDRs, one or more of the following framework residues from the 4127 VH gene (donor residues) may be retained at positions 47, 48, 49, 71, 73, 76, 78 and 94 (Kabat numbering): Leucine (L47), Isoleucine (I48), Glycine (G49), Lysine (K71), Serine (S73), Threonine (T76), Valine (V78) and Arginine (R94), respectively. In some cases, CDRH1 and CDRH2 may be mutated to remove Cysteine residues (CDRH1 variant and CDRH2 variant, respectively).

Human V-region IGHV4-38-2 plus JH4 J-region (IMGT, http://www.imgt.org/) was chosen as an alternative acceptor for the heavy chain CDRs of antibody 4127. In addition to the CDRs, one or more of the following framework residues from the 4127 VH gene (donor residues) may be retained at positions 24, 37, 47, 67, 71, 73, 76 and 78 (Kabat numbering): Alanine (A24), Valine (V37), Leucine (L47), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD22 Antibody Ab 4128

Human V-region IGKV1-5 plus JK4 J-region (IMGT, http://www.imgt.org/) was chosen as the acceptor for antibody 4128 light chain CDRs. In addition to the CDRs, one or more of the following framework residues from the 4128 VK gene (donor residues) may be retained at positions 3, 36, 63, 65, 66 and 71 (Kabat numbering): Valine (V3), Phenylalanine (F36), Lysine (K63), Aspartic acid (D65), Arginine (R66) and Tyrosine (Y71), respectively.

Human V-region IGHV3-33 plus JH4 J-region (IMGT, http://www.imgt.org/) was chosen as an acceptor for the heavy chain CDRs of antibody 4128. In addition to the CDRs, one or more of the following framework residues from the 4128 VH gene (donor residues) may be retained at positions 11, 23, 24, 48, 71, 73, 76 and 78 (Kabat numbering): Leucine (L11), Lysine (K23), Glycine (G24), Isoleucine (I48), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

Human V-region IGHV4-59 plus JK4 J-region (IMGT, http://www.imgt.org) was chosen as an alternative acceptor for the heavy chain CDRs of antibody 4128. In addition to the CDRs, one or more of the following framework residues from the 4128 VH gene (donor residues) may be retained at positions 23, 24, 37, 49, 67, 71, 73, 76 and 78 (Kabat numbering): Lysine (K23), Glycine (G24), Valine (V37), Alanine (A49), Phenylalanine (F67), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 and CDRH2 may be mutated to remove Cysteine residues (CDRH1 variant and CDRH2 variant, respectively).

CD22 Antibody Ab 4130

Human V-region IGKV1-9 plus JK4 J-region (IMGT, http://www.imgt.org) was chosen as the acceptor for antibody 4130 light chain CDRs. In addition to the CDRs, one or more of the following framework residues from the 4130 VK gene (donor residues) may be retained at positions 1, 2 and 3 (Kabat numbering): Alanine (A1), Alanine (A2) and Valine (V3), respectively.

Human V-region IGHV3-66 plus JH4 J-region (IMGT, http://www.imgt.org/) was chosen as an acceptor for the heavy chain CDRs of antibody 4130. In addition to the CDRs, one or more of the following framework residues from the 4130 VH gene (donor residues) may be retained at positions 48, 49, 67, 71, 73, 76 and 78 (Kabat numbering): Isoleucine(I48), Glycine (G49), Valine (V67), Lysine (K71), Serine (S73), Threonine (T76) and Valine (V78), respectively. In some cases, CDRH2 may be mutated to remove a Cysteine residue and/or modify a potential Asparagine deamidation site (CDRH2 variants 1-5). CDRH3 may also be mutated to modify a potential Asparagine deamidation site (CDRH3 variants 1-2).

Human V-region IGHV4-4 plus JH4 J-region (IMGT, http://www.imgt.org/) was chosen as an alternative acceptor for the heavy chain CDRs of antibody 4130. In addition to the CDRs, one or more of the following framework residues from the 4130 VH gene (donor residues) may be retained at positions 24, 71, 73, 76 and 78 (Kabat numbering): Alanine (A24), Lysine (K71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH2 may be mutated to remove a Cysteine residue and/or modify a potential Asparagine deamidation site (CDRH2 variants 1-5). CDRH3 may also be mutated to modify a potential Asparagine deamidation site (CDRH3 variants 1-2).

CD22 Antibody Ab 4132

Human V-region IGKV1-5 plus JK4 J-region (IMGT, http://www.imgt.org/) was chosen as the acceptor for antibody 4132 light chain CDRs. In addition to the CDRs, one or more of the following framework residues from the 4132 VK gene (donor residues) may be retained at positions 3 and 71 (Kabat numbering): Valine (V3) and Tyrosine (Y71), respectively.

Human V-region IGHV3-21 plus JH4 J-region (IMGT, http://www.imgt.org/) was chosen as an acceptor for the heavy chain CDRs of antibody 4132. In addition to the CDRs, one or more of the following framework residues from the 4132 VH gene (donor residues) may be retained at positions 48, 49, 71, 73, 76 and 78 (Kabat numbering): Serine (S48), Glycine (G49), Asparagine (N71), Serine (S73), Threonine (T76) and Valine (V78), respectively. In some cases, CDRH1 may be mutated to remove a Cysteine residue (CDRH1 variant). CDRH2 may also be mutated to remove a Cysteine residue and/or modify a potential Asparagine deamidation site (CDRH2 variants 1-5).

Human V-region IGHV4-4 plus JH4 J-region (IMGT, was chosen as an alternative acceptor for the heavy chain CDRs of antibody 4132. In addition to the CDRs, one or more of the following framework residues from the 4132 VH gene (donor residues) may be retained at positions 24, 48, 67, 71, 73, 76 and 78 (Kabat numbering): Alanine (A24), Serine (S48), Phenylalanine (F67), Asparagine (N71), Serine (S73), Threonine (T76) and Valine (V78), respectively. The Glutamine residue at position 1 of the human framework was replaced with Glutamic acid (E1) to afford the expression and purification of a homogeneous product. In some cases, CDRH1 may be mutated to remove a Cysteine residue (CDRH1 variant). CDRH2 may also be mutated to remove a Cysteine residue and/or modify a potential Asparagine deamidation site (CDRH2 variants 1-5).

SEQUENCE LISTING

```
Sequence total quantity: 276
SEQ ID NO: 1           moltype =    length =
SEQUENCE: 1
000

SEQ ID NO: 2           moltype = AA   length = 18
FEATURE                Location/Qualifiers
REGION                 1..18
                       note = CDRH2 of formula (II)
VARIANT                1
                       note = Xaa is C or S
VARIANT                3
                       note = Xaa is Y, D, V or N
VARIANT                4
                       note = Xaa is T, P, I, G, S or A
VARIANT                5
                       note = Xaa is G, S, or A
VARIANT                6
                       note = Xaa is S, I or T
VARIANT                7
                       note = Xaa is S, N or absent
VARIANT                8
                       note = Xaa is G, D, S, A or T
```

```
VARIANT                 9
                        note = Xaa is D, T, S, N, V or G
VARIANT                 11
                        note = Xaa is Y, D or A
VARIANT                 14
                        note = Xaa is T or S
source                  1..18
                        mol_type = protein
                        organism = synthetic construct
SEQUENCE: 2
XIXXXXXXT XYAXWAKG                                                          18

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype = AA  length = 12
FEATURE                 Location/Qualifiers
REGION                  1..12
                        note = CDRL3 has a formula (VI)
VARIANT                 6
                        note = Xaa is D or E
VARIANT                 7
                        note = Xaa is S, A or T
VARIANT                 9
                        note = Xaa is D or E
VARIANT                 10
                        note = Xaa is G, A or S
source                  1..12
                        mol_type = protein
                        organism = synthetic construct
SEQUENCE: 6
AGYKSXXDXX TT                                                               12

SEQ ID NO: 7            moltype =   length =
SEQUENCE: 7
000

SEQ ID NO: 8            moltype = AA  length = 11
FEATURE                 Location/Qualifiers
REGION                  1..11
                        note = CDRH1 formula (Ia)
VARIANT                 2
                        note = Xaa is F, I or L
VARIANT                 3
                        note = Xaa is S or D
VARIANT                 6
                        note = Xaa is S, N or G
VARIANT                 7
                        note = Xaa is S, Y, L or G
VARIANT                 8
                        note = Xaa is Y or absent
VARIANT                 10
                        note = Xaa is M or I
VARIANT                 11
                        note = Xaa is C or S
source                  1..11
                        mol_type = protein
                        organism = synthetic construct
SEQUENCE: 8
GXXFSXXXYX X                                                                11

SEQ ID NO: 9            moltype = AA  length = 11
FEATURE                 Location/Qualifiers
REGION                  1..11
                        note = CDRH1 formula (Ib)
VARIANT                 2
                        note = Xaa is F, I or L
VARIANT                 3
                        note = Xaa is S or D
VARIANT                 6
```

```
                        note = Xaa is S, N or G
VARIANT                 7
                        note = Xaa is S, Y, L or G
VARIANT                 8
                        note = Xaa is Y or absent
VARIANT                 10
                        note = Xaa is M or I
source                  1..11
                        mol_type = protein
                        organism = synthetic construct
SEQUENCE: 9
GXXFSXXXYX S                                                                       11

SEQ ID NO: 10           moltype = AA  length = 18
FEATURE                 Location/Qualifiers
REGION                  1..18
                        note = CDRH2 formula (IIa)
VARIANT                 1
                        note = Xaa is C or S
VARIANT                 3
                        note = Xaa is Y, D, V or N
VARIANT                 4
                        note = Xaa is T, P, I, G, S or A
VARIANT                 6
                        note = Xaa is S, I or T
VARIANT                 7
                        note = Xaa is S, N or absent
VARIANT                 8
                        note = Xaa is G, D, S, A or T
VARIANT                 9
                        note = Xaa is D, T, S, N, V or G
VARIANT                 11
                        note = Xaa is Y, D or A
VARIANT                 14
                        note = Xaa is T or S
source                  1..18
                        mol_type = protein
                        organism = synthetic construct
SEQUENCE: 10
XIXXGXXXXT XYAXWAKG                                                                18

SEQ ID NO: 11           moltype = AA  length = 18
FEATURE                 Location/Qualifiers
REGION                  1..18
                        note = CDRH2 formula (IIb)
VARIANT                 1
                        note = Xaa is C or S
VARIANT                 3
                        note = Xaa is Y, D, V or N
VARIANT                 4
                        note = Xaa is T, P, I, G, S or A
VARIANT                 5
                        note = Xaa is G, S, or A
VARIANT                 6
                        note = Xaa is S, I or T
VARIANT                 7
                        note = Xaa is S, N or absent
VARIANT                 8
                        note = Xaa is G, D, S, A or T
VARIANT                 9
                        note = Xaa is D, T, S, N, V or G
VARIANT                 11
                        note = Xaa is Y, D or A
source                  1..18
                        mol_type = protein
                        organism = synthetic construct
SEQUENCE: 11
XIXXXXXXXT XYASWAKG                                                                18

SEQ ID NO: 12           moltype =   length =
SEQUENCE: 12
000

SEQ ID NO: 13           moltype = AA  length = 13
FEATURE                 Location/Qualifiers
REGION                  1..13
                        note = formula (IVa)
VARIANT                 4
                        note = Xaa is Q or E
```

```
VARIANT               5
                      note = Xaa is S, N or T
VARIANT               6
                      note = Xaa is I or V
VARIANT               7
                      note = Xaa is S, Y or G
VARIANT               8
                      note = Xaa is T, S, G or N
VARIANT               9
                      note = Xaa is A, G, N, Y, T or R
VARIANT               10
                      note = Xaa is absent, N or K
VARIANT               11
                      note = Xaa is absent, E or D
VARIANT               13
                      note = Xaa is A or S
source                1..13
                      mol_type = protein
                      organism = synthetic construct
SEQUENCE: 13
QASXXXXXXX XLX                                                                    13

SEQ ID NO: 14         moltype = AA  length = 13
FEATURE               Location/Qualifiers
REGION                1..13
                      note = formula (IVb)
VARIANT               5
                      note = Xaa is S, N or T
VARIANT               6
                      note = Xaa is I or V
VARIANT               7
                      note = Xaa is S, Y or G
VARIANT               8
                      note = Xaa is T, S, G or N
VARIANT               9
                      note = Xaa is A, G, N, Y, T or R
VARIANT               10
                      note = Xaa is absent, N or K
VARIANT               11
                      note = Xaa is absent, E or D
VARIANT               13
                      note = Xaa is A or S
source                1..13
                      mol_type = protein
                      organism = synthetic construct
SEQUENCE: 14
QASQXXXXXX XLX                                                                    13

SEQ ID NO: 15         moltype = AA  length = 13
FEATURE               Location/Qualifiers
REGION                1..13
                      note = formula (IVc)
VARIANT               6
                      note = Xaa is I or V
VARIANT               7
                      note = Xaa is S, Y or G
VARIANT               8
                      note = Xaa is T, S, G or N
VARIANT               9
                      note = Xaa is A, G, N, Y, T or R
VARIANT               10
                      note = Xaa is absent, N or K
VARIANT               11
                      note = Xaa is absent, E or D
VARIANT               13
                      note = Xaa is A or S
source                1..13
                      mol_type = protein
                      organism = synthetic construct
SEQUENCE: 15
QASQSXXXXX XLX                                                                    13

SEQ ID NO: 16         moltype = AA  length = 12
FEATURE               Location/Qualifiers
REGION                1..12
                      note = formula (IVd)
VARIANT               6
                      note = Xaa is I or V
VARIANT               7
```

```
                            note = Xaa is S, Y or G
VARIANT                     8
                            note = Xaa is T, S, G or N
VARIANT                     9
                            note = Xaa is A, G, N, Y, T or R
VARIANT                     10
                            note = Xaa is absent, E or D
VARIANT                     12
                            note = Xaa is A or S
source                      1..12
                            mol_type = protein
                            organism = synthetic construct
SEQUENCE: 16
QASQSXXXXX LX                                                               12

SEQ ID NO: 17               moltype = AA  length = 11
FEATURE                     Location/Qualifiers
REGION                      1..11
                            note = formula (IVe)
VARIANT                     6
                            note = Xaa is I or V
VARIANT                     7
                            note = Xaa is S, Y or G
VARIANT                     8
                            note = Xaa is T, S, G or N
VARIANT                     9
                            note = Xaa is A, G, N, Y, T or R
VARIANT                     11
                            note = Xaa is A or S
source                      1..11
                            mol_type = protein
                            organism = synthetic construct
SEQUENCE: 17
QASQSXXXXL X                                                                11

SEQ ID NO: 18               moltype = AA  length = 11
FEATURE                     Location/Qualifiers
REGION                      1..11
                            note = formula (IVf)
VARIANT                     6
                            note = Xaa is I or V
VARIANT                     7
                            note = Xaa is S, Y or G
VARIANT                     8
                            note = Xaa is T, S, G or N
VARIANT                     9
                            note = Xaa is A, G, N, Y, T or R
source                      1..11
                            mol_type = protein
                            organism = synthetic construct
SEQUENCE: 18
QASQSXXXXL A                                                                11

SEQ ID NO: 19               moltype = AA  length = 7
FEATURE                     Location/Qualifiers
REGION                      1..7
                            note = formula (Va)
VARIANT                     1
                            note = Xaa is G, Y, L, A or S
VARIANT                     4
                            note = Xaa is T, R or K
VARIANT                     6
                            note = Xaa is A or S
source                      1..7
                            mol_type = protein
                            organism = synthetic construct
SEQUENCE: 19
XASXLXS                                                                     7

SEQ ID NO: 20               moltype = AA  length = 7
FEATURE                     Location/Qualifiers
REGION                      1..7
                            note = formula (Vc)
VARIANT                     1
                            note = Xaa is G, Y, L, A or S
VARIANT                     4
                            note = Xaa is T, R or K
source                      1..7
                            mol_type = protein
```

```
                        organism = synthetic construct
SEQUENCE: 20
XASXLAS                                                                 7

SEQ ID NO: 21           moltype = AA  length = 7
FEATURE                 Location/Qualifiers
REGION                  1..7
                        note = formula V
VARIANT                 1
                        note = Xaa is G, Y, L, A or S
source                  1..7
                        mol_type = protein
                        organism = synthetic construct
SEQUENCE: 21
XASTLAS                                                                 7

SEQ ID NO: 22           moltype = AA  length = 12
FEATURE                 Location/Qualifiers
REGION                  1..12
                        note = formula (VIa)
VARIANT                 6
                        note = Xaa is D or E
VARIANT                 7
                        note = Xaa is S, A or T
VARIANT                 9
                        note = Xaa is D or E
VARIANT                 10
                        note = Xaa is G, A or S
source                  1..12
                        mol_type = protein
                        organism = synthetic construct
SEQUENCE: 22
AGYKSXXDXX TT                                                          12

SEQ ID NO: 23           moltype = AA  length = 12
FEATURE                 Location/Qualifiers
REGION                  1..12
                        note = formula (VIb)
VARIANT                 7
                        note = Xaa is S, A or T
VARIANT                 10
                        note = Xaa is G, A or S
source                  1..12
                        mol_type = protein
                        organism = synthetic construct
SEQUENCE: 23
AGYKSDXDDX TT                                                          12

SEQ ID NO: 24           moltype =   length =
SEQUENCE: 24
000

SEQ ID NO: 25           moltype = AA  length = 15
FEATURE                 Location/Qualifiers
REGION                  1..15
                        note = formula (VIIb)
VARIANT                 2
                        note = Xaa is S, I or G
VARIANT                 5
                        note = Xaa is G, S or Y
VARIANT                 6
                        note = Xaa is T, A or S
VARIANT                 8
                        note = Xaa is S, G, V or D
VARIANT                 9
                        note = Xaa is G, S, L or absent
VARIANT                 10
                        note = Xaa is G, R, S or N
VARIANT                 11
                        note = Xaa is S, D or V
VARIANT                 12
                        note = Xaa is W, Y or absent
VARIANT                 13
                        note = Xaa is A, T, G or absent
VARIANT                 14
                        note = Xaa is N or absent
VARIANT                 15
                        note = Xaa is A or absent
source                  1..15
```

```
                        mol_type = protein
                        organism = synthetic construct
SEQUENCE: 25
QXYYXXSXXX XXXXX                                                              15

SEQ ID NO: 26           moltype = AA  length = 15
FEATURE                 Location/Qualifiers
REGION                  1..15
                        note = formula (VIIc)
VARIANT                 2
                        note = Xaa is S, I or G
VARIANT                 5
                        note = Xaa is G, S or Y
VARIANT                 8
                        note = Xaa is S, G, V or D
VARIANT                 9
                        note = Xaa is G, S, L or absent
VARIANT                 10
                        note = Xaa is G, R, S or N
VARIANT                 11
                        note = Xaa is S, D or V
VARIANT                 12
                        note = Xaa is W, Y or absent
VARIANT                 13
                        note = Xaa is A, T, G or absent
VARIANT                 14
                        note = Xaa is N or absent
VARIANT                 15
                        note = Xaa is A or absent
source                  1..15
                        mol_type = protein
                        organism = synthetic construct
SEQUENCE: 26
QXYYSSXXX XXXXX                                                               15

SEQ ID NO: 27           moltype = AA  length = 14
FEATURE                 Location/Qualifiers
REGION                  1..14
                        note = formula (VIId)
VARIANT                 2
                        note = Xaa is S, I or G
VARIANT                 5
                        note = Xaa is G, S or Y
VARIANT                 8
                        note = Xaa is S, G, V or D
VARIANT                 9
                        note = Xaa is G, S, L or absent
VARIANT                 10
                        note = Xaa is G, R, S or N
VARIANT                 11
                        note = Xaa is S, D or V
VARIANT                 12
                        note = Xaa is W, Y or absent
VARIANT                 13
                        note = Xaa is A, T, G or absent
VARIANT                 14
                        note = Xaa is A or absent
source                  1..14
                        mol_type = protein
                        organism = synthetic construct
SEQUENCE: 27
QXYYXSSXXX XXXX                                                               14

SEQ ID NO: 28           moltype = AA  length = 13
FEATURE                 Location/Qualifiers
REGION                  1..13
                        note = formula (VIIe)
VARIANT                 2
                        note = Xaa is S, I or G
VARIANT                 5
                        note = Xaa is G, S or Y
VARIANT                 8
                        note = Xaa is S, G, V or D
VARIANT                 9
                        note = Xaa is G, S, L or absent
VARIANT                 10
                        note = Xaa is G, R, S or N
VARIANT                 11
                        note = Xaa is S, D or V
```

```
VARIANT              12
                     note = Xaa is W, Y or absent
VARIANT              13
                     note = Xaa is A, T, G or absent
source               1..13
                     mol_type = protein
                     organism = synthetic construct
SEQUENCE: 28
QXYYXSSXXX XXX                                                              13

SEQ ID NO: 29        moltype = AA  length = 11
FEATURE              Location/Qualifiers
REGION               1..11
                     note = Ab 4120 CDRH1
source               1..11
                     mol_type = protein
                     organism = synthetic construct
SEQUENCE: 29
GFSFSSSYYM C                                                                11

SEQ ID NO: 30        moltype = AA  length = 11
FEATURE              Location/Qualifiers
REGION               1..11
                     note = CDRH1 variant
source               1..11
                     mol_type = protein
                     organism = synthetic construct
SEQUENCE: 30
GFSFSSSYYM S                                                                11

SEQ ID NO: 31        moltype = AA  length = 11
FEATURE              Location/Qualifiers
REGION               1..11
                     note = Ab 4126 CDRH1
source               1..11
                     mol_type = protein
                     organism = synthetic construct
SEQUENCE: 31
GIDFSSYYYM C                                                                11

SEQ ID NO: 32        moltype = AA  length = 11
FEATURE              Location/Qualifiers
REGION               1..11
                     note = Ab 4126 CDRH1 variant
source               1..11
                     mol_type = protein
                     organism = synthetic construct
SEQUENCE: 32
GIDFSSYYYM S                                                                11

SEQ ID NO: 33        moltype = AA  length = 11
FEATURE              Location/Qualifiers
REGION               1..11
                     note = Ab 4127 CDRH1
source               1..11
                     mol_type = protein
                     organism = synthetic construct
SEQUENCE: 33
GFSFSNLYYM C                                                                11

SEQ ID NO: 34        moltype = AA  length = 11
FEATURE              Location/Qualifiers
REGION               1..11
                     note = Ab 4127 CDRH1 variant
source               1..11
                     mol_type = protein
                     organism = synthetic construct
SEQUENCE: 34
GFSFSNLYYM S                                                                11

SEQ ID NO: 35        moltype = AA  length = 10
FEATURE              Location/Qualifiers
REGION               1..10
                     note = Ab 4128 CDRH1
source               1..10
                     mol_type = protein
                     organism = synthetic construct
SEQUENCE: 35
GLDFSSYWIC                                                                  10
```

```
SEQ ID NO: 36           moltype = AA   length = 10
FEATURE                 Location/Qualifiers
REGION                  1..10
                        note = Ab 4128 CDRH1 variant
source                  1..10
                        mol_type = protein
                        organism = synthetic construct
SEQUENCE: 36
GLDFSSYWIS                                                              10

SEQ ID NO: 37           moltype = AA   length = 11
FEATURE                 Location/Qualifiers
REGION                  1..11
                        note = Ab 4130 CDRH1
source                  1..11
                        mol_type = protein
                        organism = synthetic construct
SEQUENCE: 37
GFDFSGGYDI S                                                            11

SEQ ID NO: 38           moltype = AA   length = 11
FEATURE                 Location/Qualifiers
REGION                  1..11
                        note = Ab 4132 CDRH1
source                  1..11
                        mol_type = protein
                        organism = synthetic construct
SEQUENCE: 38
GFSFSSSYWI C                                                            11

SEQ ID NO: 39           moltype = AA   length = 11
FEATURE                 Location/Qualifiers
REGION                  1..11
                        note = Ab 4132 CDRH1 variant
source                  1..11
                        mol_type = protein
                        organism = synthetic construct
SEQUENCE: 39
GFSFSSSYWI S                                                            11

SEQ ID NO: 40           moltype = AA   length = 18
FEATURE                 Location/Qualifiers
REGION                  1..18
                        note = Ab 4120 CDRH2
source                  1..18
                        mol_type = protein
                        organism = synthetic construct
SEQUENCE: 40
CIYTGSSGDT YYASWAKG                                                     18

SEQ ID NO: 41           moltype = AA   length = 18
FEATURE                 Location/Qualifiers
REGION                  1..18
                        note = Ab 4120 CDRH2 variant
source                  1..18
                        mol_type = protein
                        organism = synthetic construct
SEQUENCE: 41
SIYTGSSGDT YYASWAKG                                                     18

SEQ ID NO: 42           moltype = AA   length = 18
FEATURE                 Location/Qualifiers
REGION                  1..18
                        note = Ab 4126 CDRH2
source                  1..18
                        mol_type = protein
                        organism = synthetic construct
SEQUENCE: 42
CIDPASSGTT YYATWAKG                                                     18

SEQ ID NO: 43           moltype = AA   length = 18
FEATURE                 Location/Qualifiers
REGION                  1..18
                        note = Ab 4126 CDRH2 variant
source                  1..18
                        mol_type = protein
                        organism = synthetic construct
SEQUENCE: 43
```

```
SIDPASSGTT YYATWAKG                                                          18

SEQ ID NO: 44           moltype = AA  length = 18
FEATURE                 Location/Qualifiers
REGION                  1..18
                        note = Ab 4127 CDRH2
source                  1..18
                        mol_type = protein
                        organism = synthetic construct
SEQUENCE: 44
CIDISSSGST YYASWAKG                                                          18

SEQ ID NO: 45           moltype = AA  length = 18
FEATURE                 Location/Qualifiers
REGION                  1..18
                        note = Ab 4127 CDRH2 variant
source                  1..18
                        mol_type = protein
                        organism = synthetic construct
SEQUENCE: 45
SIDISSSGST YYASWAKG                                                          18

SEQ ID NO: 46           moltype = AA  length = 18
FEATURE                 Location/Qualifiers
REGION                  1..18
                        note = Ab 4128 CDRH2
source                  1..18
                        mol_type = protein
                        organism = synthetic construct
SEQUENCE: 46
CIVTGSSDNT YYASWAKG                                                          18

SEQ ID NO: 47           moltype = AA  length = 18
FEATURE                 Location/Qualifiers
REGION                  1..18
                        note = Ab 4128 CDRH2 variant
source                  1..18
                        mol_type = protein
                        organism = synthetic construct
SEQUENCE: 47
SIVTGSSDNT YYASWAKG                                                          18

SEQ ID NO: 48           moltype = AA  length = 18
FEATURE                 Location/Qualifiers
REGION                  1..18
                        note = Ab 4130 CDRH2
source                  1..18
                        mol_type = protein
                        organism = synthetic construct
SEQUENCE: 48
CIYGGINSVT DYASWAKG                                                          18

SEQ ID NO: 49           moltype = AA  length = 18
FEATURE                 Location/Qualifiers
REGION                  1..18
                        note = Ab 4130 CDRH2 variant 1
source                  1..18
                        mol_type = protein
                        organism = synthetic construct
SEQUENCE: 49
CIYGGINAVT DYASWAKG                                                          18

SEQ ID NO: 50           moltype = AA  length = 18
FEATURE                 Location/Qualifiers
REGION                  1..18
                        note = Ab 4130 CDRH2 variant 2
source                  1..18
                        mol_type = protein
                        organism = synthetic construct
SEQUENCE: 50
CIYGGINTVT DYASWAKG                                                          18

SEQ ID NO: 51           moltype = AA  length = 18
FEATURE                 Location/Qualifiers
REGION                  1..18
                        note = Ab 4130 CDRH2 variant 3
source                  1..18
                        mol_type = protein
                        organism = synthetic construct
```

```
SEQUENCE: 51
SIYGGINSVT DYASWAKG                                                       18

SEQ ID NO: 52          moltype = AA  length = 18
FEATURE                Location/Qualifiers
REGION                 1..18
                       note = Ab 4130 CDRH2 variant 4
source                 1..18
                       mol_type = protein
                       organism = synthetic construct
SEQUENCE: 52
SIYGGINAVT DYASWAKG                                                       18

SEQ ID NO: 53          moltype = AA  length = 18
FEATURE                Location/Qualifiers
REGION                 1..18
                       note = Ab 4130 CDRH2 variant 5
source                 1..18
                       mol_type = protein
                       organism = synthetic construct
SEQUENCE: 53
SIYGGINTVT DYASWAKG                                                       18

SEQ ID NO: 54          moltype = AA  length = 17
FEATURE                Location/Qualifiers
REGION                 1..17
                       note = Ab 4132 CDRH2
source                 1..17
                       mol_type = protein
                       organism = synthetic construct
SEQUENCE: 54
CINSGTGGTA YASWAKG                                                        17

SEQ ID NO: 55          moltype = AA  length = 17
FEATURE                Location/Qualifiers
REGION                 1..17
                       note = Ab 4132 CDRH2 variant 1
source                 1..17
                       mol_type = protein
                       organism = synthetic construct
SEQUENCE: 55
CINAGTGGTA YASWAKG                                                        17

SEQ ID NO: 56          moltype = AA  length = 17
FEATURE                Location/Qualifiers
REGION                 1..17
                       note = Ab 4132 CDRH2 variant 2
source                 1..17
                       mol_type = protein
                       organism = synthetic construct
SEQUENCE: 56
CINTGTGGTA YASWAKG                                                        17

SEQ ID NO: 57          moltype = AA  length = 17
FEATURE                Location/Qualifiers
REGION                 1..17
                       note = Ab 4132 CDRH2 variant 3
source                 1..17
                       mol_type = protein
                       organism = synthetic construct
SEQUENCE: 57
SINSGTGGTA YASWAKG                                                        17

SEQ ID NO: 58          moltype = AA  length = 17
FEATURE                Location/Qualifiers
REGION                 1..17
                       note = Ab 4132 CDRH2 variant 4
source                 1..17
                       mol_type = protein
                       organism = synthetic construct
SEQUENCE: 58
SINAGTGGTA YASWAKG                                                        17

SEQ ID NO: 59          moltype = AA  length = 17
FEATURE                Location/Qualifiers
REGION                 1..17
                       note = Ab 4132 CDRH2 variant 5
source                 1..17
                       mol_type = protein
```

```
                                   -continued organism = synthetic construct
SEQUENCE: 59
SINTGTGGTA YASWAKG                                                    17

SEQ ID NO: 60          moltype = AA  length = 15
FEATURE                Location/Qualifiers
REGION                 1..15
                       note = Ab 4120 CDRH3
source                 1..15
                       mol_type = protein
                       organism = synthetic construct
SEQUENCE: 60
GPYVGYGYDL QYLYL                                                      15

SEQ ID NO: 61          moltype = AA  length = 16
FEATURE                Location/Qualifiers
REGION                 1..16
                       note = Ab 4126 CDRH3
source                 1..16
                       mol_type = protein
                       organism = synthetic construct
SEQUENCE: 61
AYGSGGSGYI GCYFDL                                                     16

SEQ ID NO: 62          moltype = AA  length = 16
FEATURE                Location/Qualifiers
REGION                 1..16
                       note = Ab 4126 CDRH3 variant
source                 1..16
                       mol_type = protein
                       organism = synthetic construct
SEQUENCE: 62
AYGSGGSGYI GSYFDL                                                     16

SEQ ID NO: 63          moltype = AA  length = 13
FEATURE                Location/Qualifiers
REGION                 1..13
                       note = Ab 4127 CDRH3
source                 1..13
                       mol_type = protein
                       organism = synthetic construct
SEQUENCE: 63
DYYSSDWGVR FNL                                                        13

SEQ ID NO: 64          moltype = AA  length = 12
FEATURE                Location/Qualifiers
REGION                 1..12
                       note = Ab 4128 CDRH3
source                 1..12
                       mol_type = protein
                       organism = synthetic construct
SEQUENCE: 64
GGGAGYSGAF DL                                                         12

SEQ ID NO: 65          moltype = AA  length = 13
FEATURE                Location/Qualifiers
REGION                 1..13
                       note = Ab 4130 CDRH3
source                 1..13
                       mol_type = protein
                       organism = synthetic construct
SEQUENCE: 65
DVSNSDHYTR LDL                                                        13

SEQ ID NO: 66          moltype = AA  length = 13
FEATURE                Location/Qualifiers
REGION                 1..13
                       note = Ab 4130 CDRH3 variant 1
source                 1..13
                       mol_type = protein
                       organism = synthetic construct
SEQUENCE: 66
DVSNADHYTR LDL                                                        13

SEQ ID NO: 67          moltype = AA  length = 13
FEATURE                Location/Qualifiers
REGION                 1..13
                       note = Ab 4130 CDRH3 variant 2
source                 1..13
```

```
                        mol_type = protein
                        organism = synthetic construct
SEQUENCE: 67
DVSNTDHYTR LDL                                                                  13

SEQ ID NO: 68           moltype = AA  length = 13
FEATURE                 Location/Qualifiers
REGION                  1..13
                        note = Ab 4132 CDRH3
source                  1..13
                        mol_type = protein
                        organism = synthetic construct
SEQUENCE: 68
EWVSGYYKDA FDL                                                                  13

SEQ ID NO: 69           moltype = AA  length = 11
FEATURE                 Location/Qualifiers
REGION                  1..11
                        note = Ab 4120 CDRL1
source                  1..11
                        mol_type = protein
                        organism = synthetic construct
SEQUENCE: 69
QASQSISTAL A                                                                    11

SEQ ID NO: 70           moltype = AA  length = 11
FEATURE                 Location/Qualifiers
REGION                  1..11
                        note = Ab 4126 CDRL1
source                  1..11
                        mol_type = protein
                        organism = synthetic construct
SEQUENCE: 70
QASQNIGSGL A                                                                    11

SEQ ID NO: 71           moltype = AA  length = 13
FEATURE                 Location/Qualifiers
REGION                  1..13
                        note = Ab 4127 CDRL1
source                  1..13
                        mol_type = protein
                        organism = synthetic construct
SEQUENCE: 71
QASQSVYGNN ELS                                                                  13

SEQ ID NO: 72           moltype = AA  length = 11
FEATURE                 Location/Qualifiers
REGION                  1..11
                        note = Ab 4128 CDRL1
source                  1..11
                        mol_type = protein
                        organism = synthetic construct
SEQUENCE: 72
QASESISNYL S                                                                    11

SEQ ID NO: 73           moltype = AA  length = 13
FEATURE                 Location/Qualifiers
REGION                  1..13
                        note = Ab 4130 CDRL1
source                  1..13
                        mol_type = protein
                        organism = synthetic construct
SEQUENCE: 73
QSSQSVYNTK DLA                                                                  13

SEQ ID NO: 74           moltype = AA  length = 11
FEATURE                 Location/Qualifiers
REGION                  1..11
                        note = Ab 4132 CDRL1
source                  1..11
                        mol_type = protein
                        organism = synthetic construct
SEQUENCE: 74
QASETISSRL A                                                                    11

SEQ ID NO: 75           moltype = AA  length = 7
FEATURE                 Location/Qualifiers
REGION                  1..7
                        note = Ab 4120 CDRL2
```

```
source                        1..7
                              mol_type = protein
                              organism = synthetic construct
SEQUENCE: 75
GASTLAS                                                                        7

SEQ ID NO: 76                 moltype = AA  length = 7
FEATURE                       Location/Qualifiers
REGION                        1..7
                              note = Ab 4126 CDRL2
source                        1..7
                              mol_type = protein
                              organism = synthetic construct
SEQUENCE: 76
YASTLAS                                                                        7

SEQ ID NO: 77                 moltype = AA  length = 7
FEATURE                       Location/Qualifiers
REGION                        1..7
                              note = Ab 4127 CDRL2
source                        1..7
                              mol_type = protein
                              organism = synthetic construct
SEQUENCE: 77
LASRLAS                                                                        7

SEQ ID NO: 78                 moltype = AA  length = 7
FEATURE                       Location/Qualifiers
REGION                        1..7
                              note = Ab 4128 CDRL2
source                        1..7
                              mol_type = protein
                              organism = synthetic construct
SEQUENCE: 78
ASSKLSS                                                                        7

SEQ ID NO: 79                 moltype = AA  length = 7
FEATURE                       Location/Qualifiers
REGION                        1..7
                              note = Ab 4130 CDRL2
source                        1..7
                              mol_type = protein
                              organism = synthetic construct
SEQUENCE: 79
GTSTLAS                                                                        7

SEQ ID NO: 80                 moltype = AA  length = 7
FEATURE                       Location/Qualifiers
REGION                        1..7
                              note = Ab 4132 CDRL2
source                        1..7
                              mol_type = protein
                              organism = synthetic construct
SEQUENCE: 80
SASTLAS                                                                        7

SEQ ID NO: 81                 moltype = AA  length = 13
FEATURE                       Location/Qualifiers
REGION                        1..13
                              note = Ab 4120 CDRL3
source                        1..13
                              mol_type = protein
                              organism = synthetic construct
SEQUENCE: 81
QSYYGTSSGG SWA                                                                13

SEQ ID NO: 82                 moltype = AA  length = 14
FEATURE                       Location/Qualifiers
REGION                        1..14
                              note = Ab 4126 CDRL3
source                        1..14
                              mol_type = protein
                              organism = synthetic construct
SEQUENCE: 82
QSHDYSSVRS YGNA                                                               14

SEQ ID NO: 83                 moltype = AA  length = 12
FEATURE                       Location/Qualifiers
REGION                        1..12
```

```
                            note = Ab 4127 CDRL3
source                      1..12
                            mol_type = protein
                            organism = synthetic construct
SEQUENCE: 83
AGYKSDSDDG TT                                                             12

SEQ ID NO: 84               moltype = AA  length = 12
FEATURE                     Location/Qualifiers
REGION                      1..12
                            note = Ab 4127 CDRL3 variant 1
source                      1..12
                            mol_type = protein
                            organism = synthetic construct
SEQUENCE: 84
AGYKSESDDG TT                                                             12

SEQ ID NO: 85               moltype = AA  length = 12
FEATURE                     Location/Qualifiers
REGION                      1..12
                            note = Ab 4127 CDRL3 variant 2
source                      1..12
                            mol_type = protein
                            organism = synthetic construct
SEQUENCE: 85
AGYKSDADDG TT                                                             12

SEQ ID NO: 86               moltype = AA  length = 12
FEATURE                     Location/Qualifiers
REGION                      1..12
                            note = Ab 4127 CDRL3 variant 3
source                      1..12
                            mol_type = protein
                            organism = synthetic construct
SEQUENCE: 86
AGYKSDTDDG TT                                                             12

SEQ ID NO: 87               moltype = AA  length = 12
FEATURE                     Location/Qualifiers
REGION                      1..12
                            note = Ab 4127 CDRL3 variant 4
source                      1..12
                            mol_type = protein
                            organism = synthetic construct
SEQUENCE: 87
AGYKSDSDEG TT                                                             12

SEQ ID NO: 88               moltype = AA  length = 12
FEATURE                     Location/Qualifiers
REGION                      1..12
                            note = Ab 4127 CDRL3 variant 5
source                      1..12
                            mol_type = protein
                            organism = synthetic construct
SEQUENCE: 88
AGYKSDSDDA TT                                                             12

SEQ ID NO: 89               moltype = AA  length = 12
FEATURE                     Location/Qualifiers
REGION                      1..12
                            note = Ab 4127 CDRL3 variant 6
source                      1..12
                            mol_type = protein
                            organism = synthetic construct
SEQUENCE: 89
AGYKSDSDDS TT                                                             12

SEQ ID NO: 90               moltype = AA  length = 12
FEATURE                     Location/Qualifiers
REGION                      1..12
                            note = Ab 4127 CDRL3 variant 7
source                      1..12
                            mol_type = protein
                            organism = synthetic construct
SEQUENCE: 90
AGYKSESDEG TT                                                             12

SEQ ID NO: 91               moltype = AA  length = 12
FEATURE                     Location/Qualifiers
```

```
REGION                  1..12
                        note = Ab 4127 CDRL3 variant 8
source                  1..12
                        mol_type = protein
                        organism = synthetic construct
SEQUENCE: 91
AGYKSESDDA TT                                                              12

SEQ ID NO: 92           moltype = AA  length = 12
FEATURE                 Location/Qualifiers
REGION                  1..12
                        note = Ab 4127 CDRL3 variant 9
source                  1..12
                        mol_type = protein
                        organism = synthetic construct
SEQUENCE: 92
AGYKSESDDS TT                                                              12

SEQ ID NO: 93           moltype = AA  length = 12
FEATURE                 Location/Qualifiers
REGION                  1..12
                        note = Ab 4127 CDRL3 variant 10
source                  1..12
                        mol_type = protein
                        organism = synthetic construct
SEQUENCE: 93
AGYKSDADEG TT                                                              12

SEQ ID NO: 94           moltype = AA  length = 12
FEATURE                 Location/Qualifiers
REGION                  1..12
                        note = Ab 4127 CDRL3 variant 11
source                  1..12
                        mol_type = protein
                        organism = synthetic construct
SEQUENCE: 94
AGYKSDADDA TT                                                              12

SEQ ID NO: 95           moltype = AA  length = 12
FEATURE                 Location/Qualifiers
REGION                  1..12
                        note = Ab 4127 CDRL3 variant 12
source                  1..12
                        mol_type = protein
                        organism = synthetic construct
SEQUENCE: 95
AGYKSDADDS TT                                                              12

SEQ ID NO: 96           moltype = AA  length = 12
FEATURE                 Location/Qualifiers
REGION                  1..12
                        note = Ab 4127 CDRL3 variant 13
source                  1..12
                        mol_type = protein
                        organism = synthetic construct
SEQUENCE: 96
AGYKSDTDEG TT                                                              12

SEQ ID NO: 97           moltype = AA  length = 12
FEATURE                 Location/Qualifiers
REGION                  1..12
                        note = Ab 4127 CDRL3 variant 14
source                  1..12
                        mol_type = protein
                        organism = synthetic construct
SEQUENCE: 97
AGYKSDTDDA TT                                                              12

SEQ ID NO: 98           moltype = AA  length = 12
FEATURE                 Location/Qualifiers
REGION                  1..12
                        note = Ab 4127 CDRL3 variant 15
source                  1..12
                        mol_type = protein
                        organism = synthetic construct
SEQUENCE: 98
AGYKSDTDDS TT                                                              12

SEQ ID NO: 99           moltype = AA  length = 13
```

```
FEATURE                     Location/Qualifiers
REGION                      1..13
                            note = Ab 4128 CDRL3
source                      1..13
                            mol_type = protein
                            organism = synthetic construct
SEQUENCE: 99
QIYYSASGSR DWT                                                              13

SEQ ID NO: 100              moltype = AA  length = 11
FEATURE                     Location/Qualifiers
REGION                      1..11
                            note = Ab 4130 CDRL3
source                      1..11
                            mol_type = protein
                            organism = synthetic construct
SEQUENCE: 100
QGGFSSSDLN V                                                                11

SEQ ID NO: 101              moltype = AA  length = 12
FEATURE                     Location/Qualifiers
REGION                      1..12
                            note = Ab 4132 CDRL3
source                      1..12
                            mol_type = protein
                            organism = synthetic construct
SEQUENCE: 101
QGYYYSSGSD YG                                                               12

SEQ ID NO: 102              moltype = AA  length = 111
FEATURE                     Location/Qualifiers
REGION                      1..111
                            note = Rabbit Ab 4120 VL region
source                      1..111
                            mol_type = protein
                            organism = synthetic construct
SEQUENCE: 102
AFELSQTPAS VEAAVGGTVT IKCQASQSIS TALAWYQQKP GQRPKLLIYG ASTLASGVSS           60
RFKGSGSGTE FTLTISDLEC ADAATYYCQS YYGTSSGGSW AFGGGTKVVV K                  111

SEQ ID NO: 103              moltype = DNA  length = 333
FEATURE                     Location/Qualifiers
misc_feature                1..333
                            note = Rabbit Ab 4120 VL region
source                      1..333
                            mol_type = other DNA
                            organism = synthetic construct
SEQUENCE: 103
gcattcgaat tgagccagac tccagcctcc gtggaggcag ctgtgggagg cacagtcacc           60
atcaagtgcc aggccagtca gagcattagc actgcattag cctggtatca gcagaaacca         120
gggcagcgtc ccaagctcct gatctatggt gcatccactc tggcatctgg ggtctcatcg         180
cggttcaaaag gcagtggatc tgggacagag ttcactctca ccatcagcga cctggagtgt        240
gccgatgctg ccacttacta ctgtcaaagc tattatggta cgagtagtgg tggttcttgg         300
gctttcggcg agggaccaa ggtggtcgtc aaa                                       333

SEQ ID NO: 104              moltype = AA  length = 124
FEATURE                     Location/Qualifiers
REGION                      1..124
                            note = Rabbit Ab 4120 VH region
source                      1..124
                            mol_type = protein
                            organism = synthetic construct
SEQUENCE: 104
QSLEESGGDL VKPGASLTLT CTASGFSFSS SYYMCWVRQS PGKGLEWIAC IYTGSSGDTY           60
YASWAKGRFT ISKTSSTTVS LQMTSLTAAD TATYFCARGP YVGYGYDLQY LYLWGPGTLV         120
TVSS                                                                      124

SEQ ID NO: 105              moltype = DNA  length = 372
FEATURE                     Location/Qualifiers
misc_feature                1..372
                            note = Rabbit Ab 4120 VH region
source                      1..372
                            mol_type = other DNA
                            organism = synthetic construct
SEQUENCE: 105
cagtcattgg aggagtccgg gggagacctg gtcaagcctg ggcatccct gacactcacc            60
tgcacagcct ctggattctc cttcagtagt agctactaca tgtgctgggt ccgccagtct         120
ccagggaagg ggctggagtg gatcgcatgc atttatactg gtagtagtgg tgacacttac         180
tacgcgagct gggcgaaagg ccgattcacc atctccaaaa cctcgtcgac cacggtgtct         240
```

```
ctgcaaatga ccagtctgac agccgcggac acggccactt atttctgtgc gagagggcct    300
tatgttggtt atggttatga tcttcaatac ttgtacttgt ggggcccggg gaccctcgtc    360
accgtctcga gt                                                        372
```

```
SEQ ID NO: 106          moltype = AA   length = 111
FEATURE                 Location/Qualifiers
REGION                  1..111
                        note = 4120 gL1 V-region IGKV1D-13 framework
source                  1..111
                        mol_type = protein
                        organism = synthetic construct
SEQUENCE: 106
AFELTQSPSS LSASVGDRVT ITCQASQSIS TALAWYQQKP GKAPKLLIYG ASTLASGVPS    60
RFSGSGSGTD FTLTISSLQP EDFATYYCQS YYGTSSGGSW AFGGGTKVEI K             111

SEQ ID NO: 107          moltype = AA   length = 126
FEATURE                 Location/Qualifiers
REGION                  1..126
                        note = 4120 gH1 V-region - IGHV3-33 framework
source                  1..126
                        mol_type = protein
                        organism = synthetic construct
SEQUENCE: 107
EVQLVESGGG LVQPGRSLRL SCAASGFSFS SSYYMCWVRQ APGKGLEWIA CIYTGSSGDT    60
YYASWAKGRF TISKDSSKTT VYLQMNSLRA EDTAVYYCAR GPYVGYGYDL QYLYLWGQGT    120
LVTVSS                                                               126

SEQ ID NO: 108          moltype = AA   length = 126
FEATURE                 Location/Qualifiers
REGION                  1..126
                        note = 4120 gH2 V-region - IGHV3-33 framework
source                  1..126
                        mol_type = protein
                        organism = synthetic construct
SEQUENCE: 108
EVQLVESGGG LVQPGRSLRL SCAASGFSFS SSYYMSWVRQ APGKGLEWIA SIYTGSSGDT    60
YYASWAKGRF TISKDSSKTT VYLQMNSLRA EDTAVYYCAR GPYVGYGYDL QYLYLWGQGT    120
LVTVSS                                                               126

SEQ ID NO: 109          moltype = AA   length = 126
FEATURE                 Location/Qualifiers
REGION                  1..126
                        note = 4120 gH4 V-region - IGHV4-38-2 framework
source                  1..126
                        mol_type = protein
                        organism = synthetic construct
SEQUENCE: 109
EVQLQESGPG LVKPSETLSL TCAASGFSFS SSYYMCWVRQ PPGKGLEWIA CIYTGSSGDT    60
YYASWAKGRF TISKDSSKTQ VSLKLSSVTA ADTAVYYCAR GPYVGYGYDL QYLYLWGQGT    120
LVTVSS                                                               126

SEQ ID NO: 110          moltype = AA   length = 126
FEATURE                 Location/Qualifiers
REGION                  1..126
                        note = 4120 gH5 V-region - IGHV4-38-2 framework
source                  1..126
                        mol_type = protein
                        organism = synthetic construct
SEQUENCE: 110
EVQLQESGPG LVKPSETLSL TCAASGFSFS SSYYMSWVRQ PPGKGLEWIA SIYTGSSGDT    60
YYASWAKGRF TISKDSSKTQ VSLKLSSVTA ADTAVYYCAR GPYVGYGYDL QYLYLWGQGT    120
LVTVSS                                                               126

SEQ ID NO: 111          moltype = AA   length = 112
FEATURE                 Location/Qualifiers
REGION                  1..112
                        note = Rabbit Ab 4126 VL region
source                  1..112
                        mol_type = protein
                        organism = synthetic construct
SEQUENCE: 111
DIVMTQTPAS VEAAVGGTVT IKCQASQNIG SGLAWYQQKP GQPPKLLIYY ASTLASGVPS    60
RFKGSGSGTQ FTLTISDLEC ADAATYYCQS HDYSSVRSYG NAFGGGTEVV VK            112

SEQ ID NO: 112          moltype = DNA   length = 336
FEATURE                 Location/Qualifiers
misc_feature            1..336
                        note = Rabbit Ab 4126 VL region
source                  1..336
```

```
                              mol_type = other DNA
                              organism = synthetic construct
SEQUENCE: 112
gacattgtga tgacccagac tccagcctcc gtgaggcag ctgtgggagg cacagtcacc      60
atcaagtgcc aggccagtca gaacattggt agtggtttag cctggtatca gcagaaacca    120
gggcagcctc ccaagctcct gatctattat gcatccactc tggcatctgg ggtcccatca    180
aggttcaaag gcagtggatc tgggacacag ttcactctca ccatcagcga cctggagtgt    240
gccgacgctg ccacttacta ctgtcaaagt catgattata gtagtgttcg gagttacggt    300
aatgctttcg gcggagggac cgaggtggtg gtcaaa                              336

SEQ ID NO: 113               moltype = AA  length = 126
FEATURE                      Location/Qualifiers
REGION                       1..126
                             note = Rabbit Ab 4126 VH region
source                       1..126
                             mol_type = protein
                             organism = synthetic construct
SEQUENCE: 113
QQHLEESGGG LVKPGGTLTL TCKASGIDFS SYYYMCWVRQ APGKGLEWVA CIDPASSGTT     60
YYATWAKGRF TISKTSSTTV TLQMTSLTAA DTATYFCARA YGSGGSGYIG CYFDLWGQGT    120
LVTVSS                                                               126

SEQ ID NO: 114               moltype = DNA  length = 378
FEATURE                      Location/Qualifiers
misc_feature                 1..378
                             note = Rabbit Ab 4126 VH region
source                       1..378
                             mol_type = other DNA
                             organism = synthetic construct
SEQUENCE: 114
cagcagcacc tggaggagtc cggggggaggc ctggtcaagc ctggaggaac cctgacactc    60
acctgcaaag cctctggaat cgacttcagt agctactact acatgtgctg ggtccgccag    120
gctccaggga aggggctgga gtgggtcgcg tgcattgatc ctgctagtag tggtactact    180
tactacgcga cctgggcgaa aggccgattc accatctcca aaacctcgtc gaccacggtg    240
actctgcaaa tgaccagtct gacagccgcg gacacggcca cctatttctg tgcgagggca    300
tatggtagtg ggggtagtgg ttatataggg tgctactttg acttgtgggg ccaaggcacc    360
ctcgtcaccg tctcgagt                                                  378

SEQ ID NO: 115               moltype = AA  length = 112
FEATURE                      Location/Qualifiers
REGION                       1..112
                             note = 4126 gL3 V-region - IGKV1-5 framework
source                       1..112
                             mol_type = protein
                             organism = synthetic construct
SEQUENCE: 115
DIVMTQSPST LSASVGDRVT ITCQASQNIG SGLAWYQQKP GKAPKLLIYY ASTLASGVPS     60
RFSGSGSGTQ FTLTISSLQP DDFATYYCQS HDYSSVRSYG NAFGGGTKVE IK            112

SEQ ID NO: 116               moltype = AA  length = 127
FEATURE                      Location/Qualifiers
REGION                       1..127
                             note = 4126 gH12 V-region - IGHV3-7 framework
source                       1..127
                             mol_type = protein
                             organism = synthetic construct
SEQUENCE: 116
EVQLVESGGG LVQPGGSLRL SCAASGIDFS SYYYMCWVRQ APGKGLEWVA CIDPASSGTT     60
YYATWAKGRF TISKDSAKTS VYLQMNSLRA EDTAVYYCAR AYGSGGSGYI GCYFDLWGQG    120
TLVTVSS                                                              127

SEQ ID NO: 117               moltype = AA  length = 127
FEATURE                      Location/Qualifiers
REGION                       1..127
                             note = 4126 gH3 V-region - IGHV3-7 framework
source                       1..127
                             mol_type = protein
                             organism = synthetic construct
SEQUENCE: 117
EVQLVESGGG LVQPGGSLRL SCAASGIDFS SYYYMCWVRQ APGKGLEWVA CIDPASSGTT     60
YYATWAKGRF TISKDSAKTS VYLQMNSLRA EDTAVYYCAR AYGSGGSGYI GSYFDLWGQG    120
TLVTVSS                                                              127

SEQ ID NO: 118               moltype = AA  length = 127
FEATURE                      Location/Qualifiers
REGION                       1..127
                             note = 4126 gH4 V-region - IGHV3-7 framework
source                       1..127
                             mol_type = protein
```

```
                        organism = synthetic construct
SEQUENCE: 118
EVQLVESGGG LVQPGGSLRL SCAASGIDFS SYYYMSWVRQ APGKGLEWVA SIDPASSGTT     60
YYATWAKGRF TISKDSAKTS VYLQMNSLRA EDTAVYYCAR AYGSGGSGYI GSYFDLWGQG    120
TLVTVSS                                                             127

SEQ ID NO: 119          moltype = AA  length = 127
FEATURE                 Location/Qualifiers
REGION                  1..127
                        note = 4126 gH13 V-region - IGHV4-4 framework
source                  1..127
                        mol_type = protein
                        organism = synthetic construct
SEQUENCE: 119
EVQLQESGPG LVKPSGTLSL TCAASGIDFS SYYYMCWVRQ PPGKGLEWVA CIDPASSGTT     60
YYATWAKGRF TISKDSSKTQ VSLKLSSVTA ADTAVYYCAR AYGSGGSGYI GCYFDLWGQG    120
TLVTVSS                                                             127

SEQ ID NO: 120          moltype = AA  length = 127
FEATURE                 Location/Qualifiers
REGION                  1..127
                        note = 4126 gH6 V-region - IGHV4-4 framework
source                  1..127
                        mol_type = protein
                        organism = synthetic construct
SEQUENCE: 120
EVQLQESGPG LVKPSGTLSL TCAASGIDFS SYYYMCWVRQ PPGKGLEWVA CIDPASSGTT     60
YYATWAKGRF TISKDSSKTQ VSLKLSSVTA ADTAVYYCAR AYGSGGSGYI GSYFDLWGQG    120
TLVTVSS                                                             127

SEQ ID NO: 121          moltype = AA  length = 127
FEATURE                 Location/Qualifiers
REGION                  1..127
                        note = 4126 gH7 V-region - IGHV4-4 framework
source                  1..127
                        mol_type = protein
                        organism = synthetic construct
SEQUENCE: 121
EVQLQESGPG LVKPSGTLSL TCAASGIDFS SYYYMSWVRQ PPGKGLEWVA SIDPASSGTT     60
YYATWAKGRF TISKDSSKTQ VSLKLSSVTA ADTAVYYCAR AYGSGGSGYI GSYFDLWGQG    120
TLVTVSS                                                             127

SEQ ID NO: 122          moltype = AA  length = 112
FEATURE                 Location/Qualifiers
REGION                  1..112
                        note = Rabbit Ab 4127 VL region
source                  1..112
                        mol_type = protein
                        organism = synthetic construct
SEQUENCE: 122
AIVMTQTPSS KSVPMGGTVT INCQASQSVY GNNELSWYQQ KPGQPPKLLI YLASRLASGV     60
PSRFSGSGSG TQFTLTISGV QCDDAATYYC AGYKSDSDDG TTFGGGTKVV VE            112

SEQ ID NO: 123          moltype = AA  length = 336
FEATURE                 Location/Qualifiers
REGION                  1..336
                        note = Rabbit Ab 4127 VL region
source                  1..336
                        mol_type = protein
                        organism = synthetic construct
SEQUENCE: 123
GCCATCGTGA TGACCCAGAC TCCATCTTCC AAGTCTGTCC CTATGGGAGG CACAGTCACC     60
ATCAACTGCC AGGCCAGTCA GAGTGTTTAT GGTAATAACG AATTATCCTG GTATCAGCAG    120
AAACCAGGGC AGCCTCCCAA GCTCCTGATC TATTTGGCAT CCAGGCTGGC ATCGGGGTC    180
CCATCGCGGT TTAGCGGCAG TGGATCTGGG ACACAGTTCA CTCTCACCAT CAGCGGCGTG    240
CAGTGTGACG ATGCTGCCAC TTACTACTGT GCAGGCTATA AAAGTGATAG TGATGATGGC    300
ACTACTTTCG GCGGAGGGAC CAAGGTGGTG GTCGAA                              336

SEQ ID NO: 124          moltype = AA  length = 122
FEATURE                 Location/Qualifiers
REGION                  1..122
                        note = Rabbit Ab 4127 VH region
source                  1..122
                        mol_type = protein
                        organism = synthetic construct
SEQUENCE: 124
QQLEESGGDL VKPGASLTLT CTASGFSFSN LYYMCWVRQA PGKGLELIGC IDISSSGSTY     60
YASWAKGRFT ISKTSSTTVT LQMTSLTAAD TATYFCARDY YSSDWGVRFN LWGQGTLVTV    120
SS                                                                  122
```

```
SEQ ID NO: 125          moltype = AA  length = 366
FEATURE                 Location/Qualifiers
REGION                  1..366
                        note = Rabbit Ab 4127 VH region
source                  1..366
                        mol_type = protein
                        organism = synthetic construct
SEQUENCE: 125
CAGCAGCTGG AGGAGTCCGG GGGAGACCTG GTCAAGCCTG GGCATCCCT GACACTCACC    60
TGCACAGCCT CTGGATTCTC CTTCAGTAAT CTCTATTACA TGTGTTGGGT CCGCCAGGCT  120
CCAGGGAAGG GGCTGGAGTT GATCGGATGC ATTGATATTA GCAGTAGTGG TAGCACTTAC  180
TACGCGAGCT GGGCGAAAGG CCGATTCACC ATCTCCAAAA CCTCGTCGAC CACGGTGACT  240
CTGCAGATGA CCAGTCTGAC AGCCGCGGAC ACGGCCACCT ATTTCTGTGC GAGAGATTAC  300
TATTCTAGTG ACTGGGGTGT TAGATTTAAC TTGTGGGGCC AGGGCACCCT CGTCACCGTC  360
TCGAGT                                                             366

SEQ ID NO: 126          moltype = AA  length = 112
FEATURE                 Location/Qualifiers
REGION                  1..112
                        note = 4127 gL3 V-region - IGKV1-5 framework
source                  1..112
                        mol_type = protein
                        organism = synthetic construct
SEQUENCE: 126
AIVMTQSPST LSASVGDRVT ITCQASQSVY GNNELSWYQQ KPGKAPKLLI YLASRLASGV   60
PSRFSGSGSG TQFTLTISSL QPDDFATYYC AGYKSDSDDG TTFGGGTKVE IK          112

SEQ ID NO: 127          moltype = AA  length = 124
FEATURE                 Location/Qualifiers
REGION                  1..124
                        note = 4127 gH3 V-region - IGHV3-9 framework
source                  1..124
                        mol_type = protein
                        organism = synthetic construct
SEQUENCE: 127
EVQLVESGGG LVQPGRSLRL SCAASGFSFS NLYYMCWVRQ APGKGLELIG CIDISSSGST   60
YYASWAKGRF TISKDSAKTS VYLQMNSLRA EDTALYYCAR DYYSSDWGVR FNLWGQGTLV  120
TVSS                                                               124

SEQ ID NO: 128          moltype = AA  length = 124
FEATURE                 Location/Qualifiers
REGION                  1..124
                        note = 4127 gH4 V-region - IGHV3-9 framework
source                  1..124
                        mol_type = protein
                        organism = synthetic construct
SEQUENCE: 128
EVQLVESGGG LVQPGRSLRL SCAASGFSFS NLYYMSWVRQ APGKGLELIG SIDISSSGST   60
YYASWAKGRF TISKDSAKTS VYLQMNSLRA EDTALYYCAR DYYSSDWGVR FNLWGQGTLV  120
TVSS                                                               124

SEQ ID NO: 129          moltype = AA  length = 124
FEATURE                 Location/Qualifiers
REGION                  1..124
                        note = 4127 gH6 V-region - IGHV4-38-2 framework
source                  1..124
                        mol_type = protein
                        organism = synthetic construct
SEQUENCE: 129
EVQLQESGPG LVKPSETLSL TCAASGFSFS NLYYMCWVRQ PPGKGLELIG CIDISSSGST   60
YYASWAKGRF TISKDSSKTQ VSLKLSSVTA ADTAVYYCAR DYYSSDWGVR FNLWGQGTLV  120
TVSS                                                               124

SEQ ID NO: 130          moltype = AA  length = 124
FEATURE                 Location/Qualifiers
REGION                  1..124
                        note = 4127 gH7 V-region - IGHV4-38-2 framework
source                  1..124
                        mol_type = protein
                        organism = synthetic construct
SEQUENCE: 130
EVQLQESGPG LVKPSETLSL TCAASGFSFS NLYYMSWVRQ PPGKGLELIG SIDISSSGST   60
YYASWAKGRF TISKDSSKTQ VSLKLSSVTA ADTAVYYCAR DYYSSDWGVR FNLWGQGTLV  120
TVSS                                                               124

SEQ ID NO: 131          moltype = AA  length = 111
FEATURE                 Location/Qualifiers
REGION                  1..111
```

```
                        note = Rabbit Ab 4128 VL region
source                  1..111
                        mol_type = protein
                        organism = synthetic construct
SEQUENCE: 131
DIVMTQTPAS VEAAVGGTVT IKCQASESIS NYLSWFQQKP GQPPKLLIYA SSKLSSGVPS    60
RFKGDRSGTE YTLTISDLEC ADAATYYCQI YYSASGSRDW TFGGGTKVVV E            111

SEQ ID NO: 132          moltype = DNA  length = 333
FEATURE                 Location/Qualifiers
misc_feature            1..333
                        note = Rabbit Ab 4128 VL region
source                  1..333
                        mol_type = other DNA
                        organism = synthetic construct
SEQUENCE: 132
gacattgtga tgacccagac tccagcctcc gtggaggcag ctgtgggagg cacagtcacc    60
atcaagtgcc aggccagtga aagcattagc aactactat cctggtttca gcagaaacca   120
gggcagcctc ccaagctcct gatctatgct tcatccaaac tgtcatctgg ggtcccatcg   180
cggttcaaag gcgatagatc tgggacagag tacactctca ccatcagcga cctggagtgt   240
gccgatgctg ccacttacta ctgtcaaatc tattattcgg ctagtggcag tcgtgattgg   300
actttcggcg gagggaccaa ggtggtcgtc gaa                                333

SEQ ID NO: 133          moltype = AA  length = 120
FEATURE                 Location/Qualifiers
REGION                  1..120
                        note = Rabbit Ab 4128 VH region
source                  1..120
                        mol_type = protein
                        organism = synthetic construct
SEQUENCE: 133
QSLEESGGDL VQPEGSLTLT CKGSGLDFSS YWICWVRQAP GKGLEWIACI VTGSSDNTYY    60
ASWAKGRFTI SKTSSTTVTL QMTSLTAADT ATYFCARGGG AGYSGAFDLW GQGTLVTVSS   120

SEQ ID NO: 134          moltype = DNA  length = 360
FEATURE                 Location/Qualifiers
misc_feature            1..360
                        note = Rabbit Ab 4128 VH region
source                  1..360
                        mol_type = other DNA
                        organism = synthetic construct
SEQUENCE: 134
cagtcgttgg aggagtccgg gggagacctg gtccagcctg agggatccct gacactcacc    60
tgcaaaggct ccgggttaga cttcagtagc tactggatat gctgggtccg ccaggctcca   120
gggaaggggc tggagtggat cgcatgcatt gttactggta gtagtgataa cacttactac   180
gcgagctggg cgaaaggccg attcaccatc tccaaaacct cgtcgaccac ggtgactctg   240
caaatgacca gtctgacagc cgcggacacg gccacctatt tctgtgcgag aggtggtggt   300
gctggttata gtggtgcctt tgacttgtgg ggccaaggga ccctcgtcac cgtctcgagt   360

SEQ ID NO: 135          moltype = AA  length = 111
FEATURE                 Location/Qualifiers
REGION                  1..111
                        note = 4128 gL1 V-region - IGKV1-5 framework
source                  1..111
                        mol_type = protein
                        organism = synthetic construct
SEQUENCE: 135
DIVMTQSPST LSASVGDRVT ITCQASESIS NYLSWFQQKP GKAPKLLIYA SSKLSSGVPS    60
RFKGDRSGTE YTLTISSLQP DDFATYYCQI YYSASGSRDW TFGGGTKVEI K            111

SEQ ID NO: 136          moltype = AA  length = 122
FEATURE                 Location/Qualifiers
REGION                  1..122
                        note = 4128 gH1 V-region - IGHV3-33 framework
source                  1..122
                        mol_type = protein
                        organism = synthetic construct
SEQUENCE: 136
EVQLVESGGG LVQPGRSLRL SCKGSGLDFS SYWICWVRQA PGKGLEWIAC IVTGSSDNTY    60
YASWAKGRFT ISKDSSKTTV YLQMNSLRAE DTAVYYCARG GGAGYSGAFD LWGQGTLVTV   120
SS                                                                  122

SEQ ID NO: 137          moltype = AA  length = 122
FEATURE                 Location/Qualifiers
REGION                  1..122
                        note = 4128 gH2 V-region - IGHV3-33 framework
source                  1..122
                        mol_type = protein
                        organism = synthetic construct
```

```
SEQUENCE: 137
EVQLVESGGG LVQPGRSLRL SCKGSGLDFS SYWISWVRQA PGKGLEWIAS IVTGSSDNTY    60
YASWAKGRFT ISKDSSKTTV YLQMNSLRAE DTAVYYCARG GGAGYSGAFD LWGQGTLVTV   120
SS                                                                 122

SEQ ID NO: 138          moltype = AA  length = 122
FEATURE                 Location/Qualifiers
REGION                  1..122
                        note = 4128 gH4 V-region - IGHV4-59 framework
source                  1..122
                        mol_type = protein
                        organism = synthetic construct
SEQUENCE: 138
EVQLQESGPG LVKPSETLSL TCKGSGLDFS SYWICWVRQP PGKGLEWIAC IVTGSSDNTY    60
YASWAKGRFT ISKDSSKTQV SLKLSSVTAA DTAVYYCARG GGAGYSGAFD LWGQGTLVTV   120
SS                                                                 122

SEQ ID NO: 139          moltype = AA  length = 122
FEATURE                 Location/Qualifiers
REGION                  1..122
                        note = 4128 gH5 V-region - IGHV4-59 framework
source                  1..122
                        mol_type = protein
                        organism = synthetic construct
SEQUENCE: 139
EVQLQESGPG LVKPSETLSL TCKGSGLDFS SYWISWVRQP PGKGLEWIAS IVTGSSDNTY    60
YASWAKGRFT ISKDSSKTQV SLKLSSVTAA DTAVYYCARG GGAGYSGAFD LWGQGTLVTV   120
SS                                                                 122

SEQ ID NO: 140          moltype = AA  length = 111
FEATURE                 Location/Qualifiers
REGION                  1..111
                        note = Rabbit Ab 4130 VL region
source                  1..111
                        mol_type = protein
                        organism = synthetic construct
SEQUENCE: 140
AAVLTQTPSP VSAAVGGTVS ISCQSSQSVY NTKDLAWYQQ KPGQPPKLLI YGTSTLASGV    60
SSRFSGSGSG TEFTLTISDL ECDDAATYYC QGGFSSSDLN VFGGGTKVVV K            111

SEQ ID NO: 141          moltype = DNA  length = 333
FEATURE                 Location/Qualifiers
misc_feature            1..333
                        note = Rabbit Ab 4130 VL region
source                  1..333
                        mol_type = other DNA
                        organism = synthetic construct
SEQUENCE: 141
gccgccgtgc tgacccagac tccatctccc gtgtctgcag ctgtgggagg cacagtcagc    60
atcagttgcc agtccagtca gagtgtttat aatacaaagg acttagcctg gtatcagcag   120
aaaccagggc agcctcccaa gctcctgatc tatggtacat ccactctggc atctggggtc   180
tcatcacggt tcagcggcag tggatctggg acagagttca ctctcaccat cagcgacctg   240
gagtgtgacg atgctgccac ttattactgt caaggcggtt ttagtagtag tgatttgaat   300
gttttcggcg agggaccaa ggtggtggtc aaa                                 333

SEQ ID NO: 142          moltype = AA  length = 123
FEATURE                 Location/Qualifiers
REGION                  1..123
                        note = Rabbit Ab 4130 VH region
source                  1..123
                        mol_type = protein
                        organism = synthetic construct
SEQUENCE: 142
QQQLEESGGD LVRPEGSLTL TCTASGFDFS GGYDISWVRQ APGKGLEWIG CIYGGINSVT    60
DYASWAKGRV TISKTSSTTV TLQMTSLTAA DTATYFCARD VSNSDHYTRL DLWGQGTLVT   120
VSS                                                                123

SEQ ID NO: 143          moltype = DNA  length = 369
FEATURE                 Location/Qualifiers
misc_feature            1..369
                        note = Rabbit Ab 4130 VH region
source                  1..369
                        mol_type = other DNA
                        organism = synthetic construct
SEQUENCE: 143
cagcagcagc tggaggagtc cggggggac ctggtcaggc ctgagggatc cctgacactc     60
acctgcacag cctctggatt cgacttcagt ggcggctacg acatttcctg ggtccgccag   120
gctccaggga aggggctgga gtggatcgga tgcatttatg gtggtatcaa tagtgtcact   180
gactacgcga gctgggcgaa aggccgagtc accatctcca aaacctcgtc gaccacggtg   240
```

```
actctgcaga tgaccagtct gacagccgcg gacacggcca cctatttctg tgcgagagat    300
gttagtaata gcgatcatta tactcggttg gatctctggg gccaaggcac cctggtcacc    360
gtctcgagt                                                            369

SEQ ID NO: 144           moltype = AA  length = 111
FEATURE                  Location/Qualifiers
REGION                   1..111
                         note = 4130 gL3 V-region - IGKV1-9 framework
source                   1..111
                         mol_type = protein
                         organism = synthetic construct
SEQUENCE: 144
AAVLTQSPSF LSASVGDRVT ITCQSSQSVY NTKDLAWYQQ KPGKAPKLLI YGTSTLASGV    60
PSRFSGSGSG TEFTLTISSL QPEDFATYYC QGGFSSSDLN VFGGGTKVEI K             111

SEQ ID NO: 145           moltype = AA  length = 124
FEATURE                  Location/Qualifiers
REGION                   1..124
                         note = 4130 gH8 V-region - IGHV3-66 framework
source                   1..124
                         mol_type = protein
                         organism = synthetic construct
SEQUENCE: 145
EVQLVESGGG LVQPGGSLRL SCAASGFDFS GGYDISWVRQ APGKGLEWIG CIYGGINSVT    60
DYASWAKGRV TISKDSSKTT VYLQMNSLRA EDTAVYYCAR DVSNSDHYTR LDLWGQGTLV    120
TVSS                                                                 124

SEQ ID NO: 146           moltype = AA  length = 124
FEATURE                  Location/Qualifiers
REGION                   1..124
                         note = 4130 gH3 V-region - IGHV3-66 framework
source                   1..124
                         mol_type = protein
                         organism = synthetic construct
SEQUENCE: 146
EVQLVESGGG LVQPGGSLRL SCAASGFDFS GGYDISWVRQ APGKGLEWIG SIYGGINSVT    60
DYASWAKGRV TISKDSSKTT VYLQMNSLRA EDTAVYYCAR DVSNSDHYTR LDLWGQGTLV    120
TVSS                                                                 124

SEQ ID NO: 147           moltype = AA  length = 124
FEATURE                  Location/Qualifiers
REGION                   1..124
                         note = 4130 gH9 V-region - IGHV4-4 framework
source                   1..124
                         mol_type = protein
                         organism = synthetic construct
SEQUENCE: 147
EVQLQESGPG LVKPSGTLSL TCAASGFDFS GGYDISWVRQ PPGKGLEWIG CIYGGINSVT    60
DYASWAKGRV TISKDSSKTQ VSLKLSSVTA ADTAVYYCAR DVSNSDHYTR LDLWGQGTLV    120
TVSS                                                                 124

SEQ ID NO: 148           moltype = AA  length = 124
FEATURE                  Location/Qualifiers
REGION                   1..124
                         note = 4130 gH5 V-region - IGHV4-4 framework
source                   1..124
                         mol_type = protein
                         organism = synthetic construct
SEQUENCE: 148
EVQLQESGPG LVKPSGTLSL TCAASGFDFS GGYDISWVRQ PPGKGLEWIG SIYGGINSVT    60
DYASWAKGRV TISKDSSKTQ VSLKLSSVTA ADTAVYYCAR DVSNSDHYTR LDLWGQGTLV    120
TVSS                                                                 124

SEQ ID NO: 149           moltype = AA  length = 110
FEATURE                  Location/Qualifiers
REGION                   1..110
                         note = Rabbit Ab 4132 VL region
source                   1..110
                         mol_type = protein
                         organism = synthetic construct
SEQUENCE: 149
DIVMTQTPAS VEAAVGGTVT IKCQASETIS SRLAWYQQKL GQPPKLLIYS ASTLASGVPS    60
RFKGSGSGTE YTLTISGVQC ADAATYYCQG YYYSSGSDYG FGGGTKVVVK               110

SEQ ID NO: 150           moltype = DNA  length = 330
FEATURE                  Location/Qualifiers
misc_feature             1..330
                         note = Rabbit Ab 4132 VL region
source                   1..330
```

```
                            mol_type = other DNA
                            organism = synthetic construct
SEQUENCE: 150
gacattgtga tgacccagac tccagcctcc gtggaggcag ctgtgggagg cacagtcacc    60
atcaagtgcc aggccagtga gaccattagt agtagattac cctggtatca gcagaagcta   120
gggcagcctc ccaaactcct gatctattct gcatccactc tggcgtctgg ggtcccatcg   180
cggttcaaag gcagtggatc tgggacagag tacactctca ccatcagcgg cgtgcagtgt   240
gccgatgctg ccacttatta ctgtcaaggc tattattata gtagtggtag tgattatggt   300
ttcggcggag ggaccaaggt ggtcgtcaaa                                    330

SEQ ID NO: 151              moltype = AA   length = 121
FEATURE                     Location/Qualifiers
REGION                      1..121
                            note = Rabbit Ab 4132 VH region
source                      1..121
                            mol_type = protein
                            organism = synthetic construct
SEQUENCE: 151
QSLEESGGDL VKPGASLTLT CTASGFSFSS SYWICWVRQA PGKGLEWSGC INSGTGGTAY    60
ASWAKGRFTI SNSSSTTVTL QMTSLTAADT ATYFCAREWV SGYYKDAFDL WGQGTLVTVS   120
S                                                                   121

SEQ ID NO: 152              moltype = DNA   length = 363
FEATURE                     Location/Qualifiers
misc_feature                1..363
                            note = Rabbit Ab 4132 VH region
source                      1..363
                            mol_type = other DNA
                            organism = synthetic construct
SEQUENCE: 152
cagtcgttgg aggagtccgg gggagacctg gtcaagcctg ggcatcccct gacactcacc    60
tgcacagcct ctggattctc cttcagtagc agctactgga tatgctgggt ccgccaggct   120
ccagggaagg ggctggagtg gagcggatgc attaatagtg gtactggtgg cactgcctac   180
gcgagctggg cgaaaggccg attcaccatc tccaattcct cgtcgaccac ggtgactctt   240
caaatgacca gtctgacagc cgcggacacg gccacctatt tctgtgcgag agaatgggtt   300
agtggttatt ataaagatgc ttttgatctc tggggccagg gcaccctggt caccgtctcg   360
agt                                                                 363

SEQ ID NO: 153              moltype = AA   length = 110
FEATURE                     Location/Qualifiers
REGION                      1..110
                            note = 4132 gL1 V-region - IGKV1-5 framework
source                      1..110
                            mol_type = protein
                            organism = synthetic construct
SEQUENCE: 153
DIVMTQSPST LSASVGDRVT ITCQASETIS SRLAWYQQKP GKAPKLLIYS ASTLASGVPS    60
RFSGSGSGTE YTLTISSLQP DDFATYYCQG YYYSSGSDYG FGGGTKVEIK              110

SEQ ID NO: 154              moltype = AA   length = 123
FEATURE                     Location/Qualifiers
REGION                      1..123
                            note = 4132 gH1 V-region - IGHV3-21 framework
source                      1..123
                            mol_type = protein
                            organism = synthetic construct
SEQUENCE: 154
EVQLVESGGG LVKPGGSLRL SCAASGFSFS SSYWICWVRQ APGKGLEWSG CINSGTGGTA    60
YASWAKGRFT ISNDSAKTSV YLQMNSLRAE DTAVYYCARE WVSGYYKDAF DLWGQGTLVT   120
VSS                                                                 123

SEQ ID NO: 155              moltype = AA   length = 123
FEATURE                     Location/Qualifiers
REGION                      1..123
                            note = 4132 gH2 V-region - IGHV3-21 framework
source                      1..123
                            mol_type = protein
                            organism = synthetic construct
SEQUENCE: 155
EVQLVESGGG LVKPGGSLRL SCAASGFSFS SSYWISWVRQ APGKGLEWSG SINSGTGGTA    60
YASWAKGRFT ISNDSAKTSV YLQMNSLRAE DTAVYYCARE WVSGYYKDAF DLWGQGTLVT   120
VSS                                                                 123

SEQ ID NO: 156              moltype = AA   length = 123
FEATURE                     Location/Qualifiers
REGION                      1..123
                            note = 4132 gH4 V-region - IGHV4-4 framework
source                      1..123
                            mol_type = protein
```

```
                         organism = synthetic construct
SEQUENCE: 156
EVQLQESGPG LVKPSGTLSL TCAASGFSFS SSYWICWVRQ PPGKGLEWSG CINSGTGGTA    60
YASWAKGRFT ISNDSSKTQV SLKLSSVTAA DTAVYYCARE WVSGYYKDAF DLWGQGTLVT   120
VSS                                                                 123

SEQ ID NO: 157           moltype = AA  length = 123
FEATURE                  Location/Qualifiers
REGION                   1..123
                         note = 4132 gH5 V-region - IGHV4-4 framework
source                   1..123
                         mol_type = protein
                         organism = synthetic construct
SEQUENCE: 157
EVQLQESGPG LVKPSGTLSL TCAASGFSFS SSYWISWVRQ PPGKGLEWSG SINSGTGGTA    60
YASWAKGRFT ISNDSSKTQV SLKLSSVTAA DTAVYYCARE WVSGYYKDAF DLWGQGTLVT   120
VSS                                                                 123

SEQ ID NO: 158           moltype = AA  length = 10
FEATURE                  Location/Qualifiers
REGION                   1..10
                         note = Ab 4447 CDRH1
source                   1..10
                         mol_type = protein
                         organism = synthetic construct
SEQUENCE: 158
GFSLSNYAVS                                                           10

SEQ ID NO: 159           moltype = AA  length = 17
FEATURE                  Location/Qualifiers
REGION                   1..17
                         note = Ab 4447 CDRH2
source                   1..17
                         mol_type = protein
                         organism = synthetic construct
SEQUENCE: 159
IIYIETGTTW YANWAKG                                                   17

SEQ ID NO: 160           moltype = AA  length = 17
FEATURE                  Location/Qualifiers
REGION                   1..17
                         note = Ab 4447 CDRH3
source                   1..17
                         mol_type = protein
                         organism = synthetic construct
SEQUENCE: 160
EPYEPYDDSN IYYGMDP                                                   17

SEQ ID NO: 161           moltype = AA  length = 13
FEATURE                  Location/Qualifiers
REGION                   1..13
                         note = Ab 4447 CDRL1
source                   1..13
                         mol_type = protein
                         organism = synthetic construct
SEQUENCE: 161
QASQSVVSGN YLA                                                       13

SEQ ID NO: 162           moltype = AA  length = 7
FEATURE                  Location/Qualifiers
REGION                   1..7
                         note = Ab 4447 CDRL2
source                   1..7
                         mol_type = protein
                         organism = synthetic construct
SEQUENCE: 162
SASTLAS                                                               7

SEQ ID NO: 163           moltype = AA  length = 13
FEATURE                  Location/Qualifiers
REGION                   1..13
                         note = Ab 4447 CDRL3
source                   1..13
                         mol_type = protein
                         organism = synthetic construct
SEQUENCE: 163
LGEFSCSSHD CNA                                                       13

SEQ ID NO: 164           moltype = AA  length = 13
```

```
FEATURE                     Location/Qualifiers
REGION                      1..13
                            note = Ab 4447 CDRL3 variant 1
source                      1..13
                            mol_type = protein
                            organism = synthetic construct
SEQUENCE: 164
LGEFSSSSHD SNA                                                              13

SEQ ID NO: 165              moltype = AA  length = 13
FEATURE                     Location/Qualifiers
REGION                      1..13
                            note = Ab 4447 CDRL3 variant 2
source                      1..13
                            mol_type = protein
                            organism = synthetic construct
SEQUENCE: 165
LGEFSCSSHD SNA                                                              13

SEQ ID NO: 166              moltype = AA  length = 13
FEATURE                     Location/Qualifiers
REGION                      1..13
                            note = Ab 4447 CDRL3 variant 3
source                      1..13
                            mol_type = protein
                            organism = synthetic construct
SEQUENCE: 166
LGEFSSSSHD CNA                                                              13

SEQ ID NO: 167              moltype = AA  length = 113
FEATURE                     Location/Qualifiers
REGION                      1..113
                            note = Rabbit Ab 4447 VL region
source                      1..113
                            mol_type = protein
                            organism = synthetic construct
SEQUENCE: 167
AQVLTQTPSP VSAPVGGTVT INCQASQSVV SGNYLAWLQQ KPGQPPKQLI HSASTLASGV           60
SSRFSGSGSG TQFTLTISGV QCEDAATYYC LGEFSCSSHD CNAFGGGTEV VVK                 113

SEQ ID NO: 168              moltype = DNA  length = 339
FEATURE                     Location/Qualifiers
misc_feature                1..339
                            note = Rabbit Ab 4447 VL region
source                      1..339
                            mol_type = other DNA
                            organism = synthetic construct
SEQUENCE: 168
gcccaagtgc tgacccagac tccgtcccct gtgtctgcac ctgtgggagg cacagtcacc           60
atcaattgcc aggccagtca gagtgttgtt agtggcaatt acctagcctg gcttcagcag         120
aaaccaggga gcctcccaa gcaactgatc cattctgcat ccactctggc atctggggtc          180
tcatcgcggt tcagcggcag tggatctggg acacaattca ctctcaccat cagcggcgtg         240
cagtgtgaag atgctgccac ttactactgt ctaggcgaat ttagttgtag tagtcatgat         300
tgtaatgctt tcggcggagg gaccgaggtg gtggtcaaa                                339

SEQ ID NO: 169              moltype = AA  length = 123
FEATURE                     Location/Qualifiers
REGION                      1..123
                            note = Rabbit Ab 4447 VH region
source                      1..123
                            mol_type = protein
                            organism = synthetic construct
SEQUENCE: 169
QSLEESGGRL VTPGTPLTLT CTVSGFSLSN YAVSWVRQAP GEGLEWIGII YIETGTTWYA           60
NWAKGRFTIS KTSTTVDLTI TSPSTEDTAT YFCAREPYEP YDDSNIYYGM DPWGPGTLVT          120
VSS                                                                       123

SEQ ID NO: 170              moltype = DNA  length = 369
FEATURE                     Location/Qualifiers
misc_feature                1..369
                            note = Rabbit Ab 4447 VH region
source                      1..369
                            mol_type = other DNA
                            organism = synthetic construct
SEQUENCE: 170
cagtcgctgg aggagtccgg gggtcgcctg gtcacgcctg gacacccct gacactcacc            60
tgcaccgtct ctggattctc cctcagtaac tatgcagtaa gctgggtccg ccaggctcca         120
ggggagggac tggaatggat cgggatcatt tatattgaaa ctggtaccac atggtacgcg         180
aactgggcga aaggccgatt caccatctcc aaaaacctcga ccacggtgga tctgacaatc        240
```

```
accagtccgt caaccgagga cacggccacc tatttctgtg ccagagaacc ttatgaacct    300
tatgatgata gtaatattta ctacggcatg gaccccctggg gcccaggcac cctcgtcacc    360
gtctcgagt                                                              369
```

```
SEQ ID NO: 171          moltype = AA   length = 113
FEATURE                 Location/Qualifiers
REGION                  1..113
                        note = 4447 gL1 V-region - IGKV1D-13 framework
source                  1..113
                        mol_type = protein
                        organism = synthetic construct
SEQUENCE: 171
AQVLTQSPSS LSASVGDRVT ITCQASQSVV SGNYLAWLQQ KPGKAPKQLI HSASTLASGV     60
PSRFSGSGSG TQFTLTISSL QPEDFATYYC LGEFSCSSHD CNAFGGGTKV EIK           113

SEQ ID NO: 172          moltype = AA   length = 113
FEATURE                 Location/Qualifiers
REGION                  1..113
                        note = 4447 gL2 V-region - IGKV1D-13 framework
source                  1..113
                        mol_type = protein
                        organism = synthetic construct
SEQUENCE: 172
AQVLTQSPSS LSASVGDRVT ITCQASQSVV SGNYLAWLQQ KPGKAPKQLI HSASTLASGV     60
PSRFSGSGSG TQFTLTISSL QPEDFATYYC LGEFSSSSHD SNAFGGGTKV EIK           113

SEQ ID NO: 173          moltype = AA   length = 126
FEATURE                 Location/Qualifiers
REGION                  1..126
                        note = 4447 gH1 V-region - IGHV3-48 framework
source                  1..126
                        mol_type = protein
                        organism = synthetic construct
SEQUENCE: 173
EVQLVESGGG LVQPGGSLRL SCAVSGFSLS NYAVSWVRQA PGKGLEWIGI IYIETGTTWY     60
ANWAKGRFTI SKDSAKNSVY LQMNSLRDED TAVYYCAREP YEPYDDSNIY YGMDPWGQGT   120
LVTVSS                                                               126

SEQ ID NO: 174          moltype = AA   length = 126
FEATURE                 Location/Qualifiers
REGION                  1..126
                        note = 4447 gH3 V-region - IGHV4-59 framework
source                  1..126
                        mol_type = protein
                        organism = synthetic construct
SEQUENCE: 174
EVQLQESGPG LVKPSETLSL TCTVSGFSLS NYAVSWVRQP PGKGLEWIGI IYIETGTTWY     60
ANWAKGRFTI SKDSSKNQVS LKLSSVTAAD TAVYYCAREP YEPYDDSNIY YGMDPWGQGT   120
LVTVSS                                                               126

SEQ ID NO: 175          moltype = AA   length = 10
FEATURE                 Location/Qualifiers
REGION                  1..10
                        note = Ab 4450 CDRH1
source                  1..10
                        mol_type = protein
                        organism = synthetic construct
SEQUENCE: 175
GFSLNNYVMV                                                            10

SEQ ID NO: 176          moltype = AA   length = 16
FEATURE                 Location/Qualifiers
REGION                  1..16
                        note = Ab 4450 CDRH2
source                  1..16
                        mol_type = protein
                        organism = synthetic construct
SEQUENCE: 176
IIYVSGNAYY ASWAKG                                                     16

SEQ ID NO: 177          moltype = AA   length = 12
FEATURE                 Location/Qualifiers
REGION                  1..12
                        note = Ab 4450 CDRH3
source                  1..12
                        mol_type = protein
                        organism = synthetic construct
SEQUENCE: 177
DAGHSDVDVL DI                                                         12
```

```
SEQ ID NO: 178            moltype = AA  length = 13
FEATURE                   Location/Qualifiers
REGION                    1..13
                          note = Ab 4450 CDRL1
source                    1..13
                          mol_type = protein
                          organism = synthetic construct
SEQUENCE: 178
QSSQSIYNNN DLA                                                        13

SEQ ID NO: 179            moltype = AA  length = 7
FEATURE                   Location/Qualifiers
REGION                    1..7
                          note = Ab 4450 CDRL2
source                    1..7
                          mol_type = protein
                          organism = synthetic construct
SEQUENCE: 179
EASKLAS                                                               7

SEQ ID NO: 180            moltype = AA  length = 11
FEATURE                   Location/Qualifiers
REGION                    1..11
                          note = Ab 4450 CDRL3
source                    1..11
                          mol_type = protein
                          organism = synthetic construct
SEQUENCE: 180
QGGGSGGDGI A                                                          11

SEQ ID NO: 181            moltype = AA  length = 11
FEATURE                   Location/Qualifiers
REGION                    1..11
                          note = Ab 4450 CDRL3 - variant 1
source                    1..11
                          mol_type = protein
                          organism = synthetic construct
SEQUENCE: 181
QGGGSGGEGI A                                                          11

SEQ ID NO: 182            moltype = AA  length = 11
FEATURE                   Location/Qualifiers
REGION                    1..11
                          note = Ab 4450 CDRL3 - variant 2
source                    1..11
                          mol_type = protein
                          organism = synthetic construct
SEQUENCE: 182
QGGGSGGDAI A                                                          11

SEQ ID NO: 183            moltype = AA  length = 11
FEATURE                   Location/Qualifiers
REGION                    1..11
                          note = Ab 4450 CDRL3 - variant 3
source                    1..11
                          mol_type = protein
                          organism = synthetic construct
SEQUENCE: 183
QGGGSGGDSI A                                                          11

SEQ ID NO: 184            moltype = AA  length = 111
FEATURE                   Location/Qualifiers
REGION                    1..111
                          note = Rabbit Ab 4450 VL region
source                    1..111
                          mol_type = protein
                          organism = synthetic construct
SEQUENCE: 184
AIDMTQTPSP VSAAVGGTVT INCQSSQSIY NNNDLAWYQQ KPGQPPKLLI YEASKLASGV      60
PSRFKGSGSG TQFTLTISGV QCDDAATYYC QGGGSGGDGI AFGGGTKVVV E               111

SEQ ID NO: 185            moltype = DNA  length = 333
FEATURE                   Location/Qualifiers
misc_feature              1..333
                          note = Rabbit Ab 4450 VL region
source                    1..333
                          mol_type = other DNA
                          organism = synthetic construct
```

```
SEQUENCE: 185
gccattgata tgacccagac tccatccccc gtgtctgcag ctgtgggagg cacagtcacc    60
atcaattgcc agtccagtca gagtatttat aataataatg acttagcctg gtatcagcag   120
aaaccagggc agcctcccaa gctcctgatc tacgaagcat ccaaactggc atctggggtc   180
ccatcgcggt tcaaaggcag tggatctggg acacagttca ctctcaccat cagtggcgtg   240
cagtgtgatg atgctgccac ttactactgt cagggcggtg gtagtggtgg tgatggcatt   300
gctttcggcg agggaccaa ggtggtcgtc gaa                                 333

SEQ ID NO: 186          moltype = AA   length = 117
FEATURE                 Location/Qualifiers
REGION                  1..117
                        note = Rabbit Ab 4450 VH region
source                  1..117
                        mol_type = protein
                        organism = synthetic construct
SEQUENCE: 186
QSVEESGGRL VTPGAPLTLT CTVSGFSLNN YVMVWVRQAP GKGLEWIGII YVSGNAYYAS    60
WAKGRFTISR TSTTVDLKVT SLTTEDTATY FCARDAGHSD VDVLDIWGPG TLVTVSS      117

SEQ ID NO: 187          moltype = DNA   length = 351
FEATURE                 Location/Qualifiers
misc_feature            1..351
                        note = Rabbit Ab 4450 VH region
source                  1..351
                        mol_type = other DNA
                        organism = synthetic construct
SEQUENCE: 187
cagtcggtgg aggagtccgg gggtcgcctg gtcacgcctg ggcacccct gacactcacc     60
tgcacagtct ctggattctc cctcaataac tatgtaatgg tctgggtccg ccaggctcca   120
gggaagggc tggaatggat cggaatcatt tatgttagtg gtaatgcata ctacgcgagc   180
tgggcaaaag gccgattcac catctccaga acctcgacca cggtggatct gaaagtgacc   240
agtctgacaa ccgaggacac ggccacctat ttctgtgcca gagatgctgg tcatagtgat   300
gtcgatgttt tggatatttg ggccccgggc accctcgtca ccgtctcgag t            351

SEQ ID NO: 188          moltype = AA   length = 111
FEATURE                 Location/Qualifiers
REGION                  1..111
                        note = 4450 gL1 V-region - IGKV1-6 framework
source                  1..111
                        mol_type = protein
                        organism = synthetic construct
SEQUENCE: 188
AIDMTQSPSS LSASVGDRVT ITCQSSQSIY NNNDLAWYQQ KPGKAPKLLI YEASKLASGV    60
PSRFSGSGSG TQFTLTISSL QPEDFATYYC QGGGSGGDGI AFGGGTKVEI K            111

SEQ ID NO: 189          moltype = AA   length = 120
FEATURE                 Location/Qualifiers
REGION                  1..120
                        note = 4450 gH1 V-region - IGHV3-66 framework
source                  1..120
                        mol_type = protein
                        organism = synthetic construct
SEQUENCE: 189
EVQLVESGGG LVQPGGSLRL SCAVSGFSLN NYVMVWVRQA PGKGLEWIGI IYVSGNAYYA    60
SWAKGRFTIS RDSSKNTVYL QMNSLRAEDT AVYYCARDAG HSDVDVLDIW GQGTLVTVSS   120

SEQ ID NO: 190          moltype = AA   length = 120
FEATURE                 Location/Qualifiers
REGION                  1..120
                        note = 4450 gH3 V-region - IGHV4-59 framework
source                  1..120
                        mol_type = protein
                        organism = synthetic construct
SEQUENCE: 190
EVQLQESGPG LVKPSETLSL TCTVSGFSLN NYVMVWVRQP PGKGLEWIGI IYVSGNAYYA    60
SWAKGRFTIS RDSSKNQVSL KLSSVTAADT AVYYCARDAG HSDVDVLDIW GQGTLVTVSS   120

SEQ ID NO: 191          moltype = AA   length = 10
FEATURE                 Location/Qualifiers
REGION                  1..10
                        note = CDRH1 dAbH1
source                  1..10
                        mol_type = protein
                        organism = synthetic construct
SEQUENCE: 191
GIDLSNYAIN                                                           10

SEQ ID NO: 192          moltype = AA   length = 16
FEATURE                 Location/Qualifiers
```

```
REGION                  1..16
                        note = CDRH2 dAbH1
source                  1..16
                        mol_type = protein
                        organism = synthetic construct
SEQUENCE: 192
IIWASGTTFY ATWAKG                                                        16

SEQ ID NO: 193          moltype = AA  length = 13
FEATURE                 Location/Qualifiers
REGION                  1..13
                        note = CDRH3 dAbH1
source                  1..13
                        mol_type = protein
                        organism = synthetic construct
SEQUENCE: 193
TVPGYSTAPY FDL                                                           13

SEQ ID NO: 194          moltype = AA  length = 12
FEATURE                 Location/Qualifiers
REGION                  1..12
                        note = CDRL1 dAbL1
source                  1..12
                        mol_type = protein
                        organism = synthetic construct
SEQUENCE: 194
QSSPSVWSNF LS                                                            12

SEQ ID NO: 195          moltype = AA  length = 7
FEATURE                 Location/Qualifiers
REGION                  1..7
                        note = CDRL2 dAbL1
source                  1..7
                        mol_type = protein
                        organism = synthetic construct
SEQUENCE: 195
EASKLTS                                                                  7

SEQ ID NO: 196          moltype = AA  length = 11
FEATURE                 Location/Qualifiers
REGION                  1..11
                        note = CDRL3 dAbL1
source                  1..11
                        mol_type = protein
                        organism = synthetic construct
SEQUENCE: 196
GGGYSSISDT T                                                             11

SEQ ID NO: 197          moltype = AA  length = 121
FEATURE                 Location/Qualifiers
REGION                  1..121
                        note = Heavy chain variable domain of anti-albumin antibody
                          (no ds)
source                  1..121
                        mol_type = protein
                        organism = synthetic construct
SEQUENCE: 197
EVQLLESGGG LVQPGGSLRL SCAVSGIDLS NYAINWVRQA PGKGLEWIGI IWASGTTFYA         60
TWAKGRFTIS RDNSKNTVYL QMNSLRAEDT AVYYCARTVP GYSTAPYFDL WGQGTLVTVS        120
S                                                                       121

SEQ ID NO: 198          moltype = AA  length = 121
FEATURE                 Location/Qualifiers
REGION                  1..121
                        note = Heavy chain variable domain of anti-albumin antibody
                          (ds)
source                  1..121
                        mol_type = protein
                        organism = synthetic construct
SEQUENCE: 198
EVQLLESGGG LVQPGGSLRL SCAVSGIDLS NYAINWVRQA PGKCLEWIGI IWASGTTFYA         60
TWAKGRFTIS RDNSKNTVYL QMNSLRAEDT AVYYCARTVP GYSTAPYFDL WGQGTLVTVS        120
S                                                                       121

SEQ ID NO: 199          moltype = AA  length = 112
FEATURE                 Location/Qualifiers
REGION                  1..112
                        note = Light chain variable domain of anti-albumin antibody
                          (no ds)
```

```
                        source          1..112
                                        mol_type = protein
                                        organism = synthetic construct
SEQUENCE: 199
DIQMTQSPSS VSASVGDRVT ITCQSSPSVW SNFLSWYQQK PGKAPKLLIY EASKLTSGVP   60
SRFSGSGSGT DFTLTISSLQ PEDFATYYCG GGYSSISDTT FGGGTKVEIK RT          112

SEQ ID NO: 200                  moltype = AA   length = 112
FEATURE                         Location/Qualifiers
REGION                          1..112
                                note = Light chain variable domain of anti-albumin antibody
                                   (ds)
                        source          1..112
                                        mol_type = protein
                                        organism = synthetic construct
SEQUENCE: 200
DIQMTQSPSS VSASVGDRVT ITCQSSPSVW SNFLSWYQQK PGKAPKLLIY EASKLTSGVP   60
SRFSGSGSGT DFTLTISSLQ PEDFATYYCG GGYSSISDTT FGCGTKVEIK RT          112

SEQ ID NO: 201                  moltype = AA   length = 847
FEATURE                         Location/Qualifiers
REGION                          1..847
                                note = Human CD22
                        source          1..847
                                        mol_type = protein
                                        organism = synthetic construct
SEQUENCE: 201
MHLLGPWLLL LVLEYLAFSD SSKWVFEHPE TLYAWEGACV WIPCTYRALD GDLESFILFH   60
NPEYNKNTSK FDGTRLYEST KDGKVPSEQK RVQFLGDKNK NCTLSIHPVH LNDSGQLGLR  120
MESKTEKWME RIHLNVSERP FPPHIQLPPE IQESQEVTLT CLLNFSCYGY PIQLQWLLEG  180
VPMRQAAVTS TSLTIKSVFT RSELKFSPQW SHHGKIVTCQ LQDADGKFLS NDTVQLNVKH  240
TPKLEIKVTP SDAIVREGDS VTMTCEVSSN PEYTTVSWL KDGTSLKKQN TFTLNLREVT   300
KDQSGKYCCQ VSNDVGPGRS EEVFLQVQYA PEPSTVQILH SPAVEGSQVE FLCMSLANPL  360
PTNYTWYHNG KEMQGRTEEK VHIPKILPWH AGTYSCVAEN ILGTGQRGPG AELDVQYPPK  420
KVTTVIQNPM PIREGDTVTL SCNYNSSNPS VTRYEWKPHG AWEEPSLGVL KIQNVGWDNT  480
TIACAACNSW CSWASPVALN VQQYAPRDVRV RKIKPLSEIH SGNSVSLQCD FSSSHPKEVQ  540
FFWEKNGRLL GKESQLNFDS ISPEDAGSYS CWVNNSIGQT ASKAWTLEVL YAPRRLRVSM  600
SPGDQVMEGK SATLTCESDA NPPVSHYTWF DWNNQSLPYH SQKLRLEPVK VQHSGAYWCQ  660
GTNSVGKGRS PLSTLTVYYS PETIGRRVAV GLGSCLAILI LAICGLKLQR RWKRTQSQQG  720
LQENSSGQSF FVRNKKVRRA PLSEGPHSLG CYNPMMEDGI SYTTLRFPEM NIPRTGDAES  780
SEMQRPPPDC DDTVTYSALH KRQVGDYENV IPDFPEDEGI HYSELIQFGV GERPQAQENV  840
DYVILKH                                                           847

SEQ ID NO: 202                  moltype = AA   length = 226
FEATURE                         Location/Qualifiers
REGION                          1..226
                                note = Human CD79a
                        source          1..226
                                        mol_type = protein
                                        organism = synthetic construct
SEQUENCE: 202
MPGGPGVLQA LPATIFLLFL LSAVYLGPGC QALWMHKVPA SLMVSLGEDA HFQCPHNSSN   60
NANVTWWRVL HGNYTWPPEF LGPGEDPNGT LIIQNVNKSH GGIYVCRVQE GNESYQQSCG  120
TYLRVRQPPP RPFLDMGEGT KNRIITAEGI ILLFCAVVPG TLLLFRKRWQ NEKLGLDAGD  180
EYEDENLYEG LNLDDCSMYE DISRGLQGTY QDVGSLNIGD VQLEKP                226

SEQ ID NO: 203                  moltype = AA   length = 229
FEATURE                         Location/Qualifiers
REGION                          1..229
                                note = Human CD79b
                        source          1..229
                                        mol_type = protein
                                        organism = synthetic construct
SEQUENCE: 203
MARLALSPVP SHWMVALLLL LSAEPVPAAR SEDRYRNPKG SACSRIWQSP RFIARKRGFT   60
VKMHCYMNSA SGNVSWLWKQ EMDENPQQLK LEKGRMEESQ NESLATLTIQ GIRFEDNGIY  120
FCQQKCNNTS EVYQGCGTEL RVMGFSTLAQ LKQRNTLKDG IIMIQTLLII LFIIVPIFLL  180
LDKDDSKAGM EEDHTYEGLD IDQTATYEDI VTLRTGEVKW SVGEHPGQE              229

SEQ ID NO: 204                  moltype = AA   length = 44
FEATURE                         Location/Qualifiers
REGION                          1..44
                                note = GCN4(7P14P) sequence
                        source          1..44
                                        mol_type = protein
                                        organism = synthetic construct
SEQUENCE: 204
ASGGGRMKQL EPKVEELLPK NYHLENEVAR LKKLVGERHH HHHH                    44
```

| | | |
|---|---|---|
| SEQ ID NO: 205 | moltype = AA length = 132 | |
| FEATURE | Location/Qualifiers | |
| REGION | 1..132 | |
| | note = GCN4(7P14P) sequence | |
| source | 1..132 | |
| | mol_type = protein | |
| | organism = synthetic construct | |

SEQUENCE: 205
```
GCTAGCGGAG GCGGAAGAAT GAAACAACTT GAACCCAAGG TTGAAGAATT GCTTCCGAAA   60
AATTATCACT TGGAAAATGA GGTTGCCAGA TTAAAGAAAT TAGTTGGCGA ACGCCATCAC  120
CATCACCATC AC                                                     132
```

| | | |
|---|---|---|
| SEQ ID NO: 206 | moltype = AA length = 262 | |
| FEATURE | Location/Qualifiers | |
| REGION | 1..262 | |
| | note = 52SR4 ds scFv sequence | |
| source | 1..262 | |
| | mol_type = protein | |
| | organism = synthetic construct | |

SEQUENCE: 206
```
DAVVTQESAL TSSPGETVTL TCRSSTGAVT TSNYASWVQE KPDHLFTGLI GGTNNRAPGV   60
PARFSGSLIG DKAALTITGA QTEDEAIYFC VLWYSDHWVF GCGTKLTVLG GGGGSGGGGS  120
GGGGSGGGGS DVQLQQSGPG LVAPSQSLSI TCTVSGFLLT DYGVNWVRQS PGKCLEWLGV  180
IWGDITDYN SALKSRLSVT KDNSKSQVFL KMNSLQSGDS ARYYCVTGLF DYWGQGTTLT  240
VSSAAHHHH HHEQKLISEE DL                                          262
```

| | | |
|---|---|---|
| SEQ ID NO: 207 | moltype = DNA length = 792 | |
| FEATURE | Location/Qualifiers | |
| misc_feature | 1..792 | |
| | note = 52SR4 ds scFv sequence | |
| source | 1..792 | |
| | mol_type = other DNA | |
| | organism = synthetic construct | |

SEQUENCE: 207
```
gatgcggtgg tgacccagga aagcgcgctg accagcagcc cgggcgaaac cgtgaccctg   60
acctgccgca gcagcaccgg cgcggtgacc accagcaact atgcgagctg ggtgcaggaa  120
aaaccggatc atctgtttac cggcctgatt ggcggcacca caaaccgcgc gccgggcgtg  180
ccggcgcgct ttagcggcag cctgattggc gataaagcgg cgctgaccat taccggcgcg  240
cagaccgaag atgaagcgat ttatttttgc gtgctgtggt atagcgacca ttgggtgttt  300
ggctgcggca ccaaactgac cgtgctgggt ggaggcggtg gctcaggcgg aggtggctca  360
ggcggtggcg gtctggcgg cggcggcagc gatgtgcagc tgcagcagag cggcccgggc  420
ctggtggcg cgagccagag cctgagcatt acctgcaccg tgagcggctt tctcctgacc  480
gattatggcg tgaactgggt gcgccagagc ccgggcaaat gcctggaatg gctgggcgtg  540
atttggggcg atggcattac cgattataac agcgcgctga aaagccgcct gagcgtgacc  600
aaagataaca gcaaaagcca ggtgtttctg aaaatgaaca gcctgcagag cggcgatagc  660
gcgcgctatt attgcgtgac cggcctgttt gattattggg gccagggcac caccctgacc  720
gtgagcagcg cggccgccca tcaccatcac catcacgaac agaaactgat tagcgaagaa  780
gatctgtaat ag                                                     792
```

| | | |
|---|---|---|
| SEQ ID NO: 208 | moltype = AA length = 8 | |
| FEATURE | Location/Qualifiers | |
| REGION | 1..8 | |
| | note = Hinge linker sequence | |
| source | 1..8 | |
| | mol_type = protein | |
| | organism = synthetic construct | |

SEQUENCE: 208
```
DKTHTCAA                                                            8
```

| | | |
|---|---|---|
| SEQ ID NO: 209 | moltype = AA length = 11 | |
| FEATURE | Location/Qualifiers | |
| REGION | 1..11 | |
| | note = Hinge linker sequence | |
| source | 1..11 | |
| | mol_type = protein | |
| | organism = synthetic construct | |

SEQUENCE: 209
```
DKTHTCPPCP A                                                       11
```

| | | |
|---|---|---|
| SEQ ID NO: 210 | moltype = AA length = 18 | |
| FEATURE | Location/Qualifiers | |
| REGION | 1..18 | |
| | note = Hinge linker sequence | |
| source | 1..18 | |
| | mol_type = protein | |
| | organism = synthetic construct | |

SEQUENCE: 210
```
DKTHTCPPCP ATCPPCPA                                                18
```

```
SEQ ID NO: 211           moltype = AA  length = 25
FEATURE                  Location/Qualifiers
REGION                   1..25
                         note = Hinge linker sequence
source                   1..25
                         mol_type = protein
                         organism = synthetic construct
SEQUENCE: 211
DKTHTCPPCP ATCPPCPATC PPCPA                                            25

SEQ ID NO: 212           moltype = AA  length = 30
FEATURE                  Location/Qualifiers
REGION                   1..30
                         note = Hinge linker sequence
source                   1..30
                         mol_type = protein
                         organism = synthetic construct
SEQUENCE: 212
DKTHTCPPCP AGKPTLYNSL VMSDTAGTCY                                       30

SEQ ID NO: 213           moltype = AA  length = 31
FEATURE                  Location/Qualifiers
REGION                   1..31
                         note = Hinge linker sequence
source                   1..31
                         mol_type = protein
                         organism = synthetic construct
SEQUENCE: 213
DKTHTCPPCP AGKPTHVNVS VVMAEVDGTC Y                                     31

SEQ ID NO: 214           moltype = AA  length = 15
FEATURE                  Location/Qualifiers
REGION                   1..15
                         note = Hinge linker sequence
source                   1..15
                         mol_type = protein
                         organism = synthetic construct
SEQUENCE: 214
DKTHTCCVEC PPCPA                                                       15

SEQ ID NO: 215           moltype = AA  length = 26
FEATURE                  Location/Qualifiers
REGION                   1..26
                         note = Hinge linker sequence
source                   1..26
                         mol_type = protein
                         organism = synthetic construct
SEQUENCE: 215
DKTHTCPRCP EPKSCDTPPP CPRCPA                                           26

SEQ ID NO: 216           moltype = AA  length = 11
FEATURE                  Location/Qualifiers
REGION                   1..11
                         note = Hinge linker sequence
source                   1..11
                         mol_type = protein
                         organism = synthetic construct
SEQUENCE: 216
DKTHTCPSCP A                                                           11

SEQ ID NO: 217           moltype = AA  length = 7
FEATURE                  Location/Qualifiers
REGION                   1..7
                         note = Flexible linker sequence
source                   1..7
                         mol_type = protein
                         organism = synthetic construct
SEQUENCE: 217
SGGGGSE                                                                7

SEQ ID NO: 218           moltype = AA  length = 6
FEATURE                  Location/Qualifiers
REGION                   1..6
                         note = Flexible linker sequence
source                   1..6
                         mol_type = protein
                         organism = synthetic construct
SEQUENCE: 218
DKTHTS                                                                 6
```

```
SEQ ID NO: 219          moltype = AA  length = 6
FEATURE                 Location/Qualifiers
REGION                  1..6
                        note = Flexible linker sequence
source                  1..6
                        mol_type = protein
                        organism = synthetic construct
SEQUENCE: 219
SGGGGS                                                                    6

SEQ ID NO: 220          moltype = AA  length = 11
FEATURE                 Location/Qualifiers
REGION                  1..11
                        note = Flexible linker sequence
source                  1..11
                        mol_type = protein
                        organism = synthetic construct
SEQUENCE: 220
SGGGGSGGGG S                                                             11

SEQ ID NO: 221          moltype = AA  length = 16
FEATURE                 Location/Qualifiers
REGION                  1..16
                        note = Flexible linker sequence
source                  1..16
                        mol_type = protein
                        organism = synthetic construct
SEQUENCE: 221
SGGGGSGGGG SGGGGS                                                        16

SEQ ID NO: 222          moltype = AA  length = 21
FEATURE                 Location/Qualifiers
REGION                  1..21
                        note = Flexible linker sequence
source                  1..21
                        mol_type = protein
                        organism = synthetic construct
SEQUENCE: 222
SGGGGSGGGG SGGGGSGGGG S                                                  21

SEQ ID NO: 223          moltype = AA  length = 26
FEATURE                 Location/Qualifiers
REGION                  1..26
                        note = Flexible linker sequence
source                  1..26
                        mol_type = protein
                        organism = synthetic construct
SEQUENCE: 223
SGGGGSGGGG SGGGGSGGGG SGGGGS                                             26

SEQ ID NO: 224          moltype = AA  length = 11
FEATURE                 Location/Qualifiers
REGION                  1..11
                        note = Flexible linker sequence
source                  1..11
                        mol_type = protein
                        organism = synthetic construct
SEQUENCE: 224
AAAGSGGASA S                                                             11

SEQ ID NO: 225          moltype = AA  length = 16
FEATURE                 Location/Qualifiers
REGION                  1..16
                        note = Flexible linker sequence
source                  1..16
                        mol_type = protein
                        organism = synthetic construct
SEQUENCE: 225
AAAGSGXGGG SGASAS                                                        16

SEQ ID NO: 226          moltype = AA  length = 21
FEATURE                 Location/Qualifiers
REGION                  1..21
                        note = Flexible linker sequence
source                  1..21
                        mol_type = protein
                        organism = synthetic construct
SEQUENCE: 226
```

```
AAAGSGXGGG SXGGGSGASA S                                          21

SEQ ID NO: 227          moltype = AA  length = 26
FEATURE                 Location/Qualifiers
REGION                  1..26
                        note = Flexible linker sequence
source                  1..26
                        mol_type = protein
                        organism = synthetic construct
SEQUENCE: 227
AAAGSGXGGG SXGGGSXGGG SGASAS                                     26

SEQ ID NO: 228          moltype = AA  length = 31
FEATURE                 Location/Qualifiers
REGION                  1..31
                        note = Flexible linker sequence
source                  1..31
                        mol_type = protein
                        organism = synthetic construct
SEQUENCE: 228
AAAGSGXGGG SXGGGSXGGG SXGGGSGASA S                               31

SEQ ID NO: 229          moltype = AA  length = 13
FEATURE                 Location/Qualifiers
REGION                  1..13
                        note = Flexible linker sequence
source                  1..13
                        mol_type = protein
                        organism = synthetic construct
SEQUENCE: 229
AAAGSGXSGA SAS                                                   13

SEQ ID NO: 230          moltype = AA  length = 28
FEATURE                 Location/Qualifiers
REGION                  1..28
                        note = Flexible linker sequence
source                  1..28
                        mol_type = protein
                        organism = synthetic construct
SEQUENCE: 230
PGGNRGTTTT RRPATTTGSS PGPTQSHY                                   28

SEQ ID NO: 231          moltype = AA  length = 11
FEATURE                 Location/Qualifiers
REGION                  1..11
                        note = Flexible linker sequence
source                  1..11
                        mol_type = protein
                        organism = synthetic construct
SEQUENCE: 231
ATTTGSSPGP T                                                     11

SEQ ID NO: 232          moltype = AA  length = 6
FEATURE                 Location/Qualifiers
REGION                  1..6
                        note = Flexible linker sequence
source                  1..6
                        mol_type = protein
                        organism = synthetic construct
SEQUENCE: 232
ATTTGS                                                           6

SEQ ID NO: 233          moltype = AA  length = 21
FEATURE                 Location/Qualifiers
REGION                  1..21
                        note = Flexible linker sequence
source                  1..21
                        mol_type = protein
                        organism = synthetic construct
SEQUENCE: 233
EPSGPISTIN SPPSKESHKS P                                          21

SEQ ID NO: 234          moltype = AA  length = 15
FEATURE                 Location/Qualifiers
REGION                  1..15
                        note = Flexible linker sequence
source                  1..15
                        mol_type = protein
                        organism = synthetic construct
```

```
SEQUENCE: 234
GTVAAPSVFI FPPSD                                                                  15

SEQ ID NO: 235          moltype = AA  length = 15
FEATURE                 Location/Qualifiers
REGION                  1..15
                        note = Flexible linker sequence
source                  1..15
                        mol_type = protein
                        organism = synthetic construct
SEQUENCE: 235
GGGGIAPSMV GGGGS                                                                  15

SEQ ID NO: 236          moltype = AA  length = 15
FEATURE                 Location/Qualifiers
REGION                  1..15
                        note = Flexible linker sequence
source                  1..15
                        mol_type = protein
                        organism = synthetic construct
SEQUENCE: 236
GGGGKVEGAG GGGGS                                                                  15

SEQ ID NO: 237          moltype = AA  length = 15
FEATURE                 Location/Qualifiers
REGION                  1..15
                        note = Flexible linker sequence
source                  1..15
                        mol_type = protein
                        organism = synthetic construct
SEQUENCE: 237
GGGGSMKSHD GGGGS                                                                  15

SEQ ID NO: 238          moltype = AA  length = 15
FEATURE                 Location/Qualifiers
REGION                  1..15
                        note = Flexible linker sequence
source                  1..15
                        mol_type = protein
                        organism = synthetic construct
SEQUENCE: 238
GGGGNLITIV GGGGS                                                                  15

SEQ ID NO: 239          moltype = AA  length = 15
FEATURE                 Location/Qualifiers
REGION                  1..15
                        note = Flexible linker sequence
source                  1..15
                        mol_type = protein
                        organism = synthetic construct
SEQUENCE: 239
GGGGVVPSLP GGGGS                                                                  15

SEQ ID NO: 240          moltype = AA  length = 12
FEATURE                 Location/Qualifiers
REGION                  1..12
                        note = Flexible linker sequence
source                  1..12
                        mol_type = protein
                        organism = synthetic construct
SEQUENCE: 240
GGEKSIPGGG GS                                                                     12

SEQ ID NO: 241          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 241
RPLSYRPPFP FGFPSVRP                                                               18

SEQ ID NO: 242          moltype = AA  length = 18
FEATURE                 Location/Qualifiers
REGION                  1..18
                        note = Flexible linker sequence
source                  1..18
                        mol_type = protein
```

```
                       organism = synthetic construct
SEQUENCE: 242
YPRSIYIRRR HPSPSLTT                                                  18

SEQ ID NO: 243         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 243
TPSHLSHILP SFGLPTFN                                                  18

SEQ ID NO: 244         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 244
RPVSPFTFPR LSNSWLPA                                                  18

SEQ ID NO: 245         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 245
SPAAHFPRSI PRPGPIRT                                                  18

SEQ ID NO: 246         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 246
APGPSAPSHR SLPSRAFG                                                  18

SEQ ID NO: 247         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 247
PRNSIHFLHP LLVAPLGA                                                  18

SEQ ID NO: 248         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 248
MPSLSGVLQV RYLSPPDL                                                  18

SEQ ID NO: 249         moltype = AA  length = 18
FEATURE                Location/Qualifiers
REGION                 1..18
                       note = Flexible linker sequence
source                 1..18
                       mol_type = protein
                       organism = synthetic construct
SEQUENCE: 249
SPQYPSPLTL TLPPHPSL                                                  18

SEQ ID NO: 250         moltype = AA  length = 18
FEATURE                Location/Qualifiers
REGION                 1..18
                       note = Flexible linker sequence
source                 1..18
```

```
                        mol_type = protein
                        organism = synthetic construct
SEQUENCE: 250
NPSLNPPSYL HRAPSRIS                                                 18

SEQ ID NO: 251          moltype = AA  length = 17
FEATURE                 Location/Qualifiers
REGION                  1..17
                        note = Flexible linker sequence
source                  1..17
                        mol_type = protein
                        organism = synthetic construct
SEQUENCE: 251
LPWRTSLLPS LPLRRRP                                                  17

SEQ ID NO: 252          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 252
PPLFAKGPVG LLSRSFPP                                                 18

SEQ ID NO: 253          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 253
VPPAPVVSLR SAHARPPY                                                 18

SEQ ID NO: 254          moltype = AA  length = 17
FEATURE                 Location/Qualifiers
REGION                  1..17
                        note = Flexible linker sequence
source                  1..17
                        mol_type = protein
                        organism = synthetic construct
SEQUENCE: 254
LRPTPPRVRS YTCCPTP                                                  17

SEQ ID NO: 255          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 255
PNVAHVLPLL TVPWDNLR                                                 18

SEQ ID NO: 256          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 256
CNPLLPLCAR SPAVRTFP                                                 18

SEQ ID NO: 257          moltype = AA  length = 11
FEATURE                 Location/Qualifiers
REGION                  1..11
                        note = Flexible linker sequence
source                  1..11
                        mol_type = protein
                        organism = synthetic construct
SEQUENCE: 257
DLCLRDWGCL W                                                        11

SEQ ID NO: 258          moltype = AA  length = 11
FEATURE                 Location/Qualifiers
REGION                  1..11
                        note = Flexible linker sequence
```

```
source                  1..11
                        mol_type = protein
                        organism = synthetic construct
SEQUENCE: 258
DICLPRWGCL W                                                            11

SEQ ID NO: 259          moltype = AA   length = 15
FEATURE                 Location/Qualifiers
REGION                  1..15
                        note = Flexible linker sequence
source                  1..15
                        mol_type = protein
                        organism = synthetic construct
SEQUENCE: 259
MEDICLPRWG CLWGD                                                        15

SEQ ID NO: 260          moltype = AA   length = 20
FEATURE                 Location/Qualifiers
REGION                  1..20
                        note = Flexible linker sequence
source                  1..20
                        mol_type = protein
                        organism = synthetic construct
SEQUENCE: 260
QRLMEDICLP RWGCLWEDDE                                                   20

SEQ ID NO: 261          moltype = AA   length = 20
FEATURE                 Location/Qualifiers
REGION                  1..20
                        note = Flexible linker sequence
source                  1..20
                        mol_type = protein
                        organism = synthetic construct
SEQUENCE: 261
QGLIGDICLP RWGCLWGRSV                                                   20

SEQ ID NO: 262          moltype = AA   length = 21
FEATURE                 Location/Qualifiers
REGION                  1..21
                        note = Flexible linker sequence
source                  1..21
                        mol_type = protein
                        organism = synthetic construct
SEQUENCE: 262
QGLIGDICLP RWGCLWGRSV K                                                 21

SEQ ID NO: 263          moltype = AA   length = 15
FEATURE                 Location/Qualifiers
REGION                  1..15
                        note = Flexible linker sequence
source                  1..15
                        mol_type = protein
                        organism = synthetic construct
SEQUENCE: 263
EDICLPRWGC LWEDD                                                        15

SEQ ID NO: 264          moltype = AA   length = 18
FEATURE                 Location/Qualifiers
REGION                  1..18
                        note = Flexible linker sequence
source                  1..18
                        mol_type = protein
                        organism = synthetic construct
SEQUENCE: 264
RLMEDICLPR WGCLWEDD                                                     18

SEQ ID NO: 265          moltype = AA   length = 16
FEATURE                 Location/Qualifiers
REGION                  1..16
                        note = Flexible linker sequence
source                  1..16
                        mol_type = protein
                        organism = synthetic construct
SEQUENCE: 265
MEDICLPRWG CLWEDD                                                       16

SEQ ID NO: 266          moltype = AA   length = 15
FEATURE                 Location/Qualifiers
REGION                  1..15
```

-continued

```
                        note = Flexible linker sequence
source                  1..15
                        mol_type = protein
                        organism = synthetic construct
SEQUENCE: 266
MEDICLPRWG CLWED                                                          15

SEQ ID NO: 267          moltype = AA  length = 18
FEATURE                 Location/Qualifiers
REGION                  1..18
                        note = Flexible linker sequence
source                  1..18
                        mol_type = protein
                        organism = synthetic construct
SEQUENCE: 267
RLMEDICLAR WGCLWEDD                                                       18

SEQ ID NO: 268          moltype = AA  length = 20
FEATURE                 Location/Qualifiers
REGION                  1..20
                        note = Flexible linker sequence
source                  1..20
                        mol_type = protein
                        organism = synthetic construct
SEQUENCE: 268
EVRSFCTRWP AEKSCKPLRG                                                     20

SEQ ID NO: 269          moltype = AA  length = 20
FEATURE                 Location/Qualifiers
REGION                  1..20
                        note = Flexible linker sequence
source                  1..20
                        mol_type = protein
                        organism = synthetic construct
SEQUENCE: 269
RAPESFVCYW ETICFERSEQ                                                     20

SEQ ID NO: 270          moltype = AA  length = 11
FEATURE                 Location/Qualifiers
REGION                  1..11
                        note = Flexible linker sequence
source                  1..11
                        mol_type = protein
                        organism = synthetic construct
SEQUENCE: 270
EMCYFPGICW M                                                              11

SEQ ID NO: 271          moltype = AA  length = 11
FEATURE                 Location/Qualifiers
REGION                  1..11
                        note = linker
source                  1..11
                        mol_type = protein
                        organism = synthetic construct
SEQUENCE: 271
SGGGGSGGGG S                                                              11

SEQ ID NO: 272          moltype = AA  length = 11
FEATURE                 Location/Qualifiers
REGION                  1..11
                        note = linker
source                  1..11
                        mol_type = protein
                        organism = synthetic construct
SEQUENCE: 272
SGGGGTGGGG S                                                              11

SEQ ID NO: 273          moltype = AA  length = 11
FEATURE                 Location/Qualifiers
REGION                  1..11
                        note = peptide sequence
source                  1..11
                        mol_type = protein
                        organism = synthetic construct
SEQUENCE: 273
GAPAPAAPAP A                                                              11

SEQ ID NO: 274          moltype = AA  length = 4
FEATURE                 Location/Qualifiers
```

```
REGION                  1..4
                        note = peptide sequence
source                  1..4
                        mol_type = protein
                        organism = synthetic construct
SEQUENCE: 274
PPPP                                                                    4

SEQ ID NO: 275          moltype = AA  length = 6
FEATURE                 Location/Qualifiers
source                  1..6
                        mol_type = protein
                        organism = synthetic construct
SEQUENCE: 275
ASGGGG                                                                  6

SEQ ID NO: 276          moltype = AA  length = 8
FEATURE                 Location/Qualifiers
source                  1..8
                        mol_type = protein
                        organism = synthetic construct
SEQUENCE: 276
ASGGGGSG                                                                8
```

The invention claimed is:

1. An antibody molecule comprising a binding domain specific to CD22, wherein the binding domain comprises a heavy chain variable domain (VH) comprising CDR H1, CDR H2, and CDR H3 and a light chain variable domain (VL) comprising CDR L1, CDR L2, and CDR L3 wherein

```
CDR H1 is SEQ ID NO: 35 or 36;
CDR H2 is SEQ ID NO: 46 or 47;
CDR H3 is SEQ ID NO: 64;
CDR L1 is SEQ ID NO: 72;
CDR L2 is SEQ ID NO: 78;
and
CDR L3 is SEQ ID NO: 99.
```

2. The antibody molecule according to claim 1, wherein VH and VL are humanised.

3. The antibody molecule according to claim 2, wherein the VH comprises a human framework region wherein at least one position in the heavy chain human framework is selected from the group consisting of position 1 is glutamic acid, position 11 is leucine, position 23 is lysine, position 24 is glycine, position 37 is valine, position 48 is isoleucine, position 49 is alanine, position 67 is phenylalanine, position 71 is lysine, position 73 is serine, position 76 is threonine and position 78 is valine, and/or the VL comprises a human framework region wherein at least one position in the light chain human framework is selected from the group consisting of position 3 is valine, position 36 is phenylalanine, position 63 is lysine, position 65 is aspartic acid, position 66 is arginine and position 71 is tyrosine, numbering according to Kabat.

4. The antibody molecule according to claim 1, comprising a VH comprising SEQ ID NO: 136, SEQ ID NO: 137, SEQ ID NO: 138 or SEQ ID NO: 139.

5. The antibody molecule according to claim 1, comprising a VL comprising SEQ ID NO: 135.

6. A composition comprising one or more antibody molecules according to claim 1.

7. An antibody molecule comprising a VH comprising SEQ ID NO: 136, SEQ ID NO: 137, SEQ ID NO: 138 or SEQ ID NO: 139 and a VL comprising SEQ ID NO: 135.

8. A nucleotide encoding an antibody molecule, wherein the antibody comprises a binding domain specific to CD22, wherein the binding domain comprises a heavy chain variable domain (VH) comprising CDR H1, CDR H2, and CDR H3 and a light chain variable domain (VL) comprising CDR L1, CDR L2, and CDR L3 wherein

```
CDR H1 is SEQ ID NO: 35 or 36;
CDR H2 is SEQ ID NO: 46 or 47;
CDR H3 is SEQ ID NO: 64;
CDR L1 is SEQ ID NO: 72;
CDR L2 is SEQ ID NO: 78;
and
CDR L3 is SEQ ID NO: 99.
```

9. The nucleotide of claim 8, wherein the VH and VL are humanised.

10. The nucleotide of claim 8, wherein the antibody comprises a VH comprising SEQ ID NO: 136, SEQ ID NO: 137, SEQ ID NO: 138 or SEQ ID NO: 139.

11. The nucleotide of claim 8, wherein the antibody comprises a VL comprising SEQ ID NO:135.

12. The nucleotide of claim 8, wherein the antibody molecule comprises a VH comprising SEQ ID NO: 136, SEQ ID NO: 137, SEQ ID NO: 138 or SEQ ID NO: 139 and a VL comprising SEQ ID NO:135.

13. A vector comprising the nucleotide of claim 8.

14. The vector of claim 13, wherein the vector is a plasmid or a viral vector.

15. The vector of claim 13, wherein the vector is capable of autonomous replication in a host cell.

16. The vector of claim 13, wherein the vector is a bacterial vector or an episomal mammalian vector.

17. The vector of claim 13, wherein the vector is capable of being integrated into the genome of a host cell.

18. A host cell comprising the nucleotide of claim 8.

19. A host cell comprising the vector of claim 13.

20. The host cell of claim 18 or claim 19, wherein the host cell is a bacterial cell.

* * * * *